US009910040B2

(12) United States Patent
Stein et al.

(10) Patent No.: US 9,910,040 B2
(45) Date of Patent: *Mar. 6, 2018

(54) MOLECULAR NETS COMPRISING CAPTURE AGENTS AND LINKING AGENTS

(71) Applicant: Sevident, Inc., San Francisco, CA (US)

(72) Inventors: Emily A. Stein, San Leandro, CA (US); Michael A. Evans, Palo Alto, CA (US)

(73) Assignee: Sevident, Inc., Hayward, CA (US)

( * ) Notice: Subject to any disclaimer, the term of this patent is extended or adjusted under 35 U.S.C. 154(b) by 782 days.

This patent is subject to a terminal disclaimer.

(21) Appl. No.: 13/938,055

(22) Filed: Jul. 9, 2013

(65) Prior Publication Data

US 2014/0080119 A1 Mar. 20, 2014

Related U.S. Application Data

(63) Continuation-in-part of application No. 13/511,364, filed on Oct. 7, 2012.

(60) Provisional application No. 61/669,261, filed on Jul. 9, 2012, provisional application No. 61/669,265, filed on Jul. 9, 2012.

(51) Int. Cl.
*G01N 33/543* (2006.01)
*G01N 33/50* (2006.01)
*G01N 33/569* (2006.01)
*B01L 3/00* (2006.01)

(52) U.S. Cl.
CPC . *G01N 33/56983* (2013.01); *G01N 33/54353* (2013.01); *G01N 33/56911* (2013.01); *G01N 33/56916* (2013.01); *G01N 33/56938* (2013.01); *B01L 3/502753* (2013.01)

(58) Field of Classification Search
CPC ................. G01N 33/54353; G01N 33/54346
See application file for complete search history.

(56) References Cited

U.S. PATENT DOCUMENTS

| | | | |
|---|---|---|---|
| 3,817,837 A | 6/1974 | Rubenstein et al. | |
| 3,850,752 A | 11/1974 | Schuurs et al. | |
| 3,939,350 A | 2/1976 | Kronick et al. | |
| 3,996,345 A | 12/1976 | Ullman et al. | |
| 4,069,352 A | 1/1978 | Parsons, Jr. | |
| 4,232,119 A * | 11/1980 | Carlsson | A61K 39/44 435/188 |

(Continued)

FOREIGN PATENT DOCUMENTS

| | | |
|---|---|---|
| CN | 1180260 C | 12/2004 |
| CN | 1925871 A | 3/2007 |

(Continued)

OTHER PUBLICATIONS

CN 201080061738.9, Fourth Office action dated Jul. 4, 2016, 5 pages of English translation.

(Continued)

*Primary Examiner* — Erik B Crawford
*Assistant Examiner* — Gary E Hollinden
(74) *Attorney, Agent, or Firm* — Arrigo, Lee & Guttman LLP; Harry J. Guttman

(57) ABSTRACT

A molecular net formed as a branched pseudorandom copolymer including two broad classes of subunits: capture agents and linking agents. The subunits self-assemble to form a structure capable of binding to predetermined targets. The binding can then be detected.

31 Claims, 60 Drawing Sheets

(56) References Cited

U.S. PATENT DOCUMENTS

| | | | |
|---|---|---|---|
| 4,275,149 A | 6/1981 | Litman et al. | |
| 4,277,437 A | 7/1981 | Maggio | |
| 4,366,241 A | 12/1982 | Tom et al. | |
| 4,434,150 A * | 2/1984 | Azad | G01N 33/532 |
| | | | 252/645 |
| 4,511,478 A | 4/1985 | Nowinski et al. | |
| 4,590,169 A * | 5/1986 | Cragle | G01N 33/54313 |
| | | | 436/519 |
| 4,756,828 A | 7/1988 | Litman et al. | |
| 4,757,004 A | 7/1988 | Routs et al. | |
| 4,778,751 A * | 10/1988 | El Shami | G01N 33/531 |
| | | | 435/7.5 |
| 4,829,101 A | 5/1989 | Kraemer et al. | |
| 4,879,215 A | 11/1989 | Weng et al. | |
| 4,883,688 A | 11/1989 | Houts et al. | |
| 4,945,205 A | 7/1990 | Litman et al. | |
| 4,960,691 A | 10/1990 | Gordon et al. | |
| 5,001,048 A | 3/1991 | Taylor et al. | |
| 5,585,481 A | 12/1996 | Arnold et al. | |
| 5,650,334 A * | 7/1997 | Zuk | G01N 33/533 |
| | | | 435/174 |
| 5,876,830 A | 3/1999 | Michl et al. | |
| 5,914,230 A * | 6/1999 | Liu | C12Q 1/6813 |
| | | | 435/6.1 |
| 5,994,089 A * | 11/1999 | Siiman | G01N 33/533 |
| | | | 435/7.24 |
| 6,074,827 A | 6/2000 | Nelson et al. | |
| 6,627,460 B1 * | 9/2003 | Lihme | G01N 33/531 |
| | | | 436/527 |
| 7,612,168 B2 | 11/2009 | Sorensen | |
| 7,615,614 B2 | 11/2009 | Hackett, Jr. et al. | |
| 7,939,283 B2 | 5/2011 | Chan et al. | |
| 2002/0137193 A1 | 9/2002 | Heller et al. | |
| 2003/0003602 A1* | 1/2003 | Vogt | G01N 33/536 |
| | | | 436/523 |
| 2003/0108972 A1 | 6/2003 | Zweig | |
| 2003/0116499 A1 | 6/2003 | Ward et al. | |
| 2003/0124623 A1 | 7/2003 | Yager et al. | |
| 2003/0149246 A1 | 8/2003 | Russell | |
| 2005/0037343 A1 | 2/2005 | Fagnani et al. | |
| 2005/0037413 A1 | 2/2005 | Park et al. | |
| 2005/0042612 A1 | 2/2005 | Hubbard et al. | |
| 2005/0112601 A1 | 5/2005 | Hassibi et al. | |
| 2006/0148096 A1 | 7/2006 | Jina | |
| 2006/0194197 A1 | 8/2006 | Spangler et al. | |
| 2006/0252074 A1 | 11/2006 | Atzesberger et al. | |
| 2007/0031283 A1 | 2/2007 | Davis et al. | |
| 2007/0117199 A1* | 5/2007 | Nimri | G01N 33/548 |
| | | | 435/287.2 |
| 2007/0281366 A1 | 12/2007 | Shimizu et al. | |
| 2008/0145949 A1 | 6/2008 | Song et al. | |
| 2008/0280778 A1 | 11/2008 | Urdea | |
| 2009/0023144 A1 | 1/2009 | Sun | |
| 2009/0214762 A1 | 8/2009 | Lewis et al. | |
| 2013/0052653 A1* | 2/2013 | Stein | G01N 33/54346 |
| | | | 435/7.1 |
| 2014/0080119 A1 | 3/2014 | Stein et al. | |
| 2014/0315759 A1 | 10/2014 | Stein et al. | |

FOREIGN PATENT DOCUMENTS

| | | |
|---|---|---|
| CN | 101514956 A | 8/2009 |
| CN | 101558301 B | 10/2009 |
| DE | 19703718 A1 | 7/1997 |
| EA | 200602280 A1 | 6/2007 |
| EP | 1577670 A2 | 9/2005 |
| EP | 2541250 A1 | 1/2013 |
| WO | 1989001335 A1 | 2/1989 |
| WO | 1993013121 A1 | 7/1993 |
| WO | 1995027902 A1 | 10/1995 |
| WO | 1995032305 A1 | 11/1995 |
| WO | 9630409 A1 | 10/1996 |
| WO | 1997007398 A1 | 2/1997 |
| WO | 1999030145 A1 | 6/1999 |
| WO | 2000007019 A1 | 2/2000 |
| WO | 2001057533 A2 | 8/2001 |
| WO | 2003025573 A1 | 3/2003 |
| WO | 2005036171 A1 | 4/2005 |
| WO | 2005072479 A2 | 8/2005 |
| WO | 2005123952 A2 | 12/2005 |
| WO | 2007067189 A2 | 6/2007 |
| WO | 2008075216 A1 | 6/2008 |
| WO | 2009135388 A1 | 11/2009 |
| WO | 2011066449 A1 | 6/2011 |

OTHER PUBLICATIONS

CN 201080061738.9, Fourth Office action dated Jul. 4, 2016, 6 pages.
CN 201080061738.9, Office action dated Jul. 2, 2014, 10 pages.
CN 201080061738.9, Office action dated Jul. 2, 2014, 7 pages of English-language summary.
CN 201080061738.9, Second Office action dated Apr. 24, 2015, 9 pages.
CN 201080061738.9, Second Office action dated Apr. 24, 2015, 9 pages of English translation.
CN 201080061738.9, Third Office action dated Dec. 23, 2015, 4 pages.
CN 201080061738.9, Third Office action dated Dec. 23, 2015, 5 pages of English translation.
English-language translation of Abstract from Thomson Innovation of Chinese Patent No. 101514956, 2 pages.
English-language translation of Abstract from Thomson Innovation of German Patent No. 19703718, 1 page.
EP 10833970.6, ESR dated Nov. 13, 2014, 9 pages.
EP 13816747.3, Partial Supplementary ESR dated Jul. 27, 2016, 8 pages.
PCT/US2010/058086, ISR/WO dated Feb. 28, 2011, 12 pages.
PCT/US2013/049779, ISR/WO dated Jan. 10, 2014, 20 pages.
PCT/US2014/029823, ISR/WO dated Aug. 28, 2014, 6 pages.
U.S. Appl. No. 13/511,364 Office Action notification dated Apr. 3, 2015, 15 pages.
U.S. Appl. No. 13/511,364 Office Action notification dated Feb. 11, 2016, 15 pages.
U.S. Appl. No. 13/511,364 Office Action notification dated Jul. 25, 2014, 7 pages.
U.S. Appl. No. 13/511,364 Office Action notification dated Sep. 25, 2013, 10 pages.
U.S. Appl. No. 13/511,364 Response filed Mar. 25, 2014, for Sep. 25, 2013, Office Action, 5 pages.
U.S. Appl. No. 13/511,364 Response filed Oct. 28, 2014, for Jul. 25, 2014, Office Action, 8 pages.
U.S. Appl. No. 13/511,364 Response filed Oct. 5, 2015, for Apr. 3, 2015, Office Action, 10 pages.
U.S. Appl. No. 13/511,364 Response filed Aug. 11, 2016, for Feb. 11, 2016, Office Action, 18 pages.
U.S. Appl. No. 14/214,556 Office Action notification dated Feb. 4, 2016, 13 pages.
U.S. Appl. No. 14/214,556 Response filed May 4, 2016, for Feb. 4, 2016, Office Action, 17 pages.
U.S. Appl. No. 14/214,556 Supplemental Response filed Aug. 15, 2016, for Feb. 4, 2016, Office Action, 17 pages.
Abrahams et al., "Assembly of porphyrin building blocks into network structures with large channels" Nature (1994) vol. 369, p. 727.
Abuknesha et al. (Abstract) "Labeling of biotin antibodies with horseradish peroxidase using cyanuric chloride." Nature Protocols, vol. 4, No. 4, pp. 452-460, Mar. 2009.
Brynda et al. "Antibody networks for surface plasmon resonance immunosensors" Sensors and Actuators B: Chemical, vol. 54, Nos. 1-2, pp. 132-136, Jan. 1999.
Chen et al., "Synthesis from DNA of a molecule with the connectivity of a cube" Nature (1991) vol. 350, No. 6319, pp. 631-633.
Cui et al., "Layer-by-layer assembly of multilayer films composed of avidin and biotin-labeled antibody for immunosensing" Biosensors & Bioelectronics (2003) vol. 18, pp. 59-67.

(56) References Cited

OTHER PUBLICATIONS

Fagan et al., "Molecular engineering of solid-state materials: organometallic building blocks" J. Am. Chem. Soc. (1989) vol. 111, pp. 1698-1719.
Jothikumar et al. (Abstract) "Design of FRET-TaqMan probes for multiplex real-time PCR using an internal positive control" Biotechniques, vol. 46, No. 7, pp. 519-524, Jun. 2009.
Koubova et al. "Detection of foodborne pathogens using surface plasmon resonance biosensors" Sensors and Actuators B: Chemical, vol. 74, Nos. 1-3, pp. 100-105, Apr. 2001.
MacGillivray et al., "Interwoven two- and three-dimensional coordination polymers through self-assembly of Cu1 cations with linear bidentate ligands" J. Chem. Soc. Chem. Commun. (1994) vol. 11, pp. 1325-1326.
Nigundi et al., "Failure of layer-by-layer multilayers composed of neutravidin-biotin-labeled antibody for sandwich fluoroimmunosensing" Biosensors & Bioelectronics (2007) vol. 22, pp. 3243-3246.
Stein et al., "Turning Down the Heat: Design and Mechanism in Solid-State Synthesis" Science (1993) vol. 259, No. 5101, pp. 1558-1564.
Su et al. "Development of immunochips for the detection of dengue viral antigens" Analytica Chimica Acta, vol. 479, No. 2, pp. 117-123, Mar. 2003.
Taylor et al. "Quantitative and simultaneous detection of four bloodborne bacterial pathogens with a multi-channel SPR sensor" Biosensors and Bioelectronics, vol. 22, No. 5, pp. 752-758, Dec. 2006.
Van Ness et al., "A versatile solid support system for oligodeoxynucleotide probe-based hybridization assays" Nucleic Acids Research (1991a) vol. 19, No. 12, pp. 3345-3350.
Van Ness et al., "The use of oligodeoxynucleotde probes in chaotrope-based hybridization solutions" Nucleic Acids Research (1991b) vol. 19, No. 19, pp. 5143-5151.
Wang et al., "Molecular Tectonics. Three-Dimensional Organic Networks with Zeolite Properties" Am. Chem. Soc. (1994) vol. 116, p. 12119.
Yaghi et al., "Hydrothermal Synthesis of a Metal-Organic Framework Containing Large Rectangular Channels" J. Am. Chem. Soc. (1995) vol. 117, No. 41, p. 10401-10402.
Yamaguchi et al., "Preparation and properties of antibody polymers" Reactive and Functional Polymers (1998) vol. 37, pp. 245-250.
Zhang et al., "Geometrically-Controlled and Site-Specifically-Functionalized Phenylacetylene Macrocycles" J. Am. Chem. Soc. (1994) vol. 116, p. 4227-4239.
CN 201480025377.0, First Office action dated Aug. 22, 2016, 17 pages.
CN 201480025377.0, First Office action dated Aug. 22, 2016, English translation, 17 pages.
EP 10833970.6, Exam report dated Sep. 22, 2016, 9 pages.
EP 13816747.3, Extended EP Search Report dated Nov. 2, 2016, 10 pages.
EP 14768268.6, Extended EP Search Report dated Jul. 21, 2016, 7 pages.
U.S. Appl. No. 13/511,364 Restriction Requirement dated Apr. 5, 2013, 5 pages.
U.S. Appl. No. 13/511,364 Response to Restriction Requirement filed Jun. 5, 2013, 5 pages.
U.S. Appl. No. 13/511,364 Advisory Action dated Nov. 18, 2014, 11 pages.
U.S. Appl. No. 13/511,364 RCE submission filed Jan. 26, 2015, 9 pages.
U.S. Appl. No. 13/511,364 Interview Summary dated Aug. 29, 2016, 4 pages.
U.S. Appl. No. 13/511,364 Statement of the Substance of the Interview filed Sep. 29, 2016, 4 pages.
U.S. Appl. No. 13/511,364 Final Office Action dated Dec. 30, 2016, 31 pages.
U.S. Appl. No. 14/214,556 Final Office Action dated Sep. 22, 2016, 23 pages.
U.S. Appl. No. 14/214,556 Interview Summary dated Nov. 1, 2016, 6 pages.
U.S. Appl. No. 14/214,556 RCE submission filed Dec. 21, 2016, 18 pages.
Brynda et al., "The detection of human beta2-microglobulin by grating coupler immunosensor with three dimensional antibody networks" Biosensors & Bioelectronics (1999) vol. 14, pp. 363-368.
CN 201480025377.0, Second Office action dated Mar. 30, 2017, 18 pages.
CN 201480025377.0, Second Office action dated Mar. 30, 2017, English translation, 17 pages.
EP 14768268.6, Examination Report dated Mar. 21, 2017, 4 pages.
U.S. Appl. No. 14/214,556 Notice of Allowance and Allowability with Interview Summary dated Mar. 27, 2017, 36 pages.
EP 10833970.6, Summons to Attend Oral Proceedings dated Dec. 6, 2017, 11 pages.

* cited by examiner

| Number of layers | 1 | 1 | 1 | 1 | 2 | 3 | 4 |
|---|---|---|---|---|---|---|---|
| Relative capture agent used per layer | 1 | 1 | 2 | 3 | 1 | 1 | 1 |
| Relative Total capture agent used | 1 | 1 | 2 | 3 | 2 | 3 | 4 |

Net fluorescence pre- and post-analyte binding assay

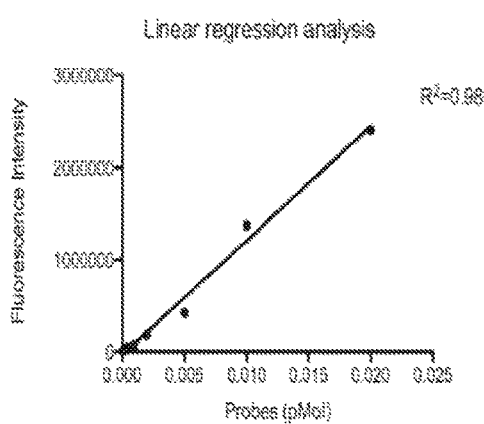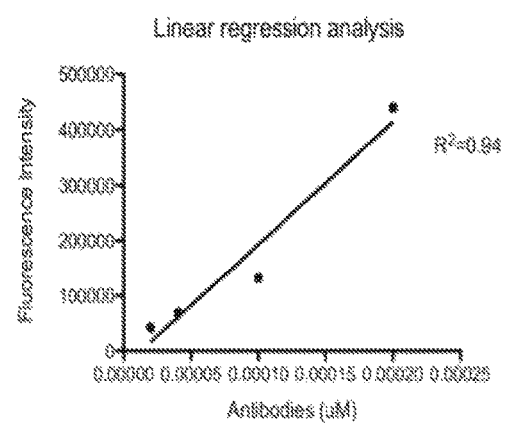
FIG. 26  FIG. 27

FIG. 43A
4310
FIG. 43B
4311
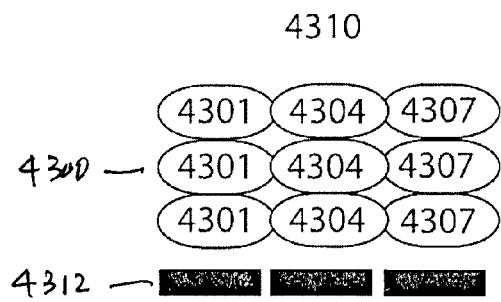
4300
4300
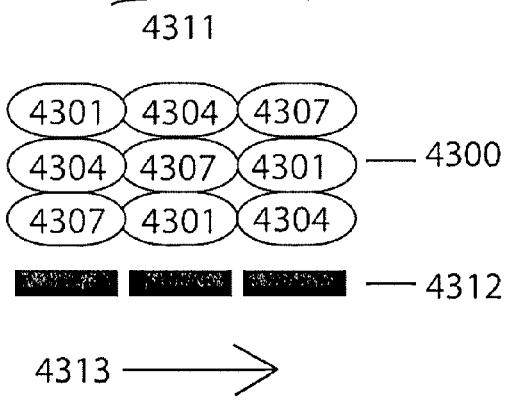
4312
4312
4313 ⟶
4313 ⟶
FIG. 43C
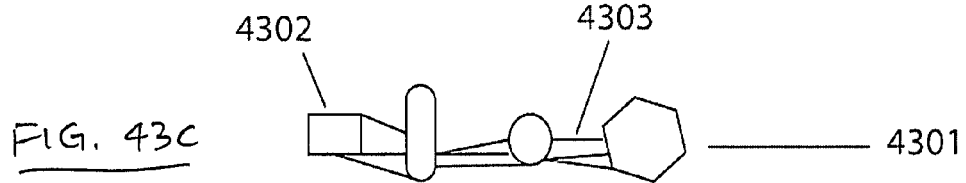
4302  4303
4301
FIG. 43D
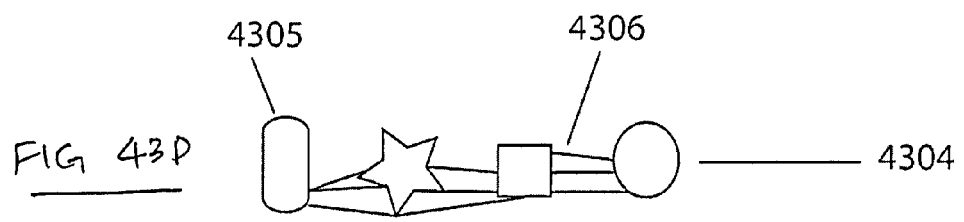
4305  4306
4304
FIG. 43E
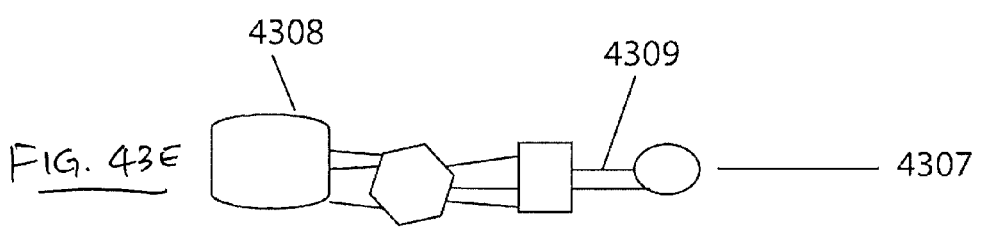
4308  4309
4307

MOLECULAR NETS COMPRISING CAPTURE AGENTS AND LINKING AGENTS

CROSS-REFERENCE TO RELATED APPLICATIONS

This application claims the benefit of U.S. provisional application Nos. 61/669,261 (filed Jul. 9, 2012) and 61/669,265 (filed Jul. 9, 2012). This application is also a continuation-in-part of U.S. patent application Ser. No. 13/511,364 (filed May 22, 2012). The entire content of each of these applications is hereby incorporated by reference.

SEQUENCE LISTING

The present application includes a Sequence Listing which has been submitted through EFS-Web and is hereby incorporated by reference in its entirety. This ASCII copy is named SEVID400.TXT, was created on Nov. 6, 2013, and has a size of 9,465 bytes.

BACKGROUND

Despite the advances in medical research, diagnostic testing strategies in current use often are not cost effective, are time-intensive, are limited in the scope of antigen tested for, and/or are labor-intensive. There is a great need for additional diagnostic methods and devices capable of detecting or assessing the health or identifying or indicating the presence of disease or disease-causing factors in humans and animals.

Diagnostic testing methods are needed for identifying or indicating the presence of various diseases, infections, and conditions.

The mammalian immune system reacts to foreign agents such as organisms and allergens through numerous recognition pathways involving the innate and adaptive immune systems. Normally, the immune system is capable of limiting or eliminating infection by a foreign organism, however, some organisms have mechanisms to evade the human immune system and can cause disease, morbidity and death. Similarly, the immune system typically generates an immune response against allografts or xenografts in organ and tissue transplant recipients causing rejection of the transplant. Further, in an increasing number of cases, the immune system is hyperactive, and reacts to self or environmental agents that it would normally be tolerant to, causing autoimmune, asthmatic or allergic responses. The aforementioned acute or chronic inflammatory states caused by infection, autoimmune and allergic diseases are significant causes of morbidity and mortality worldwide. Infectious diseases (ID) are clinically and sub-clinically manifested diseases caused by the presence of microbial organisms including pathogenic bacteria, fungi, protozoa, parasites and agents such as viruses and prions. ID are communicable diseases spread through sexual or casual contact, food, water and air. Further, infectious diseases cause significant loss to the global economy, but more importantly, they account for 16% of all deaths annually, 55% of deaths in children under the age of five years, and 26% of deaths in neonates. Many of the common IDs are largely preventable and are easy to treat once identified.

For example, rapid identification of methicillin-resistant *S. aureus* (MRSA) is highly desirable, as it is the leading cause of hospital-acquired infections (HAI). There is a need for more timely results on MRSA patient screening in clinical settings. Current technologies that exist for MRSA detection are PCR, FISH, lateral flow immunoassay, phage infection, latex agglutination or plating on selective media for MRSA sample screening; each requiring hours of incubation and sample preparation. Limitations of exclusively nucleic acid based approaches (PCR and FISH) are that multiple mutations in the target region, SCCmec, have been determined and decreased test sensitivity can result due to low probe hybridization efficiency. Limitations of traditional plating is low sensitivity and long time-to-answer. Limitations of the latex agglutination assay is the ambiguity of a positive test result, as the test must be read within a small timeframe and is not practical for many settings. Limitations of the phage-based tests require metabolically active intact cells. Limitations of current lateral flow immunoassays are the requirements to culture the organism and to prepare a sample and the high limits of detection (due to the binding of a single epitope on an analyte). Net-based assays for the detection of MRSA analytes enable multiple signatures (nucleic acid and protein) to be detected simultaneously and in a highly specific manner (refer to data on the lack of non-specific binding). The molecular net does not require sample preparation and is constructed to recognize multiple epitopes on a single analyte.

In addition, infections acquired in the community results in over 12 million ambulatory care visits/year, and are the main cause of skin and soft tissue infections in emergency departments. Currently, MRSA strain testing takes hours or days, which is too late to guide critical decisions about admission, isolation, and treatment. Additionally, acute and prolonged infections can result in an overly robust immune response leading to sepsis (septicemia), which is a serious medical condition and is the tenth leading cause of death in the US (CDC, 2003). Populations at risk of septicemia are the elderly, immunocompromised and critically ill patients. Sepsis is usually treated with intravenous fluids and antibiotics, however insufficient or delayed treatment can lead to severe sepsis characterized by organ dysfunction, hypotension, multi-organ failure and shock. Mortality rates for severe sepsis are over 60% in the United States each year. Allergies and food intolerances arise from hypersensitivity reactions of the immune system to one or more allergens. Allergic diseases affect as many as 50 to 60 million Americans and its prevalence is increasing. Food allergies account for 35-50% of all cases of anaphylaxis. More than 54% of all United States citizens are estimated to have one or more allergy (CDC). The prevalence of allergic rhinitis is approximately 35% in Europe and Australia (ECRHS). The number of ambulatory care visits in the United States with the primary diagnosis of allergic rhinitis is over 13 million in 2008. From 2000-2005, the cost of treating allergic rhinitis is increasing from $6.1 billion to $11.2 billion with more than half of the money spent on prescription medications. An allergen must be exposed to an organism to elicit a response, usually upon inhalation or ingestion. An allergen is a molecule, which causes an abnormal immunological response. Allergens tend to be protein but, can also be smaller and are called haptens.

Allergens can be bound by IgE immunoglobulins, B lymphocytes, T lymphocytes and Mast cells in the human. IgE-allergen immune complexes cause de-granulation of Mast cells and a release of histamines, locally and systemically. Histamine release can cause muscle cramps, muscle contraction, inflammation, erythema and edema of mucous membranes. Severe reactions can cause anaphylaxis and death.

Metabolic diseases (MD) comprise a large class of diseases involving disorders in metabolism. Many MD have a genetic component in addition to environmental components. Many of the genetically induced MD are due to genetic defects in enzyme function. Most MD arise due to the accumulation of enzyme substrates or enzyme products, the buildup of which is cytotoxic.

Lifestyle diseases (LD), sometimes called diseases of longevity, are diseases that appear in industrialized populations and populations with increased lifespan. Some common LD are Alzheimer's disease, atherosclerosis, hypertension, asthma, cancer, chronic liver disease, chronic obstructive pulmonary disease, Type 2 diabetes, heart disease, nephritis, osteoporosis, acne, stroke, depression, attention deficit and hyperactivity disorder, and obesity. Since the late 1990's, LD have accounted for over 60 percent of all mortality (National Center for Health Statistics, National Office of Vital Statistics).

Metabolic diseases, chronic diseases, cancers, autoimmune diseases, neuronal disorders and diseases, age-related diseases and infectious diseases are usually assessed by iterative testing strategies involving traditional physiologic measurements in the clinic, and more recently molecular assessments and measurements of molecules that are indicative of specific diseases in clinical labs. Despite the advances in medical research, there exists great need for additional diagnostics capable of detecting or assessing the health or identifying or indicating the presence of disease or disease-causing factors or disease-modifying factors in mammals. Accordingly, it is an objective of the present invention to utilize a device composing a molecular net on a polymeric platform or a kit of devices to be used in the diagnosis, detection or indication of specific aspects of health, disease, and disease-causing agents in mammals. Current diagnostic testing strategies are not cost effective, are time-intensive, are limited in the scope of antigen tested for, and/or are labor-intensive. Fast knowledge of individual health status allows for (i) appropriate medical treatment, (ii) the modification of behavior to decrease the likelihood disease incidence, morbidity, infection propagation and, (iii) the ability to save lives.

The mammalian immune system reacts to foreign agents such as organisms and allergens through numerous recognition pathways involving the innate and adaptive immune systems. Normally, the immune system is capable of limiting or eliminating infection by a foreign organism, however, some organisms have mechanisms to evade the human immune system and can cause disease, morbidity and death. Similarly, the immune system typically generates an immune response against allografts or xenografts in organ and tissue transplant recipients causing rejection of the transplant. Further, in an increasing number of cases, the immune system is hyperactive, and reacts to self or environmental agents that it would normally be tolerant to, causing autoimmune, asthmatic or allergic responses. The aforementioned acute or chronic inflammatory states caused by infection, autoimmune and allergic diseases are significant causes of morbidity and mortality worldwide.

Allergies and food intolerances arise from hypersensitivity reactions of the immune system to one or more allergens. Allergic diseases affect as many as 50 to 60 million Americans and its prevalence is increasing. Food allergies account for 35-50% of all cases of anaphylaxis. More than 54% of all United States citizens are estimated to have one or more allergy (CDC). The prevalence of allergic rhinitis is approximately 35% in Europe and Australia (ECRHS). The number of ambulatory care visits in the United States with the primary diagnosis of allergic rhinitis is over 13 million in 2008. From 2000-2005, the cost of treating allergic rhinitis is increasing from $6.1 billion to $11.2 billion with more than half of the money spent on prescription medications.

An allergen must be exposed to an organism to elicit a response, usually upon inhalation or ingestion. An allergen is a molecule, which causes an abnormal immunological response. Allergens tend to be protein but, can also be smaller and are called haptens.

Allergens can be bound by IgE immunoglobulins, B lymphocytes, T lymphocytes and Mast cells in the human. IgE-allergen immune complexes cause de-granulation of Mast cells and a release of histamines, locally and systemically. Histamine release can cause muscle cramps, muscle contraction, inflammation, erythema and edema of mucous membranes. Severe reactions can cause anaphylaxis and death.

Current diagnostic testing strategies are not cost effective, are time-intensive, are limited in the scope of antigen tested for, and/or are labor-intensive. Fast knowledge of individual health status allows for (i) appropriate medical treatment, (ii) the modification of behavior to decrease the likelihood disease incidence, morbidity, infection propagation and, (iii) the ability to save lives. The human genome project has identified 57 human genes coding for various cytochrome P450 enzymes that are involved in metabolic reactions. Cytochrome P450 isotypes and variants can interfere with drug bioactivity, drug metabolism and drug clearance and provide a confounding factor when prescribing drugs of vital importance to patients. The levels of cytochrome P450 isotypes are important factors to weigh when drugs with important side effects and drugs with narrow therapeutic windows are prescribed. There exists a need to quickly assess cytochrome P450 isotype levels in individual patients for appropriate drug selection with limited toxic effects. Thus there is also a need for genetic testing to detect cytochrome P450 isoform expression so that physicians can anticipate drug interactions in patients prior to prescribing medications.

BRIEF SUMMARY OF THE INVENTION

The invention provides a "molecular net" which may be used to detect or quantify one or more analyses in a sample. In certain embodiments, molecular nets are used for medical diagnosis and screening. A molecular net may be considered a branched pseudo7random copolymer comprising two broad classes of subunits: capture agents and linking agents. The subunits, or "monomers," self-assemble to form a structure capable of binding to predetermined targets, "or analytes," in a sample.

By contacting a sample (e.g., a drop of whole blood) with a molecular net, and detecting the presence or absence of multiple targets (e.g., pathogen proteins, nucleic acids, carbohydrates, lipids) bound by the molecular net, it is possible to determine whether one, some or all of the target molecules are present in the sample. Molecular nets find application in medical diagnostics, environmental sampling, and other uses.

In one aspect an article of manufacture is provided comprising a first portion having a capture agent composition consisting one or more species of first capture agents and one or more species of first linking agents, wherein most or essentially all capture agents in the first portion are connected by one or more first linking agents to at least one other capture agent in the first portion; a second portion having a capture agent composition consisting of a one or more species of second capture agents, wherein most or essentially all capture agents in the second portion are connected by a linking agent to at least one other capture agent in the second portion; wherein at least one species of first capture agents differs from at least one species of second capture agents; and wherein some capture agents in the first portion are connected by linking agents to capture agents in the second portion (e.g., at an interface of the portions), such that the first portion and the second portion form a continuous molecular net.

In one aspect an article of manufacture is provided comprising a first portion having a capture agent composition consisting of a first plurality of heterogeneous capture agents and a linking agent composition consisting of a first plurality of heterogeneous linking agents, wherein most or essentially all capture agents in the first portion are connected by one or more linking agents to at least one other capture agent in the first portion; a second portion having a capture agent composition consisting of a second plurality of heterogeneous capture agents and a linking agent composition consisting of a second plurality of heterogeneous linking agents, wherein most or essentially all capture agents in the second portion are connected by a linking agent to at least one other capture agent in the second portion; wherein the capture agent composition and linking agent composition of the first portion differs from the capture agent composition and linking agent composition of the second portion; and wherein at least some capture agent molecules in the first portion are connected by linking agents to at least some capture agent molecules in the second portion, such that the first portion and the second portion form a continuous molecular net.

In one aspect a branched pseudorandom copolymer is provided, comprising monomers that are capture agents and linking agents, the capture agents comprise a plurality of species of capture agents specific for different targets and the linking agents comprise a plurality of species of linking agents, wherein the co-polymer is formed under conditions under which capture agent monomers are crosslinked to each other by linking agents. In some embodiments the linking agents are homobifunctional or heterobifunctional linkers and at least some species of linking agents comprise one or more reactive groups that do not bind to some species of capture agents in the copolymer.

In one aspect, to layered, multipolymeric molecular net structure, the structure includes a base having a surface. The net structure further includes a plurality of first capture agents, the first capture agents directly connected to the base surface or connected to the base surface by one or more base linker agents. The net also includes a plurality of second capture agents and a plurality of linker agents, the second capture agents indirectly connected to the base surface by a shortest linkage having no more than one first capture agent and one or more linking agents. Each second capture agent of the molecular net, in combination with its shortest linkage, forms a multimer, or a portion of a multimer, having at least three monomer subunits, the multimer including the second capture agent, a first capture agent, and one or more linking agents.

A method of making an analytic reagent is provided, comprising forming a first layer by combining (a) a first plurality of species of capture agents, wherein said first plurality binds more than one biological target, said capture agents having capture agent reactive groups, and (b) a first linking agent or plurality of first linking agents, wherein the linking agent(s) contain reactive groups complementary to the capture agent reactive groups, under conditions in which the capture agents interconnect via the linking agent(s), thereby forming a first layer comprising a first network of interconnected capture agents; and then forming a second layer adjacent to the first layer by combining (c) a second plurality of species of capture agents, wherein said second plurality binds more than one biological target, said capture agents having capture agent reactive groups, and (d) a second linking agent or plurality of second linking agents, wherein the linking agent(s) contain reactive groups complementary to the capture agent reactive groups, under conditions in which the capture agents in the second plurality of capture agents can interconnect via the second linking agents, and wherein some capture agents in the second plurality interconnect with some capture agents in the first priority via second linking agents, to form a continuous molecular net. The method may include the step of removing unbound capture agents and linking agents prior to step (c). In some embodiments the composition of the first plurality of capture agents is different from the composition of the second plurality of capture agents. In some embodiments the linking agent(s) in step (b) are different from the linking agents in step (d). In some embodiments the method includes carrying out 1-6 additional rounds of combining capture agents and linking agents, wherein each round results in an additional portion of the molecular net.

In one aspect the invention provides an article of manufacture produced by a process described herein.

A method of simultaneously determining the presence or absence of multiple predetermined analytes in a sample is provided, the method comprising contacting the sample with an article of manufacture as described herein (e.g., above), having capture agents specific for said analytes and determining whether or not said analytes are bound by said an article of manufacture. In some embodiments determining whether or not said analytes are bound by said an article of manufacture comprises contacting the bound analytes with one or more detection reagents that bind said analyte(s). In some embodiments the detection reagents are detectably labeled with a colorimetric, fluorescent, or luminescent detectable label. In some embodiments detection reagents are selected from the group consisting or antibodies, nucleic acids, lectins and DNA binding polypeptides. In some embodiments two or more detection reagents are used, each specifically binding to a different species of analyte. In some embodiments the two or more detection reagents are labeled with the same detectable label. In other embodiments at least two of said detection reagents are labeled with different detectable labels. In some approaches a first detection reagent labeled with a first detectable label binds an analyte in the first layer and a second detection reagent labeled with a second detectable label binds an analyte in the second layer. In some embodiments binding by a first detection reagent of a captured analyte is distinguishable from binding by a second detection reagent of a different captured analyte, and wherein binding of both analytes can be distinguished from binding of only one analyte.

Provided is a device comprising a portable housing having at least one molecular net support surface; and at least one molecular net of described herein coupled to the at least one molecular net support surface.

BRIEF DESCRIPTION OF THE FIGURES

FIG. 26 shows results of a probe-based detection system binding characterization studies for MRSA.

FIG. 27 shows results of an antibody-based detection system binding characterization studies for MRSA.

FIGS. 43A-43B show two embodiments of a superplexing net. FIGS. 43C-43E show various embodiments of molecular nets.

DETAILED DESCRIPTION OF THE INVENTION

I. Definitions and Terminology

Figure 1:
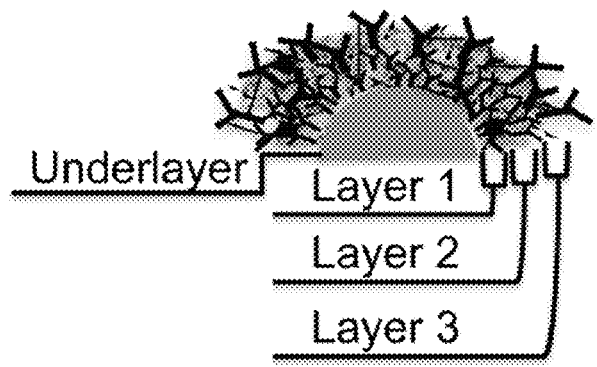
FIG. 1 is a schematic diagram of a multilayer molecular net.

Unless defined otherwise, all scientific and technical terms used herein have the same meaning as commonly understood by those skilled in the relevant art. General definitions are provided, for example, in Dictionary of Microbiology and Molecular Biology, $2^{nd}$ ed. (Singleton et al., 1994; John Wiley & Sons, New York, N.Y.) or The Harper Collins Dictionary of Biology (Hale & Marham, 1991, Harper Perennial, New York, N.Y.). Unless mentioned otherwise, the techniques employed or contemplated herein are well known standard methods in the art.

Units, prefixes and symbols are denoted in the System International de Unites (SI) accepted form. Numeric ranges are inclusive of the numbers defining the range. Unless otherwise indicated, nucleic acids are written left to right in 5' to 3' orientation. The headings provided herein are not limitations of the various aspects or embodiments of the invention, which can be had by reference to the specification as a whole. Accordingly, the terms defined immediately below are more fully defined by reference to the specification in its entirety.

By "agent" is meant a molecule or cell producing or capable of eliciting or used to obtain a specific result or response. Agents include but are not limited to inorganic molecules, organic molecules, drugs, biologics, cellular components, polypeptides, nucleic acids and environmental samples.

By "analyte" is meant a molecule that is the subject of analysis, such as being measured, and is a component of an environmental or biologic sample.

By "biologic" is meant any substance derived from a living organism or organic products produced by an organism or other biological sources and may be used to treat or prevent disease.

By "chamber" is meant a compartment or enclosed space between any two channels.

By "channel" is meant a path for the transfer of samples, fluids and solids dispersed in a fluid from one region to another.

By "competitor" is meant a molecule with similar surface chemistries and/or shape as another molecule or an analyte. The competitor molecule and the analyte are both capable of binding or specifically binding a companion molecule with nearly equal abilities. The companion molecule may have a limited number of suitable binding sites for said competitor molecule and analyte. Binding between companion molecule and analyte is subject to competitor concentration, availability, and buffer conditions.

By "non-competitor" is meant a molecule that does not have similar surface chemistries or similar shapes as an analyte and does not specifically bind to a companion molecule. Instead, a non-competitor molecule may perturb, slow down, sequester or inhibit the ability of the analyte to contact and/or bind to the companion molecule. The non-competitor molecule may also bind to an allosteric region of the companion molecule in which the analyte does not bind. Binding of non-competitor to an allosteric region may occlude or change the analyte binding region of the companion molecule. Binding between companion molecule and analyte is subject to non-competitor concentration, availability and buffer conditions.

By "filter" is meant a substance such as a cloth, polymer, paper, fibrous material or any other porous material through which fluids and molecules with a diameter that is less than the pore size of the filter can pass.

By "adapter" is meant an accessory part that connects or joins to other parts or devices.

By "wash" is meant is meant a fluid containing a buffering agent and a mixture of salts, detergents, proteins, polynucleotides, carbohydrates and/or lipids that may be applied to a device following sample injection. It may also be used to remove molecules that are non-specifically immobilized in a device or may be used to remove molecules that are specifically bound or immobilized in a device.

By "selected" is meant a process by which chemical and/or physical properties of analytes in a samples are preferentially bound or immobilized over other non-analyte materials in the sample.

By "selected against" is meant a process by which chemical and/or physical properties of unwanted sample materials are preferentially bound or immobilized and thus may allow for the indirect selection of desired sample materials.

By "molecular sieve" is meant a sieve or sifter consisting of mesh or metals or polymers that separates wanted analytes from unwanted sample materials.

By "infectious disease" is meant a disease that manifests clinically or sub-clinically in a mammal and is caused by a pathogenic agent.

By "pathogen" is meant any disease-producing agent including a virus, bacterium, or other microorganism.

By "microbial" is meant small living organisms including bacteria, viruses, fungi and protozoa.

By "bacterial" is meant pertaining to a bacterium or bacteria, which are microscopic prokaryotic organisms that may or may not cause disease in humans.

By "viral" is meant a submicroscopic microbe that causes disease. Viruses are obligate parasites and require living cells to reproduce. Viruses are composed of a genome (DNA or RNA), proteins, and may or may not have a lipid envelope.

By "parasitic" is meant a plant or animal that lives, grows and feeds on or within a human.

By "fungal" is meant a member of a class of eukaryotic microbes including mushrooms, yeasts, rusts, molds and smuts that may or may not cause disease in humans.

By "diagnostic test" is meant any kind of medical test performed to aid in the diagnosis or detection of disease. Diagnostic tests perform within a range of acceptable parameters to correctly identify the agent tested for.

By "indicator test" or "indication" is meant anything serving to point out or signal the presence of an agent or disease.

By "attachment" is meant an act of attaching or the state of being attached to a platform or binding partner.

By "crosslinker" is meant a chemical substance or agent that induces the formation of chemical crosslinks between more than one homologous and/or heterologous agent.

By "substrate" is meant the substance acted upon by an enzyme.

By "biological sample" is meant any fluid or tissue or material derived from a living or dead human which may contain immunoglobulins and/or one or more microbial-derived nucleic acid, carbohydrate, lipid and/or polypeptide. Samples include, for example, CSF, serum, blood, sputum, pleural effusion, throat swab and stools, respiratory tissue or exudates, plasma, cervical swab samples, biopsy tissue, gastrointestinal tissue, urine, feces, semen or other body fluids, tissues or materials. Samples also include bacterial cultures (from liquid or solid media) and environmental samples. A biological sample may be treated to physically disrupt tissue or cell structure, thus releasing intracellular components into a solution which may contain enzymes, buffers, salts, detergents and the like which are used to prepare the sample for analysis.

By "environmental sample" is meant any externally-derived organic or inorganic solid or fluid or particulate or molecule present outside of the body of a human that can be isolated. For example: food, water, pollen, pesticides, petroleum, latex, grass, nuts, fishes, feline saliva or other organic or inorganic-based materials. An organic environmental sample may be treated to physically disrupt tissue or cell structure, thus releasing intracellular components into a solution which may contain enzymes, buffers, salts, detergents and the like which are used to prepare the sample for analysis.

By "separating" or "purifying" or "fractionating" is meant that one or more molecules of a sample are removed from other molecules in a sample. Solid samples can be suspended in an aqueous solution that includes nucleic acids and other molecules (e.g., proteins, carbohydrates, lipids and/or nucleic acids). A separating or purifying step removes at least about 30%, preferably at least about 50%, preferably at least about 80%, and more preferably at least about 95% of the other sample components.

By "nucleic acid" or "polynucleotide" is meant a polymer of nucleosides or nucleoside analogs which have nitrogenous heterocyclic bases, or base analogs, where the nucleosides are covalently linked via a backbone structure to form a polynucleotide. Conventional RNA, DNA, and analogs of RNA and DNA are included in this term. A nucleic acid backbone may comprise a variety of known linkages, including one or more of sugarphosphodiester linkages, peptide-nucleic acid bonds ("peptide nucleic acids"; PCT No. WO 95/32305 (Hydig-Hielsen et al.)), phosphorothioate linkages, methylphosphonate linkages or combinations of known linkages. Sugar moieties of the nucleic acid may be ribose or deoxyribose, or similar compounds having known substitutions, e.g., 2' methoxy and/or 2' halide substitutions. Nitrogenous bases may be conventional bases (A, G, C, T, U), known base analogs (e.g., inosine; see The Biochemistry of the Nucleic Acids 5-36, Adams et al., ed., 11$^{th}$ ed., 1992), or known derivatives of purine or pyrimidine bases (PCT No. WO 93/13121 (Cook)) and a "basic" residues in which the backbone includes no nitrogenous base for one or more residues (U.S. Pat. No. 5,585,481 (Arnold et al.)). A nucleic acid may comprise only conventional sugars, bases and linkages, as found in RNA and DNA, or may include both conventional components and substitutions (e.g., conventional bases linked via a methoxy backbone, or a nucleic acid including conventional bases and one or more analogs).

By "probe" is meant a nucleic acid oligomer that hybridizes specifically to a target sequence in a nucleic acid or its complement, preferably in an amplified nucleic acid, under conditions that promote hybridization, thereby allowing detection of the target or amplified nucleic acid. Detection may either be direct (i.e., resulting from a probe hybridizing directly to the target sequence or amplified nucleic acid) or indirect (i.e., resulting from a probe hybridizing to an intermediate molecular structure that links the probe to the target sequence or amplified nucleic acid). A probe's "target" generally refers to a sequence in (i.e., a subset of) a larger nucleic acid sequence that hybridizes specifically to at least a portion of the probe sequence by standard hydrogen bonding (base pairing). Sequences that are "sufficiently complementary" allow stable hybridization of a probe oligomer to a target sequence, even if the two sequences are not completely complementary. A probe may be labeled or unlabeled, depending on the detection method used, which methods are well known in the art.

By "polypeptides" is meant organic compounds made up of amino acids that are covalently linked through a peptide bond, that are a major constituent of living cells. Polypeptides can be segments of a protein or can compose an entire protein. Proteins can be cleaved through enzymatic, chemical or mechanical cleavage to give rise to polypeptides.

By "allergen" is meant any epitope on an antigen that is recognized by the immune system By "non-specific binding" is meant any molecule that interacts with another molecule in a non-specific and transient manner. An example of this is the interaction of one molecule with an overall positive charge with a molecule that has an overall negative charge, however the association is not tight and dissociation is likely in the presence of mild salts.

By "antigen" is meant any substance that, when introduced into the body, is recognized by the immune system. Antigens can be, but is not limited to, allergens and other non-self molecules.

By "allergy" is meant an inappropriate and harmful response of the immune system to normally harmless substances, called allergens.

By "immunoglobulins" is meant a family of soluble protein molecules produced and secreted by B cells in response to an antigen or by hybridomas in the laboratory, which is capable of binding to that specific antigen. Isotypes of immunoglobulins are IgM, IgG, IgA, IgY, IgD and IgE.

By "class of molecule" is meant molecules that are grouped together by reason of common attributes, characteristics, qualities, traits, chemistries, and/or activities.

By "nanochannel" is meant a channel with architectural dimensions of 1-10,000 Angstroms.

By "microchannel" is meant a channel with architectural dimensions of 10,000100,000,000,000 Angstroms.

By "nanopocket" is meant a pocket with a diameter of 1-10,000 Angstroms.

By "micropocket" is meant a pocket with a diameter of 10,000-100,000,000,000 Angstroms.

By "sepsis" is meant a serious medical condition characterized by a systemic inflammatory response that can lead to multi-organ failure and death and is characterized by a cytokine storm in response to microbial products in the blood, urine, lungs, skin and other tissues.

By "corona" is meant an atmospheric-pressure dielectric barrier discharge, corona discharge, barrier discharge, atmospheric-pressure plasma, atmospheric-pressure glow discharge, atmospheric-pressure non-equilibrium plasma, silent discharge, atmospheric-pressure partially ionized gas, filamentary discharge, direct or remote atmospheric-pressure discharge, externally sustained or self-sustained atmospheric-pressure discharge, and the like and is to be distinguished from sub-atmospheric and vacuum-pressure electrical discharges or processes. However, the corona may occur in the gaseous atmosphere of specific compositions, i.e., in a controlled atmosphere.

By "extracellular matrix" or "extracellular matrices" is meant a combination of more than one of the following excreted cellular products: peptides, proteins, glycoproteins, lipids, polysaccharides, water and other organic molecules. Examples of extracellular matrix components are alginate slime, fibrinogen, chondrocyte pericellular matrix, and cartilage.

By "substrate" is meant the substance acted upon by an enzyme.

By "aptamer" is meant a class of molecules including single- or double-stranded nucleic acids (DNA or RNA) between 30 and 70 nucleotides in length and can have a molecular weight of 9-20 kDa). Aptamers can also be peptides and nucleic acid-peptide hybrids. Aptamers possess a high specificity and affinity for their target molecules.

By "filtration" is meant the mechanical, physical or chemical operation which is used for the separation of analytes from fluid samples by immobilizing said analytes so that only the non-analytes and the fluid from the samples can pass.

By "sponge" is meant porous framework of molecules characterized by readily adsorbing or immobilizing molecules from a fluid sample.

By "photovoltaic cell" is meant one or an array of material such as crystalline silicon, cadmium telluride, and copper indium selenide that can convert light energy into direct current electricity.

By "compressive strength" is meant the capacity of a material to withstand axially directed pushing forces. When the limit of compressive strength is reached, materials are crushed, producing fractoluminescence (also called triboluminescence).

By "metachromatic" is meant a change in color that can be the result of the presence or absence of heat.

II. Overview

The invention provides "molecular nets" which may be used in diagnostic and other applications to detect analytes in a sample. Single and multilayer molecular nets may be incorporated into medical devices to aid in diagnosis and other devices for sample analysis.

A molecular net contains capture agents. Molecular nets can contain a heterogeneous population of organic and inorganic molecules that can be linked together by a combination of electrostatic interactions and covalent bonding in a non-uniform manner. The arrangement and spacing of molecular components of the molecular net can generate an nonuniform multi-dimensional stable architecture, with different densities of capture agents and cross-linkers per unit volume in different regions. An effect of the nonuniformity is that different layers or regions may have different porosity.

The identity and arrangement of the molecular capture components within the molecular net can confer multiple different surface chemistries per unit volume of molecular net. The multiple binding affinities, surface chemistries, activities, or other properties of the heterogeneous capture components that make up the molecular net can confer multiplexing capabilities; and wherein the capture components can be arranged and bound together in an architecture that can possess a high density of binding surfaces per unit volume and can enable enhanced multiplexing capabilities.

In a molecular net, different capture agents (or "capture components") may bind the same analyte, e.g., a multiple of the same analyte in a sample can specifically bind more than one heterogeneous capture component in a molecular net. Conversely, heterogeneous analytes in a sample may specifically bind a multiple of the same capture component in a molecular net. In some cases heterogeneous analytes in a sample can specifically bind more than one heterogeneous capture component in a molecular net.

As noted above and discussed in detail below, molecular nets typically have multiple layers. Thus, the net may be built in a layered or striated manner. For example, the initial layer may be a homogeneous or heterogeneous mixture of one or more types of polypeptides and/or other molecules (e.g., polynucleotides) adsorbed to a polymeric surface or glass surface; followed by the addition of one or more chemical crosslinkers. This may be followed by addition of homogeneous or heterogeneous mixtures of one or more different molecules, followed by cross-linkers.

In a device, one or more molecular nets can be absorbed, stacked, layered, suspended, or floated to form a testing volume. The overall surface topology of the net can be described as patchwork of non-uniform, heterogeneous textures connected by chemical linkages. For example, the net can have the structure of a layered lattice or a plurality of staggered lattices. The chemical or physical properties of the polymer determines the adsorption or repulsion of the first layer of the molecular net. Differential chemical or physical properties of the polymer confer sub-localization of specific components in the first layer onto specific regions of the polymer. Subsequent layers of the net are preferentially linked to the previous layer of the net.

The molecular net may be fabricated using crosslinkers of various arm lengths ranging, for example and not limitation, from 2 to 17 Angstroms. In fabricating a layer, cross-linkers may be added or may be applied in a sequential fashion to attach, immobilize, and stabilize the capture components in a random or semi-oriented directionality. The arrangement or distribution of components in the net will be affected by the size and surface chemistry of capture component relative to the neighboring chemistry of the net. Capture components of different sizes and shapes are linked together through one or more than one crosslink; whereby the crosslinked capture components may be surface exposed or may be built into the internal structure of the net. The overall structure of the net may be designed to include regions that are specifically formulated and located to identify and segregate properties of elements of the test sample.

In some embodiments, the molecular net is a large polymeric heterogeneous network containing five or more different capture components, such as but not limited to proteins and/or polynucleotides and/or other molecules that are immobilized or linked in three-dimensional space to promote analyte binding.

The molecular net may be attached or fitted to a polymeric device. For example, one or more molecular nets can be formed; placed; adsorbed; adhered; glued; crosslinked; and/or fitted onto a polymeric; and/or non-porous; and/or corona etched; and/or molded; surface with one or more surface chemistry.

A molecular net device may have a testing area with one or a series of molecular nets that can be oriented in a defined volume and can be used to perform one or more analyte binding tests. The device may have a lumen. A feature of some devices is the non-uniform distribution of binding sites along the luminal surfaces of the device including the molecular nets, luminal coatings, filters and sieves that my be present in a device. The surface may provide a uniform distribution of binding sites across sections within the device but may not in other areas of the device.

A test device can contain a plurality of molecular nets, wherein each molecular net contains a plurality of different capture components that can detect different analytes from more than one species; wherein a single sample can contain analytes from more than one species and whereby bound analytes are indicative of an infection. A device can contain multiple test volumes containing multiple different molecular nets to capture multiple different analytes from a sample. Said device can contain containment chambers that can hold buffers, solutions, washes, detection molecules, catalysts, and other molecules that aid in the detection of specific analytes bound and immobilized to said molecular nets. Said device can contain a plurality of different analyte detection molecules conjugated to one or more class of detectable molecules, whereby the presence of analyte can be detected by the immobilization of said detectable molecules. Said device can contain solutions that can contain catalysts, substrates and other molecules involved in an enzymatic or chemical reaction; whereby the detectable molecules on said analyte detection molecules can interact chemically with the catalysts and substrates to produce a detectable signal if analyte detection molecules are immobilized by one or more different analyte bound to one or more molecular net. Said device can contain one or more signal sensors or signal amplifiers connected in series or in parallel to detect and propagate signals. Said device can contain one or more of the same amplifiers and sensors or can contain one or more different amplifier and sensor.

The use of molecular nets as part of tests, devices and methods described herein provides for the simultaneous testing of sample protein, lipid, carbohydrate, nucleic acid analytes, and combinations thereof, using affinity-based, physicochemical, electrochemical, magnetic or enzymatic analyses in under 1 hour.

One aspect of the present invention relates to any arrangement, use, method, test and device that employs the molecular nets described herein. In preferred embodiments, the molecular nets are dense heterogeneous multi-layered network of multiples of different capture molecules constructed by interlinking to form unique and distinct topologies and binding surfaces with quantifiable physical, electrical, vibrational, thermal, spatial, magnetic, and chemical properties. Pores, channels and pockets can be present throughout one or more layer of a molecular net. In certain embodiments, a molecular net is covalently or non-covalently linked via chemical crosslinkers or mixed with polyethylene glycol to increase the stability of the capture molecules, or to generate spatial distances between capture molecules that can vary within or between layers of the molecular net.

Without wishing to be bound by theory, it is believed that stacking or layers of molecular net increases the analyte binding sites in a vertical column of molecular net so as to allow for positioning immobilized analyte in such a manner as to generate a focal signal.

Also disclosed herein are methods by which molecular nets can be constructed, processed and arranged on a planar surface or a bead surface.

The molecular nets and/or an arrangement of layers of molecular nets can include an array of structures and can be formed or attached to planar or bead surfaces to enable enhanced binding capacity and detection of various analytes simultaneously. Also disclosed are devices employing multiple different molecular nets or layers of molecular nets configured within one or more testing area to facilitate the capture, immobilization and detection of multiple different analytes. In certain embodiments, the analytes are allergens, allergen-specific immune cells and/or allergen-specific immune products in a biologic, food or environmental sample.

III. Fabrication and Properties of Molecular Nets

A. Composition and Structure of Molecular Nets

In its most basic form, a molecular net is a branched pseudorandom copolymer comprising two broad classes of subunits: capture agents and linking agents. The subunits, or "monomers," self-assemble to form a structure capable of binding to predetermined targets, "or analytes," in a sample. By contacting a sample (e.g., a drop of whole blood) with a molecular net, and detecting the presence or absence of multiple targets (e.g., pathogen proteins) bound by the molecular net, it is possible to determine whether one, some or all of the target molecules are present in the sample. Molecular nets find application in medical diagnostics, environmental sampling, and other uses.

As will become apparent, the molecular net structure provides a number of advantages over conventional diagnostic devices.

A simple ("single layer") molecular net will be described first, followed by a description of more complex ("multi-layer") molecular nets. The single layer net is described in part to facilitate understanding of multilayer nets. Multilayer nets are the preferred form for many applications. A device of the invention (including single sample devices) may contain one or several single or multilayer nets.

As noted, molecular nets can be described as a branched polymer comprising capture agents and linking agents.

1. Capture Agents

Capture agents are macromolecules that specifically bind to an analyte or target. For illustration and not limitation, examples of capture agents include antibodies, antigens, ligands, antiligands, receptors, nucleic acids, and lectins, which specifically bind to antigens, antibodies, antiligands, ligands, receptor ligands, complementary nucleic acids, and carbohydrates, respectively. Examples of classes of capture agents are provided in TABLE 1. In general, the interaction between an analyte and a capture agent is non-covalent.

Capture agents contain at least two, and usually several or many, reactive groups with which linker functional groups (described below) can react to form a covalent linkage. Exemplary reactive groups are the amino-terminus and lysine-amino groups of polypeptides and the 3'-hydroxyl group in nucleic acids. Additional examples of reactive groups found on capture agents are provided in TABLE 1. In some cases, a biological capture agent, such as an immunoglobulin, can be derivatized to add a reactive group not associated with the agent in nature. For example, an oligonucleotide may be modified by addition of an amine group. In some embodiments of the invention, the biological capture agent is not so derivatized but comprises only the reactive groups normally associated with the class of biological molecule.

Capture components may include, but are not limited to: polypeptides; antibodies; polynucleotides; carbohydrates; enzymes; lipids; small molecule drugs; biologic therapeutics; vaccine components; allergens; hormone-binding molecules; lipid binding molecules; cholesterol binding molecules; enzyme substrates; mammalian cellular components; mammalian cellular products; viral components; viral products; bacterial cellular components; bacterial products; parasite cellular components; parasite products; fungal cellular components; fungal products; prions; viroids; viroid products; extra cellular matrix components; mammalian cytokines; mammalian cytokine receptors; mammalian soluble receptors and orphan receptors; ligands and other molecules.

In some embodiments, the molecular net is composed of polypeptide and/or nucleic acid capture molecules that are linked together by one or more than one chemical cross-linker in a manner that preserves the three-dimensional structure and binding capacity of said capture molecules.

In referring to molecular nets, the following terms may be used to describe capture agents in an individual net: One may refer to a single molecule (e.g., a single antibody molecule), a single species (e.g., many antibody molecules with the same target specificity), multiple species (e.g., species of antibodies that recognize different targets), or single or multiple separate classes of classes of capture agents (e.g., nucleic acids, antibodies, aptamers, etc., see TABLE 1). Capture agents may also be described by reference to target specificity (e.g., a polyclonal antibody mixture that binds multiple distinct epitopes of a common target molecule can be referred to as a single species with reference to target specificity).

TABLE 1

Exemplary Capture Agents

| CAPTURE AGENT CLASS | EXEMPLARY LIGAND BOUND BY CAPTURE AGENT | REACTIVE GROUPS FOR LINKING |
|---|---|---|
| 1 Antibodies | Antigens<br>Protein A<br>Protein G<br>$F_c$ Receptors<br>Immune cells containing $F_c$ receptors<br>Complement protein C1q | Amines, Carboxyls |
| 2 Nucleic Acids (for hybridization)<br>DNA<br>RNA<br>Peptide Nucleic Acids | Complementary nucleic acids<br>Nucleic acid binding proteins<br>Restriction endonucleases<br>Exonucleases | Carboxyls, Hydroxyls |
| 3 Apatamers<br>Nucleic acid aptamers<br>Polypeptide aptamers | | Amines, Carboxyls, Hydroxyls, Sulfhydryls |
| 4 Receptors | Antigens<br>Cytokines<br>Ligands<br>Steroids<br>Drugs less than 500 Daltons<br>RNA<br>DNA | Amines, Carboxyls, Hydroxyls, Sulfhydryls |
| 5 Antigens | Polyclonal antibodies from serum or other biological fluid | Amines, Carboxyls, Hydroxyls, Sulfhydryls |
| 6 Antiligands<br>Penicillin binding proteins<br>Drug-modifying enzymes<br>Multi-drug efflux pumps | Antibiotics<br>Antifungal drugs<br>Antiprotozoal drugs | Amines, Carboxyls, Hydroxyls, Sulfhydryls |
| 7 Carbohydrates<br>Lectins | Lectin-binding proteins<br>Complement protein C3<br>Polyclonal antibodies from serum or other biological fluid | Carboxyls, Hydroxyls |
| 8 Lipids<br>Lipid A | Polyclonal antibodies from serum or other biological fluid<br>Lipid binding protein (eg. LPS binding protein (LBP))<br>Lipid modifying enzymes | Carboxyls, Hydroxyls |
| 9 Nucleic acid binding proteins and peptides | DNA, RNA | Amines, Carboxyls |

DNA binding proteins may be used as capture agents. For illustration and not limitation, examples include:
Nucleic acid-binding polypeptides which contain leucine-rich repeats and, optionally the following motifs: LXZL (SEQ ID NO: 1) and FXZL (SEQ ID NO: 2) and VXZL (SEQ ID NO: 3), where L=leucine, F=phenylalanine, V=valine, X=glycine or serine or proline or threonine, and Z=asparagine or arginine or glycine or threonine.
Nucleic acid-binding polypeptides comprising the sequence (SEQ ID NO: 4)
VPTLEELNLSYNNIMTVPAL.

Nucleic acid-binding polypeptides comprising the sequence (SEQ ID NO: 5)
LGNLTHLSLKYNNLTVVPRNLPSSLEYLLLSYNRIVKLAPED.

Nucleic acid-binding polypeptides comprising the sequence (SEQ ID NO: 6)
LSRLEGLVLKDSSLSWLNASWFRGLGNL.

other peptides derived from toll-like receptor 9 that contain leucine-rich repeats.
In some examples, single-stranded DNA binding polypeptides can contain the following motif: FGXZ (SEQ ID NO: 7), whereby F=phenylalanine, G=glycine, X=arginine or lysine, Z=leucine or valine or serine or alanine or glycine or phenylalanine or tryptophan or aspartate or histidine.
Single-stranded DNA binding polypeptides can contain the following motif: FGXZ (SEQ ID NO: 8), whereby F=phenylalanine, G=glycine, X=arginine or lysine, Z=leucine, valine, serine, alanine, glycine, phenylalanine, tryptophan, asparagine or histidine.
In some examples, single-stranded RNA binding polypeptides can contain the following motifs: FGKI (SEQ ID NO: 9) and RGF, whereby F=phenylalanine, G=glycine, K=lysine, I=isoleucine and R=arginine.
DNA binding domains from single-stranded DNA binding proteins such as *Escherichia coli* ETEC H10407 [Accession CBJ04410.1], *Salmonella enterica* [ADK62159.1, ZP_03346359.1], *Klebsiella pneumo-* niae [YP_003517675.1, YP_003517470.1], *Enterobacter cloacae* [YP_003610832.1], *Pseudomonas aeruginosa* [ZP_06876710.1, NP_252922.1] and others.

Peptides containing polyarginine, polylysine or combinations of arginine and lysine regions 8-22 amino acids in length.

Single-stranded RNA binding polypeptides can contain the following motifs: FGKI and RGF, whereby F=phenylalanine, G=glycine, K=lysine, I=isoleucine and R=arginine.

For example, the net may contain 1-50 heterogeneous polynucleotide binding proteins; said polynucleotide binding proteins have inherent binding affinity in the form of hydrogen bonding and/or ionic or electrostatic interactions with specific polynucleotide sequences; and may be capable of non-specific interactions with many RNA or DNA fragments or chromosomes or plasmids.

Antibodies

For example, the molecular net may contain 1-50 different antibodies; each directed against 1-50 different characteristics (epitopes) of an analyte; or that can bind between 1-50 different epitopes on 1-50 heterogeneous analytes in a sample; and where each antibody of the net may have a maximum binding potential of 2 analytes.

Examples of antibody capture agents include antibody against: cytochrome P450 family members; isoforms; and other members (such as but not limited to: P450 1A2, 2B6, 2C8, 2C9, 2C19, 2D6, 2E1, 3A4, 3A5, 3A7, and other isoforms); and/or cytochrome P450 substrates (such as but not limited to: caffeine, haloperidol, estradiol, naproxen, propranolol, verapamil, celecoxib, methadone, cerivastatin, ibuprofen, losartan, tamoxifen, diazepam, lansoprazole, omeprazol, propafenone, clomipramine, haloperidol, codeine, halothane, azithromycin, diazepam, tacrolimus, cyclosporine, verapamil, atorvastatin, lovastatin, simvastatin, progesterone, aprepitant, dexamethasone, taxol and other substrates); and/or cytochrome P450 inhibitors (such as but not limited to: ciprofloxacin, cimetidine, fluoroquinolones, interferon, trimethoprim, fluconazole, fluvastatin, isoniazid, lovastatin, lansoprazole, rabeprazole, chloramphenicol, cimetidine, celecoxib, clemastine, quinidine, clarithromycin, aprepitant, erythromycin, imatinib and other inhibitors); and/or cytochrome P450 inducers (such as but not limited to: insulin, omeprazole, rifampin, phenobarbital, carbamazepine, norethindrone, dexamethasone, isoniazid, phenobarbital, glucocorticoids, efavirenz, troglitazone and other inducers).

Other examples of antibody capture agents include antibodies against non-protein and/or protein markers for bone; muscular; epithelial; endothelial; endocrine; renal; hepatic; neural; vascular; coronary; and cellular health and/or damage; cytotoxicity; and/or inflammation; and wherein capture components can be nucleic acid binding polypeptides and can bind nucleic acid analytes containing single nucleotide polymorphisms that can indicate susceptibility to: drug toxicity; disease; drug incompatibility; drug efficacy; and other indicators of health and/or disease. Other binding molecules may also be used.

Other examples of antibody capture agents include combinations of one or more antibody against: human ferritin; lipid A; bacterial lipopolysaccharide; bacterial peptidoglycan; lipoteichoic acid; teichoic acid; mycolic acid; bacterial flagella; fimbriae; pilin; pili; glycocalyx; slime layer; capsule; bacterial heat shock proteins; bacterial lipoproteins; bacterial siderophores; and other bacterial products;

Capture components can be a combination of one or more single-stranded DNA binding polypeptide; and wherein capture components can be a combination of one or more antibody; polypeptide; lipid; carbohydrate; and/or divalent cation; that can specifically bind: human ferritin; lipid A; bacterial lipopolysaccharide; bacterial peptidoglycan; lipoteichoic acid; teichoic acid; mycolic acid; bacterial flagella; fimbriae; pilin; pili; glycocalyx; slime layer; capsule; bacterial heat shock protein; bacterial glycoprotein; bacterial lipoprotein; bacterial siderophores; and other bacterial products.

Other examples of antibody capture agents include combinations of one or more antibody against: aflatoxin; fumonisins; and other fungal toxins; chitin; ergosterol; fungal lipoprotein; fungal glycoprotein; and other fungal products.

Capture components can be a combination of one or more antibody against chitin; chitinase; chitin-binding domain and/or MQMTKAEFTFANRLKHDDLEEIYSELSD QFPYWD (SEQ ID NO: 10) (GenBank accession number 157801001); YITCLFRGARCRVYSGRSC CFGYY-CRRDFPGSIFGTCSRRNF (SEQ ID NO: 11) (GenBank accession number 126030190); or any other polypeptide that can bind chitin; and wherein capture components can be a combination of one or more antibody; polypeptide; lipid; and/or carbohydrate that can specifically bind aflatoxin; chitin; ergosterol; fungal lipoprotein; fungal glycoprotein; fungal toxin; and other fungal products.

Other examples of antibody capture agents include combinations of one or more antibody against: interferon-alpha; interferon-beta; viral capsid protein; viral spike protein; viral integrase; viral hemagglutinin; viral neuraminidase; viral reverse transcriptase; viral glycoprotein; viral lipoprotein; and other viral products; and wherein capture components can be a combination of one or more single-stranded DNA binding polypeptides; single-stranded RNA binding polypeptides; double-stranded DNA binding polypeptides; double-stranded RNA binding polypeptides; and other molecules that can bind viral nucleic acid; and wherein capture components can be a combination of one or more antibody; polypeptide; lipid; and/or carbohydrate that can specifically bind human interferon-alpha; human interferon-beta; viral capsid protein; viral spike protein; viral integrase; viral hemagglutinin; viral neuraminidase; viral reverse transcriptase; viral glycoprotein; viral lipoprotein; and other viral products.

Capture agents can be molecules that can bind cytochrome P450 molecules; and/or genes; and/or substrates; and/or inducers; and/or inhibitors; and other molecules that encode; and/or modify; and/or regulate cytochrome P450 molecules.

Polynucleotides

For example, the net may contain 1-500 different polynucleotides; which have inherent binding affinity in the form of hydrogen bonding and/or ionic or electrostatic interactions against 1-500 specific polynucleotides; or which can bind 1-500 different polynucleotide binding proteins through hydrogen bonding; ionic bonding; and/or electrostatic interactions in a complex solution.

Other Capture Agents

Molecular nets can contain capture components such as LPS binding proteins, CD14, polymyxin B and other molecules that can bind lipid A, endotoxin and/or lipopolysaccharide, and other microbial lipids; and whereby capture components can be antibodies that can bind peptidoglycan, flagellin, pilA, fimbriae, heat shock proteins and other bacterial products that induce inflammation; and/or whereby capture components can be antibodies that can bind fungal cellular components and fungal products; and/or whereby capture components can be antibodies that can bind viral components and viral products; and/or whereby capture components can be antibodies that can bind mammalian pro-inflammatory cytokines such as histamine, TNF, IL-1beta, INFgamma; and other molecules involved in sepsis.

Molecular nets can contain capture components that can bind growth factor receptors and other tumor cell markers on the surface of tumor cells; and whereby said molecular nets can immobilize said tumor cells within the column; cartridge; tubing; and other device; and whereby non-tumor cells can pass through said device.

Molecular nets can contain capture components that can bind and immobilize T cell receptors, B cell receptors, major histocompatibility complexes, and other antigen recognition cell surface markers on the surface of cells; and whereby said molecular nets can bind and immobilize specific cell products; and whereby said molecular nets can immobilize immune cells and/or immune cell products within the column; cartridge; tubing; and other device; and whereby un-immobilized cells and cell products and fluid can pass through said device; and whereby said un-immobilized agents can be returned to the biologic source.

Molecular nets can contain capture components such that can bind heavy metal, cholesterol, triglycerides, low density lipoprotein, high density lipoprotein, cytokines, insulin, hormones, drugs and other molecules that can be abnormally elevated in mammals.

Molecular nets can contain capture components that can be organic and inorganic molecules and/or living microbial cells that can bind and/or absorb and/or store chemicals such as petroleum, heavy metals, petro-chemicals, gasoline, herbicides, pesticides, and other environmental contaminants.

Still other examples of capture agents are bio-available forms of metals such as iron, manganese, magnesium, and others; extracellular matrices such as alginate slime, fibrinogen, fibronectin, collagens, and others; antibodies such as strain-specific antibodies, species-specific antibodies, anti-TNF, anti-peanut protein, anti-chitin, anti-tropomyosin, anti-peptidoglycan, anti-lipid A, anti-lipopolysaccharide, anti-flagellin, anti-pilA, anti-fimbrae, anti-lipoteichoic acid, anti-ferritin, anti-CCP, anti-interferon alpha, anti-interferon beta, anti-interferon gamma, anti-aflatoxin, anti-chit1, anti-desferrioxamine B, anti-ferrichrome, anti-2,2-dipyridyl, anti-rhodotorulic acid, and others; antigens such as pilA, pili, flagellin, flagella, heat-shock proteins, citrullinated proteins, and others; receptors such as steroid receptors, pheromone receptors, TNF receptor I, TNF receptor II, IFN-alpha receptor I, IFN-alpha receptor II, galactose receptors, sialic acid receptors, mannose receptors, and others; ligands such as sialic acid, mannose, tumor necrosis factor and others; enzymes such as chitinases and others; substrates such as chitin, tropomyosin, and others; cells such as non-clonal and clonal T cells, non-clonal and clonal B cells, macrophages, dendritic cells, neuronal cells, cardiac myocytes, endothelial cells, monocytes, fibroblasts, stromal cells, beta cells, epithelial cells, lung epithelial cells, skeletal myocytes, microglia, Kuppfer cells, mast cells, basophils, neutrophils, keratinocytes and others; intact or disrupted microbes from one or more Genus, species, or strain, such as *Acinetobacter baumannii, Acinetobacter* sp., *Staphylococcus aureus, Staphylococcus* sp., *Streptococcus* sp., *Mycobacterium* sp., *Neisseria* sp., *Salmonella* sp., *Shigella* sp., *Chlamydia* sp., *Borrelia* sp., *Klebsiella pneumonia, Klebsiella* sp., *Eschericia* sp. *Pseudomonas* sp., *Treponema* sp., *Mycoplasma* sp., *Adenoviridae* sp., *Herpesviridae* sp., *Poxyiridae* sp., *Parvoviridae* sp., *Reoviridae* sp., *Picornaviridae* sp., *Togaviridae* sp., *Orthomyxoviridae* sp., *Rhabdoviridae* sp., *Retroviridae* sp., *Hepadnaviridae* sp., *Flaviviridae* sp., *Candida* sp., *Aspergillus* sp., *Plasmodium* sp., *Amoeba* sp., and others; drugs such as steroids, non-steroidal anti-inflammatory molecules, beta-blockers, statins, and others; biologics such as adalumimab, infliximab, etanercept, PEG-sTNF-RI, and others; binding domains such as chitin binding domains and others; binding proteins such as flg15, lipopolysaccharide binding protein, actin, and others; nucleic acid binding proteins such as single-stranded DNA binding proteins and others; nucleic acids containing ribosomal DNA sequences; nucleic acids containing genes or gene segments; sense RNA, anti-sense RNA; carbohydrate-binding molecules such as dectin-1, retrocyclin 2, lectins, mannan-binding proteins and others; defensins; antigen-recognition molecules such as TLR1, TLR2, TLR3, TLR4, TLR5, TLR7, TLR8, TLR9 and others; antigen-presentation molecules such as major histocompatability complex I and major histocompatability complex II and others; orphan receptors such as soluble TNF receptors and others.

2. Linking Agents

Linking agents (or "linkers") are used to connect capture agents to each other. A large number of suitable linkers are known in the art and many are commercially available. See, for example, Hermanson, G. T., BIOCONJUGATE TECHNIQUES $2^{nd}$ Edition, 2008, Elsevier Inc., Oxford, which is incorporated herein by reference. Most often, linking agents are bifunctional (either homo-bifunctional or hetero-bifunctional). Bifunctional linking agents have two functional groups, each of which can bind to reactive groups of a capture molecule. (Solely for ease of reference, chemically reactive groups on capture agents are referred to as "reactive groups" while chemically reactive groups on linkers are referred to as "functional groups.") For illustration and not limitation, examples of bifunctional linking agents are provided in TABLE 2. Functional groups commonly used in commercially available linkers include amide, azide, imide, and ester. In certain embodiments tri-functional or multifunctional linking agents may be used. Examples of multifunctional linking agents include hydroxymethylphosphino linkers and triazene linkers.

In addition to the nature of linker functional groups, an important linker property is effective length, which is approximately the distance between two capture agents linked to the same linker molecule. For purposes of description, effective length can be considered approximately the same as the published extended chain length (in angstroms (Å)). For example, the linker succinimidyl 4-formylbenzoate (SFB) has a length of about 6 Å while the linker 5bis-dPEG6 NHS ester has a length of about 36 Å. Linker length can also be characterized by reference to the number of carbons in a chain, by reference to a number of repeating units (e.g., ethylene glycol units) in the linker, etc. Different molecular nets may be constructed using different linkers or different combinations of linkers and, in certain versions of the molecule net, linker length(s) may vary from layer to layer of a multilayer structure. In these contexts, it will be appreciated that reference to preferred linker lengths is intended only to be approximate.

Linkers may be divided, for example, into four catagories based on length:
i) Zero length linkers (1-Ethyl-10-[10-dimethylaminopropyl]carbodiimide hydrocloride (EDC))
ii) Short, non-selective linkers (e.g. formaldehyde, glutaraldehyde)

iii) Linkers with lengths in the range of about 6 to about 40 Å
iv) Linkers with lengths>40 Å

EDC promotes the linkage of amino and carboxy moieties, but does not result in a physical linker, per se. Short, non-selective linkers may be used to stabilize molecular net layers. Numerous linkers with lengths in the range of about 6 to about 40 Å are described in the scientific literature; examples are provided in TABLE 2. Linkers with lengths>40 Å are described in the scientific literature or can be made as described in EXAMPLE 12.

In some embodiments a molecular net, or molecular net layer, contains at least one linker with length in the range of about 6 to about 40 Å. In some embodiments a molecular net, or molecular net layer, contains at least one, at least two, at least three, or more than three linkers with length in the range of about 6 to about 40 Å and/or one or more linkers with length greater than 40 Å. In some embodiments a molecular net, or molecular net layer, contains at least one linker that is not formaldehyde or glutaraldehyde and/or at least one linker that is not a zero length linker.

It will be appreciated that preferably linkers are used which do not form homopolymers. When multiple species of linkers are used in fabrication of a molecular net, the linkers and/or linking conditions are selected to minimize formation of linker-only heterooligomers or polymers.

Long linkers may be useful in certain nets or net layers, such as molecular nets in which cells are captured. In some cases, long linkers can be prepared as described in EXAMPLE 12. Briefly, in this method a linear biopolymer (polysaccharide, polypeptide, or polynucleotide) is linked by two heterobifunctional linkers so that the resulting molecule comprises two reactive groups separated by the length of the biopolymer plus linkers.

The crosslinkers may bind more than one capture component; and may bind more than one type of capture component in a manner that preserves the two or three-dimensional structure of the capture components, and may preserve the secondary; tertiary; or quaternary structures of the capture components. Preferably the binding of at least one analyte recognition motif or binding site of the capture components is preserved.

Exemplary chemical crosslinkers include [N-e-Maleimidocapropyl]succinimide ester (EMCS), ethylene glycol bis[succinimidylsuccinate] (EGS), NHS-(PEG)n-maleamide, NHS-(PEG)n-NHS, and where n can be 1 to 50; whereby the chemical crosslinkers can be between 2 and 200 Angstroms in length.

Cross-linkers may be applied at various concentrations ranging from 1 nanomolar to 1 milimolar. Cross-linkers and concentrations will be selected to achieve molecular net stability under various conditions such as, for example temperatures of 0 to 45 degrees Celsius, buffer conditions such as 0 to 800 milimolar salt and 0 to 11% detergent. Cross-linkers are selected so that the fabricated nets withstand lyophilization followed by rehydration.

TABLE 2

| Linker | Reactive Groups | Reactive Towards | Approximate Length (Å) |
|---|---|---|---|
| sulfodisuccinimidyl tartarate, | | Primary amines | 6.4 |
| DTSSP (3,3'-Dithiobis(sulfosuccinimidyl) propionate) | | Primary amines | 12 |
| (1-Ethyl-3-(3-dimethylaminopropyl) carbodiimide hyrochloride, binds primary amines and carboxyl groups | | Primary amines and carboxyl groups | |
| N-Sulfosuccinimidyl-6-(4'-azido-2'-nitrophenylamino) hexanoate (sulfo-SANPAH) | NHS ester/aryl azide | Amino group-to-nonselective | 18.2 |
| N-Succinimidyl-6-(4'-azido-2'-nitrophenylamino) hexanoate (ZAMPA) | nitrophenyl azide/NHS ester | Amino group-to-nonselective | 18.2 |
| Succinimidyl 4-hydrazinonicotinate acetone hydrazone (SANH), C6-succinimidyl 4-hydrazinonicotinate acetone hydrazone (C6SANH) | Hydrazide | Amino groups | 6.7 (SANH) 14.4 (C6SANH) |
| Succinimidyl 4-hydrazidoterephthalate hydrochloride (SHTH) | Hydrazide | Amino groups | 7.9 |
| Succinimidyl 4-formylbenzoate (SFB) CAS Registry Number 60444-78-2 | Benzoate | Amino groups | 5.8 |
| C6-succinimidyl 4-formylbenzoate (C6-SFB) | Benzoate | Amino groups | 13.5 |
| Bis-[b-(4-Azidosalicylamido)ethyl]disulfide (BASED) | Aryl azide | Nonselective | 21.3 |
| p-Azidobenzoyl hydrazide (ABH) | Aryl azde/Hydrazide | Nonselective-to-carbohydrate | 11.9 |
| N-[k-Maleimidoundecanoic acid]hydrazide (KMUH) | Maleimide/hydrazide | Sulfhydryl-to-carbondyl (aldehyde)/carboxyl groups | 19.0 |
| 106627-54-7 | NHS ester | Amino groups | |
| 4-[p-Azidosalicylamido]butylamine (ASBA) | Aryl azide | Nonselective (or primary amine) | 16.3 |
| [N-e-Maleimidocaproic acid]hydrazide (EMCH) | Hydrazide | Oxidized carbohydrates | 11.8 |
| [N-e-Maleimidocaproyloxy]succinimide ester (EMCS) CAS Registry Number 55750-63-5 | Maleimide/NHS ester | Sulfhydryl-to-amino group | 9.4 |
| Succinimidyl 6-(4,4'-azipentanamido)hexanoate (LC-SDA) | NHS-LC-Diazirine | Amine-to-nonselective | 12.5 |
| Sulfosuccinimidyl 6-(4,4'-azipentanamido)hexanoate (Sulfo-LC-SDA) | Sulfo-NHS-LC/Diazirine | Amine-to-nonselective | 12.5 |
| N-[p-Maleimidophenyl]isocyanate (PMPI) | Isocyanate/Maleimide | Hydroxyl-to-sulfhydryl | 8.7 |
| 4-(4-N-Maleimidophenyl)butyric acid hydrazide hydrochloride (MPBH) CAS Registry Number 70539-42-3 | Hydrazide | Oxidized carbohydrates | |
| ethylene glycol bis[succinimidylsuccinate] (EGS) | NHS esters | Amino groups | 16.1 |
| 5bis-dPEG6 NHS Ester; di-(N-hydroxysuccinimidyl)-4,7,10,13,16-pentaoxanonadeca-1,19,dioate (BS(PEG)9) | NHS esters | Amino groups | 35.8 |

TABLE 2-continued

| Linker | Reactive Groups | Reactive Towards | Approximate Length (Å) |
|---|---|---|---|
| 5bis-dPEG6 NHS Ester; di-(N-hydroxysuccinimidyl)-4,7,10,13,16-pentaoxanonadeca-1,19,dioate (BS(PEG)5) | NHS esters | Amino groups | 21.7 |
| Succinimidyl-[4-(psorlaen-8-yloxy)]-butyrate (SPB) | NHS ester/Psoralen | Amine-to-DNA | 8.6-9.5 |
| NHS-(PEG)n-maleamide | NHS ester/Maleamide | Amine-to-Sulfhydryl | Dependent on PEG length |
| NHS-(PEG)n-NHS | NHS esters | Amine-to-Amine | Dependent on PEG length |
| B-[Tris(hydroxymethyl)phosphino] propionic acid (THPP) | Hydroxymethyl-phosphine groups | Primary and secondary amines | Tri-functional 3.03 |
| (bis[sulfosuccinimidyl] suberate ($BS^3$) | NHS esters | Primary amines | 11.4 |
| 1-Ethyl-10-[10-dimethylaminopropyl]carbodiimide hydrochloride (EDC) (CAS 25952-53-8) | Carbodiimide | Amine-to-Carboxyl | 0 |
| Formaldehyde | Active hydrogen groups | Nonselective | 2 |
| glutaraldehyde | Active hydrogen groups | Nonselective | ~6 |
| Maleamide | Maleamide | Sulfhydryls | ~4 |
| Cyanuric Chloride | Chloride | Amine | 6 |

In certain embodiments, the linker is degradable, for example, either due to chemical or thermal instability. Exemplary degradable linkers include PEG derivatives, poly(alkylene oxides), hydroxyalkyl acid esters, polyethylenimine triethyleneglycol (PEI-TEG), poly(spermine ketal ester), poly(spermine ester), amide linkers, thiol conjugation chemistry and the like. Exemplary degradable nucleic acid binding molecular nets include ones with polypeptides such as poly-arginine or poly-lysine or nucleic acid binding domains as capture agents and linkers such as $BS(PEG)_9$, poly(alkylene oxides), hydroxyalkyl acid esters, polyethylenimine triethyleneglycol (PEI-TEG), poly(spermine ketal ester), poly(spermine ester) or $BS^3$.

In other embodiments, the properties of the linkers are responsive to environmental conditions (pH, temperature, redox, chemistry, etc.) such that affinity of capture agents for analytes is altered. As the length and configuration changes, the properties of the molecular net may change. Exemplary linkers of this type include poly(N-isopropylacrylamide), poly(ethylene glycol)diacrylate, N,N'-methylenebisacrylamide, N-vinyl-2-pyrrolidone, and 2-hydroxy-ethyl methacrylate.

Molecular nets that are degradable or with properties responsive to environmental conditions find use in conditions where it is desirable to capture, and then selectively release analytes. Site-specific delivery of agents (drugs, biologics or nucleic acids) can be facilitated by the designed release of agents from a molecular net. Current problems with agent delivery include toxicity, poor distribution, lack of targeting and inefficient release. Other problems with agent delivery include unfavorable pharmacodynamic and/or pharmacokinetic profiles in the body and within specific tissues. Design of a molecular net to perform the following functions enable more effective dosing strategies: (i) capture agents of the molecular net designed to protect the agent, (ii) capture agents of the molecular net designed to target the net to a particular tissue or cell type, (iii) capture agents or linking agents of the molecular net designed to be susceptible to tissue-specific or subcellular conditions, (iv) capture agents or linking agents of the molecular net can be designed for a timed release of agent.

B. Fabrication of Molecular Nets

To produce molecular nets of the invention, capture agents with reactive groups ("capture agent reactive groups") are combined with linkers having complementary functional groups ("linker functional groups"). In this context, "complementary" means the two groups interact to form a covalent chemical bond.

In one approach, the molecular net is prepared by combining at least one (and more often more than one) species of capture agent and at least one (and often more than one) species of linking agent. Assuming bifunctional linking agents are used, the capture agents and linkers are combined under conditions in which most of the linking agent molecules in the net are conjugated to two capture agents and each capture agent is linked to one or more other capture agents via a linker. It will be expected that, depending on the linker(s) and capture agent(s), some linkers may form intramolecular bonds with a single capture agent molecule, but conditions of solvent, pH, buffers, temperature, monomer concentration and the like are selected to promoter linking of different capture agent molecules to each other. It will be recognized that unlinked or singly linked capture agents may be enmeshed in the molecular net if not washed out during fabrication, but most or essentially all (e.g., >95% or >99%) of capture agents are linked to at least one other capture agent.

It will be recognized that if multifunctional linking agents are used, individual linkers may be conjugated to more than two capture agents.

In the resulting molecular net, capture agents are linked directly to each other to form an amorphous three dimensional structure, in contrast to structures in which, for example, a plurality of capture agents such as antibodies are individually linked to an underlying substrate or polymer strand(s).

The resulting molecular net may be described, for purposes of description rather than definition, as a branched pseudorandom copolymer in which the monomers are capture agents and linking agents.

The molecular net may be called a random copolymer because given a mixture of multiple species of bi- or multi-functional linking agents, capture agents with multiple reactive groups, and multiple species of capture agents, the resulting branched polymer has an unpredictable, irregular, networked structure.

The molecular net may be called a pseudorandom copolymer because in contrast to a truly random polymer (a) linkers bind capture agents but preferably do not bind linkers, and capture agents bind linkers but not other capture agents and (b) not every reactive group on a linker can bind to reactive groups on any capture molecule (for example, in a composition containing antibody and DNA capture agents, and sulfo-NHS linkers and succinimidyl-[4(psorlaen-8-yloxy)]-butyrate (SPB) linkers, the sulfo-NHS linker will link antibodies but will not react with the nucleic acids while the SPB heterobifunctional linkers will bind an antibody to a DNA).

For illustration, a molecular net may be formed by (1) depositing a solution containing the capture agent or agents (typically a pooled capture agent composition) at a site, and (2) adding the linker or linkers (typically a pooled linker composition) to the capture agent solution, under conditions in which the linkers and capture agents form a cross-linked net. The capture agents may, for example, be deposited on a planar surface (e.g., on a hydrophobic substrate). Typically the net is self-assembling following mixture of the linkers and capture agents. However, it is not excluded that in some embodiments a chemical catalyst or other agent (e.g., light activation of photoactivatable linkers) might be used to promote formation of the net. The fabrication process is described in more detail below.

After the monomers are combined and the net forms, it is sometimes useful to quench the binding reaction (e.g., using small molecules that render the linkers unreactive) and/or remove any unlinked capture agent and/or linker. For example, unlinked monomers can be removed by washing the net using an aqueous buffer, optionally containing detergent.

Exemplary substrates are discussed below. The substrate may be an inert material, a porous material (e.g., nitrocellulose), a material derivatized to bind the net, etc. Suitable substrates for making molecular nets include, but are not limited to nitrocellulose, polystyrene, and polyurethane. If the substrate includes reactive groups the first layer of the net may bind covalently with the substrate. In some cases the monomers are combined within a removable mold.

In some embodiments, as discussed below, the net may be formed over an "elevated molecular base" or "underlayer" such as a base of uncrosslinked polypeptides. When the underlayer is proteinaceous it may comprise one or more or all of the capture agents present in the first layer of the net, or may comprise other proteins (e.g., BSA) or molecules (e.g., carbohydrates). In an alternative embodiment, the "underlayer" does not include capture agents (e.g., does not include capture agents found in the net layers). In an alternative embodiment, the "underlayer" is cross-linked only with glutaraldehyde or formaldehyde.

In an alternative approach, nets may be formed by combining linkers and capture agents in a syringe or other container and extruding the mixture into a liquid whereupon cross-linking occurs.

Optionally, a molecular net (or molecular net layer) can be stabilized by contacting the net with formaldehyde or glutaraldehyde, typically 0.037 mM for 15 min at ambient temperature In some embodiments, one or more layer of molecular net can be extruded, cut into with a sharp edge, a laser or other method; and fitted together.

C. Capture Agent and Linker Compositions

In some embodiments, the molecular net comprises only a single species of capture agent (e.g., anti-interferon-alpha antibodies). More often, the molecular net comprises multiple different (heterogeneous) species of capture agents having different binding specificities (e.g., anti-interferon-alpha antibodies, anti-interferon-beta antibodies, and antiviperin antibodies). Often the molecular net comprises multiple classes of capture agents (e.g., anti-interferon-alpha antibodies, DNA binding molecules and oligonucleotides).

Similarly, the net can contain one or multiple species of linkers.

Methods for selecting capture agents and combinations of capture agents are described below.

D. Multilayer Molecular Nets

Although simple molecular nets have useful properties, in preferred embodiments more complex molecular nets are formed. Simple nets, made in one step, can be referred to as "one-region" or "one-layer" nets, the terms being used interchangeably. More complex nets can be referred to as "multiple layer," "two-layer," "three-layer" etc. molecular nets. Multilayer nets may have 2, 3, 4, 5, 6, 7, 8, 9, 10 or more layers. Molecular nets used for diagnostic purpose usually have at least two layers and often have more than two layers (e.g., 3-8 layers).

A two-layer net is prepared by fabricating a one-layer net, as described above, and fabricating a second molecular net by combining the one-layer net with at least one (and more often more than one) species of capture agent and at least one (and more often more than one) species of linking agent. It is convenient, although not entirely accurate, to visualize the process of making additional net layers as pipetting solutions of capture agents and linkers on top of the one-layer net to form a distinct second layer disposed above the first layer, optionally making a third layer, etc., resulting in a generally cylindrical structure or in a generally concentric series of hemispherical layers. FIG. 1 illustrates a multilayer molecular net.

Often, the linkers and capture agents are selected so that the composition of the one layer of a multilayer net differs from the composition of at least one other layer. In some embodiments the at least one other layer is an adjacent layer. In some embodiments the linkers and capture agents are selected so that the composition of the one layer of a multilayer net differs from all other layer of the net. For example, in some versions the composition of a second layer is distinct from the composition of a first layer. Thus, a second layer may differ from a first layer in terms of the capture agent composition and/or linker composition. Two layers may have different porosity as a result of the selection of agents and linkers. For illustration and not limitation, examples of two-layer molecular nets are shown in TABLE 3.

TABLE 3

| | Layer 1 | Layer 2 |
|---|---|---|
| Capture agents | dsDNA binding peptides | Antibodies against PBP2a |
| Linking agents | EDC | EDC |
| Capture agents | dsDNA binding peptides | Antibodies against interferon-alpha and interferon-beta |
| Linking agents | EMCS | EDC |
| Capture agents | dsDNA binding peptides and antibodies against LPS and antibodies against lipoteichoic acid | dsDNA binding peptides and antibodies against LPS and antibodies against lipoteichoic acid |
| Linking agents | EMCS and EDC | BS(PEG)9 |

As will be apparent to the careful reader, the porous nature of the molecular net means that linkers and capture agents added in the second step will not necessarily remain entirely "on top" of the first layer. Rather, linkers and agents may migrate into the "pores" of the first layer. However, such migration can be limited so that while both populations of linkers and capture agents may be somewhat intermingled at the interface between the first and second layers, the bottom of the first layer (assuming for the moment a cylindrical structure) of the resulting multilayer net will have the composition of the linkers and capture agents added in the first step, and the top of top-most or outer-most layer of the multilayer net will have the composition of the linkers and capture agents added in the second step.

A result of this intermingling is that the composition at the interface between two layers may be somewhat different from components used to form either of the two layers.

The interface between two layers with the same capture agent and linker composition (such as a multilayer net in which each layer has the same composition) will also differ from non-interface regions of the net. Typically, the concentration of capture agents and linkers is higher in the interface as a consequence of the fabrication process. That is, forming a first layer using 1 microliter each of capture agent and linker solutions and then forming a second layer (and interface) by adding 1 microliter each of capture agent and linker solutions to the preformed first layer will result in a different density and distribution of capture agents and linkers than forming a single layer from 2 microliters each of capture agent and linkers.

In one embodiment, a multilayer net may have one layer as a core and additional layer(s) formed as concentric hemispheres or shell(s) surrounding the core. However, other shapes are possible. For example, although multilayer molecular nets may have a roughly cylindrical or roughly rectangular shape. For example, a multilayer net may be narrower at one end than at the other (e.g., cone shaped). In preferred embodiments the layers are configured so that a liquid (e.g., sample) contacting with the uppermost (or outermost) layer can flow consecutively through each subsequent layer. That is, not all "layers" are simultaneously or equally accessible.

It will be recognized that the linkers added in the second step, in addition to cross-linking capture agents added in the second step to each other, will also link capture agents in the first layer with those added in the second layer, thus binding the layers to each other.

We have discovered that multilayer nets with particular linker and capture agent compositions in each linker are endowed with a number of valuable properties. For example, molecular nets have the ability to simultaneously capture different multiple classes of analytes of different sizes and with different chemistries. This allows for simultaneous detection of multiple indicia of infection (for example) which in turn provides higher confidence in the result. In addition, we have observed that molecular nets achieve high signal-to-noise ratios and low non-specific binding relative to other detection approaches. For a given footprint, the molecular net configuration facilitates binding and detection of more analyte per unit area, resulting in a more easily detectable signal (e.g., a visually detectable color signal). In addition, molecular nets are readily adaptable to a variety of device formats and are stable and storable.

E. Detection of Bound Targets

Analytes bound to the molecular net may be detected using conventional methods consistent with the nature of the analyte. Most often the immobilized analyte is bound by a detectably labeled antiligand, unbound labeled antiligand is washed out of the net and the label detected. For example, protein analytes (including cells and cell fragments) may be detected using antibodies that specifically bind the target protein. Carbohydrate analytes may be detected using labeled lectins or other carbohydrate binding agents. Nucleic acid analytes may be detected using detectably labeled complementary nucleic acids or using nucleic acid binding proteins. Exemplary nucleic acid binding proteins include double-stranded DNA binding proteins such as bZIP, topoisomerases, zinc-finger containing proteins, helix-turnhelix protein, nucleases, and others; and single-stranded DNA binding proteins, DNA polymerases and others. In addition, we have developed novel binding proteins, as described herein below.

Alternatively, the antiligand may be unlabeled and then associated with label after it has bound to the bound analyte. For example, an unlabeled goat IgG may be associated with an analyte bound by a capture agent, and then detected using detectably labeled mouse anti-goat IgG antibody. As another example, biotin-conjugated antiligands may be used, and then detected using strepavidin-conjugated detectable labels.

In a different embodiment, a bound enzyme may be detected (although not necessarily localized) by adding a substrate that can be enzymatically converted to produce a detectable signal or a bound substrate may be detected by addition of an enzyme and reagents that produce a detectable signal. In some cases the capture agent itself may undergo a conformational change after binding to the analyte so that a detectable signal is emitted and/or so that the analyte-capture agent complex can be detected.

A heterogeneous combination of analyte detection molecules, or detection reagents, can be used simultaneously to detect analytes bound by capture agents. Exemplary analyte detection molecules include aptamers; polyribonucleic acid probes; polydeoxyribonucleic acid probes; peptides; proteins; antibodies; functional or non-functional enzymes; substrate-binding domains; glycoproteins; lipoproteins; carbohydrates; glycolipids; receptors; ligand binding domains; ligands; lipids; cholesterols; sterols; drugs; biologics; antibiotics; antibacterials; anti-virals; anti-mycotics; anti-parasitics; mammalian cells; and microbes; and whereby said heterogeneous analyte detection molecules can be labeled with one or more detectable label; wherein binding of one or more type of analyte detection molecules to one or more type of analyte immobilized by one or more capture components belonging to one or more molecular net can generate a signal or can generate an enhanced signal; and can indicate a positive test.

It will be appreciated that these examples are for illustration and not limitation, and that many other approaches are possible. For example, analytes may be associated with detectable label prior to immobilization.

Numerous detectable labels are known in the art, such as colorimetric, fluorescent, radioactive, luminescent, phosphorescent, enzymatic tags (e.g., alkaline phosphatase, luciferase) affinity tags and the like. In principle any type of detectable label may be used. However, most preferred are labels suitable for colorometric and/or fluorescent detection. Visible labels detectable by the naked eye without specialized equipment have certain advantages. Labels that emit signal without the addition of additional substrates or reagents may provide a more rapid and less expensive readout.

Examples of fluorescently detectable labels include Cy3, Cy5, FITC, PE, Alexa, fluorescein, fluorescein-isothiocyanate, Texas red, rhodamine, green fluorescent protein, enhanced green fluorescent protein, lissamine, phycoerythrin, Cy2, Cy3, Cy3.5, Cy5, Cy5.5, Cy7, SyBR Green and the like. Colormetically detectable labels include dyes, colloidal gold or silver, colored latex beads.

One or more class of analyte detection molecules can be conjugated to one or more specific detectable molecule such as: enzyme such as horseradish peroxidase, alkaline phosphatase, ATPase, adenylate kinase, beta-lactamase, urease, lactase, pyruvate dehydrogenase, carbonic anhydrase, catalase, fumarase, superoxide dismutase, dihydrofolate reductase, cyclooxygenase, kinase, phosphatase, luciferase, cytochrome P450 oxidase, and other oxidoreductases, transferases, hydrolases, lyases, isomerases, and ligases; ultrafine particles such as nanoparticles, nanocrystals, nanoclusters, nanopowders, and others made from carbon, silica, ceramics, polymers, glass, and material composites; fluorophores such as 9,10-diphenylaanthracene, 1-chloro-9,10-diphenylanthracene, 2-chloro-9,10diphenylanthracene, 9,10-bis(phenylethynyl)anthracene, 1-chloro-9,10bis(phenylethynyl)anthracene, 2-chloro-9,10-bis(phenylethynyl)anthracene, 1,8-dichloro-9,10-bis(phenylethynyl)anthracene, 2,4-di-tert-butylphenyl 1,4,5,8-tetracarboxynapthalene diamide, rhodamine B, 5,12-bis(phenylethynyl)naphthacene, violanthrone, 16,17-(1,2-ethylenedioxy) violanthrone, 16,17-dihexyloxyviolanthrone, 16,17-butyloxyviolanthrone, N,N'-bis(2,5-di-tert-butylphenyl)-3,4,9,10-perylenedicarboximide, 1-N,Ndibutylaminoanthracene, 6-methylacridinium iodide, Cy3, Cy5, Cy7, Pacific Blue, FITC, PE, DiA, Nile Red, Toto1 and 3, Yoyo1 and 3, SYBR green, Sytox orange, Popo1 and 3, Bobo1 and 3, Evoblue-30, DY-485, DY-500, DY-554, DY-633, DY-613, DY-590, DY-650, DY490XL, DY-520XL, DY-480XL, Alexa488, Alexa 647, ProQ Emerald, ProQ Diamond, IRDye 700DX, Adams apple red 680, Adirondack Green 520, Birch Yellow 580, Snake-Eye Red 900 and other fluorophores; redox dependent labels such as 2,2'-bipyridine (Ru complex), nitrophenanthroline (Fe complex), N-phenylanthranilic acid, 1,10-phenanthroline (Fe complex), N-ethoxychrysoidine, 2,2'-bipyridine (Fe complex), 5-6-dimethylphenanthroline (Fe complex), o-dianisidine, sodium diphenylamine sulfonate, diphenylbenzidine, diphenylamine, viologen, and others; pH-dependent redox labels such as sodium 2,6-dibromophenol-indophenol, sodium 2,6-dichlorophenol-indophenol, sodium o-cresol indophenol, thionine, methylene blue, indigotetrasulfonic acid, indigotrisulfonic acid, indigocarmine, indigomono sulfonic acid, phenosafranin, safranin T, neutral red, and others; visible dyes such as coomassie brilliant blue, Sypro Ruby, silver stain, and others; substrates such as luciferin, oxygen, luminol, hydrogen peroxide, adenosine monophosphate, adenosine diphosphate, adenosine triphosphate, para-nitrophenylphosphate, and others; radioisotopes such as tritium, carbon-14, phosphorus-33, phosphorus-32, technetium-99, molybdenum-99, sulfur-35, and others; polymers such as polystyrene sulfonate latex and other; colloids such as colloidal crystal, colloidal metal, 10-60 nm colloidal gold particles, 10-80 nm colloidal silver particles and others; magnetic particles such as hematite, stainless steel, copper, iron, magnetite, zinc, alloys, nickel, cobalt, gadolinium, and others; hydrogen peroxide, and phenyl oxalate ester.

The detectable labels on the analyte detection molecules can be conjugated separately with dyes such as: 3-3'-Diaminobenzidine tetrahydrochloride; 1,9-Dimethylmethylene blue chloride; bromocresol purple; bromophenol blue; bromothymol blue; di-Camphorquinone; fluorescein; gentian violet; gum mastic; leishman stain; methyl purple; nitroblue tetrazolium chloride; phenol red; rosolic acid; saffron; szechrome; thiazole orange; methylene blue chloride; chlorotriazine dyes such as but not limited to cibacron blue 3GA, procion red H-E7B, procion green H-4G and yellow H-E3G; triazine dyes; hematoxylin stains; eosin; acid fushin; picric acid; Wright's stain; aldehyde fuschin; metanil yellow; silver salt; toluidine blue; periodic acid-Schiff stain; Masson's trichrome stain; Mallory's trichrome stain; Weigert's elastic stain; Heidenhains' azan tricrome stain; silver stain; Orcein stain; Sirius red F3BA; nuclear fast red; alcian blue; iodine; luxol fast blue; neutral red; Sudan black B; oil red O; Nile red; crystal violet and other visible dyes.

Methods for conjugating or otherwise associating or incorporating labels into an antiligand (for example) are well known in the art.

Methods of detecting signal from an immobilized label are similarly well known, and are dependent on the nature of the label. Many devices are available for such detection including transilluminator, colorimeters, fluorometers, luminometers, and the like.

Multiple Analyte Detection

Molecular nets are powerful tools, in part, because they are well adapted for simultaneous detection of multiple different analytes. In principle, a single detection system may be used to detect each of several different analytes bound by a net. For example, in a net in which capture agents bind "analytes W, X, Y, and Z" each of the detection system antiligands could be labeled with the same detectable label. This would make it possible to determine whether none, or at least one, of the analytes had been captured, but would not permit easy discrimination between binding of allow some analytes (e.g., W and Y) and not others (e.g., X and Z). This can be addressed by localizing capture moieties to particular layers. For example, if layer 1 contains analytes W and X, layer 2 contains analytes X and Y, and layer 3 contains analytes Y and Z, if bound detectable signal is observed in only layer 3, it can be inferred the sample contains analyte Z but not analytes W, X or Y. However, this requires localizing signal to a particular layer, which may not be convenient.

Alternatively, analytes W, X, Y, and Z can each be differentially labeled (e.g., with a different color dye) and presence or absence of an analyte can be deduced based on the labels observed. It will be appreciated that the two approaches (differential labeling, and inference based on binding in a particular layer) can combined. Finally, samples can be assayed using multiple nets, such as by using a device with multiple nets. For example, a device with three multi-layer nets may be used in which the first net has capture agents for analytes W and X, the second net has capture agents for analytes X and Y, and the third net has capture agents for analytes Y and Z.

Colorimetric mixing refers to the reflectance spectra emanating from one or more molecular source in the presence of light. Said reflection can be regular or diffuse in nature and can be single or multiple scattering. When detectable signals are bound in different layers of multilayer nets (layered or stacked nets) the bound colored detectable molecules conjugated to analyte detection molecules can produce a different color; wherein colorimetric mixing can occur; wherein one or more metachromatic reaction can occur; whereby the presence of color detection labels in a test volume can be a positive test; and whereby said colored analyte detection molecules can be bound to one or more analyte immobilized by one or more capture component held by crosslinking within one or more molecular net; and whereby said colored analyte detection molecules can be bound to analyte in a dense and closely-packed manner; and whereby said colored analyte detection molecules can be magnified by lenses; can be polarized by magnetic polarization; can be sensed by sensors; and can be visually assessed per unit test volume; and can be visually assessed earlier than conventional methods; and can signal a positive test faster than many conventional methods.

Disclosed is one or more molecular net and/or an arrangement of molecular net pieces; whereby the arrangement of capture molecules and the respective specific surface chemistries of capture molecules and the respective binding preferences for specific analytes can be arranged in sections within the molecular net; whereby the binding and immobilization of specific analytes to specific capture molecules can generate a pattern of detection; and whereby the pattern of detection can be determined by the immobilization of specifically labeled analyte detection molecules; and whereby said labeled detection molecules can provide one or more signal; and whereby the patterning and/or arrangement and/or timing of signal can provide information in a binary or analytical test. can in combination: produce a different positive signal; can produce an intensified signal;

The degree of binding of analyte detection molecules to the molecular net can be monitored by photography; by eye, or using test device sensors can monitor the degree of binding and/or intensity of binding of analyte detection molecules to the molecular net by: vibrational frequency and changes thereof; thermal conductance and changes thereof; heat production and changes thereof; iridescence and changes thereof; electrical conductance and changes thereof; electrical potential and changes thereof; magnetic fields and changes thereof; light production and changes thereof; light diffraction and changes thereof; colorimetric absorbance and changes thereof; chromatic spectra and changes thereof; electromagnetic potential and changes thereof; electrochemical potential and changes thereof; electrochemical chromatic spectra and changes thereof; phosphorescence and changes thereof; fluorescence absorbance and changes thereof; chemiluminescence and changes thereof; electroluminescence and changes thereof; sonoluminescence and changes thereof; mechanoluminescense and changes thereof; piezoluminescence and changes thereof; fractoluminescence and changes thereof; thermoluminescence and changes thereof; triboluminescence and changes thereof; redox potential and changes thereof; pH and changes thereof; and others methods of sensing or monitoring detection molecule binding per unit volume of molecular net in a testing area; and whereby signal can be enhanced by: the presence of an amplifier; incubation time; heat; light; photons; acid; base; magnification lenses; electrical current; filters; polarization; and others; and whereby signal can be transmitted to and can be propagated by: central processing unit; processors; microprocessors; arithmetic logic units; data storage; flash memory; transmitters; modulators, storage devices; computer hardware; universal serial bus; personal computers; simple computers; embedded computers; computer networking abilities; ethernet and others; and whereby signals can be analyzed with conventional algorithms and can be analyzed with conventional software.

By "sonoluminescence" is meant the emission of short burst of light from imploding bubbles in a liquid when excited by sound. Under an acoustically driven field, a bubble moves until the final stages of collapse.

By "mechanoluminescence" is meant light emission resulting from any mechanical action on a solid. Mechanical actions can include, but are not limited to the application of ultrasound, pulling force, pushing force, twisting force and others.

By "fractoluminescence" is meant light emission resulting from mechanical stress applied to molecules to produce molecular fractures. Can also be applied to molecular interaction, whereby fractures can occur within and between interaction pairs.

By "thermoluminescence" is meant light emission resulting from a reaction between species trapped in a rigid matrix wherein light is released as a result of an increase in temperature.

By "triboluminescence" is meant light emission resulting from the rubbing together of the surface of certain solids. Can also occur when solids are crushed.

By "piezoluminescence" is meant light emission resulting from a change in pressure of certain solids.

By "photovoltaic cell" is meant one or an array of material such as crystalline silicon, cadmium telluride, and copper indium selenide, that can convert light energy into direct current electricity.

By "metachromatic" is meant a change in color that can be the result of the presence or absence of heat.

By "colorimetric mixing" is meant the reflectance spectra emanating from one or more molecular source in the presence of light. Said reflection can be regular or diffuse in nature and can be single or multiple scattering.

In one embodiment, a device can detect one or more different analyte in a sample by light production from an enzymatic reaction. Whereby analytes can be bound to one or more molecular net per test volume and can bind one or more class of analyte detection molecule per test volume. Said analyte detection molecules can be conjugated to one or multiple light producing enzymes and can be immobilized on one or more molecular net per test volume. A light producing reaction can occur when enzyme substrate is present. A light producing reaction can be amplified when a catalyst is present. A light producing reaction can be amplified when one or more light harnessing devices is present. Said light from a light producing reaction can be focused, amplified, and directed when one or more light harnessing devices are present, such as optic fibers, photodiodes, semiconductors and others. Said light from a light producing reaction can be detected by sensors such as solar cells, solar films, photomultiplier tubes and other photon sensors that can generate voltage or current from photon energy.

In another embodiment, a device can detect one or more different analyte in a sample by light production from a chemical reaction. Whereby analytes can be bound to one or more molecular net per test volume and can bind one or more class of analyte detection molecule per test volume. Said analyte detection molecules can be conjugated to one or multiple light producing dyes and can be immobilized on one or more molecular net per test volume. A light producing reaction can occur when one or more nucleophilic molecule is present. A light producing reaction can be amplified when a catalyst is present. A light producing reaction can be amplified when one or more light harnessing devices is present. Said light from a light producing reaction can be focused, amplified, and directed when one or more light harnessing devices are present, such as optic fibers, photodiodes, semiconductors and others. Said light from a light producing reaction can be detected by sensors such as solar cells, solar films, photomultiplier tubes and other photon sensors that can generate voltage or current from photon energy.

F. Making Molecular Nets with Desired Specificity

The molecular net is particularly well adapted for detecting multiple different analytes. It will be appreciated that the particular analytes bound and detected by a particular net or device will vary with the intended use of the article. By way of example, when it is desired to detect the presence of an infectious bacterial pathogen, a single net or device can be used to detect multiple indicia of infection such as, for example, the presence of pathogen protein, the presence of pathogen nucleic acids, the presence of pathogen cells, the presence of pathogen carbohydrates, the presence of a host immune response to infection, and the like. By simultaneously detecting multiple independent indicia of infection, molecular nets allow determinations to be made with greater confidence.

Molecular nets can also be adapted to simultaneously immobilize and/or detect analytes of differing sizes. In some cases, what is being immobilized are small analytes or fragments of larger analytes. In other cases, the analytes are larger analytes, complexes, or cells containing certain analytes. Since the upperlayers are less sterically constrained to due fewer crosslinks, they are more accessible to larger analytes. Therefore, the smaller analytes and fragments bind to underlayers of a molecular net, while the larger analytes, complexes, and cells bind to upperlayers of a molecular net. Thus the nets can be used for stratified analyte binding due to the spacing of interconnected capture molecules within one or more layers of a molecular net or by the placement of adjacent molecular nets. An example is the simultaneous immobilization/detection of fungal spore proteins, allergens, which only include an epitope of the allergen, and a fragment of an allergen.

At least four primary design elements must be addressed in designing a molecular net. They are (in arbitrary order):

First, a particular set of analytes must be selected that the assay will provide useful information to a physician or operator.

Second, capture agents must be selected to detect the presence or absence of the particular set of analytes.

Third, the detection systems for each analyte must be selected.

Fourth, linkers must be selected and the particular linker and capture agent compositions of each layer of the net must be determined.

Selection of Analytes

In the diagnostic context, analytes may be selected to identify and/or differentiate infections cased by different infectious agents. Preferably, multiple analytes are selected for the (or each of the) infectious agents. In some embodiments at least one, two, three or all four of the following pathogen markers are detected: (1) pathogen protein, (2) pathogen nucleic acid, (3) pathogen polysaccharide, (4) pathogen lipid. In some embodiments at least one, two three or all four of the following host markers are detected (1) complement activation; (2) antipathogen antibodies; (3) interferon; (4) lectin binding proteins; (5) acute phase proteins; (6) 8-hydroxydeoxyguanosine (8-OH-dGUA); (7) antimicrobial peptides (AMPs); (8) LPS binding protein (LBP). TABLE 4 provides examples of analytes that may be used to detect infections, as well as exemplary corresponding capture agents. It will be recognized that TABLE 4 is for illustration and is not intended to be comprehensive.

TABLE 4

| CONDITION OR INFECTIOUS AGENT | ANALYTES | CAPTURE AGENT |
|---|---|---|
| Staphylococcus aureus | S. aureus peptidoglycan; S. aureus SsaA; TSST-1; α-toxin; S. aureus capsular polysaccharides; nuc DNA sequence; | Antibodies against (1) S. aureus peptidoglycan; (2) S. aureus SsaA; (3) TSST-1; (4) α-toxin; (5) Lectin binding protein; Complement protein C3; DNA binding peptide 1; DNA binding peptide 2 |
| Methicillin-resistant S. aureus | S. aureus PBP2a; mec A DNA sequence; mec I DNA sequence; mec R DNA sequence | Antibodies against S. aureus PBP2a; DNA binding peptide 1; DNA binding peptide 2; DNA binding peptide 6 |
| General viral | interferon-alpha interferon-beta IPS-1 (MAVS) viperin (cig5) | Antibodies against (1) interferon-alpha; (2) interferon-beta; (3) IPS-1 (MAVS); (4) viperin (cig5) |
| Sepsis | lipid A lipopolysaccharide peptidoglycan teichoic acid 16s DNA sequence LPS binding protein (LBP) Procalcitonin Soluble TREM-1 | Antibodies against (1) lipid A; (2) peptidoglycan; (3) teichoid acid; (4) lipopolysaccharide; (5) LPS binding protein (LBP); (6) pro-calcitonin; (7) sTREM-1 DNA binding peptide 1 DNA binding peptide 2 DNA binding peptide 6 |
| General fungal | Chitin; Chitinase; Galactomannan (1→3)-β-D-Glucan Amphotericin Fungal toxins 18s rDNA sequences | Antibodies against (1) chitin; (2) chitinase; (3) galactomannan; (4) (1→3)-β-D-Glucan; (5) amphotericin (6) fungal toxins Chitin binding peptide 1 Chitin binding peptide 2 DNA binding peptide 7 |
| Bacterial | Lipopolysaccharide (Gram negative); Lipid A (Gram negative); LPS binding protein (immune response against Gram negative); Acylated lipopeptide (Mycoplasma and Gram negative); Peptidoglycan (Gram positive); | Antibodies against (1) lipopolysaccharide; (2) lipid A; (3) LPS binding protein (LBP); (4) peptidoglycan; (5) teichoic acid; (6) penicillin binding proteins; (7) mycoloyl arabinogalactan (8) arabinomannan; (9) HSP65; DNA binding peptide 1 DNA binding peptide 2 DNA binding peptide 6 |

TABLE 4-continued

| CONDITION OR INFECTIOUS AGENT | ANALYTES | CAPTURE AGENT |
|---|---|---|
| | Teichoic acid (Gram positive); Penicillin binding proteins (Gram positive); Mycoloyl arabinogalactan ((Mycobacteria); Arabinomannan (Mycobacteria); HSP65 (Mycobacteria); 16S-23S rRNA spacer region sequences (Mycobacteria); hsp65 DNA sequences (Mycobacteria) | |

Selection of Capture Agents and Detection Systems

In selecting capture agents and detection systems, specificity for a particular analyte may come from the capture agent, the detection system, or both. See TABLE 5.

TABLE 5

| Capture Agent | Detection System |
|---|---|
| Non-specific or partially-specific Example: nonspecific DNA binding protein | Specific Example: labeled nucleic acid probe |
| Specific Example: antibodies against capsular polysaccharides | Non-specific or partially-specific Example: Complement protein C3 and lectin binding proteins |
| Specific Example: antibody binds one epitope of protein analyte | Specific Example: antibody binds second epitope of protein analyte |

Selection of Linkers and Particular Linker and Capture Agent Compositions of Each Layer The fourth design element can be selected based on a combination of broad guidelines and empirical tests. Typically, combinations of capture agents are selected to provide redundancy in detection of a pathogen or other analyte. For example, a net for detection of bacterial infection may detect whole bacterial, a bacterial protein, a bacterial nucleic acid and a bacterial lipopolysaccharide all indicative of the infection. This redundancy provided higher confidence and greater sensitivity to the assay. Usually, in multilayer nets in which the porosity varies from layer to layer, porosity tends to decrease moving from the outside of the net to the interior, or moving from one end of the net (e.g., top) to the other (e.g., bottom) so that sample flowing through the net flows through higher porosity layers first, and increasingly lower porosity layers thereafter. Generally the concentration of capture agent is dictated by peak analyte concentration in the clinical or other sample and the sensitivity of the detection system.

Empirical tests are required to design a molecular net with suitable properties. The empirical tests may involve:

(a) creating numerous different candidate molecular nets for each contemplated set of capture agents by combining a plurality of individual aliquots of the set of capture agents with a plurality of individual aliquots of one or more sets of linking agents to produce a plurality of molecular nets with different compositions, wherein optionally the concentration of individual capture agents and/or linkers varies from molecular net to molecular net;

(b) assessing the ability of each net to bind analytes, wherein said assessing comprises contacting the nets with a sample containing the analytes, typically for 5 to 60 minutes, and determining which nets most efficiently bind said analytes, thereby identifying one or more lead nets;

(c) combining one or more said lead nets with one or more second sets of capture agents, which may be the same as the first set, adding one or more of linking agents under conditions in which a multilayer net forms, and assessing the ability of each multilayer net to bind the first and second analytes, wherein said assessing comprises contacting the multilayer nets with a sample containing the analytes, and determining which multilayer nets most efficiently bind said analytes.

(d) repeating step (c) to add multiple net layers;

(e) assessing the nonspecific background and sensitivity of the candidate nets and selecting those with acceptable low background and sensitivity.

Notwithstanding the broad discussion above, it will be appreciated that there are numerous other factors involved in designing a diagnostic or other assay system.

F. The Three-Dimensional Structure of Molecular Nets

The molecular nets described herein may be understood as three-dimensional structures with a pseudo-random composition including at least capture agents and linking agents. The structure and dimensionality of the molecular nets may be better understood with reference to certain exemplary configurations that molecular nets may assume.

Figure 35:
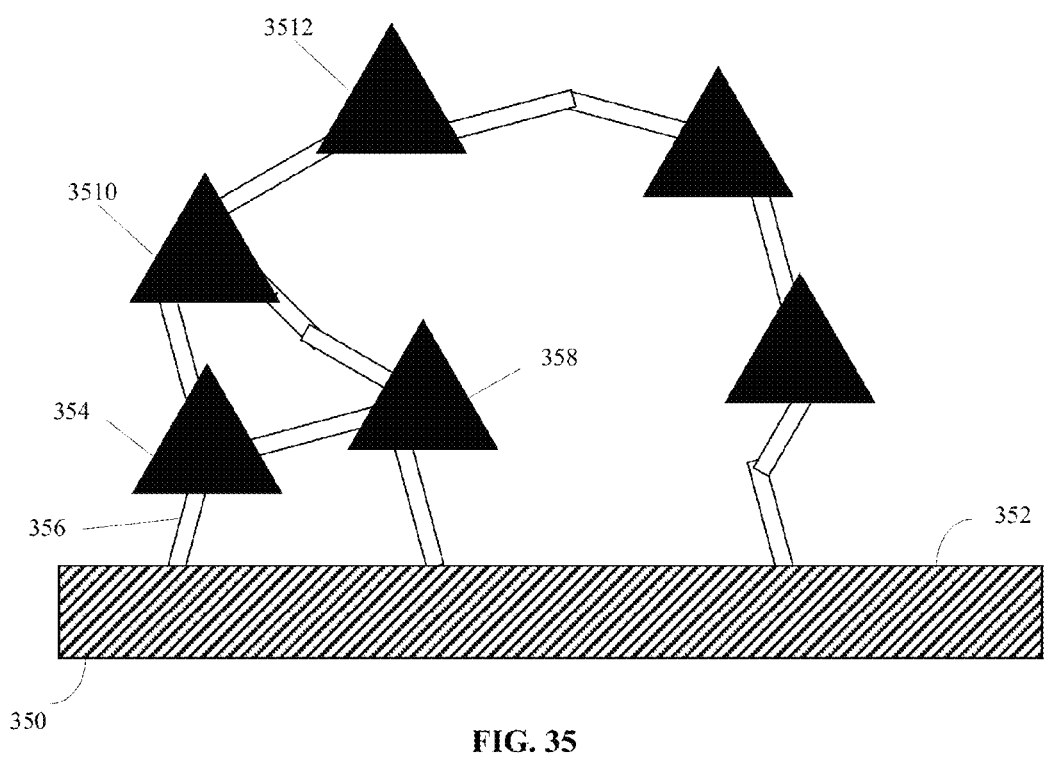
FIG. 35 is a schematic, cross-sectional diagram of molecular net formed on base.

FIG. 35 is a schematic diagram of molecular net formed on base 350, a polystyrene base having a top surface 352. The molecular net includes a single species of monoclonal antibody capture agent, a number of which are depicted. While the capture agents are identical in structure, their relationship, or linkage, to surface 352 varies. Capture agent 354 can be considered a first-order capture agent, as it is connected to surface 352 by a shortest linkage path (via linker 356) that does not include any other capture agents. Capture agent 354 is linked to surface 352 by alternative paths that do include one or more other capture agents (e.g., capture agent 358); however, the linkage having the least number of intervening capture agents is defined as the shortest linkage and defines the order of a capture agent, with respect to the surface of the base. Thus, capture agent 3510 is a second-order capture agent, as its shortest linkage includes one additional capture agent (capture agent 354 or 358). Similarly, capture agent 3512 is a third-order capture agent having a shortest linkage including two other capture agents.

Figure 36:
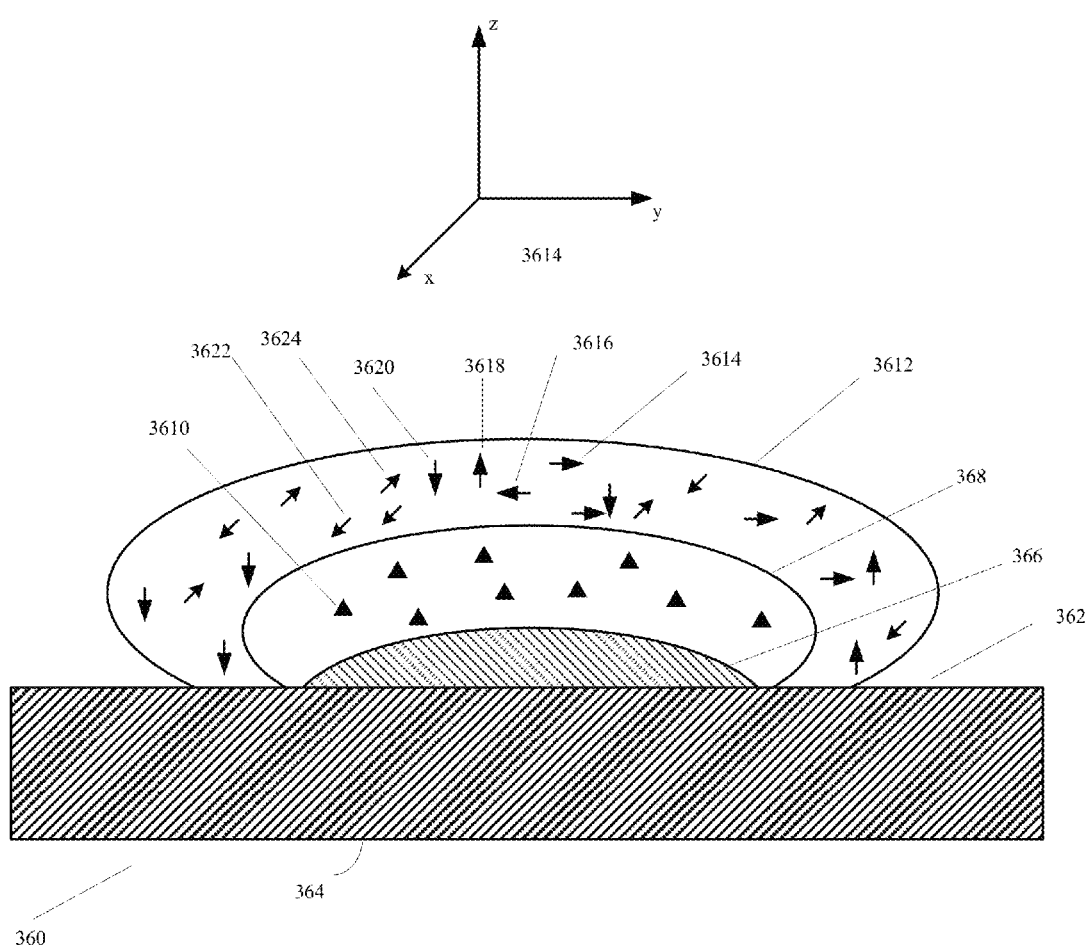
FIG. 36 is a cross-sectional diagram of molecular net formed on base having a top surface with a raised portion formed as an underlayer.

FIG. 36 depicts a schematic, cross-sectional view of a two-layered molecular net. The net is formed on base 360, which has a top surface 362. Unlike base 350 depicted in FIG. 35, base 360 of FIG. 36 includes two distinguishable regions: polystyrene region 364 and raised underlayer 366, formed from formaldehyde-crosslinked bovine serum albumin that has been allowed to set. Thus, top surface 362 is substantially flat in some portions and convex in the region above underlayer 366. In alternative embodiments (not depicted) a base having topographical features similar to top surface 362 may be affected directly in base formed of a single material, such as micro-textured polystyrene. Returning to FIG. 36, a first molecular net layer 368 is formed over 366. Layer 368 includes a plurality of nucleic acid capture agents 3610. A second molecular net layer 3612 is formed over first layer 368. Second layer 3612 includes several structurally identical monoclonal IgG antibodies, depicted as arrows. IgGs are capture agents having bilateral symmetry, in which orientation is relevant to their capture properties. As depicted, the heads of each arrow indicates the variable-region end of the IgG and the tail of each arrow depicts the constant-region end of each IgG. While not shown, the first and second layers of the molecular net are circular in shape, when viewed from above, in plan view.

Due to the pseudo-random nature of the molecular nets, Second layer 3612 includes capture agents having different orientations, which may be more easily understood with reference to three-axis Cartesian diagram 3614. For example, IgG 3612 depicts three axes: axis y having a positive direction towards the right of the figure; axis z having a positive direction towards the top of the figure; and axis x having a positive direction outwards (towards the viewer) from the plane of the figure. Thus, the cross-section viewing plane may be understood as plane y-z, with plane x-y (and plane x-z) extending outwards (towards the viewer) and inwards (away from the viewer) from the viewing plane.

With reference to Cartesian diagram 3614, IgG 3614 faces in the positive y-direction. In contrast, IgG 3616 faces in the negative y-direction, rotated 180° from IgG 3614, in any plane. IgG 3618 faces in the positive z-direction, rotated 90° counterclockwise from IgG 3614. IgG 3620 faces in the negative z-direction, rotated 90° clockwise from IgG 3614. IgG 3622 faces in the positive x-direction, outwards from the plane of view and rotated 90° from IgG 3614, in the x-y plane. IgG 3624 faces in the negative x-direction, outwards from the plane of view and also rotated 90° from IgG 3614, in the x-y plane.

Thus, it is understood that the pseudo-random of the molecular nets allows for the individual capture agents in the molecular net to be oriented in any direction.

Figure 37:
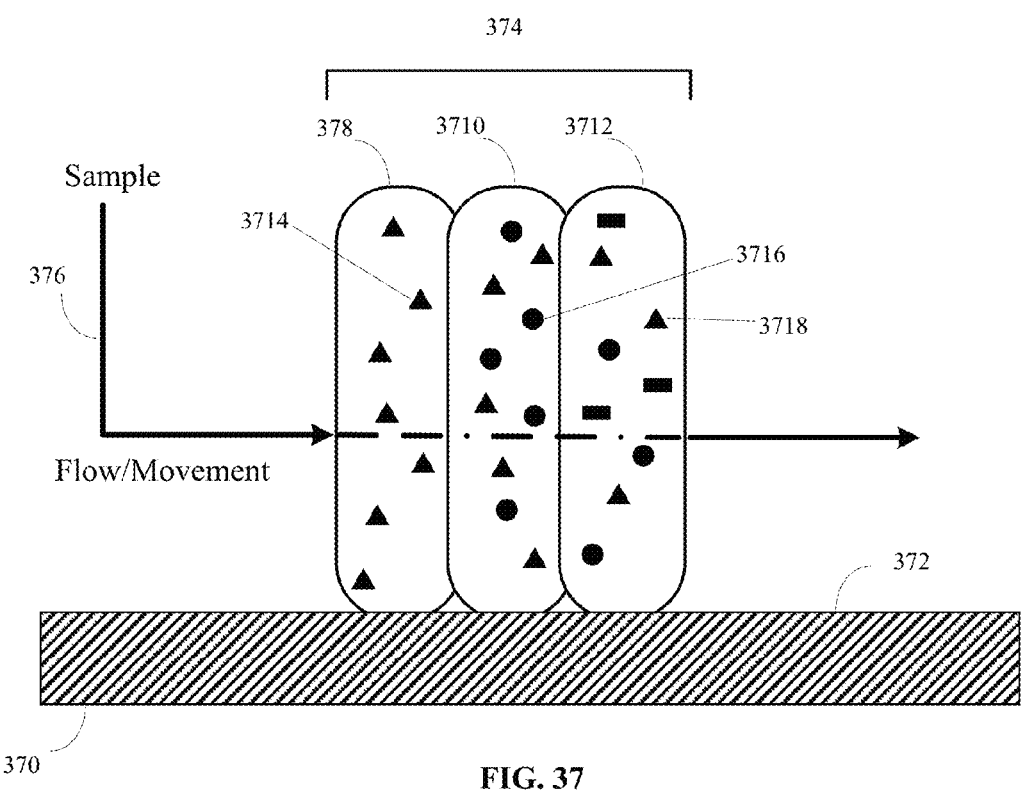
FIG. 37 is a cross-sectional diagram of molecular net formed on base in a system having substantially unidirectional flow.

FIG. 37 depicts a schematic, cross-sectional view of a three-layered molecular net 374, formed on base 370, a polystyrene base having a top surface 372. Molecular net 374 is formed in a capillary having substantially unidirectional flow of sample, as shown by arrow 376. Each of the three layers of molecular net 374 is formed to present a large surface area to flow of sample. First layer 378 includes nucleic acid capture agent 3714 specific to a first target. Second layer 3710 includes nucleic acid capture agents 3714 and also protein capture agent 3716 specific to a second target. Third layer 3712 nucleic acid capture agent 3714 and protein capture agent 3716 and also includes IgG capture agents 3718 specific to a third target. Thus, molecular net 374 allows for sequential, targeted capture of targets of interest in the direction of flow. In alternative embodiments, molecular nets similar to molecular net 374 may be used in a filtering capacity.

Figure 38A:
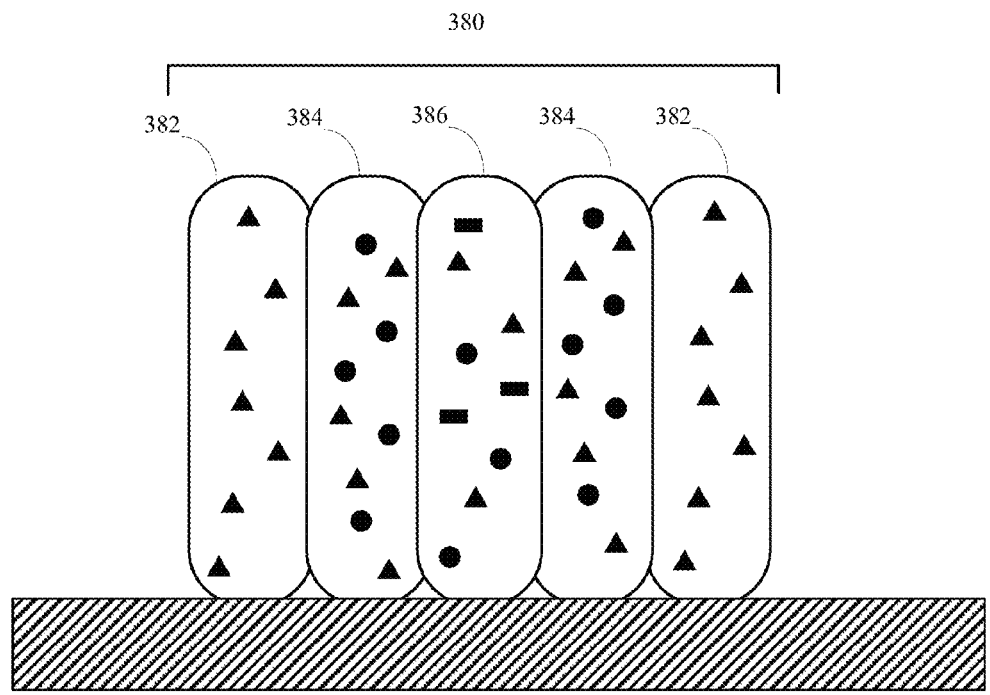
FIG. 38A is a cross-sectional diagram of molecular net formed on base in a system having multidirectional flow.

FIG. 38A depicts a five-layered molecular net 380 similar to molecular net 374 of FIG. [37]. However, the flow of sample in FIG. 38 is not unidirectional; rather, sample molecules move towards net 380 via multidirectional diffusion. Thus, molecular net 380 is formed of two an outer layer 382, an intermediate layer 384, and an inner layer 386.

Figure 38B:
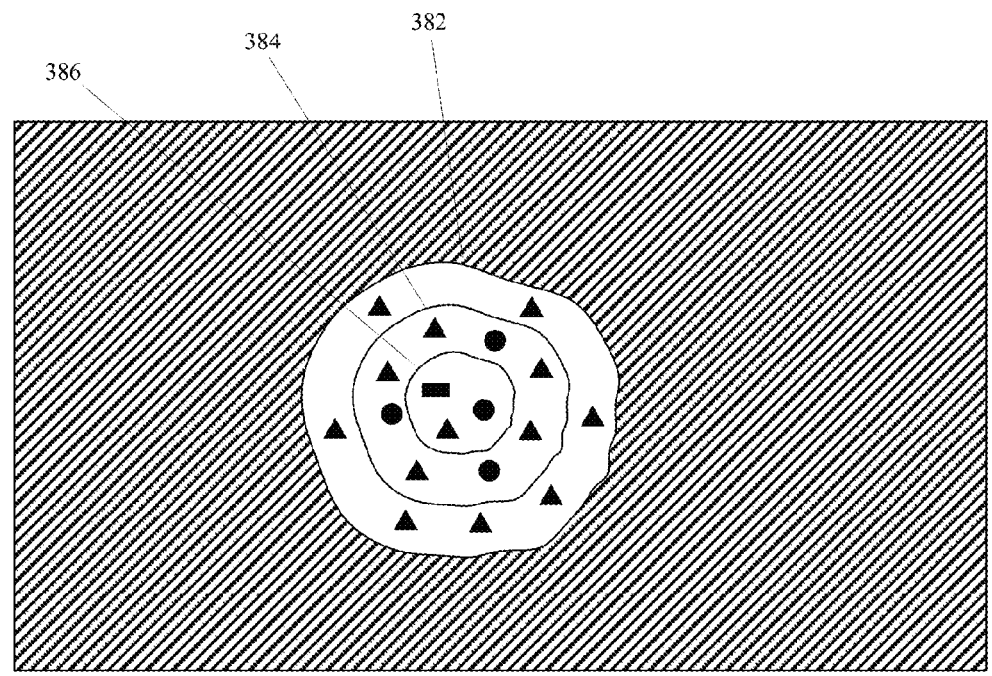
FIG. 38B is plan view of the same molecular net.

FIG. 38B is a plan view of molecular net 380. As shown, inner layer 386 is substantially circular. Intermediate layer 384 is substantially ring-shaped and disposed around inner layer 386. Finally, outer layer 382 is also ring-shaped and disposed around intermediate layer 384.

Figure 39:
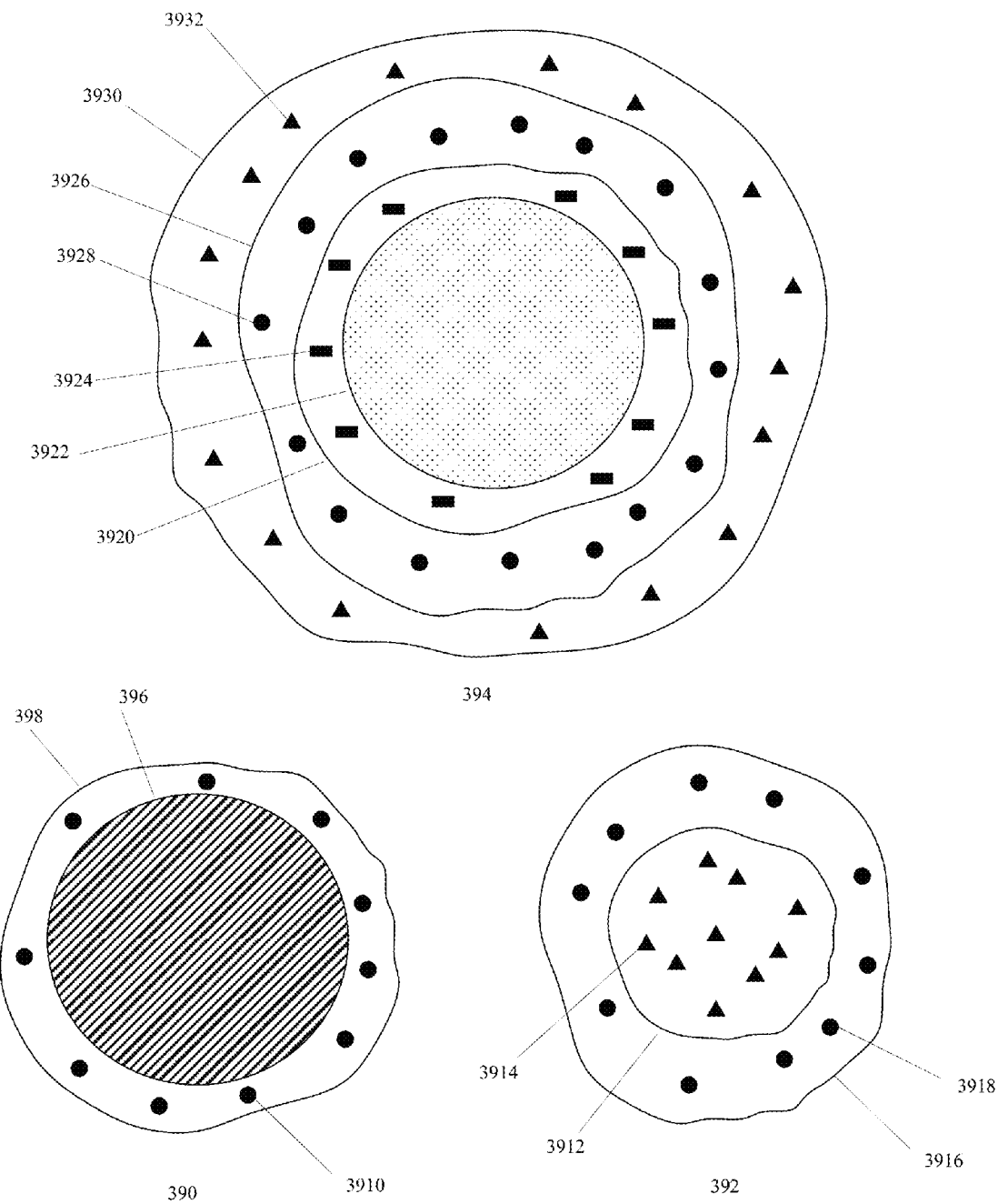
FIG. 39 is a cross-sectional diagram of three substantially spherical molecular nets.

FIG. 39 depicts three cross-sectional views of three different molecular nets, 390, 392, and 394. Each of the nets is substantially spherical in shape.

Molecular net 390 is a single-layer molecular net, formed on polystyrene bead 396. Net layer 398 includes capture agents 3910.

Molecular net 392 is a two-layer molecular net, formed without a non-net base Inner net 3912 is a self-supporting, roughly spherical molecular net having capture agents 3914 that are specific to a first target. Second molecular net layer 3916 is formed over inner net layer 3912. Second molecular net layer 3916 includes capture molecules 3918 that are specific to a second target.

Molecular net 394 is a three-layer molecular net useful for containment and/or delivery of a compound. The first net layer 3920 is formed around a bolus 3922 of a compound, such as an active pharmaceutical ingredient (API). In alternative embodiments, the API may be intermixed with one or more molecular net layers, instead of being provided as a separate bolus. First net layer 3920 includes capture agents 3924 specific to the API. First net layer 3920 serves at least several purposes: protection of API bolus 3922 from the external environment; containment of API bolus 3922; and controlled release of API bolus 3922. Second net layer 3926 includes capture agents 3928, specific to an external target. Second net layer 3926 may operate as a filter targeted to compounds in the environment that may detrimental to the API. Third net layer 3930 includes capture agents 3932, specific to an external target that is indicative of a location of interest (e.g., proteins specific to a target organ or location on an in vitro assay plate).

IV. Use of Molecular Nets

Molecular nets have use as a means to attach to specific analytes. Such molecular nets can be used to capture and immobilize specific analytes so that they can be detected by other means. Alternatively, these molecular nets have analyte-specific capture agents with properties that change upon binding to analyte.

Molecular nets having the have broad application in medical diagnostics, such as for point of care determination of the presence and nature of an infectious agent, detecting signs of cancer, inflammation and chronic diseases, determining drug susceptibility, veterinary diagnostics, and the like. In this application, a biological sample (e.g., blood, urine, saliva, stool, wound exudate, etc.) is contacted with one or more molecular nets and the presence or absence of analyte(s) is determined.

In addition to medical diagnostic applications molecular nets of the invention may be used for other types of analyte detection including for food, water and environmental testing (e.g., to detect chemical or biological contaminants), biothreat assessment, and the like. Molecular nets may also be used for affinity filtration of blood to remove drugs, autoreactive cells, cellular products, toxins, pathogens, or immune factors, and for drug screening.

Samples may be processed prior to their application to a molecular net. For example, samples may be disrupted by mechanical, enzymatic or chemical disruption. Tissues, cells, or other complexes of molecules may be processed using mechanical, enzymatic and chemical disruption to render analytes of interest bindable by the net. By "mechanical disruption" is meant a mechanized method for disrupting tissues, cells, or other complexes of molecules to release the constituent molecules, e.g. by grinding, sonication, etc. By "enzymatic activity or disruption" is meant a method for disrupting tissues, cells, or other complexes of molecules to release the constituent molecules using enzymes. By "exposure to chemicals or chemical disruption" is meant a method of disrupting tissues, cells, or other complexes of molecules to release the constituent molecules by chemicals such as oxidants, reducing agents, detergents, salts, heat, enzymes, phenol/chloroform, nucleophiles and other agents. Sample preparations may be processed by filtration and centrifugation and the like. In some embodiments, sample preparation is carried out in a device containing a molecular net(s).

In some embodiments a sample is disrupted by a molecular net, such as the top most net in a layered molecular net or the first net in a device containing a series of molecular nets. For example the net can be a wash net and can contain a combination of detergents; solvents; acids; bases; surfactants; salts; reducing agents, oxidizing agents and other molecules; and can be used to wash samples; whereby said wash net can lyse; bind; degrade; weaken the structural integrity of: mammalian cells, protozoa, bacteria, fungi, plants, viruses and products thereof; and whereby said wash net can release soluble proteins, peptides and other organic molecules from larger molecular complexes within food, fluids, tissues or environmental samples.

For diagnostic purposes the basic molecular net is one that binds analytes (e.g., "analyte binding nets"). However, "auxiliary nets" with other functions may also be used, for example, for sample processing. The auxiliary nets may be configured as one or more layers in a multilayer net. Alternatively, auxiliary nets may be used in series in a circuit of multiple nets (some or all of which may be multilayer nets). For example and not limitation, a biological sample might pass though a lysis net to lyse cells, a size exclusion net to remove unlysed cells or debris, and then a multilayer analyte binding net in which analytes are bound and detected. Examples of auxiliary nets are lysis nets, wash nets, size exclusion nets, and enzymatic nets.

A "lysis net" is a molecular net containing molecules capable of lysing mammalian and microbial cells, such as lysozyme, detergent, chelators, performs, membrane-attack complex, salts, and other molecules capable of cytolysis.

A "wash net" is a molecular net containing a buffering agent and/or a mixture of salts, pH, detergents, chelators, metals, proteins, polynucleotides, carbohydrates and/or lipids that may be located in a device. It may also be used to bind or immobilize sample molecules non-specifically and can be used to remove or lyse cells in a sample.

A "size-exclusion net" is a molecular net containing molecules that are arranged in a way to generate irregular pore sizes between molecules. The pore sizes are generated in part by the length and nature of the reactive arms of the chemical crosslinkers and the surface chemistry on the neighboring molecules. The physical shape and size of the neighboring molecules also contribute to the pore sizes.

A "enzymatic net" is a molecular net containing one or more types of enzyme that can have one or more substrate specificity. The enzymatic net can also contain essential cofactors for the enzymes. The purpose of the enzymatic net is to interact with specific substrate in the sample and to generate the respective product that can be detected when immobilized on a subsequent net such as a positive selection net.

Negative selection nets and positive selection nets are types of analyte binding nets. A "negative selection net" is a molecular net containing a mixture of salts, detergents, chelators, metals, proteins, polynucleotides, carbohydrates and/or lipids, drugs, antibiotics, and other molecules that may be located in a device. It may also be used to bind or immobilize sample molecules based on the absence of specific surface chemistries or affinities or properties and can be used to immobilize subsets of cells in a sample. A "positive selection net" is a molecular net containing capture molecules that specifically immobilize specific analytes in a sample. Said net can be located in a device. It can also be used to bind or immobilize sample molecules based on the presence of specific surface chemistries or affinities or properties and can be used to specifically immobilize subsets of cells in a sample.

Any number of formats may be used for contacting the sample and molecular net(s) as well as for washing and detection steps. In one embodiment, nets are fabricated in wells of a microtiter plate and conventional manual or robotic fluid transfers are used to conduct the assay. In another embodiment, a dipstick format is used in which the net(s) is attached to a substrate which is contacted with sample and detection reagents. Other formats include, without limitation, chips, cartridges, cards, cubes, discs, adaptors, and plates.

After analytes are bound in a molecular net a wash step is sometimes included to improve specificity, sensitivity and/or signal. A buffer system that may be used in sample preparation or in washing steps in a device. Hydrophobic sites at a surface commonly give rise to an increase in non-specific binding because physisorption of proteins to surfaces is mediated by hydrophobic interactions. Additionally, an excess of charged groups also generally increases the probability of non-specific binding. For example, some proteins possess a net positive charge at neutral pH and will tend to associate with negatively charged surfaces. In some embodiments, buffer systems that may contain high salt and detergent concentrations may decrease non-specific binding on important detection surfaces in a device. Buffers may be applied to enhance or quench; one or more detectable signal. For example and not limitation, buffers can contain hydrogen peroxide; bleach; oxidizing agents; chelators; aptamers; organic molecules; substrates; and inorganic molecules.

Molecular Nets for Capture of Nucleic Acid

In some embodiments, the capture agents are cationic peptides which bind nucleic acid. The cationic peptides may include poly-Arginine, poly-Lysine, or a combination of both residues linked together by primary amine-reactive crosslinkers such as $BS^3$ and BS-(PEG)9. Without wishing to be bound by theory, it is believed that cationic peptides non-specifically bind the poly-phosphate backbone of nucleic acids such as dsDNA, ssDNA, ssRNA, dsRNA, and any other nucleic acids, natural or artificial, having a negatively charged backbone. In other embodiments, the capture agents are antibodies against nucleic acid binding proteins, such as histones and DNA/RNA polymerases. In some embodiments, the capture agent is specific for nucleic from certain sources. For example, a capture agent that has high affinity for eukaryotic promoters, histones, single-stranded binding proteins, and transcription factors, will bind with increased affinity to human and other eukaryotic nucleic acid.

Molecular nets of this type can be manufactured according to any of the previously described methods. An exemplary method of manufacture is to combine a heterogenous mixture of antibodies and cationic peptides (of 9-40 amino acids) into amine-free buffer, add stock concentrations of cross-linkers directly into the peptide mixtures, cure, and repeat as needed to construct additional layers.

Molecular nets which bind nucleic acids can be used for isolation of nucleic acids from a sample. Advantageously, methods which use molecular nets can isolate nucleic acid in the presence of other non-nucleic acid species such as protein.

The molecular nets having the nucleic acid binding peptides or antibodies as capture agents can be designed to avoid interference of non-nucleic acid species. For example, interference of non-nucleic acid species with binding can be reduced by adjusting the length of linkers to limit the pore or pocket size within and throughout the net. The size dimensions of a nucleic acid-binding net can be the angstrom length of linker plus angstrom length of the nucleic acid binding peptides or antibodies against nucleic acid binding. The size dimensions of a different species of molecular net can be the angstrom length of linker and the angstrom length of a nucleic acid binding peptide. For example, the pore/pocket size can exclude larger molecules such a globular proteins. Interference of non-nucleic acid species can also be reduced by constructing a molecular net with an overall positive charge, which repels hydrophobic molecules and molecules having an overall positive charge due to repulsive forces.

In some embodiments a molecular net having a nucleic acid binding peptide or antibody also has capture agents for proteins which associate tightly with nucleic acid, thus increasing capture of nucleic acids.

Nucleic acid molecular nets can be used in devices which amplify nucleic acid, for example devices which perform isothermal PCR or RT-PCR. In such molecular nets, the capture agents may be nucleic acid binding polypeptides.

Molecular Nets as Cages

In another aspect, molecular nets have use as physical structure to encapsulate agents regardless of their specific properties. Exemplary agents include therapeutic molecules and cells. The composition of the layers can be adjusted to provide the best protection from the environment in which is the employed. Alternatively, the net can include degradable components such that the agent can be released from the net.

These molecular nets can include components which have affinity for certain types of surface chemistries and thus serve to both encapsulate and localize agents. Further, the properties of degradable molecular nets can be adjusted by using linkers of different distance, thermal instability, or chemical instability.

V. Examples of Diagnostic (Analyte Binding) Molecular Nets

A. Bacterial Net

In one embodiment, a test can contain a plurality of molecular nets, wherein one molecular net can be a bacterial net and can contain capture components that can specifically bind: host response molecules that are specifically induced in response to a bacterial infection, bacterial DNA, flagella, pili, fimbrae, capsules, S-layers, peptidoglycan, bacteria-specific polymerases, bacteria-specific heat-shock proteins, mannose and other surface polysaccharides, bacterial ribosomal subunits, and other bacteria-specific molecules.

A bacterial net can contain capture components specific for Gram-positive bacteria and their products, such as lipoteichoic acid, bacteriocins, Gram-positive specific peptidoglycan-binding proteins, and other indications of a Gram-positive bacterial infection. A bacterial net can contain capture components specific for Gram-negative bacteria and their products, such as lipopolysaccharide, lipid A, outer membrane pumps, outer membrane binding proteins specific for Gram-negative bacteria, and other indications of a Gram-negative bacterial infection. A test can also contain a viral net, wherein capture components can specifically bind: viral nucleic acids, capsid proteins, spike proteins, hemagglutinin, neuraminidase, viral polymerases, reverse transcriptases, viral products, host molecules that are specifically induced in response to a viral infection, and anti-viral cytokines such as interferon-alpha and interferon-beta. A test can also contain a fungal net, wherein capture components can specifically bind: host response molecules that are specifically induced in response to a bacterial infection, chitin, aflatoxin, fungal glycoproteins, fungal polysaccharides, diacylated ureas, and other fungi-specific molecules. A test can also contain a protozoan net, wherein capture components can specifically bind host response molecules that are specifically induced in response to a protozoan infection, protozoa-specific carbohydrate structures, protozoa-specific glycoproteins, protozoa-specific DNA sequences, and other protozoa-specific molecules.

In another embodiment, a test can contain Gram-negative, Gram-positive, and bacterial nets in a stacked or layered arrangement. Analyte detection molecules can be labeled with different detection labels; and whereby analyte binding to more than one molecular net can produce enhanced signal, mixed signals, multiple signals, and different signals. An example of such positive test outcomes can be the presence of blue signal to indicate a sample positive for bacteria, in combination with the presence of a red signal to indicate a sample positive for Gram-positive bacteria, whereby the combination of red and blue signal produces a purple signal. Another example of such positive test outcomes can be the presence of blue signal to indicate a sample positive for bacteria, in combination with the presence of a yellow signal to indicate a sample positive for Gram-negative bacteria, whereby the combination of blue and yellow signal produces a green signal.

B. Total Tumor Necrosis Factor Net

In one preferred embodiment, a test can contain a molecular net that can measure total tumor necrosis factor (TNF) in a sample. Said TNF net can contain capture components that can capture and immobilize: soluble TNF ligand; soluble TNF receptors I and II; soluble TNF receptor fragments that can bind TNF ligand, such as TNF-BP-I, TNF-BP-2, and other TNF-BPs; anti-TNF antibodies; TNF:anti-TNF antibody complexes; TNFR:anti-TNFR antibody complexes; TNF:TNFR:anti-TNFR antibody immune complexes; TNF:TNF-BP1:anti-TNF antibody complexes; TNF:TNF-BP-2:anti-TNF antibody complexes; TNF:TNFBP-1:anti-TNF-BP antibody complexes; TNF:TNF-BP-2:anti-TNF-BP antibody complexes; and other TNF-bound complexes in a sample. Said TNF test can contain one or more TNF net whereby said TNF net can be composed of capture components such as but not limited to: anti-TNF antibodies; anti-TNFR antibodies; anti-TNF-BP-1 antibodies; anti-BP-2 antibodies; TNFR-I; TNFR-II; heparin; and other TNF-binding molecules. Said TNF test can contain wash buffers to remove non-bound sample molecules. Said TNF test can contain analyte detection molecules that can be labeled with one or more indicator molecule. Wherein the binding of said analyte detection molecules to bound analyte following wash steps can be considered a positive test.

C. Antibiotic Resistance Test

In another embodiment, a test can be an antibiotic resistance test and can contain one of the aforementioned microbial nets that can capture and immobilize whole organism in a living state; and whereby said test can employ differentially labeled analyte detection molecules to identify resistance; or targets of resistance; or methods conferring resistance.

In one embodiment, a test can be an antibiotic resistance indicator test using an extracellular matrix net to capture and immobilize whole bacteria in a living state, and whereby said test can employ differently-labeled detection molecules; whereby said detection molecules are labeled antibiotics; whereby each class of antibiotic is labeled with a different indicator; whereby said living bacteria is incubated in the presence of a heterogeneous population of labeled detection molecules; whereby a wash is applied; whereby bound detection molecule(s) can indicate antibiotic-susceptibility.

D. Extracellular Matrix Net

In another preferred embodiment, a test can contain one or more extracellular matrix nets, whereby said extracellular matrix net can be used to capture and immobilize bacteria or any other microbe or any mammalian cell. Said capture components can specifically bind one or more surface glycoprotein, polysaccharide, mannose, protein, lipid, glycolipid, lipoprotein or other surface molecule. Said test can be used to bind living cells; and whereby said test can employ specific analyte detection molecules; and whereby said taste can be used to analyze the characteristics, dynamics, properties and response of said bound cells.

E. Infection Surveillance Indicator Test

In another embodiment, a test can be an infection surveillance indicator test using bacterial, viral, fungal and protozoan molecular nets, or a combination thereof, to identify one or more host-specific indication of an infection and one or more microbe-specific indication of an infection.

F. MRSA Net

In one embodiment, molecular nets are used in tests which detect MRSA.

The captured MRSA analytes can be detected using antibodies directed against epitopes on MRSA protein Pbp2a and nucleic acid probes directed again the MRSA SCCmec region. The antibodies and nucleic acid probes can be conjugated to FITC.

Other markers that are part of MRSA's protein signature include those listed in the following table, along with potential vendors for antibody capture agents directed to such markers.

| MRSA Protein Marker | Antibody Vendors |
| --- | --- |
| Pbp2a | AbCam, AbD Serotec, GenWay Biotech |
| MecR | Covance, Pierce, Genscript |
| VraRS | Covance, Pierce, Genscript |
| PhoU | Covance, Pierce, Genscript |
| PstS | Covance, Pierce, Genscript |
| PstC | Covance, Pierce, Genscript |
| PstA | Covance, Pierce, Genscript |
| PstB | Covance, Pierce, Genscript |
| PVL (LukF and LukS) | Covance, Pierce, Genscript |

-continued

| MRSA Protein Marker | Antibody Vendors |
| --- | --- |
| alpha-toxin | AbCam, GenWay Biotech |
| Phenol-soluble modulin alpha | Covance, Pierce, Genscript |

Other markers that are part of MRSA's nucleic acid signature include those listed in the following table, along with potential vendors for probe capture agents directed to such markers.

| MRSA Nucleic Acid Marker | Probe Vendors |
| --- | --- |
| agr Group I and Group III | IDT |
| mecA | IDT |
| mecR | IDT |
| fmtA | IDT |
| sarA | IDT |
| tcaA | IDT |
| msrR | IDT |
| vraRS | IDT |
| SCCmec | IDT |

G. Sepsis Net

In another embodiment, molecular nets are used in tests which determine sepsis etiology. For example, such a test may identify the sepsis as bacterial gram-positive, bacterial gram-negative, viral, or fungal.

F. Allergen Identification

The molecular nets described herein can be used for simultaneous immobilization, and subsequent detection if desired, of allergen-specific immune cells and allergen-specific immune cell products. The allergen of interest can be of a biologic or non-biologic origin. The allergen may be an antigenic fragment, or region of, or an entire allergen. In certain embodiments, the analytes are allergens, IgE, mast cells, allergen-specific immune cells and/or allergen-specific immune products in a biologic, food or environmental sample.

In another preferred embodiment, a test can be used to identify allergens in a food or environmental sample whereby said test contains one or more molecular nets to capture and immobilize whole or processed allergens; whereby test can produce one or more signals in one or more test area; and whereby said testing area contains one or more molecular net and can be dense in volume; and whereby the dense nature of the molecular net-analyte-detection molecular complex can produce an intensified positive signal; and can produce a faster signal per unit volume.

The capture molecules may be one or a combination of antibodies against human IgE, or an antigenic fragment, a region of an allergen, an entire allergen, or an allergen complex. In some embodiments, the capture agents are multiple antibodies against the constant region of human IgE that form a molecular net with affinity for one or a combination of allergens. In other embodiments, the capture agents are multiples of the same or multiples of different but related antigenic fragments, allergens, allergen complexes, or allergenic organisms that form a molecular net with affinity to one or a combination of IgEs, mast cells, allergen-specific T cells, or allergen-specific B cells in a sample.

Preferred embodiments of the capture agents for certain analytes are provided in the below Table:

TABLE 6

| CAPTURE AGENT | ANALYTE | APPLICATION |
|---|---|---|
| Allergenic fragment | IgE, T cell, B cell, Mast cell | Allergy/hypersensitivity testing |
| Allergenic peptide | IgE, T cell, B cell, Mast cell | Allergy/hypersensitivity testing |
| Allergen, whole | IgE, T cell, B cell, Mast cell | Allergy/hypersensitivity testing |
| Allergen complex | IgE, T cell, B cell, Mast cell | Allergy/hypersensitivity testing |
| Antibodies against histamine | Histamine | Allergy/hypersensitivity testing |
| Histamine binding domain of histamine receptor | Histamine | Allergy/hypersensitivity testing |
| Antibodies against one or more allergenic fragment | Allergen (fragment, whole and complexed forms) | Food and environmental testing |
| Antibodies against one or more allergenic peptide | Allergen (fragment, whole and complexed forms) | Food and environmental testing |
| Antibodies against one or more allergen | Allergen (fragment, whole and complexed forms) | Food and environmental testing |
| Antibodies against one or more allergen | Allergen (fragment, whole and complexed forms) | Food and environmental testing |

In a certain embodiments, the molecular nets described herein have the composition described in the below table:

TABLE 7

| NET LAYER | CAPTURE AGENT | EXAMPLE OF ONE OR MORE CAPTURE AGENTS | EXAMPLE OF ONE OR MORE ANALYTES |
|---|---|---|---|
| Under-layers | Antibodies against epitopes on one or multiple allergens (related) | Antibodies against soy protein Antibodies against soybeans | Fragments of soy protein Fragments of proteins from soybeans or plant source |
| Upper-layers | Antibodies against epitopes on one or multiple allergens (related) | Antibodies against soy protein Antibodies against soybeans | Fragments and whole soy protein Fragments and whole proteins from soybeans or plant source |
| Outer-layer | Antibodies against epitopes on one or multiple allergens (related) | Antibodies against soy protein Antibodies against soybeans | Fragments, whole protein and complexes of soy proteins Fragments, whole protein and complexes of proteins from soybeans or plant source |

In certain embodiments, the allergens that are immobilized and detected by molecular nets include the following:
Animal products including, but not limited to,
    Fel d 1 (cat allergy)
    fur and dander
    cockroach calyx
    wool
    dust mite excretion
Drugs including, but not limited to,
    penicillin
    sulfonamides
    salicylates (also found naturally in numerous fruits)
    local anaesthetics
Foods including, but not limited to,
    celery and celeriac[24]
    corn or maize
    eggs (typically albumen, the white)
    fruit including, but not limited to,
        pumpkin
    legumes including, but not limited to,
        beans
        peas
        peanuts
        soybeans
    milk
    seafood
    sesame
    soy
    tree nuts including, but not limited to,
        pecans
        almonds
    wheat
Insect stings including, but not limited to,
    bee sting venom
    wasp sting venom
    mosquito stings
Mold spores
Other
    latex
    metal
Plant pollens (hay fever) including, but not limited to,
    grass including, but not limited to, ryegrass, timothy-grass
    weeds including, but not limited to, ragweed, plantago, nettle, artemisia vulgaris, chenopodium album, sorrel
    trees including, but not limited to, birch, alder, hazel, hornbeam, aesculus, willow, poplar, platanus, tilia, olea, Ashe juniper In other embodiments, these allergens can instead be used in molecular nets as capture agents for immune cells and immune cell products.

In certain embodiments, molecular nets can be used in a dipstick device to assess the presence of allergens in the environment and an individual's immune response. For example, the device may be a lateral chromatography device where an environmental sample is applied to a first region containing a molecular net to immobolize allergens from the sample, and then a blood sample is applied upstream of the environmental sample. The blood sample comes in contact with the immobilized allergen, and then moves downstream to a region containing molecular net which immobilizes histamine, activated immune cells, and immune cell products. This multi-pronged approach allows simultaneous testing for: (i) antibodies and immune cell in a blood sample that react to an environmental sample and (ii) the presence of allergens in an environmental sample.

VI. Devices Containing Molecular Nets

The invention provides an analytical device for determining the presence or amount of one or more analyte in a sample using molecular nets. The device can comprise an array of internal structures, chambers and channels; whereby one or more of said structures can have a surface supporting and/or immobilizing one or more molecular net that can be covalently or non-covalently attached; or fitted; to a surface, which may be made from an organic polymer such as polystyrene or polyethylene; metal; nitrocellulose; polyvinylidene fluoride; fibrous material; glass or other materials, and whereby the immobilized molecular net can be capable of binding more than one different kind of analyte in a sample. Molecular nets can be formed; placed; adsorbed; adhered; glued; crosslinked; and/or fitted onto a surface. Surfaces may be, without limitation, porous non-porous; corona etched and/or molded and may have more than one surface chemistries. Surfaces may be planar, beads, or other. Exemplary beads include agarose beads, polymeric beads, glass beads, metallic beads or fibrous beads. Molecular nets may be used to coat beads in Luminex or similar immunoassays.

The device can also comprise a plurality of molecular nets in one or more arrangement; in one or more testing area of a device, or whereby individual molecular nets can be separated into separate testing areas, wherein all testing areas can be exposed to said test sample or a separated, semi-purified, or fractionated test sample to enable one or more analyte to be immobilized by multiple capture molecules in one or more molecular net in one or more testing area of said device.

Disclosed is a device containing one or more molecular net, or molecular net walls, containing interspersed capture molecules and modified metal nanoparticles; whereby analyte binding can alter the physical, magnetic, electrical, chemical, vibrational, compressive, colorimetric, thermal, and spatial properties of said molecular nets or molecular net walls; whereby said altered properties can be a signal and can be detected by sensors to produce information in a binary or analytical test of said device.

The device may contain entry ports; channels; partitions; buffer storage chambers; sample processing chambers; sample detection chambers; waste containment chambers; efflux ports; and other compartments. Compartments may contain reagents required for an assay, such as buffers, washes, nucleic acid primers, enzymes, chemicals, substrates, catalysts and other molecules needed for sample processing and/or analyte amplification; nucleic acid probes, antibodies, polypeptides, enzymes and other labeled analyte detection molecules; substrates, chemical catalysts, co-factors, and other molecules in signal-producing reactions; amplifiers, lenses, filters, and other agents involved in signal amplification; and photodetectors, semiconductors, and other agents in signal detection.

Luminal polymeric surfaces of channels may be coated with one or more than one of the following: integrins; poly-arginine peptides; amino acids with an overall positive charge in neutral, acidic and basic solutions; polycationic lipids; recombinant receptors; metals; metal oxides; single-stranded DNA binding proteins; ethylene diamine tetraacidic acid; ethylene glycol tetraacetic acid; collectins; antibodies; protein A; protein G; recombinant ligands; pattern-recognition receptors (PRR); domains from PRRs; domains of proteins containing pathogen-associated molecular patterns (PAMPS); lyophilized or gel detergents such as tween-20, tween-80, CHAPS, octylthioglucosides, tritonX-100, and/or NP40; sodium dodecyl sulfate; salmon sperm DNA; lipopolysaccharide binding proteins (LBP); and any other molecules that preferentially covalently or non-covalently bind components in a raw or semi-purified sample. Internal binding surfaces of the device may be washed by pressure changes; mechanical shearing; vibration; fluid waves; sound waves; gas microbubbles; pH gradients; detergents; salinity changes; viscosity changes; temperature changes; and flow-rate changes; and may remove non-specific binding of molecules in one or more chambers.

The device may be adapted for a method of detecting multiple different analytes in a sample by pulling sample into testing volume of a device that can contain molecular nets and/or molecular net pieces arranged in a landscape that confers microfluidic and/or nanofluidic properties to the sample as it passes through the device; and/or by dropping molecular nets and/or pieces of molecular nets into a contained sample; whereby said molecular nets and pieces thereof may contain microchannels and nanochannels and surface chemistries that can confer microfluidics and/or nanofluidics within and surrounding the molecular net (and pieces thereof); digital microfluidics; and/or using continuous-flow and/or non-continuous-flow microfluidics; and/or nanofluidics to move sample through a testing volume containing molecular nets arranged in a landscape that confers microfluidics and/or nanofluidics.

In this manner multiple different analytes are detected in a sample in a manner that can produce one or a combination of multiple different signals in one or more zone of molecular net; and/or in one or more zone of molecular net pieces; and/or in one or more location within a device.

Molecular nets may be used in an environmental filtration unit, whereby molecular nets are used to remove specific analytes from a sample; whereby molecular nets can be introduced into a liquid environment; or whereby molecular nets can be placed in pipes and/or tubing and/or hosing and liquid sample can be moved through the pipes and/or tubing and/or hosing to immobilize analytes from said sample.

Molecular nets may be used as molecular walls, whereby sample analyte can bind one or multiple molecular walls simultaneously; and whereby the binding of analyte can be detected; analyzed; and/or quantified; by the change in molecular net properties within a defined volume of the detection chamber of a device. Sample analyte immobilization can be detected and/or quantified by, for example, the absolute value and/or change in: physical resistance; shape; light scattering properties; chemical properties; physical compressive forces; electrical potential; vibrational frequency; magnetism; thermal absorbance; conductance; and other physical and electrochemical properties that the analytes confer to the molecular net upon immobilization.

Molecular nets may be used as molecular sponges for the purpose of absorbing and immobilizing analytes and removing them from sample; whereby molecular nets can be deposited in a sample and whereby capture components can bind and/or interact with said analytes and whereby said analytes can be removed from sample when and if molecular nets are removed from sample; and/or whereby the moving of unbound sample beyond molecular nets can separate; filter; and/or fractionate; the sample.

Molecular nets used for the purpose of biologic sample filtration may be packed into a column, cartridge, pipe, tubing, hose, and other device; whereby molecular nets contain capture components that can bind analytes that are cells and analytes that are cell products of specific reactivity through affinity-based interactions; and whereby non-analytes and fluid can pass through said molecular nets and can be returned to the biologic source.

The devices may have molecular nets that contain capture components that can bind growth factor receptors and other tumor cell markers on the surface of tumor cells; and whereby said molecular nets can immobilize said tumor cells within the column; cartridge; tubing; and other device; and whereby non-tumor cells can pass through said device.

The devices may have molecular nets that contain capture components that can bind and immobilize T cell receptors, B cell receptors, major histocompatibility complexes, and other antigen recognition cell surface markers on the surface of cells; and whereby said molecular nets can bind and immobilize specific cell products; and whereby said molecular nets can immobilize immune cells and/or immune cell products within the column; cartridge; tubing; and other device; and whereby un-immobilized cells and cell products and fluid can pass through said device; and whereby said un-immobilized agents can be returned to the biologic source.

The devices may have molecular nets that contain capture components that can bind heavy metal, cholesterol, triglycerides, low density lipoprotein, high density lipoprotein, cytokines, insulin, hormones, drugs and other molecules that can be abnormally elevated in mammals.

The devices may have molecular nets that contain capture components that can be organic and inorganic molecules and/or living microbial cells that can bind and/or absorb and/or store chemicals such as petroleum, heavy metals, petro-chemicals, gasoline, herbicides, pesticides, and other environmental contaminants.

Molecular nets may be contained within a vacutainer device, whereby the negative pressure of the vacutainer pulls sample into testing volume containing one or more molecular net; and wherein sample analytes can be immobilized by said molecular net; and wherein immobilized analytes can be detected within vacutainer device; or wherein molecular nets with bound analytes can be removed from the vacutainer device and can be placed in a second device for analyte detection.

The device, in some embodiments, is made of a combination of chemically sensitive molecules and/or polymers which may be applied in layers over a molding to form an ordered system of channels and chambers, capable of simultaneously detecting many different kinds of analytes in biological or environmental samples rapidly. An aspect of the device is that the ordered system of channels and chambers may be formed using a microfabrication process, thus minimizing sample size and allowing the device to be manufactured in an inexpensive manner.

In another embodiment, a multilayer net is immobilized in a device and sample flows sequentially thought the layers of the net. Alternatively, a device may comprise multiple molecular nets and is configured so that a sample flows through several nets. In either case, samples may flow by capillary action or by active pumping. Other transport methods (e.g., electophoresis) are also possible, but methods requiring specialized equipment are less convenient in several respects.

Preferably the device is a self-contained handheld device. Typically the device contains a port or compartment for introduction of the biological sample, as well as compartments containing detection reagents and any other reagents necessary for the assay. Other reagents may include buffers and sample processing agents (e.g., cell lysis solution). In embodiments in which detection systems generate a signal that cannot be analyzed visually (e.g., other than a colorimetric system) the device may include elements for detecting signal, or may be coupled to an instrument for detection of signal. In some embodiments the sample may be processed prior to coming in contact with the net(s), for example to lyse cells, remove cells or concentrate samples.

Accordingly, disclosed is an analytical device for determining the presence or amount of an analyte in a test sample. The device can comprise an array of structures, where one or more of said structures have a surface providing an molecular net covalently or non-covalently attached or fitted to a polymeric surface. The immobilized molecular net is capable of binding more than one analyte in a sample.

The device can also comprise a plurality of molecular nets separated into chambers wherein all are exposed to said test sample or a sub-fractionated population of the test sample to enable one or more analyte to be immobilized by interacting with capture molecules of each molecular net.

The device can comprise an array of structures, where each structure has a surface providing an immobilized molecular net covalently or non-covalently attached to said structure, and capable of specifically binding an analyte; a plurality of molecular nets separated on the device surface within separate chambers wherein said test sample containing one or more analyte, passes through the network of channels and passes through one or more filter, sieve or molecular net whereby the test sample is progressively fractionated and flows into one or more than one chamber, each chamber containing one or more molecular net composed of different capture components; a buffer system to reduce or inhibit non-specific interaction between fractionated sample agents and the molecular net, a labeled reagent comprising a specific binding member conjugated to a detectable label, where said detectable label is capable of producing a signal when immobilized by binding analyte which is immobilized on a molecular net to indicate the presence or amount of said analyte in a test sample.

The device may contain one or more detection chambers, said chamber contains one or more molecular net immobilized by friction, suspension or attachment to a surface of the chamber, wherein said molecular net is capable of binding at least one kind of analyte population from a fractionated sample by injecting said sample into the device; injection of a washing buffer into the device to remove non-specific binding of sample to the molecular net; injection of a detection solution whereby detection agents specifically bind immobilized analyte; and injection of a washing buffer into the device to remove of unbound detection agents.

The devices may generate differential diagnostic signals for both individual analytes and mixtures of analytes. The devices may separate desired analytes from undesired analytes. The devices may separate analytes differently in separate regions within the device such that in one region analytes A and B are selected for and in another region of the device, analytes A and B are selected against, thereby selecting for analytes C, D, E and F. The device, in some embodiments, is made of a combination of chemically sensitive molecules and/or polymers which may be applied in layers over a molding to form an ordered system of channels and chambers, capable of simultaneously detecting many different kinds of analytes in biological or environmental samples rapidly. An aspect of the device is that the ordered system of channels and chambers may be formed using a microfabrication process, thus minimizing sample size and allowing the device to be manufactured in an inexpensive manner.

In one example of a device, a main channel may be contiguous with the sample port and may lead to a branch point or node where multiple subsequent channels may be present. Each subsequent channel may contain a filter and/or a sieve and lead to a chamber wherein said chamber may contain a selection features in the form of filters and/or sieves and/or molecular nets supported by and fastened to chamber features. The chamber may be connected to an additional channel and may lead to a second chamber containing a different molecular net supported by and fastened to chamber features. A channel may lead from the second chamber to a waste efflux port.

In another example of a device may contain a sample inlet port connected to a continuous channel with a series of different filters of increasingly smaller pore sizes to select for sub-cellular molecules or viruses and may lead to a node of channels leading to one or more chambers. Each chamber may contain one or more molecular net and may be connected by another channel to a waste efflux port.

In another example, a device may contain a sample inlet port connected to an alternating series of channels and chambers. Each channel may consist of an increasing gradient of selection molecules attached to the luminal surface of the channel and may bind specific sample components through interacting surface chemistries. Said channels may be connected to a node that may be connected to chambers that may contain a molecular net composed of capture molecules that may bind molecules in a sample that have similar surface chemistry as the analytes of interest but may preferentially bind to the net whereas the analytes of interest pass uninhibited into the attached channel that may lead to the final chamber or may lead to a sample access port.

In another embodiment, a device may contain a sample inlet port and may contain a wicking agent that is contiguous with a channel. The channel may contain a series of different molecular nets whereby sample from the inlet port slowly diffuses into and throughout the channel. Said molecular nets contain capture components of different surface chemistries and conformations allowing for maximum binding of undesired components in a sample. Remaining sample components may then be removed by suction through a sample access port.

In another embodiment, a device may contain a mixture of selection features including: gradient coatings on luminal surface, filters, sieves, and molecular nets and may be located in channels and may be located in chambers. Said selection features may be attached to the luminal surface or may be suspended or may be fitted against a luminal lip.

In another embodiment, a device for sample preparation with selectable features may distinguish sample components based on size, affinity, surface chemistry, shape, hydrophobicity, hydrophilicity, and activity.

In another embodiment, a device may contain luminal surfaces with raised physical features and may be composed of polymer and may contain surface chemistry that promotes binding of specific molecules such as components in a molecular net.

In one preferred embodiment of a device, a polymeric device may contain ports at both ends of the device. The device may have directionality in that the device may have a sample inlet port and sample outlet port. The device may contain a large continuous channel and said channel may contain a series of different filters and/or sieves and/or molecular nets attached to channel features.

In another example, the inlet and outlet ports may be Luer lock style connectors. The inlet and outlet ports may be female Luer lock connectors. The use of female Luer lock connectors will allow a fluid to be introduced via a syringe. Typically syringes include male Luer lock connector at the dispensing end of the syringe. For liquid samples, the Luer lock connectors may allow samples to be transferred directly from a syringe by the application of force at the syringe plunger into said inlet port of the device.

In another example, a device is an adapter linking two different syringes. One syringe may contain raw sample and the sample may be pushed into the adapter and through the adapter device to separate undesired sample from analytes. The other syringe may be connected to the opposite end of the adapter device and receive semi-purified or purified analytes.

In another example, a device may have layered sections that are assembled to produce a system of channels and chambers in which sample is passed from the outermost layer, through multiple inner layers and is passed to the opposing outermost layer. Said sample may be purified in part or in whole as it passes through the sequential layers of the device to produce semi-purified or purified analytes that may be present for analyses.

In another example, a device may include an external surface with transparent and translucent polymers serving as the window surface of a chamber.

Exemplary Systems:

Embodiments of the invention include apparatuses for analyzing a sample for the presence of a specific type of analyte using a molecular net. In some embodiments, such an apparatus includes one or more sensors operationally coupled to the molecular net. These sensors can provide a signal that is indicative or non-indicative of the presence of the certain analyte caught within the net, and thus originally present within the sample. In some embodiments, the lack of a signal may be indicative or non-indicative of the presence of the certain analyte within the sample.

In some embodiments, energy may be applied to the sensors to cause certain analytes to generate signals. The energy can be applied to the molecular net by the sensor, where portions of the molecular net emit a response signal (e.g., fluorescence, vibration). In some embodiments, the presence of the analyte alone will cause the sensor to generate a signal. For example, the molecular net may be structurally attached to one or more piezoelectric sensors, where the capture of the analyte causes the structure of the molecular net to change (e.g., stiffen, contract) and thus apply mechanical strain to the piezoelectric sensor. Under this strain, the piezoelectric sensor emits an electrical signal indicative of the presence of the analyte.

The systems and devices disclosed herein generally include a structure, which may be a housing or a sub-housing of a greater structure, to hold one or more molecular nets. The structures generally include one or more support surfaces configured to support one or more molecular nets. In some embodiments, such support surfaces form at least a portion of a chamber configured to hold a fluid sample. Accordingly, in some embodiments it is understood that a "chamber" is a structural element including one or more support surfaces. In some embodiments, the structures are modular and/or portable. In some embodiments, the structure is a relatively small (i.e., handheld) cartridge which can interface with a computing device. In some embodiments, the structures include moveable parts, which may be physically actuated for processing a sample.

Figure 8A:
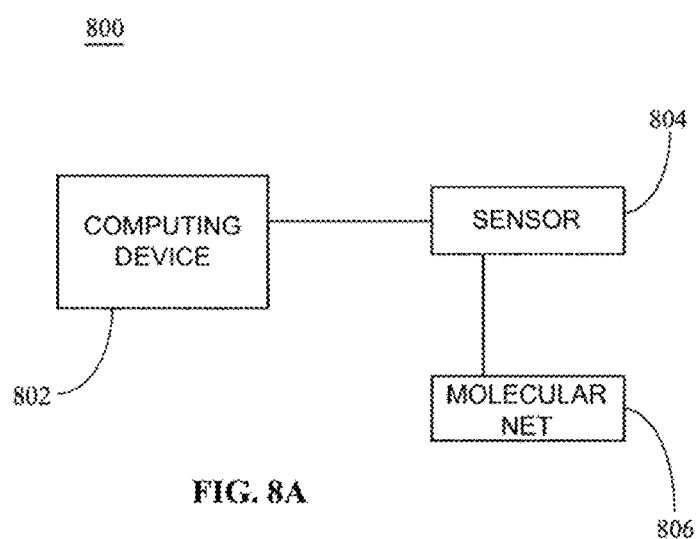
FIG. 8A shows a schematic diagram for an apparatus for capturing an analyte using a molecular net.

FIG. 8A shows a simplified schematic diagram of an exemplary analyte detection system 800, according to an embodiment of the invention. System 800 includes a computing device 802. The computing device 802 generally includes at least one processor for executing machine instructions. The computing device 802 may be connected to additional subsystems such as a printer, keyboard, fixed disk, monitor, which is coupled to a display adapter. Peripherals and input/output (I/O) devices, which couple to an I/O controller, can be connected to the computing device 802 by any number of means known in the art, such as a serial port. For example, a serial port or a different external interface (e.g., USB, wireless, etc.) can be used to connect the computing apparatus to a wide area network such as the Internet, a mouse input device, or a scanner. The interconnection via the system bus allows the processor to communicate with each subsystem and to control the execution of instructions from system memory or the fixed disk, as well as the exchange of information between subsystems. The system memory and/or the fixed disk may embody a computer readable medium.

System 800 also includes at least one sensor 804 operationally coupled to the computing device 802. The sensor 804 is generally configured as described herein, and may include an integrated or non-integrated amplifier. A molecular net 806 is shown operationally coupled to the sensor 804. It should be understood that in some embodiments, the molecular net 806 can include a plurality of molecular nets. It should further be understood that the molecular net 806 can be configured similarly to any of the molecular nets disclosed herein, and combinations thereof.

In use, a sample that potentially contains a certain analyte is physically applied to the molecular net 806, which is preconfigured to capture that certain analyte. The sensor 804 detects the presence of the certain analyte and sends an appropriate signal to the computing device 802. The computing device 802 processes the signal to indicate to a use whether or not the analyte is present within the molecular net, and thus originally within the sample. However, in some embodiments, it should be understood that the lack of a predetermined signal can be indicative of the presence of the certain analyte. For example, the sensor 804 may apply a certain electromagnetic wavelength (e.g., laser light) to the sample, where absorbance of the wavelength by the analyte is indicative of its presence. Thus, detecting the absence of the certain wavelength will show a positive indication.

The system 800, in some embodiments, can include one or more structures for holding the computing device 802 and/or sensor 804 and/or the molecular net 806. Various materials and configurations are possible for these structures. In some embodiments, the structures may be constructed from polymers and/or metals. For example, a structure may be configured as a sheet metal or molded plastic housing having a plurality of outer and inner walls for structurally supporting physical aspects of the system 800. Portions of the structures can be configured as tubes, chambers, and ducts to route samples through the system 800. Additional aspects, such as pumps, power supplies, and electrical hardware can also make up the system 800. In some embodiments, the sensor 804 and the molecular net 806 can be configured within a modular structure that separately interfaces with the computing device 802. An example of such a sub-system is shown in FIG. 8B as device 808.

Figure 8B:
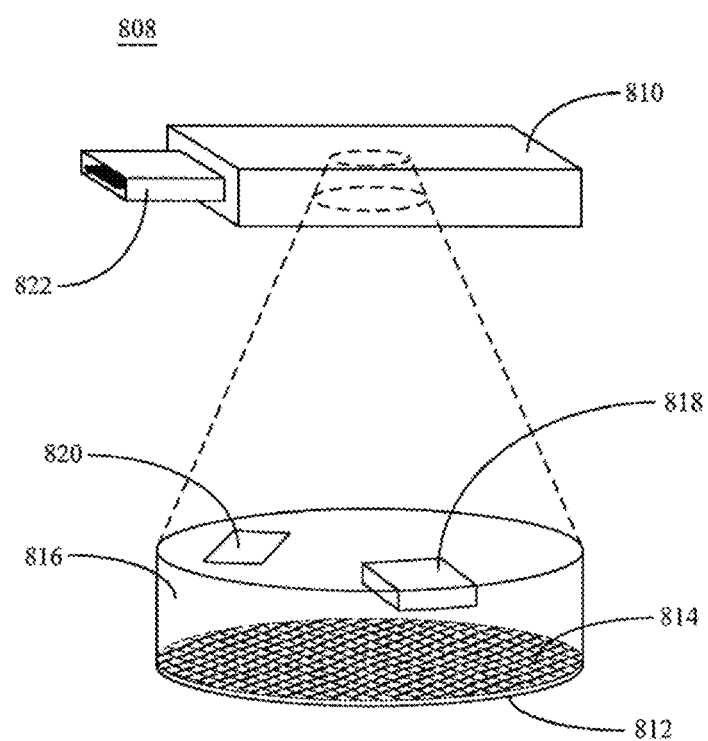
FIG. 8B shows a close-up view of an apparatus for capturing an analyte using a molecular net.

FIG. 8B shows a perspective and detail view of an exemplary device 808, according to an embodiment of the invention. The device 808 includes a structure 810, which is shown as a portable elongate housing. The structure 810 includes at least one surface 812 configured for supporting a molecular net 814. The surface 812 may be configured according to the molecular net support surfaces and substrates described herein. The surface 812 defines at least a portion of a sample detection chamber 816. A sensor 818 can be coupled to the surface 812 or to another surface defining the sample detection chamber 816. The sample detection chamber 816 will generally include an inlet port or other opening for physical application of a sample to the molecular net 814. The structure may include a viewing window 820 to confirm the application of the sample and/or for viewing a visual indication of the presence of a certain analyte caught within the molecular net 814. The sensor may also include a connector 822 operatively coupled to the sensor 818. The connector 1822 may be configured according to a known connector standard (e.g., USB) for connection to the computing system 802.

Figure 8C:
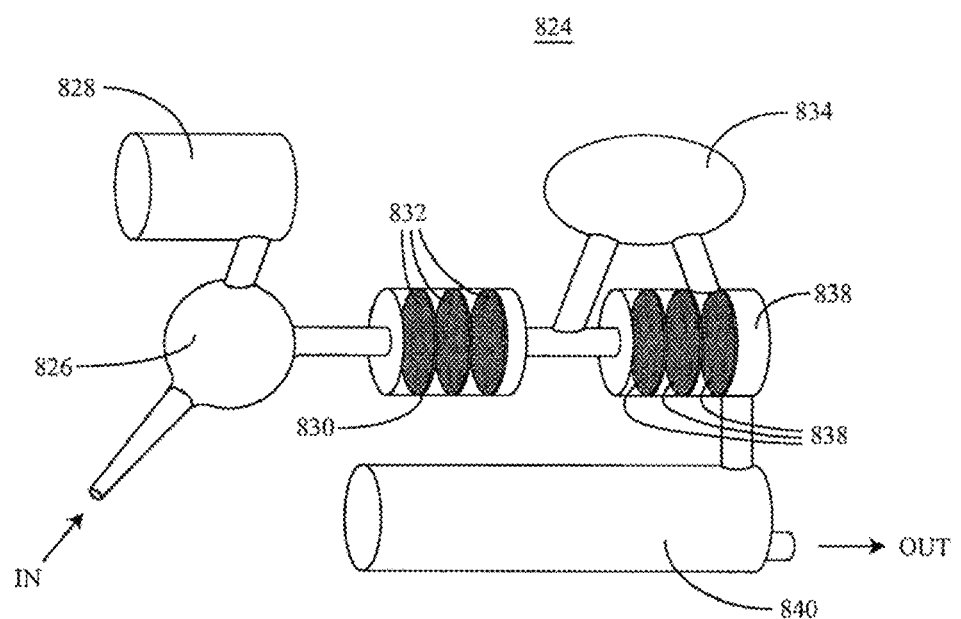
FIG. 8C shows a side view of a multi-chambered apparatus for capturing an analyte using a molecular net.

FIG. 8C shows an exemplary multi-chambered system 824, according to an embodiment of the invention. The system 824 is configured as an isothermal nucleic acid affinity testing system using molecular nets. The system 824 includes a modification chamber 826 where a sample may be processed (e.g., denatured, modified, etc.) via chemical alteration. The modification chamber 826 is generally where a detection process begins, and thus includes an inlet port. A buffer holding chamber 828 is in fluid communication with the modification chamber 826. The buffer holding chamber 828 is configured to release modifying and/or processing agents and/or a buffer solution into the modification chamber 826. An amplification chamber 830 is in down-stream fluid communication with the modification chamber 826. The amplification chamber 830 can include one or more molecular nets 832 that subdivide the amplification chamber 830 by spanning across one or more connective surfaces.

The molecular nets 832 within the amplification chamber 830 can include amplification factors, such as enzymes, which amplify the detectable presence of one or more certain types of analytes passing through the amplification chamber 830. These enzymes can be configured to bind with the analytes. A wash chamber 834 is shown in fluid communication with the amplification chamber 830 and/or a detection chamber 836. The wash chamber 834 is configured to store a wash fluid which is releasable into the amplification chamber 830 and/or the detection chamber 836. The detection chamber 836 is configured to include one or more molecular nets 838, that are in turn configured to capture one or more specific types of modified and/or processed and/or amplified analytes. The molecular nets 838 are configured to subdivide the detection chamber 834. Resulting wash fluid, including unbound portions of the sample, can be routed to a waste chamber 840, which is in fluid communication with the detection chamber 836, for release out of an outlet port.

Understandably, other configurations of system 824 are possible. In some embodiments, the amplification chamber 830 and/or the wash chamber 834 can be configured as detection chambers, in a similar manner to detection chamber 836. In further embodiments, one or more sensors may be positioned within the chambers for detection of one or more certain types of analytes. In yet further embodiments, one or more valves are positioned between chambers to selectively cause fluid communication between the chambers. For example, to release buffer solution and/or wash fluid at certain times during the testing process. In yet further embodiments, positive and/or negative pressure via a fluidly coupled pump causes the sample fluid to enter into an entry port, pass through the various chambers, and outlet out through an outlet port.

Figure 8D:
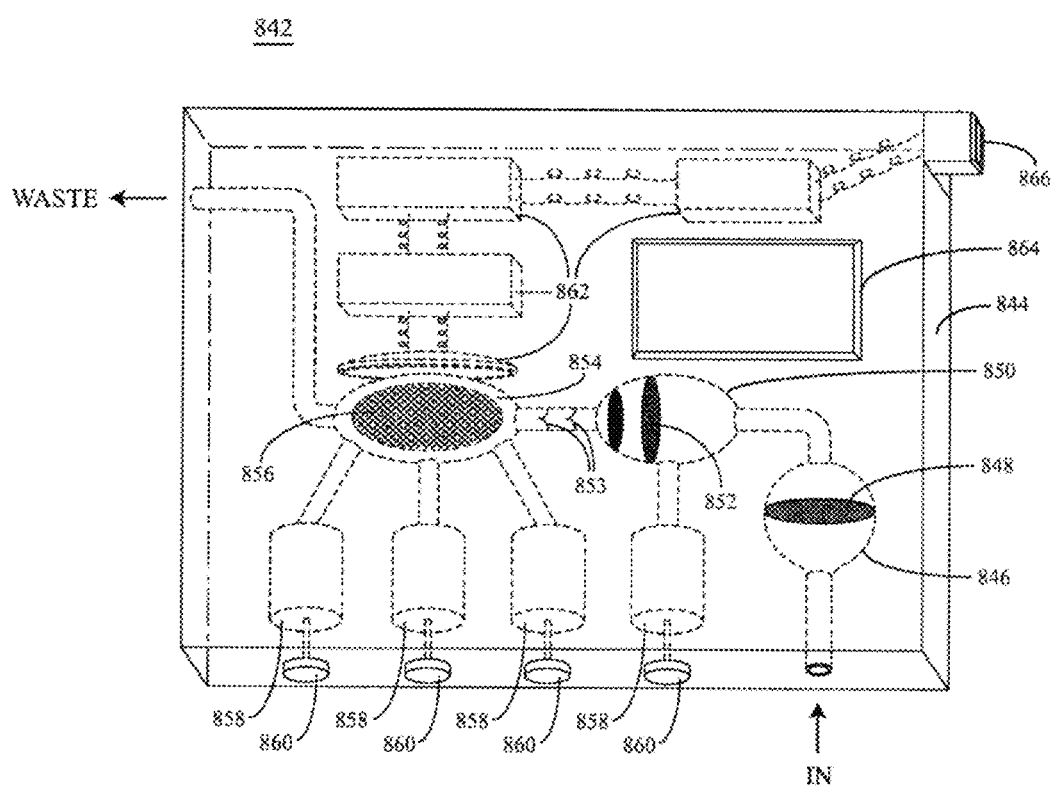
FIG. 8D shows a top view of a multi-chambered apparatus for capturing an analyte using a molecular net.

FIG. 8D shows another exemplary multi-chambered system 842, according to an embodiment of the invention. The system 842 includes a structure 844 for housing various chambers and other components. The system 842 also includes a filtration chamber 846 which supports a filter 848. The filtration chamber 846 is generally in fluid communication with an entry port for receiving a sample. The filter 848 can be configured as a wash net, filter element, or a sieve. A wash filtration chamber 850 is in fluid communication with the filter chamber 848. The wash filtration chamber 850 includes one or more filters 852 which are configured to prevent certain portions of a sample from passing through. A detection chamber 854 is in fluid communication with the wash filtration chamber 850; these chambers may be separated by one or more one-way fluid valves 853 to prevent backwash. The detection chamber 854 includes at least one molecular net 856, that is configured to capture at least one certain type of analyte.

The system 842 further includes a plurality of holding chambers 858. Each holding chamber 858 may include one or more types of fluid, such as washes, reagents, buffers, etc. Each holding chamber 858 may be configured to release a respective fluid upon user actuation of at least one of a plurality of switches 860, which are shown here as push buttons. The switches 860 can be configured to activate electro-mechanical or mechanical valves. In some embodiments, the switches are not user actuated in a direct and contemporaneous manner, but are configured to actuate via the occurrence of an event, such as the triggering of the one-way valves 853, various detectors, and/or other mechanisms.

The system 842 further includes a computing device 862, which can be configured similarly to the exemplary computing device 802. The computing device 862 can include sensors, amplification circuitry, and signal processing circuitry configured to detect the presence of a certain analyte caught within the molecular net 856. A display 864 can be coupled to the computing device 862 for displaying test results and configurations. In some embodiments, the display 864 is a touch screen which can accept user inputs to control the switches 860 and other aspects of the system 842. An external interface 866 (e.g., USB port) can be connected to the computing device 862 to output data from the computing device 862.

Figure 8E:
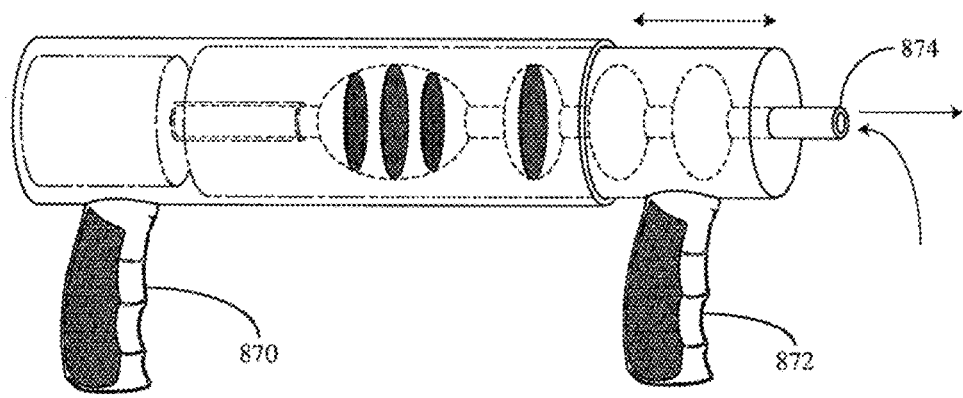
FIG. 8E shows a side view of an portable multi-chambered gun apparatus for capturing an analyte using a molecular net.

FIG. 8E shows an exemplary multi-chambered gun device 868, according to an embodiment of the invention. The gun device 868 includes a plurality of fluidly connected chambers configured similarly with respect to the chambers of devices 824 and 826, and generally includes at least one molecular net. However, the gun device 1068 includes a back portion 870 moveably connected to a front portion 872. As shown, the front portion 872 is completely withdrawn into the back portion 870. Relative actuation of the back portion 870 away from the front portion 872 results in negative relative pressure within the chambers, and thus will draw in a sample or buffer into a port 874 of the gun device 868 for testing or buffering of a sample. Conversely, relative actuation of the back portion 870 towards from the front section 872 results in positive relative pressure within the chambers, and thus will expel a sample or buffer out from the port 874 after potential capture of a certain analyte within the molecular net.

Detection Components

Devices may also contain signal detectors (i.e., sensors), such as photomultiplier tubes; photovoltaic cell; multi-crystalline silicon foil; thin-film photovoltaic; photovoltaic wafer; photovoltaic module; light harvesting printable materials; copper-indium-galliumselenide based solar electric systems; monocrystalline silicon; polycrystalline silicon; tandem junction thin film silicon; photodiode; semiconductor diode; and other photodetectors capable of converting light energy into either current or voltage.

In some embodiments, a device may include different sensor arrays mounted within respective chambers. A device (or testing volume/net in a device) may include one or more optical fibers that can be connected to one or more signal amplifier; and can contain one or more signal detector; and can transmit one or more detected signal to one or more electrical circuit; and can transmit electrical information to a computer for analysis.

Exemplary Detection Arrangements

Figure 9A:
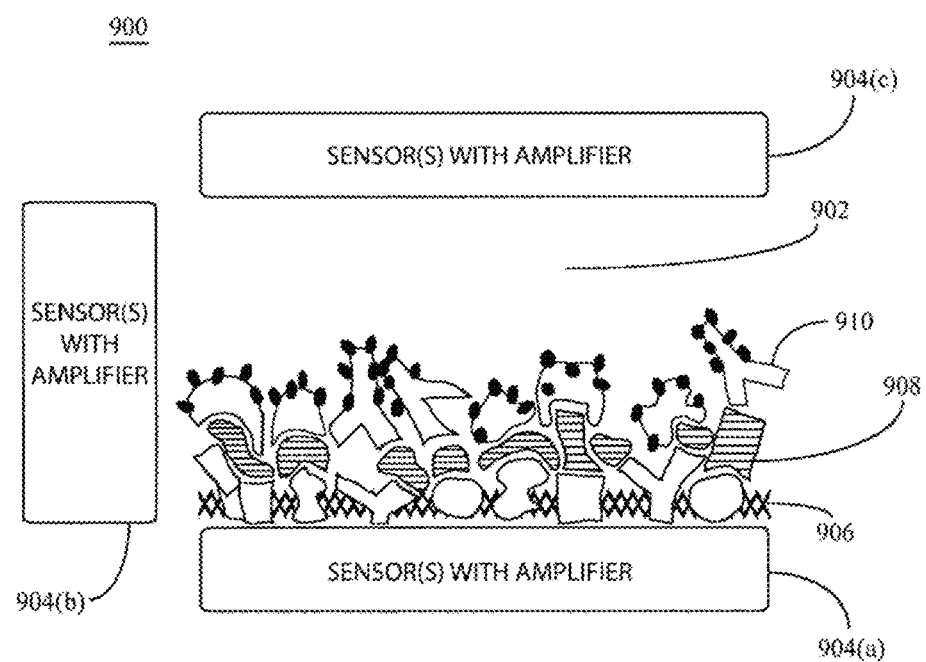
FIGS. 9A and 9B show respective exemplary sensor arrangements.

FIG. 9A shows a detailed schematic of an exemplary sensor arrangement 900, according to an embodiment of the invention. The sensor arrangement 900 is used to perform a method of analyte detection using a molecular net. The sensor arrangement 900 is configured within a chamber 902 having a plurality sensors 904 that define at least some portions of the chamber 902. Each sensor 904 may include amplification circuitry/devices, which amplify the presence of analytes and/or the signal produced by the sensors 904. Each sensor 904 may be configured in a different manner to detect different aspects of an analyte, or a plurality of different types of analytes. In some embodiments, the sensors 904 can be configured to detect a predetermined movement, temperature, electrical potential, light (UV/visible), vibration, rigidity, acidity, basicity, pH changes, energy conductance (current, thermal, etc.) mechanical tension, mechanical torsion, elasticity, magnetic fields, and combinations thereof.

A molecular net 906 constructed from various capture molecules and cross-linkers is shown coupled to at least one of the sensors 902($a$). Further shown is a plurality of analytes 908 captured by the molecular net 906, and a plurality of detection molecules 906 bound to the analytes via an amplifying process. Understandably, many analytes lack properties that are easily detectable by commonly available sensors. To compensate for this, the detection molecules 910 include readily circuitry delectable properties, and are used to bind to the analytes and thus allow for their detection. For example, the detection molecules 910 may be bound with a ferrous substance and the sensor 904($a$) may include a piezoelectric strain detector. The remaining sensors 904($b$)($c$), and/or the sensor 904($a$), can include permanent magnets or electromagnets. These magnets can cause the detection molecules 910 to pull away from, or towards, the molecular net 906 with a force which causes the piezoelectric strain detector to emit a electrical signal, and thus indicate the presence of the analytes 908. In another example, the detection molecules 910 may be bound with a conductive or resistive substance, which alters the conductive and/or capacitive relationship between the sensors 904. In another example, the detection molecules 910 may be bound with a fluorescent substance, which allows the sensors 904 to detect the presence of a certain wavelength of light when exposed to a different wavelength of light. In another example, each sensor 904 includes a molecular net. Understandably, many more sensor arrangements are possible.

Figure 9B:
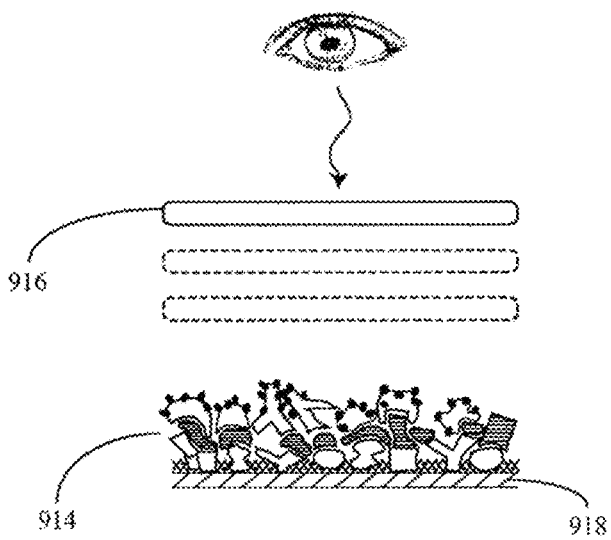

FIG. 9B shows a detailed schematic of an exemplary sensor arrangement 912, according to an embodiment of the invention. The sensor arrangement 912 includes a molecular net 914 configured similarly to the molecular net 906 of FIG. 9A. However, in this arrangement the detection molecules are configured to bind to certain substances having a certain visible color, or several colors. One or more microscopic lenses 916 can be arranged in view of the molecular net 914, to provide a view of the colors for a naked eye. Thus, in some embodiments, the analytes are detectable without a need to apply energy to the sensor arrangement 912. In some embodiments, the molecular net 914 is arranged in a specific manner, to show a predetermined symbol, such as a letter or number. In some embodiments, a support surface 918 for holding the molecular net is transparent, to allow light to pass through. In some embodiments, the support surface 918 can include a simple light source circuit, such as an LED switchably coupled to a battery, to provide light of a specific wavelength or white light.

Figure 9C:
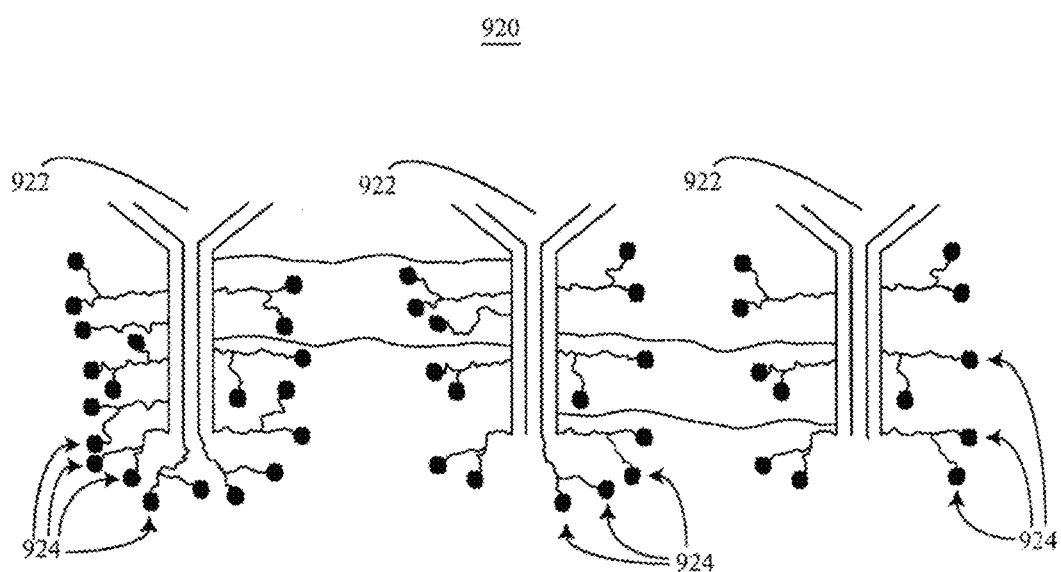
FIG. 9C shows an arrangement of a plurality of cross-linked detection molecules.

FIG. 9C shows an exemplary molecular arrangement 920 of a plurality of crosslinked detection molecules, according to an embodiment of the invention. The detection molecules 922 are configured to bind to one or more certain analytes. The detection molecules 922 can be chemically cross-linked to one another and/or PEGylated to signal amplification factors 924, which are depicted as dark-filled circles. The amplification factors 924 are present to enhance signal or to provide the presence of a signal. The amplification factors 924 can include enzymes, metal nanoparticles, dyes, fluorophores, chemicals, cofactors, substrates, and combinations thereof.

Figure 9D:
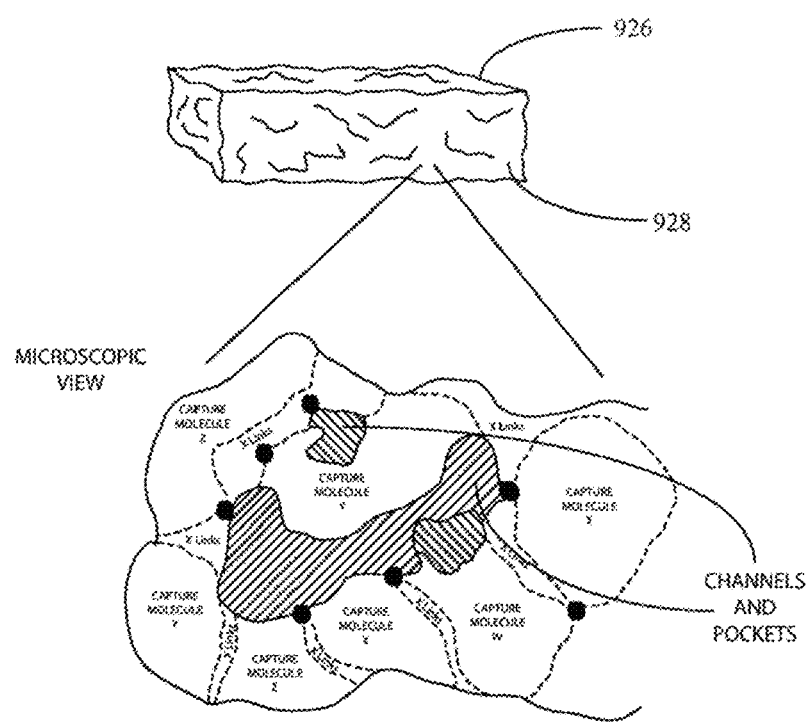
FIG. 9D shows a molecular net configuration.

FIG. 9D shows an exemplary molecular net configuration 926, according to an embodiment of the invention. A macroscopic view of the molecular net configuration 926 is shown having irregular surfaces 928. The molecular net configuration 926 can include irregular densities, pockets and channels, multiple surface chemistries, and other physical properties. This is shown in the microscopic view where different types of capture molecules and amplification elements are connected via cross-links. The channels and pockets provide a relatively large surface area for capturing analytes, and thus makes efficient use of a compact molecular net. Such channels and pockets can be formed by aerating the molecular net before and/or during the cross-linking process. In some embodiments, non-binding microparticles can be used to provide the channels and pockets before and/or during the cross-linking process. These non-binding microparticles can be removed after the cross-linking process by various methods, such as flushing, evaporation, or dissolving, and thus provide the empty spaces for the channels and pockets.

Exemplary Devices, Subsystems, and Structural Aspects

As previous noted with reference to FIG. 8A, various combinations of the sensors and molecular nets disclosed herein can be configured within a modular structure that separately interfaces with an external computing device, such as computing device 802. Conversely, some embodiments do not require a computing device. In one example, such an embodiment is shown in FIG. 10A.

Figure 10A:
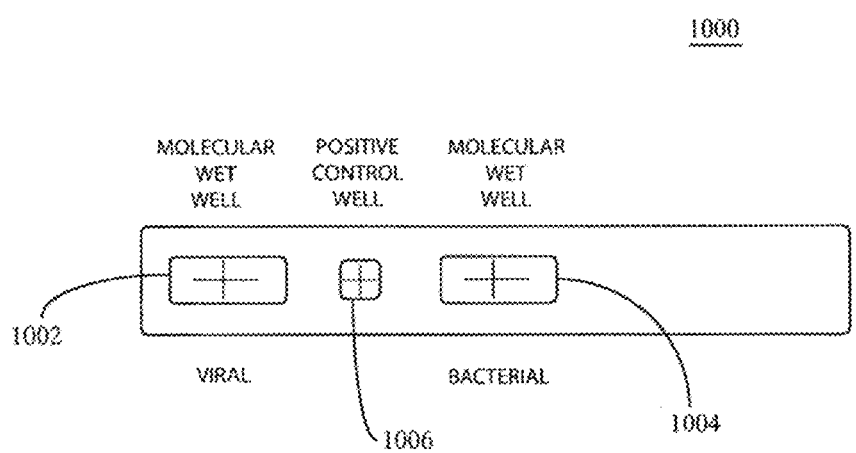
FIG. 10A shows an exemplary testing device for detecting the presence of various analytes.

FIG. 10A shows an exemplary testing device 1000 for detecting the presence of various analytes, according to an embodiment of the invention. The device 1000 is configured as an elongate structure having a plurality of wells. In some embodiments, the device 1000 is configured as a disposable plastic stick. Each well can include a specific molecular net respectively configured to indicate the presence of a specific analyte. For example, well 1002 can include a molecular net configured to indicate the presence of a specific virus by showing a previously non-visible symbol upon application of a sample. In a similar manner, well 1004 can be configured to indicate the presence of a specific bacteria. In a similar manner, well 1006 can be configured as a positive control well to confirm the operational functionality well 1002 and well 1004 if no viral and bacterial symbols appear.

Figure 10B:
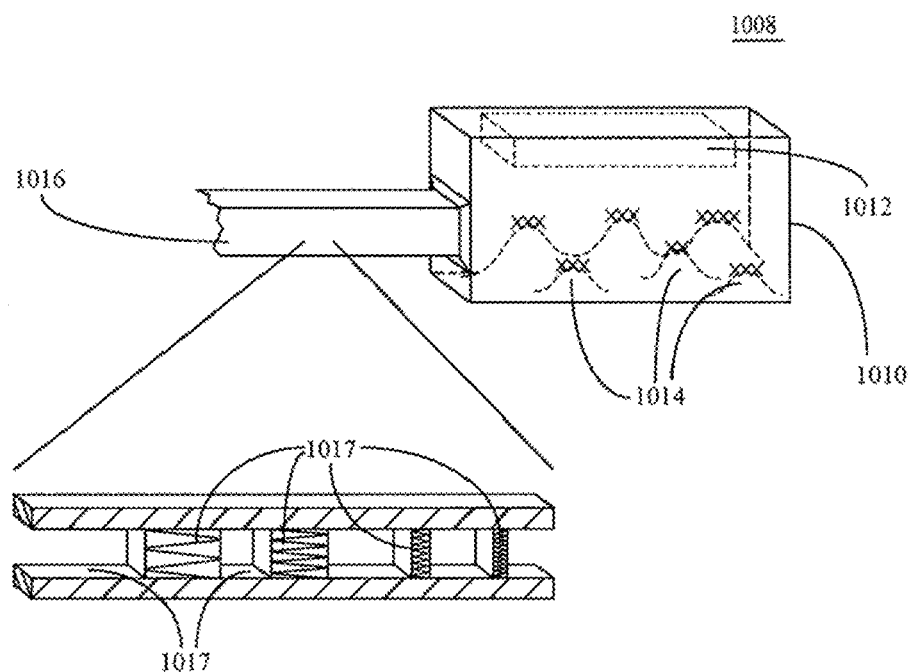
FIG. 10B shows a perspective a close-up view of a testing chamber.
Figure 10C:
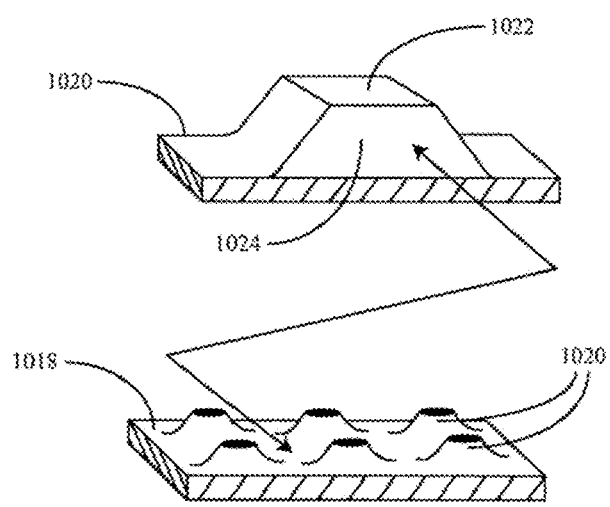
FIG. 10C shows a detailed view of the testing chamber of FIG. 10B.

FIGS. 10B and 10C show a simplified structural depiction of an exemplary testing chamber 1008, according to an embodiment of the invention. The chamber 1008 includes an interior surface 1010 which supports one or more sensors 1012 and one or more molecular nets 1014. A sample can be introduced into the chamber 1008 via an attached tube or channel 1016. The channel 1016 can include luminal surfaces, various filters, and sieves (collectively 1017) for removing portions of a sample. As shown in FIG. 10C, a portion 1018 of the interior surface 1010 includes physical features 1020 to support molecular nets. The physical features are configured as multifaceted protrusions with binding and non-binding surfaces. The top surfaces 1022 can support the molecular nets, while the side surfaces 1024 can be configured to reduce the non-specific binding of analytes. These physical features can also be used within the channel 1016, for example, the physical features can be located on the channel walls to detect specific analytes and also filter out other analytes.

Figure 10D:
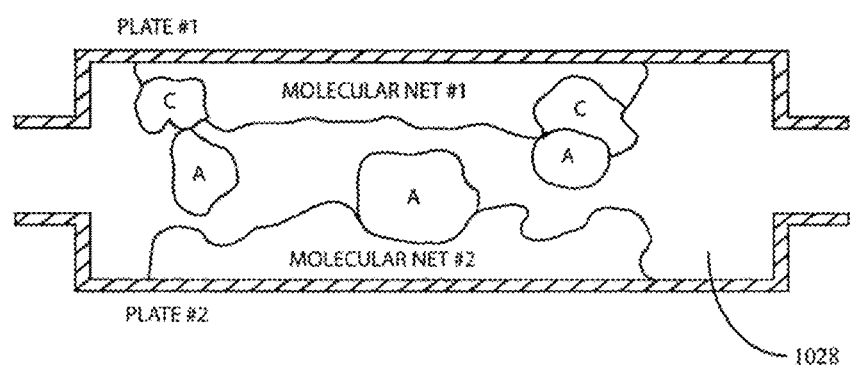
FIG. 10D shows a molecular net arrangement.

FIG. 10D shows a simplified schematic of an exemplary molecular net arrangement 1026, according to an embodiment of the invention. In this arrangement 1026, the detection of analytes can be accomplished by immobilizing analytes via binding by molecular nets on the chamber walls 1028 of a test chamber. The manner of binding is configured by the molecular nets to alter physical, chemical, magnetic, electrical, mechanical, light scattering, light refracting, and/or light reflecting properties of the walls. The chamber walls are generally calibrated to known qualities of the properties, both before and after testing. Sensors can be used to ascertain these properties for determining whether an analyte is bound to the molecular net.

Figure 11A:
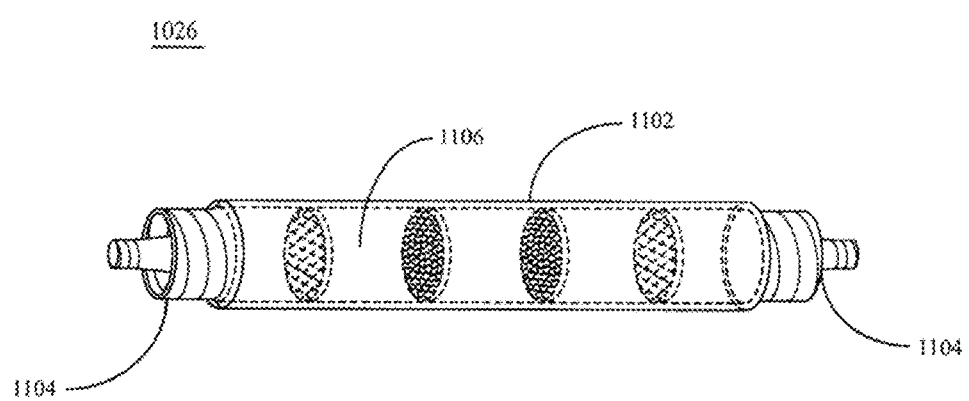
FIG. 11A shows a perspective view of an adapter.

FIG. 11A shows a perspective view of an exemplary adapter 1100 for sample processing and/or sample fractionation, according to an embodiment of the invention. The adapter 1100 is configured as an elongate tube 1102 having attachment features 1104 for fluidic connection to sample introduction and removal devices, such as syringes and tubes. In this example, Luer style connectors are shown at each end of an internal lumen 1106. Various filters and sieves fractionate the lumen 1106 into sub-areas. The filters, sieves, and luminal surfaces of the lumen can include molecular nets to capture certain analytes. In use, an unprocessed sample may be applied into one end via a first syringe. When the sample almost completely fills the lumen, a second syringe can be attached to the other end and then filled with reapplication of the first syringe. In this manner, the second syringe is filled with a purified or processed sample that does not contain the analytes captured by the filters, sieves, and walls of the lumen.

Figure 11B:
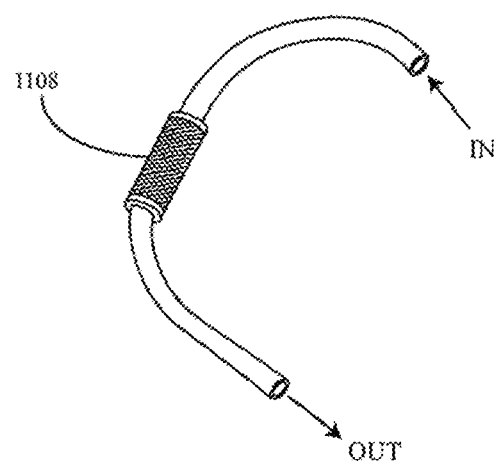
FIG. 11B shows a side view of an filtration unit.

FIG. 11B shows a side view of an exemplary filtration unit 1108, according to an embodiment of the invention. In a similar manner to adapter 1100, the filtration unit 1108 includes one or more internal molecular nets configured as filters, sieves, and/or luminal surfaces. The filtration unit 1108 is configured as a tubular cartridge, and is readily replaceable with an identical or similar cartridge after saturation with analytes, as indicated by the presence of a signal. The filtration unit 1108 can be configured within a closed circuit and intake and expel fluid to the same sample source. In some embodiments, the filtration unit 1108 is configured to bind cells, cellular remains, cellular debris, cellular products, metals, chelators, drugs, biologics, nitrogens, cytokines, nucleic acids, proteins, viruses, fungi, protozoa, and other molecules and/or agents which can be removed from a biologic sample.

Figure 12:
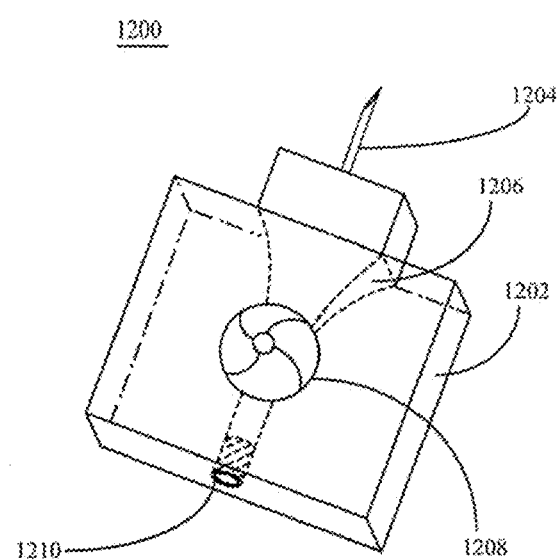
FIG. 12 shows a perspective view of a sharp containing device.

FIG. 12 shows a perspective view of an exemplary sharp containing device 1200, according to an embodiment of the invention. The device 1200 includes a structure 1202 configured as a plastic cartridge. A micro or macro-needle 1204 extends from the structure 1202, and is in fluid communication with an internal polymeric chamber 1206 or tube. The chamber 1206 can include various hydrophobic or hydrophilic coating chemistries. A deformable and resilient bulb 1208 extends from the top of the structure 1202, and is in fluid communication with the chamber 1206. A sample port 1208 opposes the needle 1204, and is also in fluid communication with the chamber 1206. The sample port 1208 can include an adapter to connect to a syringe or diagnostic device. The chamber 1206 includes one or more molecular nets, and may also include one or more sensors. In use, the needle 1204 can be applied into target tissue to access vasculature. The bulb 1208 is then pumped to draw blood into the chamber 1206 and onto the molecular net. A syringe or diagnostic device can then be attached to the sample port 1210 to determine the presence of an analyte within the molecular net.

Figure 13A:
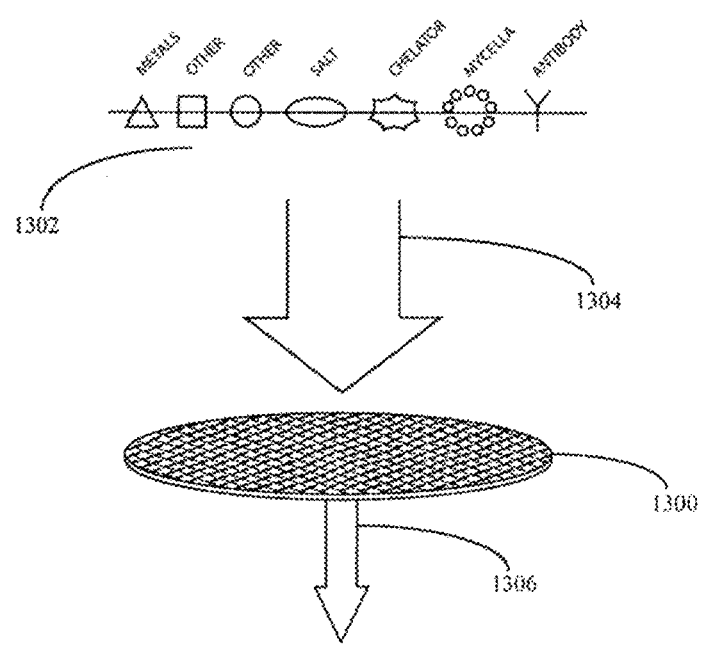
FIG. 13A shows a perspective view of an wash net.

FIG. 13A shows a perspective view of an exemplary wash net 1300, according to an embodiment of the invention. The wash net 1300 is constructed from a molecular net, which is configured with 1302 to filter a sample containing one or more undesired analytes. The wash net 1300 can be sized to manually and flexibly span a container or tube in a lab or field setting, or alternatively pre-housed in a filter frame assembly. In use, the wash net 1300 can be applied to cover the opening of a container, such as a bowl or graduated cylinder. An unfiltered sample 1304 can then be poured onto the wash net 1300 in a manner which results in a filtered sample 1306 flowing into the container.

Figure 13B:
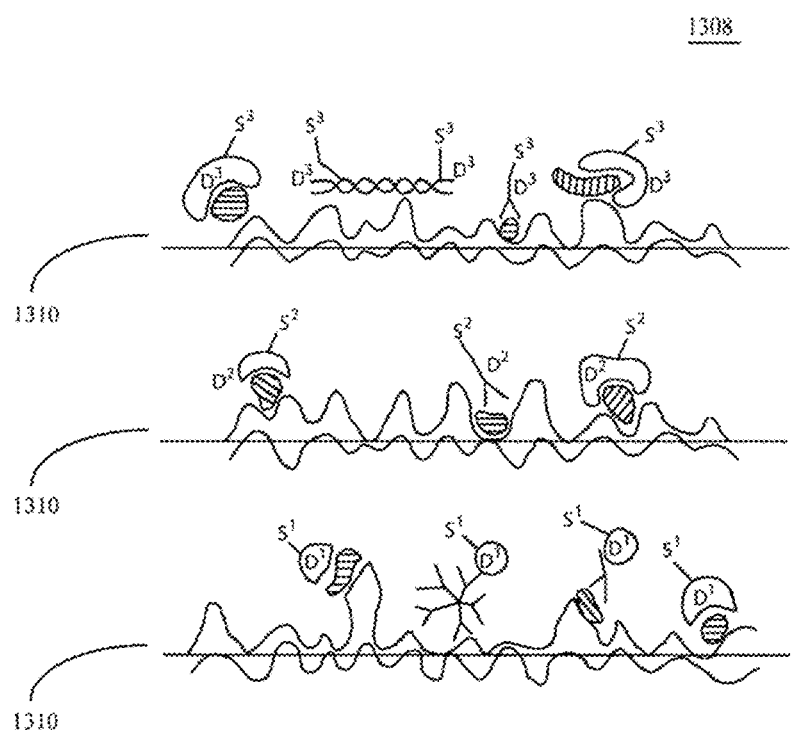
FIG. 13B shows a schematic depiction of a multiplexing network.

FIG. 13B shows a schematic depiction of an exemplary multiplexing network 1308 of molecular nets, according to an embodiment of the invention. A plurality of molecular nets 1310 are layered, stacked, or suspended over one another, and can further be attached to a greater structure, such as a detection label. Each molecular net includes various detection molecules configured to produce one or more signals ($S^1$, $S^2$, $S^3$) Examples of signals include, without limitation, colorimetric, fluorescent, luminescent, and phosphorescent signals. The detection molecules can be configured to produce a single signal or multiple signals (e.g., multiple colors) upon capture of one or more certain analytes. For example, $S^1$=blue, $S^2$=red, and $S^3$=yellow. Further, $S^1+S^2$=purple and $S^1+S^3$=green. Tying signals (e.g., colors) and/or combinations of signals to specific types of analytes via respective detection molecules, can thus visually indicate the presence of various analytes.

Figure 13C:
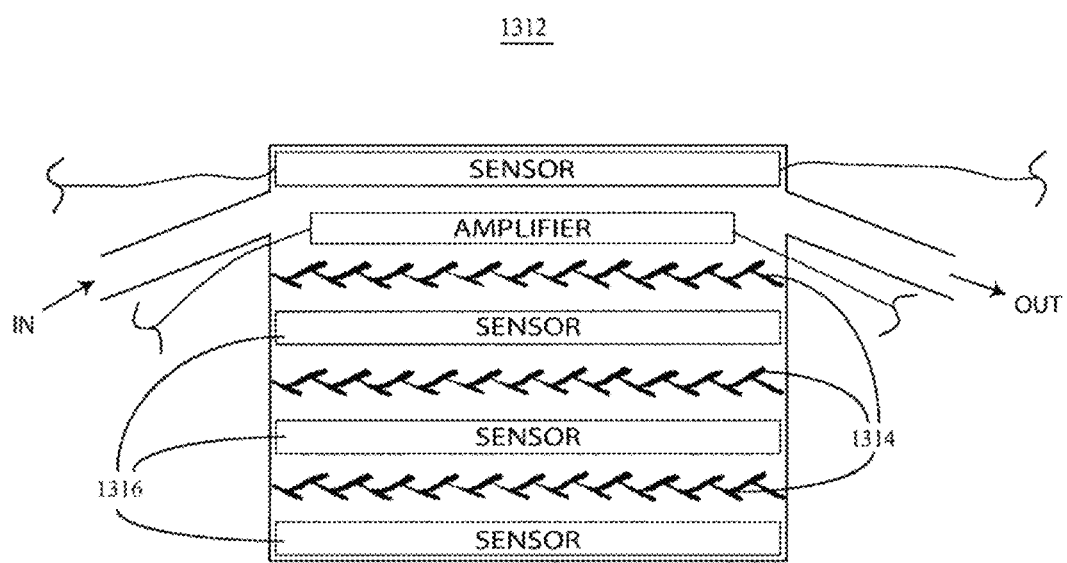
FIG. 13C shows a schematic depiction of a test volume.

FIG. 13C shows a schematic depiction of an exemplary test volume 1312, according to an embodiment of the invention. The test volume 1312 is configured as a chamber with an inlet and outlet. The test volume 1312 houses a plurality of molecular nets 1314 stacked in an alternating manner with a plurality of sensors. The sensors 1316 can be configured to detect light or other wave energies, and can include silicon solar cells, dye-sensitized solar cells, polymeric solar cells, organic solar cells, and/or single or multisided nanoantennas on polymers. The test volume 1312 further includes an amplifier 1318 coupled to the sensors 1316. The amplifier can be configured as a luminescent solar concentrator made of silicon or polymer materials, and can be connected to a silicon or polymeric multi junction PV solar cell. The amplifier can also be configured as concentrating photovolatics or a network of nanoantennas. In use, a sample is made to fill the test volume, which can cause one or more kinds of analytes to be captured by the molecular nets. The presence of the analytes can affect the propagation of light and energy through the test volume 1312, which is detectable by the sensors 1316. Measured properties of luminance and/or heat and/or thermophotovolatic from the sensors 1316 can then be compared with expected properties that are indicative or non-indicative of the presence of analytes, and accordingly determine their presence in the sample.

Figure 14A:
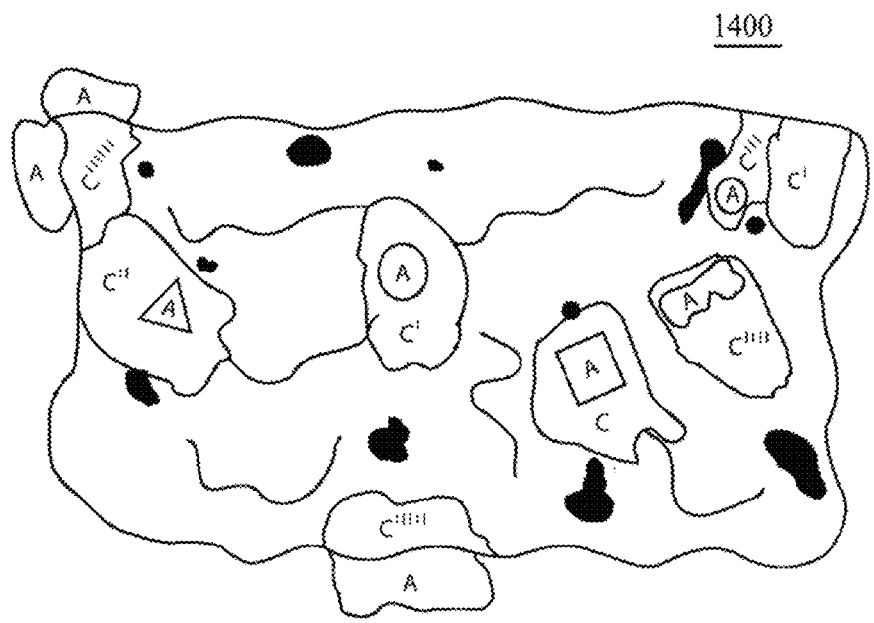
FIG. 14A shows a simplified depiction of a molecular net configured as a sponge.
Figure 14B:
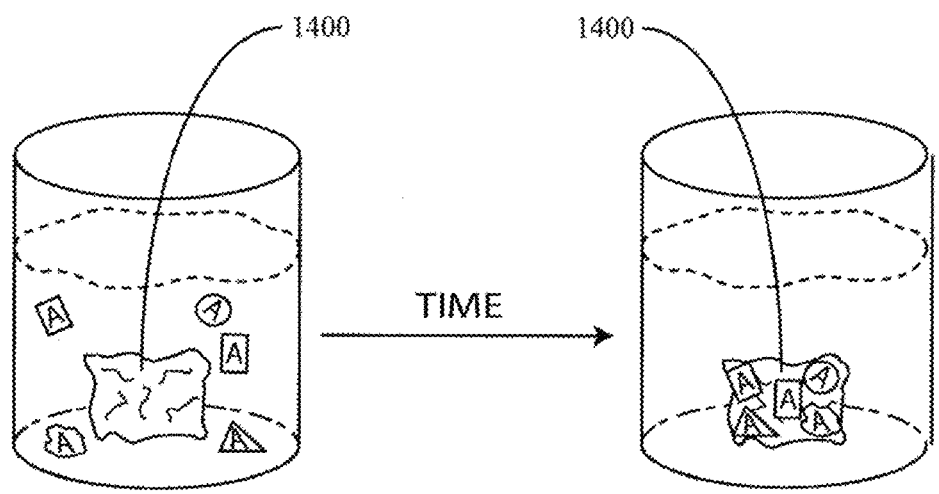
FIG. 14B shows the net in a container holding a sample.

FIG. 14A shows a simplified depiction of an exemplary molecular net configured as a sponge 1400, according to an embodiment of the invention. The sponge 1400 is constructed from an open-cell (macro or micro) absorbent molecular net structure, similarly to a artificial or organic sponge. In some embodiments, the sponge is constricted from a hybrid of artificial sponge material (e.g., open cell polymeric foam) interlaced with molecular nets. As shown in FIG. 14B, in use, the sponge 1400 can be placed in a container holding a sample. The sponge 1400 over time can absorb analytes "A" via physical interaction with capture molecules "C" of the sponge 1400. This occurs due to the absorbent properties of the sponge that forcibly draw in the sample fluid. The sponge 1400 can be removed from the sample after saturation, and analyzed for the presence of analytes.

Figure 15A:
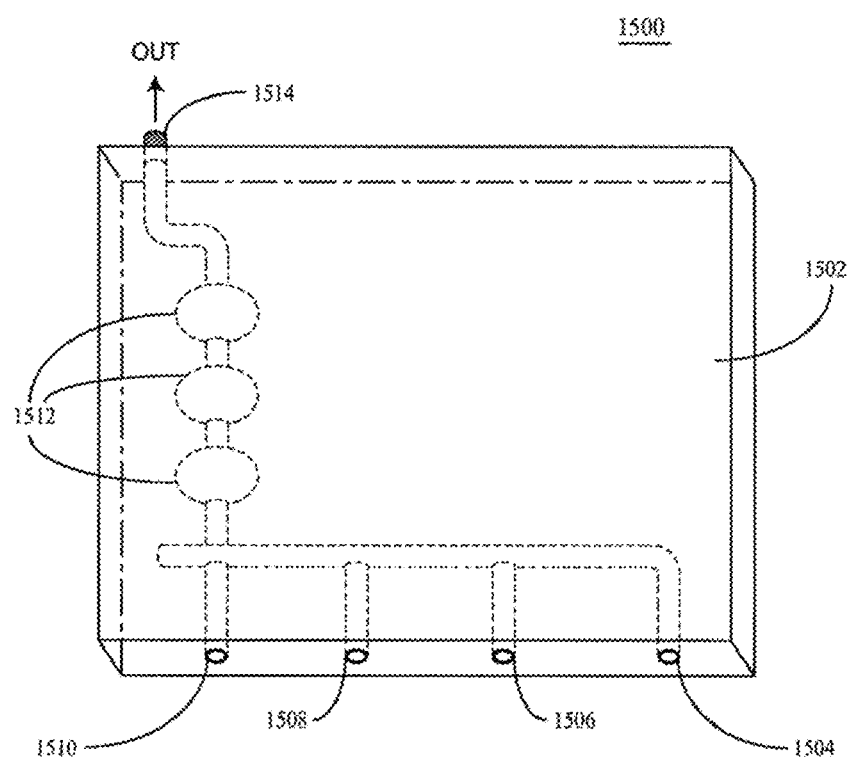
FIGS. 15A-17 show respective perspective views of various multi-chambered devices.

FIG. 15A shows a top view of an exemplary multi-chamber device 1500, according to an embodiment of the invention. The device 1500 includes a structural housing 1502 having internal tubes and chambers. The device includes an inlet port 1504, first wash inlet 1506, detection reagent inlet 1508, and second wash inlet 1510, all in fluid communication with a main channel 1511. The main channel 1511 is in further fluid communication with a plurality of test chambers 1512 containing one or more molecular nets. The main channel 1511 eventually terminates at a waste port. In use, a sample can be introduced into the main channel 1511 at the inlet port 1504 via positive or negative pressure. The sample may be chemically altered due to influx of various washes and reagents at inlets 1504, 1506, and 1508. Thus, when the sample reaches the test chambers 1512, it will be chemically altered as compared to when originally introduced into the device 1500.

Figure 15B:
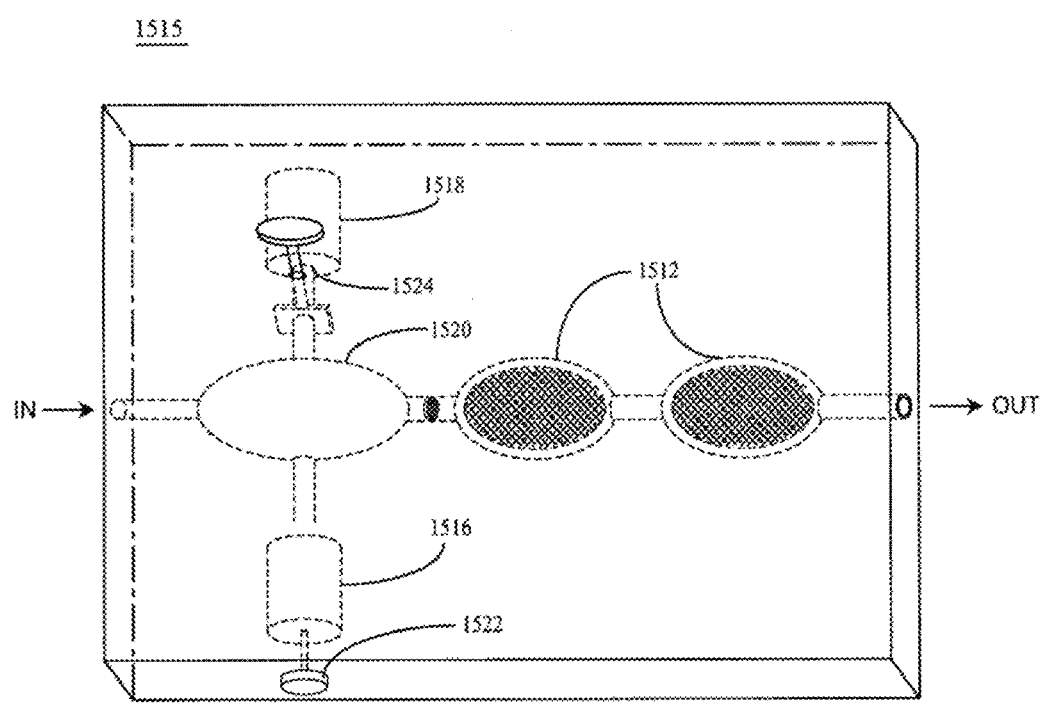

FIG. 15B shows a top view of another exemplary multi-chamber device 1515, according to an embodiment of the invention. The device 1515 is configured similarly to the device 1500 of FIG. 15A. However, the device 1515 includes internal chambers 1516, 1518 which are in fluid communication with a sample distribution chamber 1520. The internal chambers 1516 and 1518 can hold various reagents, enzymes, washes, chemicals, and the like. The internal chambers 1516 and 1518 can be made to be in fluid communication with the sample distribution chamber 1520 via actuation of a switch 1522 and pull-tab 1524, respectively. In use, a sample is initially introduced into the distribution chamber 1520. A user can then manually activate the switch 1522 and pull-tab 1524 in a desired order to release substances into sample distribution chamber 1520 and cause the sample to chemically change before or during introduction into the test chambers 1512.

Figure 16:
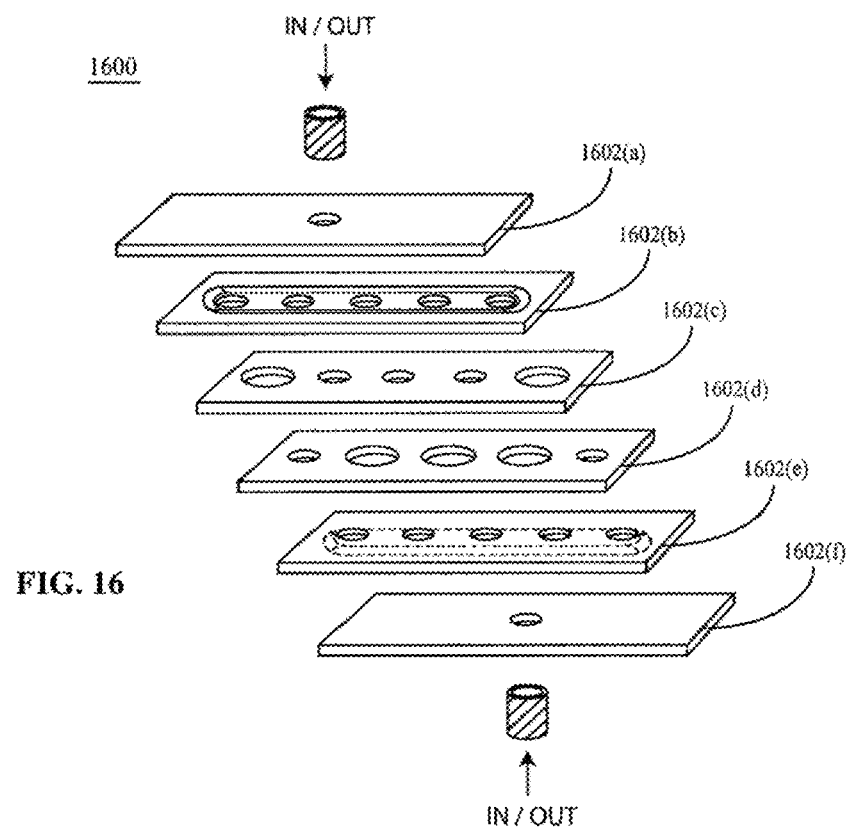

FIG. 16 shows an exploded view of another exemplary multi-chamber device 1600, according to an embodiment of the invention. The device 1600 is constructed form a plurality of layers 1602(*a-f*), each having one or more openings. When the layers 1602(*a-f*) are assembled, the openings form channels and chambers traveling horizontally and/or vertically within the device 1600. The channels and chambers may include one or more molecular nets. In use, a sample may migrate horizontally or vertically within and throughout the device to fill each chamber. Accordingly, the chambers can then be analyzed for the presence of different types analytes. Sensors can be imbedded within each layer to output signal. Alternatively, each layer can be removed and read by a reader.

Figure 17:
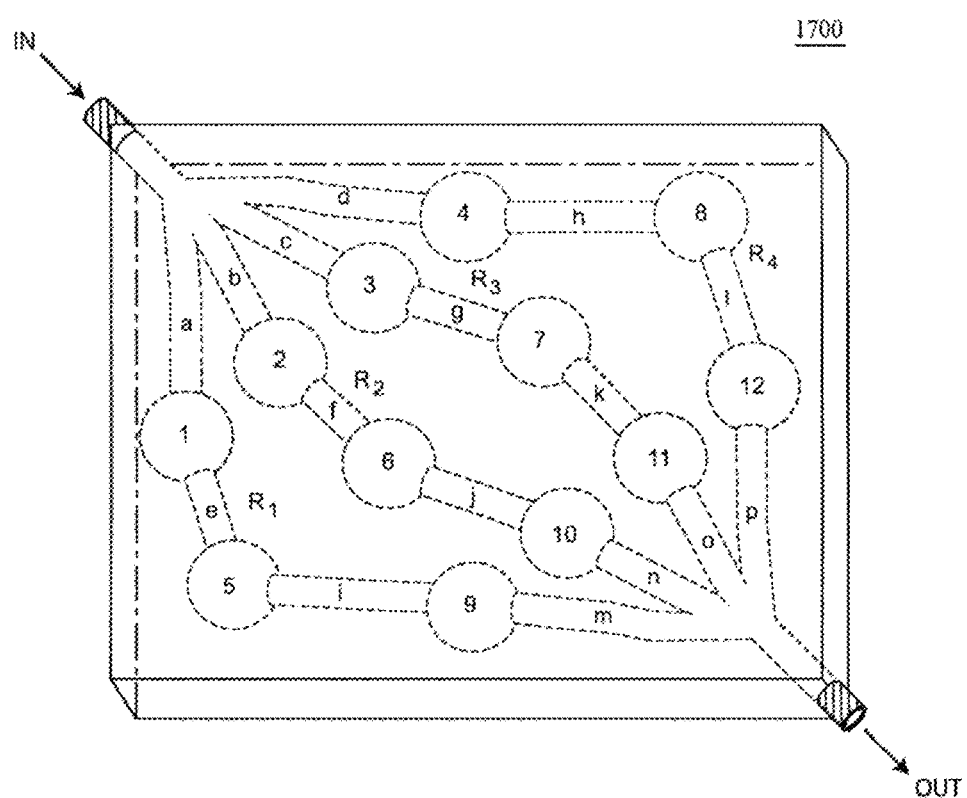

FIG. 17 shows a top view of another exemplary multi-chamber device 1700, according to an embodiment of the invention. The device 1700 is constructed in a similar manner to device 1500. However, device 1500 includes four distinct routes ($R_1$, $R_2$, $R_3$, $R_4$) for differential detection of sample analytes. Each route R1-4 includes a plurality of chambers (1-12) interconnected by a plurality of channels (a-p). Each chamber can include different molecular nets with different chemical and mechanical sample preparation features, selection features, filtration features, fractionation features, sensors, access points, and/or data input/output points. Each channel can include different luminal coatings, selection features, and/or filtration features. In use, a sample may migrate throughout the device to fill each test chamber. The chemistry of selection and fractionation features in combination with sensors may then determine the presence of one or more types of analytes within each test chamber.

VI. Examples

Example 1: Molecular Net to Detect Viral Infection

This prophetic example describes fabrication of a three-layer molecular net for detection of a viral infection. The net binds 1) Interferon alpha; 2) Interferon beta, 3) Viral MAVS and 4) Viral Viperin.

Materials

| Capture Agents | |
|---|---|
| 1) Polyclonal Antibodies against interferon-alpha | (stock = 1 mg/mL) |
| 2) Polyclonal Antibodies against interferon-beta | (stock = 1 mg/mL) |
| 3) Polyclonal Antibodies against IPS-1 (MAVS) | (stock = 1 mg/mL) |
| 4) Polyclonal Antibodies against viperin (cig5) | (stock = 1 mg/mL) |
| Linkers | |
| 5) EGS | (stock = 25 mM in DMSO) |

Methods
1. Mix capture agents 1-4 (antibodies) in a 1:1:1:1 ratio.
2. Underlayer—Add a 10 uL aliquot containing 100 ug of antibody mixture to substrate (nitrocellulose) surface. Let absorb overnight at 4° C. Remove remaining liquid including any non-immobilized antibodies.

First Layer
3. Pipette 10 uL of the antibody mixture onto the underlayer. Immediately add 1 uL EGS. Incubate at room temp for 1 hr.
4. Quench by adding 10 uL of 50 mM Tris buffer pH 7.5, let sit for 10 min.
5. Remove remaining liquid by pipette. Wash net 3× times by pipetting 50 uL PBS pH 7.4 onto net and removing.

Additional Layers
6. Repeat steps 4-7 to generate second layer
7. Repeat steps 4-7 to generate third layer Lyophilize or add 50 uL PBS+0.001% sodium azide and store at 4° C. until use

TABLE 8

Multilayer Molecular Net Content

| Layer | Capture Agent(s) | Linker(s) |
|---|---|---|
| First | Antibodies against IFN-α, IFN-β, IPS1, viperin | EGS |
| Second | " | " |
| Third | " | " |

Example 2: Molecular Net to Detect Bacterial Infection

This prophetic example describes fabrication of a three-layer molecular net for detection of a bacterial infection. The net binds 1) Gram negative bacterial lipopolysaccharide, 2) Gram negative bacterial lipid A, 3) Gram positive bacterial teichoic acid, and 4) CpG bacterial DNA.

Materials

| Capture Agents | |
|---|---|
| 1) Polyclonal Antibodies against lipopolysaccharide | (stock = 1 μg/mL) |
| 2) Polyclonal Antibodies against lipid A | (stock = 1 μg/mL) |
| 3) Polyclonal Antibodies against peptidoglycan | (stock = 1 μg/mL) |
| 4) Polyclonal Antibodies against teichoid acid | (stock = 1 μg/mL) |
| 5) DNA binding peptide 1 (VLFGKLA) (SEQ ID NO: 12). | (stock = 1 mg/mL) |
| 6) DNA binding peptide 2 (VMFGKLA) (SEQ ID NO: 13) | (stock = 1 mg/mL) |
| 7) DNA binding peptide 6 (VFFGRLA) (SEQ ID NO: 14) | (stock = 1 mg/mL) |
| Linkers | |
| 8) EGS | (stock = 25 mM in DMSO) |
| 9) EMCS | (stock = 25 mM in DMSO) |
| 10) BS(PEG)$_9$ | (stock = 250 mM in DMSO) |

Methods
1. Mix capture agents 1-4 (antibodies) in a 1:1:1:1 ratio into Tube A (1 ug/mL)
2. Mix capture agents 5-7 (DNA binding peptides) in a 1:1:1:1 ratio into Tube B (1 mg/mL)
3. Mix equal parts Tube A+Tube B in new Tube C
4. Underlayer Add a 10 uL aliquot from Tube C to substrate (nitrocellulose) surface. Let absorb overnight at 4° C. Remove remaining liquid including any non-immobilized antibodies.

First Layer
1. Pipette] 10 uL of Tube C mixture onto underlayer. Immediately add 1 uL each EGS, BS(PEG)$_9$ and EMCS. Incubate at room temp for 1 hr
2. Mix by slightly shaking the surface back and forth within a 5 cm distance 5 to 10 times.
3. Quench by adding 10 uL of 50 mM Tris buffer, let sit for 10 min
4. Remove remaining liquid by pipette, wash 3 times with 50 uL PBS by pipette Additional Layers
1. Repeat steps 1-4 to generate second layer
2. Repeat steps 5-8 to generate third layer
3. Lyophilize or add 50 uL PBS+0.001% sodium azide and store at 4° C. until use.

TABLE 9

Multilayer Molecular Net Content

| Layer | Capture Agent(s) | Linker(s) |
|---|---|---|
| First | Antibodies and DNA Binding Peptides | EGS, BS(PEG)9, EMCS |
| Second | " | EGS, BS(PEG)9, EMCS |
| Third | " | EGS, BS(PEG)9, EMCS |

Figure 2:
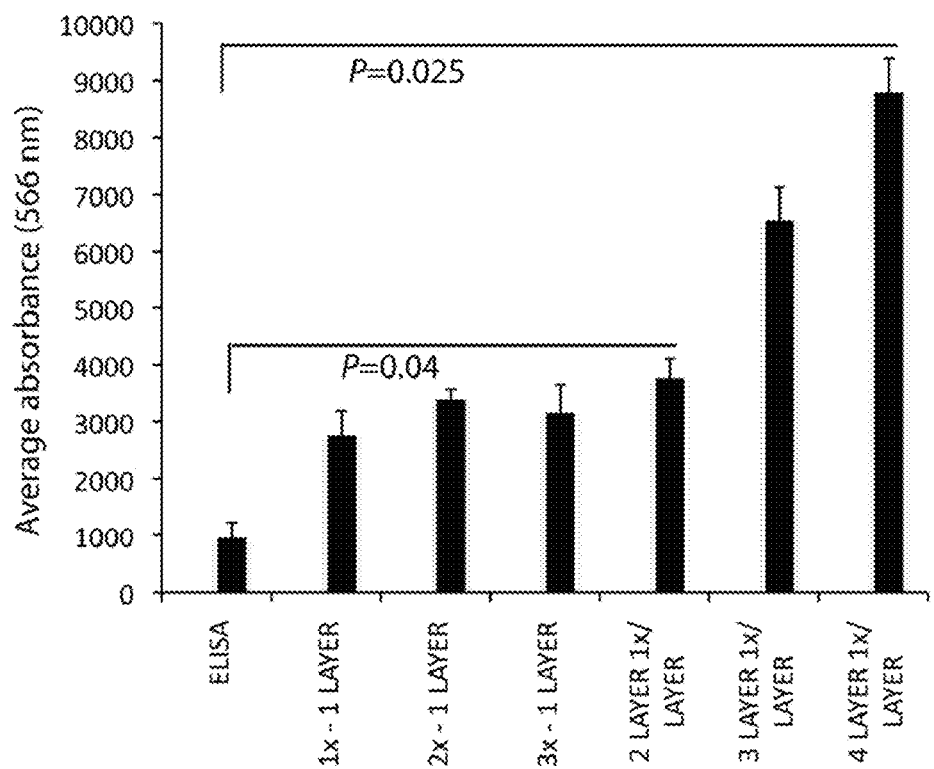
FIG. 2 shows effect of layer number on analyte binding.

Example 3: Multilayer Nets are Superior to Single Layer Nets Made with the Same Capture Agent Content Single layer, 2-layer, 3-layer and 4-layer nets were prepared which bind 1) bacterial peptidoglycan, 2) lipoteichoic acid, 3) bacterial lipopolysaccharide, 4) bacterial lipid A and 5) bacterial CpG DNA. As shown in FIG. 2 multilayers were more effective at binding analyte than single layers made using the same total amount of capture agent.

Materials

| Capture agents for bacterial nets | |
|---|---|
| 1) antibodies against peptidoglycan | |
| 2) antibodies against lipid A | |
| 3) antibodies against lipopolysaccharide | |
| 4) DNA binding peptide 1 (VLFGKLA) | (stock = 1 mg/mL) |
| 5) DNA binding peptide 2 (VMFGKLA) | (stock = 1 mg/mL) |
| 6) DNA binding peptide 6 (VFFGRLA) | (stock = 1 mg/mL) |
| Linkers | |
| 7) EMCS | (stock = 25 mM) |
| 8) EDC | (stock = 25 mM) |
| 9) BS(PEG)$_9$ | (stock = 25 mM) |
| Non-fat milk | (100%) |
| Phosphate buffered saline pH 7.4 | |
| 50 mM Tris buffer pH 7.5 | |
| Polystyrene substrate | |

Two, Three and Four Layered Nets
1) Mix antibodies against: lipid A and lipopolysaccharide and peptidoglycan in a 1:1:1 ratio into Tube A (1 ug/mL)
2) Mix DNA binding peptides at 1:1 ratio into Tube B (1 mg/mL)
3) Mix anti-bacterial antibodies and DNA binding peptides at 1:1 ratio in Tube C First Layer
4) Add [pipette] 10 uL of tube C mixture to surface to generate 1$^{st}$ layer
5) Immediately add [pipette] 1 uL EGS, EMCS and BS(PEG)$_9$ on spotted tube C mixture and mix by slightly shaking the surface back and forth within a 5 cm distance 5 to 10 times
6) Let sit for 1 hr at room temperature
7) Quench by adding [pipette] 10 uL of 50 mM Tris buffer, let sit for 10 min
8) Remove remaining liquid by pipette, wash 3 times with 50 uL PBS by pipette Second, third and fourth layers were prepared by repeating steps 11-15, above, each time pipetting the components onto the already formed layer(s). The resulting nets were stored at 4 degrees C. in PBS and 0.001% sodium azide and stored at 4 degrees Celsius until use.

Single Layer Nets with 1×, 2×, or 3× Concentration of Capture
1) Mix antibodies against: lipid A and lipopolysaccharide and peptidoglycan in a 1:1:1 ratio into Tube A (1 ug/mL (1×), 10 ug/mL (2×), 100 ug/mL (3×))
2) Mix DNA binding peptides at 1:1 ratio into Tube B (1 mg/mL (1×), 10 mg/mL (2×), 100 mg/mL (3×))
3) Mix anti-bacterial antibodies and DNA binding peptides at 1:1 ratio in Tube 1×C, 2×C, 3×C First Layer
4) Add [pipette] 10 uL of each tube C (1×C-3×C) mixture to surface to generate 1st layer
5) Immediately add [pipette] 1 uL EGS, EMCS and BS(PEG)$_9$ on spotted tube C mixture and mix by slightly shaking the surface back and forth within a 5 cm distance 5 to 10 times
6) Let sit for 1 hr at room temperature
7) Quench by adding [pipette] 10 uL of 50 mM Tris buffer, let sit for 10 min
8) Remove remaining liquid by pipette, wash 3 times with 50 uL PBS by pipette
9) Add 50 uL PBS+0.001% sodium azide and store at 4 degrees Celcius until use (can also lyophilize and store at room temperature or 4 degrees until use).

Assay Procedure
1) Single, double, triple and quadruple layered nets were built in triplicate and compared to the ELISA format (un-crosslinked absorbed capture molecules) and single nets with 1×, 2× and 3× concentrations of capture components in the presence of equimolar concentrations of EGS, EMCS and BS(PEG)$_9$ were built.
2) EDTA-treated whole blood samples were spiked with 50 pg/mL of bacterial acylated lipoptrotein labeled with rhodamine and added at 10 µL/well.
3) Samples and detection molecules were incubated for 15 minutes (or 60 minutes for ELISA) at room temperature
4) Wells were washed with 300 uL phosphate buffered saline (PBS), 0.05% Tween20, and 10% albumin (wash buffer).
5) Wells were excited at 549 nm and absorbance was measured at 566 nm by plate reader.

Results

This is an example of the principle of multi-layered nets and inherent binding capacity. Single, double, triple and quadruple layered nets were built in triplicate with capture components at a 1× concentration per layer in wells of a polystyrene plate. Single layered nets with 1×, 2× and 3× concentrations of capture components were also constructed. All nets in this experiment were built using EGS, EMCS and BS(PEG)9 crosslinkers. Net performance was compared against the standard ELISA format (standard ELISA format=un-crosslinked absorbed capture molecules). EDTA-treated whole blood samples were spiked with 50 pg/mL of bacterial acylated lipoprotein and added to each well at 10 µL/well. Samples and detection molecules were incubated for 15 minutes with each molecular net (or 60 minutes for ELISA) and washed with phosphate buffered saline (PBS), 0.05% Tween-20, and 10% albumin (wash buffer). Absorbance at 566 nm was measured by plate reader. Values represent the mean absorbance of triplicate nets. Error bars represent the standard error of the mean (SEM). P-values were obtained by unpaired student t-test. See FIG. 2.

The data represent multiple molecular nets incubated with or without excess analyte (acylated lipoprotein) in whole blood for 15 minutes, prior to wash and fluorescence analysis. The data demonstrate the importance of layering of a molecular net and the inherent binding capacity of layered molecular nets. The data also point to the significance of the layering in that 3× capture is not better than a 3 layered net with the same number of capture agents in the net.

Example 4: Example of the Value of Layered Nets in Binding Capacity of Specific Analytes in a Mixed Blood Sample To compare the properties of a layered net and a non-layered net having the same volume two bacterial capture net variants were constructed (12 replicates per variant) and evaluated for the ability to bind two bacterial analytes with very different chemical properties.

3-layered nets were constructed with capture molecules, and linkers BS(PEG)$_9$, EMCS and EGS. A single layered net of equivalent volume as the 3-layered net was constructed using the same linkers and the same number of capture molecules, BS(PEG)$_9$, EMCS and EGS.

Clinical concentrations of fluorophore-labeled bacterial analytes were spiked into whole blood and incubated with each net variant for 15 minutes and then washed off. Immobilized analyte was measured by fluorescence emission at 525 and 566 nm.

Nets were Prepared which Bind
1) bacterial peptidoglycan
2) lipoteichoic acid
3) bacterial lipopolysaccharide
4) bacterial lipid A
5) bacterial CpG DNA Materials

| Capture agents for bacterial nets | | |
|---|---|---|
| 4) | antibodies against peptidoglycan | |
| 5) | antibodies against lipid A | |
| 6) | antibodies against lipopolysaccharide | |
| 4) | NA binding peptide 1 (VLFGKLA) | (stock = 1 mg/mL) |
| 5) | DNA binding peptide 2 (VMFGKLA) | (stock = 1 mg/mL) |
| 6) | DNA binding peptide 6 (VFFGRLA) | (stock = 1 mg/mL) |
| Linkers | | |
| 7) | EMCS | (stock = 10 µM) |
| 8) | EDC | (stock = 2.5 µM) |
| 9) | BS(PEG)$_9$ | (stock = 5 µM) |

Non-fat milk (100%)
Phosphate buffered saline pH 7.4
50 mM Tris buffer pH 7.5
Polystyrene surface Methods for Building Layered Nets
9) Mix antibodies against: lipid A and lipopolysaccharide and peptidoglycan in a 1:1:1 ratio into Tube A (1 ug/mL)
10) Mix DNA binding peptides at 1:1 ratio into Tube B (1 mg/mL)
11) Mix anti-bacterial antibodies and DNA binding peptides at 1:1 ratio in Tube C
12) Add [pipette] 10 uL of tube C mixture to surface to generate 1$^{st}$ layer
13) Immediately add [pipette] 1 uL EGS, EMCS and BS(PEG)$_9$ on spotted tube C mixture and mix by slightly shaking the substrate back and forth within a 5 cm distance 5 to 10 times
14) Let sit for 1 hr at room temperature First, Second and Third Layers
1) Add [pipette] 10 uL of tube C mixture to underlayer to generate 1$^{st}$ layer
2) Immediately add [pipette] 1 uL EGS, EMCS and BS(PEG)$_9$ on spotted tube C mixture and mix by slightly shaking the surface back and forth within a 5 cm distance 5 to 10 times
3) Let sit for 1 hr at room temperature Steps 1-3 were repeated to add layers 2 and 3, with the capture agent and linker mixtures being pipetted onto the existing lower layer(s).

Methods for Building Single Layered Nets with a Volume Equivalent to Layered Nets
1. Mix antibodies against: lipid A and lipopolysaccharide and peptidoglycan in a 1:1:1 ratio into Tube A (1 ug/mL)
2. Mix DNA binding peptides at 1:1 ratio into Tube B (1 mg/mL)
3. Mix anti-bacterial antibodies and DNA binding peptides at 1:1 ratio in Tube C
4. Add [pipette] 40 uL of tube C mixture to surface to generate 1st layer
5. Immediately add [pipette] 4 uL EGS, EMCS and BS(PEG)9 on spot from tube C mixture and mix by slightly shaking the surface back and forth within a 5 cm distance 5 to 10 times
6. Let sit for 1 hr at room temperature
7. Remove remaining liquid by pipette, wash 3 times with 50 uL PBS by pipette Block nets with 100% non-fat milk for 30 minutes at room temperature Assay Procedure
1) Single or triple-layered nets of equivalent volume were built in replicates of 12.
2) EDTA-treated whole blood samples were spiked with 50 pg/mL of bacterial acylated lipoprotein labeled with rhodamine and added at 10 µL/well or 5 pg/mL of bacterial muramyl dipeptide labeled with FITC and added at 10 µL/well.
3) Samples were incubated for 15 minutes at room temperature.
4) Wells were washed with 300 uL phosphate buffered saline (PBS), 0.05% Tween-20, and 10% albumin (wash buffer).
5) Wells were excited at 490 nm and 549 nm and absorbance was measured at 525 nm and 566 nm, respectively, by plate reader.

Results

Figure 3:
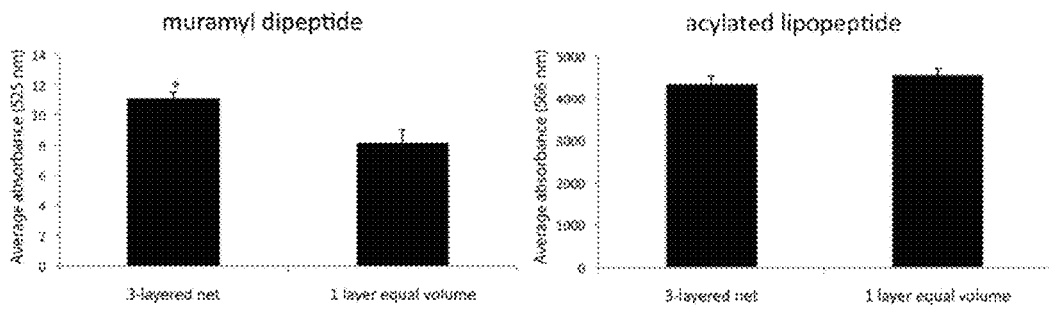
FIG. 3 shows binding properties of a layered net and a non-layered net.

The results are summarized in FIG. 3. Values represent the average fluorescence detected in the 12 replicates of each net variant. Error bars represent the standard error of the mean (SEM). The unpaired student t-test was used to compare significance. Significance was determined between the 3-layered nets and 1-layered nets of equal volume in binding muramyl dipeptide (P-value=0.005). There was no significant difference in acylated lipoprotein binding between 3-layered nets and 1-layered nets with equal volume.

This net is optimized to bind signatures of the bacterial peptidoglycan, the carbohydrate components, N-acetyl muramic acid (NAM) and N-acetyl glucosamine (NAG) and the protein component, a di-, tri- or penta-peptide (muramyl dipeptide). This example of molecular net is not optimized to detect a hydrophobic analyte connected to the peptidoglycan such as a bacterial acylated lipoprotein. However, modification of the molecular net to favor the interaction of an acylated lipoprotein by the incorporation of lipophilic capture agents and increased interlinkages can be performed.

Example 5: Bacterial Analyte Binding to Net Using Whole Blood

The data represent a number of studies analyzing the binding of numerous bacterial (and human) signatures to a molecular net designed to immobilize bacterial signatures. The data show (i) that the net can bind very low levels of numerous analytes in whole blood, (ii) that the net can bind numerous molecules with different surface chemistries simultaneously, (iii) the net can bind more analyte more rapidly than the ELISA and (iv) the net excludes the binding of a notoriously sticky protein, human fibrinogen, for which it was not designed to bind.

Figure 4:
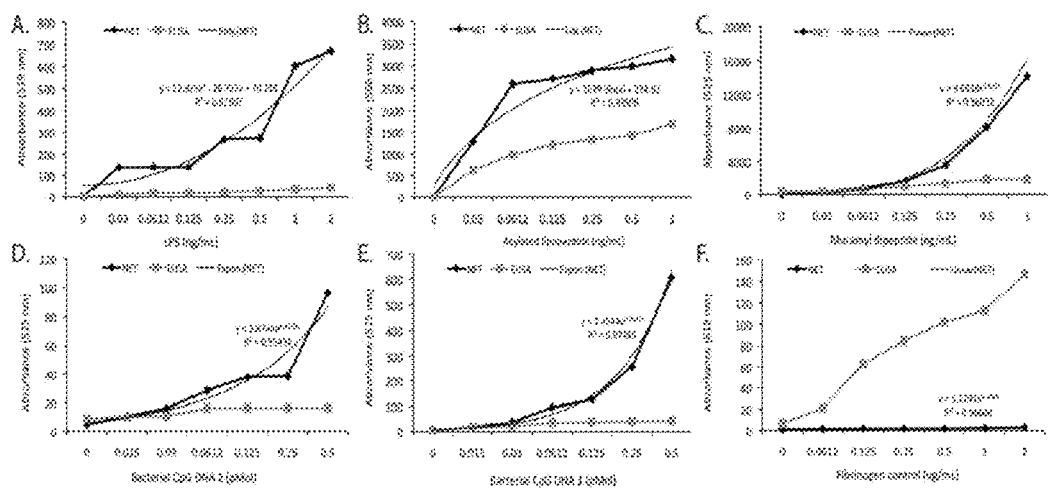
FIG. 4 shows show a comparison of the multi-analyte binding capabilities of an ELISA and a molecular net.

This example and FIG. 4 show a comparison of the multi-analyte binding capabilities of the ELISA and the molecular net. Fluorophore-labeled bacterial analytes (A, lipopolysaccharide; B, acylated lipopeptide; C, muramyl dipeptide; D and E, bacterial CpG oligonucleotides; and F, human fibrinogen as control) were spiked into EDTA-treated whole blood at clinically-relevant concentrations with replicates of the ELISA or molecular net constructed with capture components against the bacterial antigens: outer membrane components of Gram negative bacteria (lipopolysaccharide and lipid A) and cell wall components of Gram positive bacteria (peptidoglycan) and bacterial CpG DNA. Due to limitations in fluorophores, LPS and CpG DNA 2 were spiked into the same blood samples, acylated lipopeptide and CpG DNA 1 were spiked into the same blood samples and muramyl dipeptide and fibrinogen were spiked into the same blood samples. Samples were incubated with the ELISA for 60 minutes or the molecular net for 15 minutes prior to wash. Fluorescence was evaluated using a fluorescent plate reader. Values represent the average fluorescence emitted by immobilized analytes in the ELISA format (grey line) or the molecular net (black line).

Nets were prepared which bind:
6) bacterial peptidoglycan
7) lipoteichoic acid
8) bacterial lipopolysaccharide
9) bacterial lipid A
10) bacterial CpG DNA Materials

| Capture agents for bacterial nets | |
|---|---|
| 7) polyclonal antibodies against peptidoglycan | (stock = 1 mg/mL) |
| 8) polyclonal antibodies against lipid A | (stock = 1 mg/mL) |
| 9) polyclonal antibodies against lipopolysaccharide | (stock = 1 mg/mL) |
| 4) NA binding peptide 1 (VLFGKLA) | (stock = 1 mg/mL) |
| 5) NA binding peptide 2 (VMFGKLA) | (stock = 1 mg/mL) |
| 6) NA binding peptide 6 (VFFGRLA) | (stock = 1 mg/mL) |
| Linkers | |
| 7) MCS | (stock = 2M) |
| 8) GS | (stock = 1.5M) |
| 9) BS(PEG)9 | (stock = 1M) |
| 10) formaldehyde | (stock = 0.115% v/v) |
| Non-fat milk | (100%) |
| Phosphate buffered saline | pH 7.4 |
| 50 mM Tris buffer | pH 7.5 |
| Polystyrene | |

Methods for Building Layered Nets
15) Mix antibodies against: lipid A and lipopolysaccharide and peptidoglycan in a 1:1:1 ratio into Tube A (1 mg/mL)
16) Mix DNA binding peptides at 1:1 ratio into Tube B (1 mg/mL)
17) Mix anti-bacterial antibodies and DNA binding peptides at 1:1 ratio in Tube C First Layer
18) Add [pipette] 10 L of tube C mixture to surface to generate 1st layer
19) Immediately add [pipette] 4 μL of each of the following: formaldehyde, EGS, EMCS and BS(PEG)9 on spots from tube C mixture and mix by slightly shaking the surface back and forth within a 5 cm distance 5 to 10 times
20) Let sit for 1 hr at room temperature Second Layer
21) Add [pipette] 10 μL of tube C mixture to surface to generate 2st layer
22) Immediately add [pipette] 4 μL of EGS and then 4 L of EMCS on spotted tube C mixture and mix by slightly shaking the surface back and forth within a 5 cm distance 5 to 10 times
23) Let sit for 1 hr at room temperature Third Layer
24) Add [pipette] 10 μL of tube C mixture to surface to generate 3st layer
25) Immediately add [pipette] 4 μL of each of the following: EGS, EMCS and BS(PEG)9 on spotted tube C mixture and mix by slightly shaking the surface back and forth within a 5 cm distance 5 to 10 times
26) Let sit for 1 hr at room temperature Fourth Layer
27) Add [pipette] 10 μL of tube C mixture to surface to generate 4th layer
28) Immediately add [pipette] 4 μL EGS, EMCS and BS(PEG)9 on spotted tube C mixture and mix by slightly shaking the surface back and forth within a 5 cm distance 5 to 10 times
29) Let sit for 1 hr at room temperature
30) Removed remaining liquid by pipette, wash 3 times with 50 μL PBS by pipette
31) Blocked nets with 100 μL of 100% non-fat milk for 30 minutes at room temperature Methods for ELISA Coating
8) Mix antibodies against: lipid A and lipopolysaccharide and peptidoglycan in a 1:1:1 ratio into Tube A (1 mg/mL)
9) Mix DNA binding peptides at 1:1 ratio into Tube B (1 mg/mL)
10) Mix anti-bacterial antibodies and DNA binding peptides at 1:1 ratio in Tube C
11) Coated 50 μL of Tube C per well and let absorb overnight at 4° C.
12) Washed wells 3×100 μL with PBS
13) Blocked with 100 μL of 100% non-fat milk for 30 minutes at room temperature Assay Procedure
1) EDTA-treated whole blood from eight pooled donors was divided into 19 aliqots for serial dilutions.
2) 5 fluorophore-labeled bacterial analytes and 1 fluorophore-labeled human analyte (as control) with different surface chemistries were used.
3) Two kinds of analytes per dilution set was set up (LPS+CpG DNA 2; acylated lipoprotein+CpG DNA 1; and muramyl dipeptide+fibrinogen)
4) Serial dilutions of 1:2 dilution were performed with the following analytes:
   a. Lipopolysaccharide—Range: 0.03-2 ng/mL
   b. Acylated lipopeptide—Range: 0.03-1 ng/mL
   c. Muramyl dipeptide—Range: 0.03-1 ng/mL
   d. CpG ODN 1—Range: 0.015-0.5 pMol
   e. CpG ODN 2—Range: 0.015-0.5 pMol
   f. Human fibrinogen—Range: 0.06-2 μg/mL
5) 20 μL of PBS was added to each well
6) 5 μL of each dilution was added to each well and incubated for 15 minutes (for nets) and 60 minutes (ELISA) at room temperature
7) Wells were washed once with 300 uL phosphate buffered saline (PBS), 0.05% Tween-20, and 10% albumin (wash buffer)
8) Wells were excited at 490, 495, 549, 592 nm and absorbance was measured at 525, 519, 566 and 618 nm, respectively, by plate reader.

Example 6: Molecular Net to Detect *Staphylococcus aureus* Infection

This prophetic example describes fabrication of a three-layer molecular net for detection of a *Staphylococcus aureus* infection. The net binds 1) *Staphylococcus aureus;* 2) *S. aureus* peptidoglycan, 3) *S. aureus* SsaA, 4) *S. aureus* TSST-1, 5) *S. aureus* α-toxin, 6) Capsular polysaccharides, and 7) Bacterial CpG DNA.

Materials

| Capture Agents | | |
|---|---|---|
| 1) Polyclonal Antibodies against *Staphylococcus aureus* | (stock = 1 µg/mL) | |
| 2) Polyclonal Antibodies against *S. aureus* peptidoglycan | (stock = 1 µg/mL) | |
| 3) Polyclonal Antibodies against *S. aureus* SsaA | (stock = 1 µg/mL) | |
| 5) Polyclonal Antibodies against TSST-1 | (stock = 1 µg/mL) | |
| 5) Polyclonal Antibodies against α-toxin | (stock = 1 µg/mL) | |
| 6) Complement C3 | (stock = 1 ug/mL) | |
| 7) Lectin binding protein | (stock = 1 ug/mL) | |
| 8) DNA binding peptide 1 (VLFGKLA) | (stock = 1 mg/mL) | |
| 9) DNA binding peptide 2 (VMFGKLA) | (stock = 1 mg/mL) | |
| 10) DNA binding peptide 6 (VFFGRLA) | (stock = 1 mg/mL) | |
| Linker | | |
| 11) EGS | (stock = 25 mM in DMSO) | |
| 12) EMCS | (stock = 25 mM in DMSO) | |
| 13) BS(PEG)$_9$ | (stock = 250 mM in DMSO) | |
| 14) Formaldehyde | (stock = 37% v/v) | |

Methods

1. Mix capture agents 1-7 (antibodies and protein receptors) in a 1:1:1:1 ratio into Tube A (1 ug/mL)
2. Mix capture agents 8-10 (DNA binding peptides) at 1:1:1:1 ratio into Tube B (1 mg/mL)
3. Add equal parts from Tube A and Tube B to new Tube C First Layer 4. Pipette] 10 uL of Tube C mixture onto substrate (polystyrene). Immediately add 1 uL each EGS, EMCS and BS(PEG)9. Incubate at room temp for 1 hr.
5. Mix by slightly shaking the surface back and forth within a 5 cm distance 5 to 10 times
6. Quench by adding 10 uL of 50 mM Tris buffer, let sit for 10 min
7. Remove remaining liquid by pipette, wash 3 times with 50 uL PBS by pipette Second Layer 8. Repeat steps 4-7; then add 10 uL of a 0.1% w/v solution of formaldehyde in PBS, let sit for 10 minutes at room temperature.

Third Layer

9. Repeat steps 4-8 to generate.

Lyophilize or add 50 uL PBS+0.001% sodium azide and store at 4° C. until use.

TABLE 10

Multilayer Molecular Net Content

| Layer | Capture Agent(s) | Linker(s) |
|---|---|---|
| First | Antibodies, DNA binding proteins, lectin, C3 | EGS, BS(PEG)$_9$, EMCS |
| Second | Antibodies, DNA binding proteins, lectin, C3 | EGS, BS(PEG)$_9$, EMCS |
| Third | Antibodies, DNA binding proteins, lectin, C3 | EGS, BS(PEG)$_9$, EMCS |

Example 7: Molecular Net to Detect Infection by Methicillin-Resistant *Staphylococcus aureus*

This prophetic example describes fabrication of a three-layer molecular net for detection of infection by methicillin-resistant *Staphylococcus aureus*. The net binds penicillin binding protein 2a (PBP2a) and Bacterial CpG DNA.

Materials

| Capture Agents | |
|---|---|
| 1) Antibodies against PBP2a (clones AC10, 332/423, 198) | (stock = 1 µg/mL) |
| 2) DNA binding peptide 1 (VLFGKLA) | (stock = 1 mg/mL) |
| 3) DNA binding peptide 2 (VMFGKLA) | (stock = 1 mg/mL) |
| 4) DNA binding peptide 7 (RRRRRRRRRRRR) (SEQ ID NO: 38) | (stock = 1 mg/mL) |
| 5) pAb *S. aureus* | (stock = 1 µg/mL) |
| 6) mAb *S. aureus* IgM | (stock = 1 µg/mL) |
| 7) mAb Enterotoxin A/B/C1/C2/D/E clone S13 | (stock = 1 µg/mL) |
| 8) mAb *S. aureus* clone 704 | (stock = 1 µg/mL) |
| 9) pAb protein A | (stock = 1 µg/mL) |
| Linkers | |
| 5) BMPH | (stock = 285 nM) |
| 6) EGS | (stock = 5.9-6.03 uM) |
| 7) EMCS | (stock = 0.03 uM) |
| 8) BS$^3$ | (stock = 14.4 uM) |
| 8) Formaldehyde | (stock = 37% w/v) |

Detection Agents

9) Dye-labeled *S. aureus* probe (SEQ ID NO: 35)
GCCAGCAGCGCGGTAATACG
(GenBank accession no. M87484)

10) Dye-labeled *S. aureus* probe (SEQ ID NO: 36)
GGACTACCAGGGTATCTAATCC
(GenBank accession no. M87484)

11) Dye-labeled *S. aureus* probe (SEQ ID NO: 15)
GGTATGTGGAAGTTAGATTGGGATATAGG

12) Dye-labeled *S. aureus* probe (SEQ ID NO: 16)
AATAGAGAAAAAAAAAAGATGGCAAAG

13) Dye-labeled *S. aureus* probe (SEQ ID NO: 17)
AATAGAGAAAAGAAAAAAGATGGCAAAG

14) Dye-labeled *S. aureus* probe (SEQ ID NO: 18)
AGATGTGCACAGTTATTACACATAT

10) Dye-labeled *S. aureus* probe (SEQ ID NO: 19)
GCTATTATTTACTTGAAATGAAAGACTGCGGAGGCTAACT 11) Dye-labeled *S. aureus* probe (SEQ ID NO: 20)
ACGACAAVVATGCAVVAVVTG
(GenBank accession number X68417)

11) Dye-labeled mecA probe (SEQ ID NO: 21)
GCAATACAATCGCACTACATTAATAG
(GenBank accession no. X52593)

-continued

12) Dye-labeled mecA probe
    CATTTTGAGTTCTGCAGTACCG (SEQ ID NO: 22)
    (GenBank accesssion no. X52593)

13) Dye-labeled mecA probe
    TCATAGCGTCATTATTCC (SEQ ID NO: 23)

14) Dye-labeled mecA probe
    ATCACTTGGTATATCTTCACC (SEQ ID NO: 24)

15) Dye-labeled mecA probe
    TATCCACCCTCAAACAGGTGAATT (SEQ ID NO: 25)

16) Dye-labeled mecA-mecRI probe
    CCAAACCCGACAACTAC (SEQ ID NO: 26)

17) Dye-labeled mecA-mecRI probe
    CGTGTCAGATACATTTCG (SEQ ID NO: 27)

18) Dye-labeled mecI probe
    CCGGAATTCGCATATGGATTTCAC (SEQ ID NO: 28)

19) Dye-labeled mecI probe
    GATGGTTCGTAGGTTATGTTG (SEQ ID NO: 29)

20) Dye-labeled mecI probe
    CGGATCCGAAATGGAATTAATATAATG (SEQ ID NO: 30)

21) Dye-labeled mecI probe
    CGGAATTCGACTTGATTGTTTCCT (SEQ ID NO: 31)

Bovine serum albumin (BSA) (stock=1 mg/mL)

Methods

1. PBP2a antibodies are diluted to (1 ug/mL) in Tube A
2. Mix DNA binding peptides at 1:1 ratio into Tube B (1 mg/mL)
3. Mix antibodies against PBP2a and DNA binding peptides at 1:1 (volume:volume) ratio in Tube C Underlayer 4. Add [pipette] 5 uL of BSA onto substrate
5. Immediately add [pipette 1 uL EDC to spotted BSA, add 1 uL of formaldehyde to spotted BSA
6. Mix by slightly shaking the surface back and forth within a 5 cm distance 5 to 10 times
7. Let sit at room temperature for 1 hr [this step will make a highly crosslinked base to serve a structural role]
8. Quench by adding [pipette] 10 uL of 50 mM Tris buffer, let sit for 10 min
9. Remove remaining liquid by pipette, wash 3 times with 50 uL PBS by pipette First Layer 10. Add [pipette] 10 uL of tube A mixture to surface to generate $1^{st}$ layer
11. Immediately add [pipette] 1 uL DTSSP on spotted tube A mixture and mix by slightly shaking the surface back and forth within a 5 cm distance 5 to 10 times [to build longer spacer arms between a subset of capture molecules].
12. Wait 5 minutes then add 1 uL sulfo DST to spot and mix by slightly shaking the surface back and forth within a 5 cm distance 5 to 10 times [to build shorter spacer arms between a subset of capture molecules and generate a completed $2^{nd}$ layer—$1^{st}$ layer to capture fragmented PBP2a analyte]
13. Let sit for 1 hr at room temperature
14. Quench by adding [pipette] 10 uL of 50 mM Tris buffer, let sit for 10 min
15. Remove remaining liquid by pipette, wash 3 times with 50 uL PBS by pipette Second Layer 16. Add 5 uL of tube B to the top of the layered capture molecules
17. Quickly add 1 uL of DTSSP on spotted tube B mixture and mix by slightly shaking the surface back and forth within a 5 cm distance 5 to 10 times [to build nucleic acid capture layer 1]
18. Let sit for 1 hr at room temperature
19. Quench by adding [pipette] 10 uL of 50 mM Tris buffer, let sit for 10 min
20. Remove remaining liquid by pipette, wash 3 times with 50 uL PBS by pipette Third Layer 21. Add 10 uL of tube C to the layered net
22. Immediately add [pipette] 1 uL DTSSP on spotted mixture and mix by slightly shaking the surface back and forth within a 5 cm distance 5 to 10 times [this step enables one to build longer spacer arms between a subset of capture molecules]
23. Wait 5 minutes then add 1 uL sulfo DST to spot and mix by slightly shaking the surface back and forth within a 5 cm distance 5 to 10 times [this step enables one to build shorter spacer arms between a subset of capture molecules and generate a completed 3rd layer—this layer can capture fragmented or larger or whole PBP2a analyte and fragmented or larger or whole nucleic acids]
24. Quench by adding [pipette] 10 uL of 50 mM Tris buffer, let sit for 10 min
25. Remove remaining liquid by pipette, wash 3 times with 50 uL PBS by pipette
26. Add 50 uL PBS+0.001% sodium azide and store at 4 degrees Celcius until use (can also lyophilize and store at room temperature or 4 degrees until use).

TABLE 11

Multilayer Molecular Net Content

| Layer | Capture Agent | Linkers |
|---|---|---|
| First | Antibodies | DTSSP, DST |
| Second | DNA binding peptides | DTSSP |
| Third | Antibodies and DNA binding peptides | DTSSP, DST |

Example 8: Gram Negative Bacterial Sepsis Assay

Figure 5:
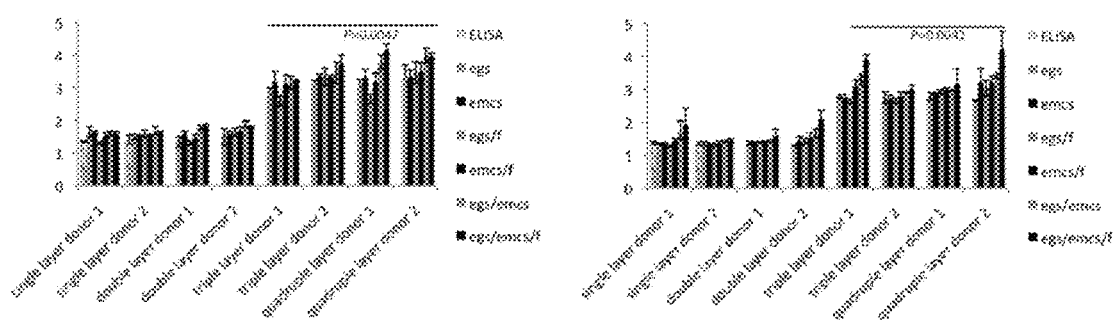
FIG. 5 shows binding by a molecular net for diagnosing septicemia.

This example demonstrates that the molecular net designed to capture signatures from gram negative bacteria can bind clinically-relevant levels of endotoxin and whole CFU in unprocessed blood samples within 15 to 30 minutes. See FIG. 5.

Background

This example describes a molecular net for diagnosing septicemia in a patient from a blood sample. Septic patients can have 5-1000 pg/mL LPS and 0-200 CFU/mL of bacteria in their blood. A net is prepared which binds 1) lipopolysaccharide (LPS). 2) Lipid A, 3) bacterial CpG DNA, 4) acylated lipoprotein and 6) *Eschericia coli* bacteria.

Materials

| Capture Agents | |
|---|---|
| 1) Antibodies against lipopolysaccharide (LPS) | (stock = 1 μg/mL) |
| 2) Antibodies against lipid A | (stock = 1 μg/mL) |
| 3) DNA binding peptide 1 (VLFGKLA) | (stock = 1 mg/mL) |
| 4) DNA binding peptide 2 (VMFGKLA) | (stock = 1 mg/mL) |
| 5) DNA binding peptide 6 (VFFGRLA) | (stock = 1 mg/mL) |
| Linkers | |
| 5) EMCS | (stock = 25 mM) |
| 7) EDC | (stock = 25 mM) |
| 8) Formaldehyde | (stock = 3.7% v/v) |

Detection System
1) Dye-conjugated antibodies against lipopolysaccharide
2) Dye-conjugated antibodies against lipid A 3) Dye-conjugated
   CCTTCCTCCCAACTTAAAGTGCTT (Pseudomonas) (SEQ ID NO: 3)

4) Dye-conjugated
   GGAGTAAAGTTAATACCTTTGCTCATT (Escherichia) (SEQ ID NO: 33)

5) Dye-conjugated
   ACGACAGCCATGCAGCACCT (SEQ ID NO: 34)
   (GenBank Accession number AF233451)

Bovine serum albumin (BSA) (stock=1 mg/mL)
Phosphate buffered saline pH 7.4
50 mM Tris buffer pH 7.5
Polystyrene surface Methods
1. Mix anti-lipid A and lipopolysaccharide antibodies in a 1:1 ratio into Tube A (1 ug/mL)[1]
2. Mix DNA binding peptides at 1:1 ratio into Tube B (1 mg/mL)
3. Mix anti-PBP2a antibodies and DNA binding peptides at 1:1 ratio in Tube C Underlayer
4. Add [pipette] 5 uL of BSA onto surface
5. Immediately add [pipette 1 uL EDC to spotted BSA, add 1 uL of formaldehyde to spotted BSA
6. Mix by slightly shaking the surface back and forth within a 5 cm distance 5 to 10 times
7. Let sit at room temperature for 1 hr [this step will make a highly crosslinked base to serve a structural role]
8. Quench by adding [pipette] 10 uL of 50 mM Tris buffer, let sit for 10 min
9. Remove remaining liquid by pipette, wash 3 times with 50 uL PBS by pipette First Layer
10. Add [pipette] 10 uL of tube A mixture to surface to generate $1^{st}$ layer
11. Immediately add [pipette] 1 uL DTSSP on spotted tube A mixture and mix by slightly shaking the surface back and forth within a 5 cm distance 5 to 10 times [to build longer spacer arms between a subset of capture molecules]
12. Wait 5 minutes then add 1 uL sulfo DST to spot and mix by slightly shaking the surface back and forth within a 5 cm distance 5 to 10 times [to build shorter spacer arms between a subset of capture molecules and generate a completed $2^{nd}$ layer—$1^{st}$ layer to capture fragmented PBP2a analyte]
13. Let sit for 1 hr at room temperature
14. Quench by adding [pipette] 10 uL of 50 mM Tris buffer, let sit for 10 min
15. Remove remaining liquid by pipette, wash 3 times with 50 uL PBS by pipette Second Layer
16. Add 5 uL of tube B to the top of the layered capture molecules
17. Quickly add 1 uL of DTSSP on spotted tube B mixture and mix by slightly shaking the surface back and forth within a 5 cm distance 5 to 10 times [to build nucleic acid capture layer 1]
18. Let sit for 1 hr at room temperature
19. Quench by adding [pipette] 10 uL of 50 mM Tris buffer, let sit for 10 min
20. Remove remaining liquid by pipette, wash 3 times with 50 uL PBS by pipette Third Layer
21. Add 10 uL of tube C to the layered net
22. Immediately add [pipette] 1 uL DTSSP on spotted mixture and mix by slightly shaking the surface back and forth within a 5 cm distance 5 to 10 times [this step enables one to build longer spacer arms between a subset of capture molecules]
23. Wait 5 minutes then add 1 uL sulfo DST to spot and mix by slightly shaking the surface back and forth within a 5 cm distance 5 to 10 times [this step enables one to build shorter spacer arms between a subset of capture molecules and generate a completed $3^{rd}$ layer—this layer can capture fragmented or larger or whole PBP2a analyte and fragmented or larger or whole nucleic acids]
24. Quench by adding [pipette] 10 uL of 50 mM Tris buffer, let sit for 10 min
25. Remove remaining liquid by pipette, wash 3 times with 50 uL PBS by pipette
26. Add 50 uL PBS+0.001% sodium azide and store at 4 degrees Celcius until use (can also lyophilize and store at room temperature or 4 degrees until use).

The Assay Procedures were as Follows:
1. Layered nets were built in replicates according to methods above and blocked in 20% BSA in PBS for 30 minutes.
2. Block was removed from the wells containing nets and washed with PBS
3. Human whole blood samples were spiked with *E. coli* or purified LPS
4. Samples were then incubated with 50 uL of a 1:46 dilution of dye-labeled detection system with each net for 30 minutes
5. Nets were washed with 0.3 mL PBS, 0.5% Tween-20, 0.75% albumin and 0.5% casein (wash buffer) and quickly rinsed with PBS
6. The wells were measured in each well by plate reader

TABLE 12

Multilayer Molecular Net Content

| Layer | Capture Agent | Linkers |
|---|---|---|
| First | Antibodies | DTSSP, DST |
| Second | DNA binding peptides | DTSSP |
| Third | Antibodies and DNA binding peptides | DTSSP, DST |

Example 9: Screening Molecular Nets for Enhanced Detection of Analytes of a Bacterial or Viral Infection 30 net candidates were screened in triplicate in polystyrene wells. In each case the capture agents were antibodies against the outer-membrane of gram-negative bacteria (lipopolysaccharide and lipid A) and bacterial DNA binding peptides, with the variables being (i) the combination of chemical crosslinking agent(s) and (ii) the number of net layers. As a reference (hereinafter referred to as "ELISA"), the capture agent mixture without crosslinking agents was adsorbed to the substrate and analytes bound and detected.

Nets were Prepared which Bind
1) human interferon-α
2) human interferon-β

Nets were Prepared which Bind
1) bacterial peptidoglycan
2) bacterial lipopolysaccharide Materials

| Capture Agents for viral infection nets | | |
|---|---|---|
| 1) | Anti-human interferon- antibodies | (stock = 1 mg/mL) |
| 2) | Anti-human interferon- antibodies | (stock = 1 mg/mL) |
| Capture Agents for bacterial infection nets | | |
| 1) | Anti-lipopolysaccharide antibodies | (stock = 1 mg/mL) |
| 2) | Anti-peptidoglycan antibodies | (stock = 1 mg/mL) |
| Linkers | | |
| 1) | Formaldehyde | (stock = 16% w/v) |
| 2) | EGS | (stock = 25 mM in DMSO) |
| 3) | EMCS | (stock = 25 mM in DMSO) |

Samples
1) EDTA-treated virus-infected whole blood from female donor 1
2) DTA-treated virus-infected whole blood from female donor 2
3) EDTA-treated whole blood from healthy male donor 1
4) EDTA-treated whole blood from healthy male donor 2
5) CFUs from bacterial colony isolated on a streaked plate (source=human sample)

Biotinylated Detection Agents for Viral Infection Nets
1) Anti-human interferon-α antibodies
2) Anti-human interferon-β antibodies Biotinylated Detection Agents for Bacterial Infection Nets
1) Anti-lipopolysaccharide antibodies
2) Anti-peptidoglycan antibodies Phosphate buffered saline (PBS)
Tween-20
50 mM Tris buffer pH 7.5
Egg albumin
Skim milk Methods Preparation of Detection Molecules
1. For biotin reconstitution, biotin was equilibrated to room temperature and then resuspended in 0.246 mL of DMSO to give a final concentration of 83 mM biotin.
2. 50 μL of each antibody type was combined in a single tube (one for viral and one for bacterial) and brought to room temperature before the addition of 8 uL of biotin to reach a final concentration of 6.8 mM biotin/tube.
3. Each reaction was incubated in the dark at room temperature for 90 minutes until the reaction was complete.
4. The pooled detection molecules were dialyzed overnight in PBS at 4° C.
5. Long-term storage in PBS at −20° C.

Procedure for ELISA Coating
1. Pooled detection molecules at a 1:1 ratio of capture agents for viral nets.
2. Pooled detection molecules at a 1:1 ratio of capture agents for bacterial nets.
3. Coated ELISA by adding 10 uL of viral or bacterial capture components (approximately 10 ug capture components/well) into wells of a polystyrene plate O/N at 4° C.
4. Next day, removed polystyrene plates from 4° C., allowed them to reach room temperature, washed wells with ELISA format to remove unabsorbed viral and bacterial capture molecules.

Procedure for Net Construction
1. To wells where bacterial and viral nets were to be constructed, added 10 uL of viral or bacterial capture components+1 uL of each crosslinker to respective wells
2. Mixed briefly by shaking plate
3. Let stand for 1 hour
4. Removed unbound capture molecules, washed with PBS
5. Repeated steps 3 through 6 for additional layers
6. Blocked nets in 100% nonfat milk for 20 minutes at room temperature Assay Procedure
1. Single, double, triple and quadruple layered nets were built in triplicate according to methods above.
2. EDTA-treated whole blood samples (for viral net: blood taken from a virally-infected individual diluted 1:1000 in PBS; for bacterial net: a bacterial colony diluted 1:1500 in PBS and then diluted 1:5 in whole blood) and added to each net at 10 μL/well.
3. To samples, biotinylated detection molecules were added at 5 L/well
4. Samples and detection molecules were incubated with each net for 15 minutes (or 60 minutes for ELISA)
5. Wells were washed with 0.3 mL phosphate buffered saline (PBS), 0.05% Tween-20, and 10% egg albumin (wash buffer).
6. For detection step, goat anti-biotin conjugated to colloidal gold (20 nm) particles antibodies were used at a 1:1000 dilution in skim milk and incubated for 30 minutes at room temperature (10 L/well).
7. The wells were washed with 0.3 mL wash buffer per well
8. The absorbance in each well was measured by plate reader Number and composition of layers are 1, 2, 3, and 4 layers composed of formaldehyde (F), and/or EMCS, and/or EGS, alone or in combination (TABLE 13).

TABLE 13

Molecular Net Content In Screening Experiment

| Layer | Capture Agent | Linkers |
|---|---|---|
| First | Antibodies | EGS, EMCS, EGS + EMCS, EGS + F or EMCS + F |
| Second | Antibodies | EGS, EMCS, EGS + EMCS, EGS + F or EMCS + F |
| Third | Antibodies | EGS, EMCS, EGS + EMCS, EGS + F or EMCS + F |

TABLE 13-continued

Molecular Net Content In Screening Experiment

| Layer | Capture Agent | Linkers |
|---|---|---|
| Fourth | Antibodies | EGS, EMCS, EGS + EMCS, EGS + F or EMCS + F |

Example 10: Detection of Gram Negative Bacteria and Analytes from Gram Negative Bacteria in Human Blood EDTA-treated whole blood was spiked at concentrations found in clinical sepsis patient blood (spiked with a mixture of the following: acylated lipoprotein-30 pg/mL; LPS-3 pg/mL; *E. coli* DNA-0.06 pMol; *E. coli*-40 CFU/mL and *Candida albicans* (yeast control) 40 cells/mL). 50 uL of spiked sample was incubated in triplicate molecular nets with 5 uL of the Gram-negative colorimetric detection system and incubated for 15 minutes. For the ELISA wells, 50 uL of the identical blood sample was incubated for 60 minutes prior to the addition of 5 uL of detection system (same as used with the molecular nets), and was incubated for 30 minutes at room temperature. Wells were washed with 300 uL of wash buffer and plates were quantified reading absorbance at 510 on a plate reader.

Molecular nets were prepared to immobilize the following analytes associated with gram-negative bacterial infections:
  lipopolysaccharide
  lipid A-acylated lipoprotein
  CpG bacterial DNA
  Gram-negative bacterial CFU
Net Composition and Fabrication

| Capture agents- | | |
|---|---|---|
| 1) | Antibodies against lipopolysaccharide | (stock = 1 ug/mL) |
| 2) | Antibodies against lipid A | (stock = 1 ug/mL) |
| 3) | Antibodies against peptidoglycan | (stock = 1 ug/mL) |
| 3) | NA binding peptide 1 (VLFGKLA) | (stock = 1 mg/mL) |
| 4) | NA binding peptide 2 (VMFGKLA) | (stock = 1 mg/mL) |
| 5) | NA binding peptide 6 (VFFGRLA) | (stock = 1 mg/mL) |
| Linkers are- | | |
| 1) | BS(PEG)$_9$ | (stock = 7.9 mM in DMSO) |
| 2) | EGS | (stock = 2.5 mM in DMSO) |
| 3) | EMCS | (stock = 1.4 mM in DMSO) |
| 4) | Formaldehyde | (stock = 3.7% v/v in ddH2O) |

Molecules to be Detected by Gram-Negative Detection System
  1) Gram negative bacterial CFUs
  2) Gram negative outer membrane
  3) Lipopolysaccharide
  4) Lipid A
  5) Acylated lipopeptide
  6) Gram negative CpG 16s rDNA
Molecules in Gram-Negative Detection System
  1) polyclonal antibodies against lipid A (stock=1 mg/mL)
  2) polyclonal antibodies against lipopolysaccharide (stock=1 mg/mL)
  3) Gram-negative bacterial probe 5'-biotin-ACGACAGC-CATGCAGCACCT stock=500 pmol)

Dyes
  1) 'Super black' dye concentrate
  2) 'Royale blue' dye concentrate
Phosphate buffered saline (PBS)
Tween-20
50 mM Tris buffer pH 7.5
Avidin (from egg white)
Skim milk
Polystyrene surface
Methods
Colorimetric Labeling of Detection Systems
1) A mixture of the following was generated and called 'blue-black1'-1 part blue, 2 parts black.
2) To biotinylated DNA probes: 100 pmol per probe was incubated with 50 μL of 100% egg white (source of avidin) in phosphate buffered saline to a total volume of 100 μL; binding reaction took place overnight at 4° C.
3) Added avidin-bound DNA probes to respective tubes containing 100 μL dye and 50 L of antibodies to a tube
4) Incubated with dye for 48 hrs at 4° C.
5) Added 3.7% (w/v) final formaldehyde to conjugate adsorbed dyes, incubated at RT or 1 hr
6) Dialyzed in 50× volume of phosphate buffered saline O/N at 4° C.
7) Next day, replaced phosphate buffered saline with fresh saline buffer, incubated/N at 4° C.
8) Next day, replaced phosphate buffered saline with fresh saline buffer, incubated O/N at 4° C.
9) Removed from dialysis cassette and assessed binding using net assays
Procedure for ELISA Coating
1. Pooled detection molecules at a 1:1 volume-per-volume ratio of capture agents for bacterial nets.
2. Coated ELISA by adding 10 uL of bacterial capture components (approximately 10 ug capture components/well) into wells of a polystyrene plate O/N at 4° C.
3. Next day, removed polystyrene plates from 4° C., allowed them to reach room temperature, washed wells with ELISA format to remove unabsorbed viral and bacterial capture molecules.
Procedure for Net Construction
Underlayer
32) Add [pipette] 10 μL of capture mixture to surface
33) Immediately add [pipette] 5 μL formaldehyde on spotted capture molecules and mix by slightly shaking the surface back and forth within a 5 cm distance 5 to 10 times
34) Let sit for 1 hr at room temperature
First Layer
35) Add [pipette] 10 μL of capture mixture to surface to generate $1^{st}$ layer
36) Immediately add [pipette] 1 μL of EGS and then 4 μL of EMCS and then 2 uL of BS(PEG)$_9$ on capture mixture and mix by slightly shaking the surface back and forth within a 5 cm distance 5 to 10 times
37) Let sit for 1 hr at room temperature
Second Layer
38) Add [pipette] 10 μL of capture mixture to surface to generate $2^{nd}$ layer
39) Immediately add [pipette] 1 μL of EGS and then 4 μL of EMCS and then 2 uL of BS(PEG)$_9$ on capture mixture and mix by slightly shaking the surface back and forth within a 5 cm distance 5 to 10 times
40) Let sit for 1 hr at room temperature
Third Layer
41) Add [pipette] 10 μL of capture mixture to surface to generate $3^{rd}$ layer 42) Immediately add [pipette] 1 μL of EGS and then 4 μL of EMCS and then 2 uL of BS(PEG)$_9$ on capture mixture and mix by slightly shaking the surface back and forth within a 5 cm distance 5 to 10 times
43) Let sit for 1 hr at room temperature
44) Removed remaining liquid by pipette, wash 3 times with 50 μL PBS by pipette
45) Blocked nets with 100 μL of 1:1 ratio of egg white and 100% non-fat milk for 30 minutes at room temperature Assay Procedure
1. Triple layered nets were built in triplicate according to methods above.
2. EDTA-treated whole blood samples were spiked with a mixture of the following: acylated lipoprotein—30 pg/mL; LPS—3 pg/mL; *E. coli* DNA—0.06 pMol; *E. coli*—40 CFU/mL and *Candida albicans* (yeast control)—40 cells/mL and added at 50 μL per well
3. To samples, detection molecules were added at 5 μL/well
4. Samples and detection molecules were incubated with each net for 15 minutes (or 60 minutes for ELISA)
5. Wells were washed with 0.3 mL phosphate buffered saline (PBS), 0.05% Tween-20, and 10% egg albumin (wash buffer).
6. The absorbance in each well was measured by plate reader Number and composition of bacterial capture net composed of Formaldehyde, BS(PEG)$_9$, EGS and EMCS (TABLE 14).

TABLE 14

Molecular Net Content In Screening Experiment

| Layer | Capture Agent | Linkers |
|---|---|---|
| Underlayer | Antibodies and DNA capture molecules | Formaldehyde |
| First | Antibodies and DNA capture molecules | EGS, EMCS, BS(PEG)$_9$ |
| Second | Antibodies and DNA capture molecules | EGS, EMCS, BS(PEG)$_9$ |
| Third | Antibodies and DNA capture molecules | EGS, EMCS, BS(PEG)$_9$ |

Figure 6:
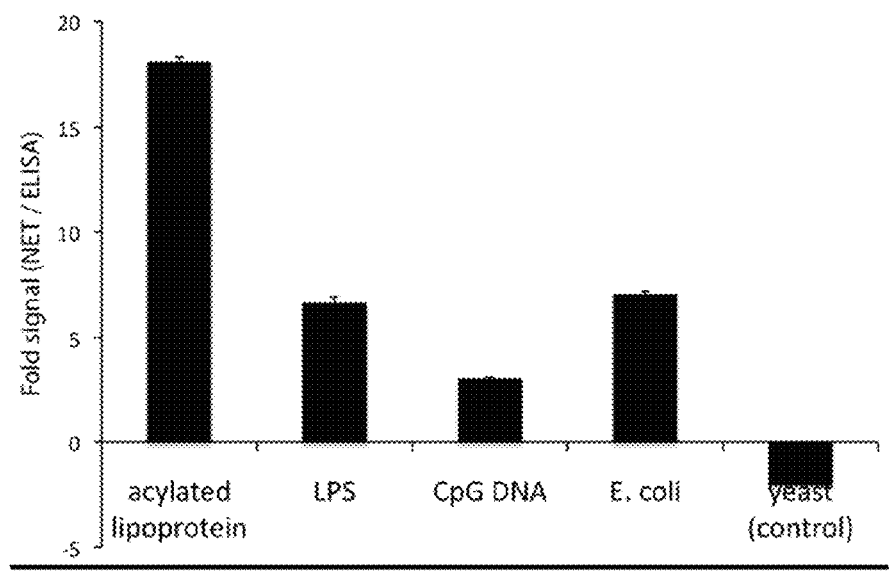
FIG. 6 shows signal to noise ratios in an assay for Gram negative bacterial infection.

Results are shown in FIG. 6. The data from FIG. 6 demonstrate that multiple analytes, each having a plurality of surface chemistries can be immobilized on the same net within 15 minutes in a complex blood sample. Additionally, the data demonstrate the specificity of the molecular net built to capture gram-negative analytes, as the yeast analytes did not bind. Conventional testing examines the presence of CFUs in blood by culture or the presence of endotoxin in blood by the Limulus lysate assay. The significance of the current invention is the reduction in time-to-answer (15 minutes) and the scope of different analytes that can be tested for in a single sample (whole cells, proteins, nucleic acids, polysaccharides and lipids that are characteristic of gram-negative bacteria).

Example 11: Detection of Gram Negative and Gram Positive Bacterial Cells in Blood

*Listeria monocytogenes* cells (Gram positive) and *E. coli* cells (Gram negative) were spiked at 20 CFU/mL into whole blood from a human donor. Fungal cells (20 cells/mL) were included as a negative control.

Molecular nets were prepared to immobilize the following analytes associated with gram-negative and gram-positive bacterial infections:
lipopolysaccharide
lipid A
acylated lipoprotein
CpG bacterial DNA
Gram-negative bacterial CFU
Gram-positive bacterial CFU
Peptidoglycan Net Composition and Fabrication

| Capture agents- | | |
|---|---|---|
| 1) | Antibodies against lipopolysaccharide | (stock = 1 ug/mL) |
| 2) | Antibodies against lipid A | (stock = 1 ug/mL) |
| 3) | Antibodies against peptidoglycan | (stock = 1 ug/mL) |
| 4) | DNA binding peptide 1 (VLFGKLA) | (stock = 1 mg/mL) |
| 5) | DNA binding peptide 2 (VMFGKLA) | (stock = 1 mg/mL) |
| 6) | DNA binding peptide 6 (VFFGRLA) | (stock = 1 mg/mL) |
| Linkers are- | | |
| 1) | BS(PEG)$_9$ | (stock = 7.9 mM in DMSO) |
| 2) | EGS | (stock = 2.5 mM in DMSO) |
| 3) | EMCS | (stock = 1.4 mM in DMSO) |
| 4) | formaldehyde | (stock = 3.7% v/v in ddH2O) |

Molecules to be detected by Gram-negative detection system
7) Gram negative bacterial CFUs
8) Gram negative outer membrane
9) Lipopolysaccharide
10) Lipid A
11) Acylated lipopeptide
12) Gram negative CpG 16s rDNA Molecules to be Detected by Gram-Positive Detection System
13) Peptidoglycan
14) Gram positive CpG 16s rDNA Molecules in Gram-Negative Detection System
1) polyclonal antibodies against lipid A (stock=1 mg/mL)
2) polyclonal antibodies against lipopolysaccharide (stock=1 mg/mL)
3) Gram-negative bacterial probe 5'-biotin-ACGACAGC-CATGCAGCACCT (stock=500 pmol)

Molecules in Gram-Positive Detection System
1) antibodies against peptidoglycan (stock=1 mg/mL)
2) Gram-positive bacterial probe 5'-biotin-ACGACAAC-CATGCACCACCTG (SEQ ID NO: 37) (stock=100 pmol)

Dyes
3) 'Super black' dye concentrate
4) 'Royale blue' dye concentrate
Phosphate buffered saline (PBS)
Tween-20
50 mM Tris buffer pH 7.5
Avidin (from egg white)
Skim milk
Polystyrene surface Methods
Colorimetric Labeling of Detection Systems
10) A mixture of the following was generated and called 'blue-black1'—1 part blue, 2 parts black for the Gram-negative detection system.

11) A mixture of the following was generated and called 'black'—1 part black for the Gram-positive detection system.
12) To biotinylated DNA probes: 100 pmol per probe was incubated with 50 μL of 100% egg white (source of avidin) in phosphate buffered saline to a total volume of 100 μL; binding reaction took place overnight at 4° C.
13) Added avidin-bound DNA probes to respective tubes containing 100 μL dye and 50 uL of antibodies to a tube
14) Incubated with dye for 48 hrs at 4° C.
15) Added 3.7% (w/v) final formaldehyde to conjugate adsorbed dyes, incubated at RT for 1 hr
16) Dialyzed in 50× volume of phosphate buffered saline O/N at 4° C.
17) Next day, replaced phosphate buffered saline with fresh saline buffer, incubated O/N at 4° C.
18) Next day, replaced phosphate buffered saline with fresh saline buffer, incubated O/N at 4° C.
19) Removed from dialysis cassette and assessed binding using net assays Procedure for ELISA Coating
1. Pooled detection molecules at a 1:1 volume-per-volume ratio of capture agents for bacterial nets.
2. Coated ELISA by adding 10 uL of bacterial capture components (approximately 10 ug capture components/well) into wells of a polystyrene plate O/N at 4° C.
3. Next day, removed polystyrene plates from 4° C., allowed them to reach room temperature, washed wells with ELISA format to remove unabsorbed viral and bacterial capture molecules.

Procedure for Net Construction
Underlayer
46) Add [pipette] 10 μL of capture mixture to surface
47) Immediately add [pipette] 5 μL formaldehyde on spotted capture molecules and mix by slightly shaking the surface back and forth within a 5 cm distance 5 to 10 times
48) Let sit for 1 hr at room temperature
First Layer
49) Add [pipette] 10 μL of capture mixture to surface to generate $1^{st}$ layer
50) Immediately add [pipette] 1 μL of EGS and then 4 L of EMCS and then 2 uL of BS(PEG)$_9$ on capture mixture and mix by slightly shaking the surface back and forth within a 5 cm distance 5 to 10 times
51) Let sit for 1 hr at room temperature
Second Layer
52) Add [pipette] 10 μL of capture mixture to surface to generate $2^{nd}$ layer
53) Immediately add [pipette] 1 μL of EGS and then 4 μL of EMCS and then 2 uL of BS(PEG)$_9$ on capture mixture and mix by slightly shaking the surface back and forth within a 5 cm distance 5 to 10 times
54) Let sit for 1 hr at room temperature
Third Layer
55) Add [pipette] 10 μL of capture mixture to surface to generate $3^{rd}$ layer
56) Immediately add [pipette] 1 μL of EGS and then 4 μL of EMCS and then 2 uL of BS(PEG)$_9$ on capture mixture and mix by slightly shaking the surface back and forth within a 5 cm distance 5 to 10 times
57) Let sit for 1 hr at room temperature
58) Removed remaining liquid by pipette, wash 3 times with 50 μL PBS by pipette
59) Blocked nets with 100 μL of 1:1 ratio of egg white and 100% non-fat milk for 30 minutes at room temperature Number and composition of bacterial capture net composed of Formaldehyde, BS(PEG)$_9$, EGS and EMCS (TABLE 15).

TABLE 15

Molecular Net Content In Screening Experiment

| Layer | Capture Agent | Linkers |
| --- | --- | --- |
| Underlayer | Antibodies and DNA capture molecules | Formaldehyde |
| First | Antibodies and DNA capture molecules | EGS, EMCS, BS(PEG)$_9$ |
| Second | Antibodies and DNA capture molecules | EGS, EMCS, BS(PEG)$_9$ |
| Third | Antibodies and DNA capture molecules | EGS, EMCS, BS(PEG)$_9$ |

Assay Procedure
1. Triple layered nets were built in triplicate according to methods above.
2. EDTA-treated whole blood samples were spiked with a mixture of the following: *Listeria monocytogenes*—40 CFU/mL, *Eschericia coli*—40 CFU/mL and *Candida albicans* (yeast control)—40 cells/mL and added at 50 μL per well
3. To samples, detection molecules were added at 5 μL/well
4. Samples and detection molecules were incubated with each net for 15 minutes (or 60 minutes for ELISA)
5. Wells were washed with 0.3 mL phosphate buffered saline (PBS), 0.05% Tween-20, and 10% egg albumin (wash buffer).
6. The absorbance in each well was measured by plate reader.

Figure 7:
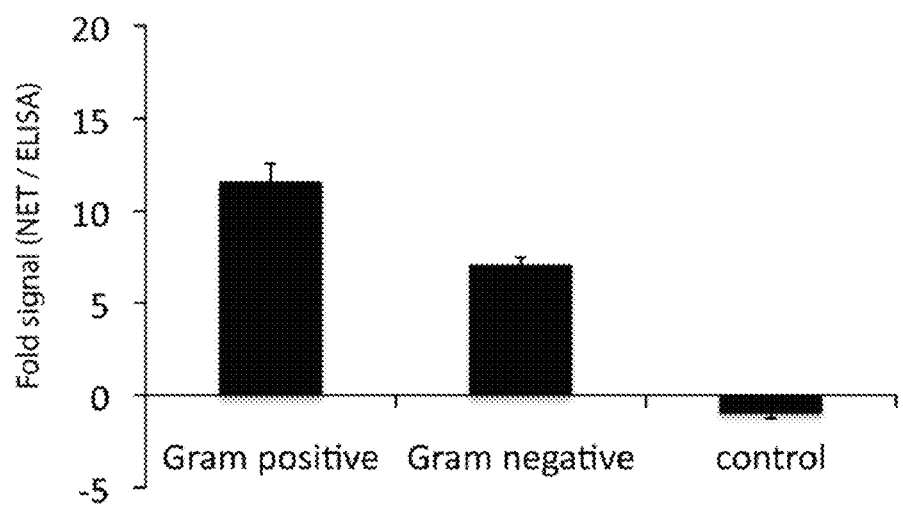
FIG. 7 shows detection of Gram negative bacteria and analytes from Gram negative bacteria in human blood.

Results are shown in FIG. 7. The data demonstrate the ability of an application of the invention to produce a visible signal when net-immobilized analytes were detected by the chromogenic detection system. Additionally, the data demonstrate that a net built to capture analytes that are highly abundant on bacteria can produce a visible signal when incubated in the presence of chromogenic detection systems that detect gram-negative bacteria or gram-positive bacteria. Lastly, the molecular nets and the gram-negative and gram-positive detection systems demonstrate specificity in that they did not recognize yeast analytes.

Example 12: Methods for Generating Extended Linkages

Extended linkers may be used to make an especially porous layer. Extension molecules can be made/purchased that contain one or more than one kind of the following: free amines, hydroxyls, carboxyls or sulfhydryls. Examples of extension molecules:
PROTEIN: Poly-Argenine (5 to 50 amino acids linked into a polypeptide chain)
PROTEIN: Poly-Lysine (5 to 50 amino acids linked into a polypeptide chain)
CARBOHYDRATE: Cellulose CARBOHYDRATE: Amylose
CARBOHYDRATE: Xylan
NUCLEIC ACID: Salmon sperm DNA
Methods:
1. A homogeneous population of an extension molecule can be mixed with a homogeneous population of heterobifunctional crosslinker, such that only one functional end of each molecule of crosslinker is bound to an extension molecule to give rise to the following construct: Example: EMCH-{Amylose}-EMCH 2. The extended linkage reaction can be quenched with 50 nM Tris pH 7.5
3. The extended linkages can be separated from unlinked monomers by size exclusion chromatography and by dialysis.
4. The extended linkages can be mixed with capture molecules to generate a layer in a molecular net. Example: sulfhydryl-containing capture molecule-EMCH-Amylose-EMCH-sulhydryl-containing capture molecule

Example 14: Positive Binding Events can be Monitored by a Shift in the Fluorescent Intensity (FI) of a Net This example demonstrates that molecular nets can be used to detect MRSA directly in a non-sandwich assay format. In this example, the net properties are pre-determined, the sample is incubated with the net, and the shift in net properties is measured.

TABLE 17

Use of some MRSA detection system components as capture components in a net for direct detection of MRSA in a sample

| Capture Agent | Modification | Vendor | Amt of Stock Used (ug for Ab and pMol for probe) |
|---|---|---|---|
| mAb MRSA clone 332/423 | Biotin | AbD Serotec | 1 |
| mAb MRSA clone 198 | Biotin | AbCam | 1 |
| mAb MRSA clone AC10 | Biotin | AbCam | 1 |
| ACACCATTTTATATTGAGCATCTACT | Biotin | IDT | 1 |
| ACACCATTTTACCACGTTCTGATTTT | Biotin | IDT | 1 |
| ACACCATTCCACATTGTTT | Biotin | IDT | 1 |
| ACACCAGTCATTTCTACTTCACCATTA | Biotin | IDT | 1 |
| ACACCATGTTATGTTTTTAAGAAGC | Biotin | IDT | 1 |
| ACACCAGATAAATCTTTAAGTACAAG | Biotin | IDT | 1 |

Nets were built by the following: 1 ug/mL of each biotinylated antibody and 1 pMol of each biotinylated probe were mixed. Biotinylated capture components were pre-incubated for 30 minutes at 37° C. with avidin-fluorophore (Invitrogen) at a 1:3 ratio and served as the capture components for the net. Underlayers (2 uL each) were built using a mixture of 1:1 10% (w/v) albumin and 37% (w/v) formaldehyde and cured for 15 minutes. Three layered nets were constructed (2.5 uL per layer) with fluorophore-labeled capture components and working linker stock containing $BS^3$ (363 nM), BMPH (27.5 nM), EMCS (750 nM) and EGS (150 nM) at a 2:0.5 ratio of capture-to-linker.

Net fluorescence was measured for 48 nets prior to block in 0.5% BSA. Nets were rinsed and incubated with methicillin-resistant *S. aureus* (MRSA) or methicillin-sensitive *S. aureus* (MSSA as control) for 30 minutes. Nets were washed with 2.5% albumin+0.005% Tween and rinsed with PBS prior to reading.

Figure 18:
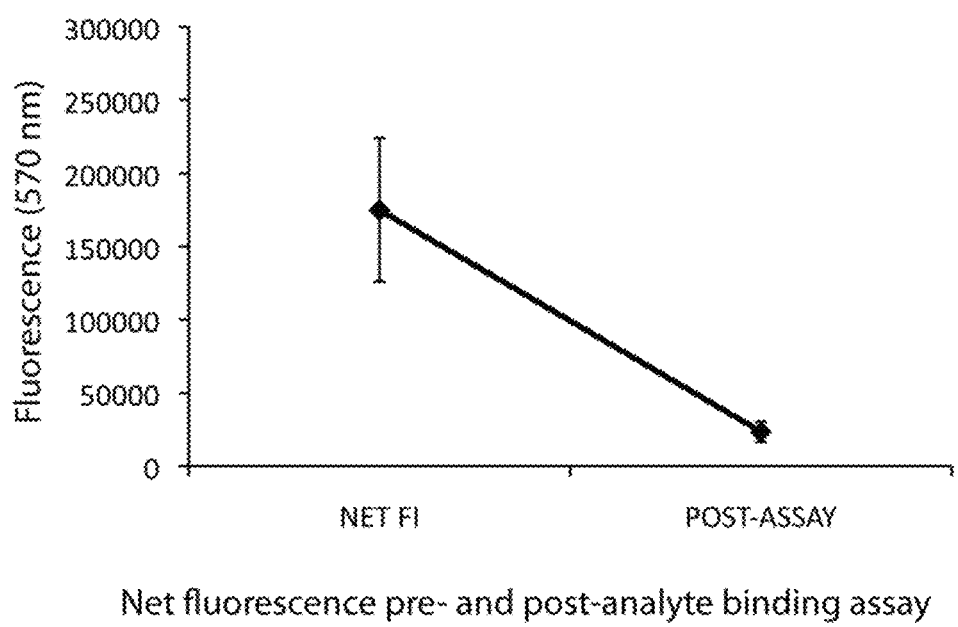
FIG. 18 shows that positive binding events can be monitored by a shift in the fluorescent intensity (FI) of a net.

See FIG. 18 for the results. Data represent 48 rhodamine-labeled *S. aureus* nets. Data from these studies and the net specificity binding studies (see Example 22) demonstrate that molecular nets can be used for direct detection of specific analytes in complex samples. Molecular nets can be constructed to possess measurable properties such as fluorescence, luminescence, absorbance, magnetism, vibrational frequency, etc., that can be pre-determined. The binding of analyte(s) to a molecular net changes the value of the measured property and can indicate a positive binding event. In this example, layers 1-3 of the molecular nets contained fluorescence that was reduced by direct analyte binding. In other examples, nets can contain underlayers or individual layers with the measurable signal. Direct detection testing minimizes reagent handling and user error. Few platforms are capable of direct binding studies and must rely on amplification of a signal to indicate binding (eg, ELISA). The molecular net can be designed to contain the appropriate number of signal generating molecules orientated in meaningful manner within the net to facilitate sensitivity and produce a measurable reduction in signal when an analyte binds.

Example 15: Changes in Net Fluorescent Intensity can be Monitored to Indicate a Specific Binding Event This example demonstrates that molecular nets can be used to detect MRSA directly in a non-sandwich assay format. In this example, the net properties are pre-determined, the sample is incubated with the net, and the shift in net properties is measured. Nets were built with BS3, BMPH, EMCS and EGS as linkers and fluorescent antibodies against *S. aureus*, and DNA binding probes against nuc as capture components.

TABLE 18

Use of *S. aureus* detection system components as capture components in a net for direct detection of *S. aureus* in a sample

| Capture Agent | Modification | Vendor |
|---|---|---|
| mAb *S. aureus* IgM | Biotin | Millipore |
| mAb Enterotoxin A/B/C1/C2/D/E clone S13 | Biotin | AbD Serotec |
| mAb *S. aureus* clone 704 | Biotin | AbCam |
| mAb *S aureus* | Biotin | AbCam |
| ACACCACATTGGTTGACCTTTGRACATTAA | Biotin | IDT |
| ACACCAGATGGAAAAATGGTAAACGAAG | Biotin | IDT |

Net fluorescence was measured for 11 nets prior to incubation with 20 CFU methicillin-resistant *S. aureus* or *S. epidermidis* (as control) and post assay (following analyte incubation, nets were washed and read).

Figure 19:
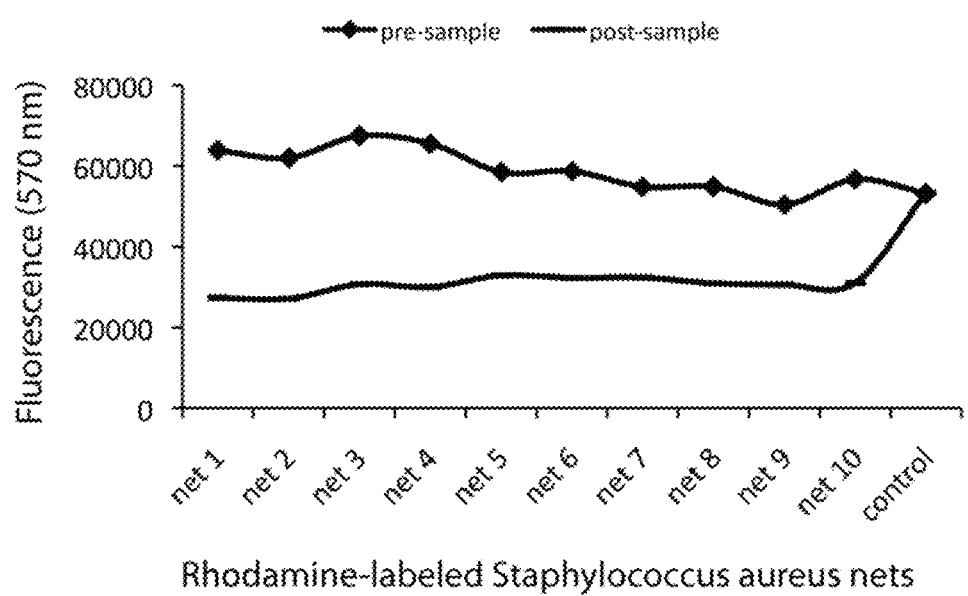
FIG. 19 shows that changes in net fluorescent intensity can be monitored to indicate a specific binding event.

See FIG. 19 for the results. Data represent the fluorescence of rhodamine-labeled *S. aureus* nets pre- and post-analyte (*S. aureus* nets 1-10 and *S. epidermidis* control). Data in this example demonstrate that nets can be constructed to selectively bind a single species in a complex sample, and that the net can differentiate between 2 species in the same genus.

Example 16: Positive Analyte Binding to Nets can Induce Altered Net Properties This example demonstrates that molecular nets can be used to detect MRSA directly in a non-sandwich assay format. In this example, the net properties are pre-determined, the sample is incubated with the net, and the shift in net properties is measured. Nets were built with BS3, BMPH, EMCH and EGS as linkers and fluorescently labeled antibodies against *S. aureus*, DNA binding peptides as capture components. This experiment was performed under the same conditions from Example 15.

Figure 20:
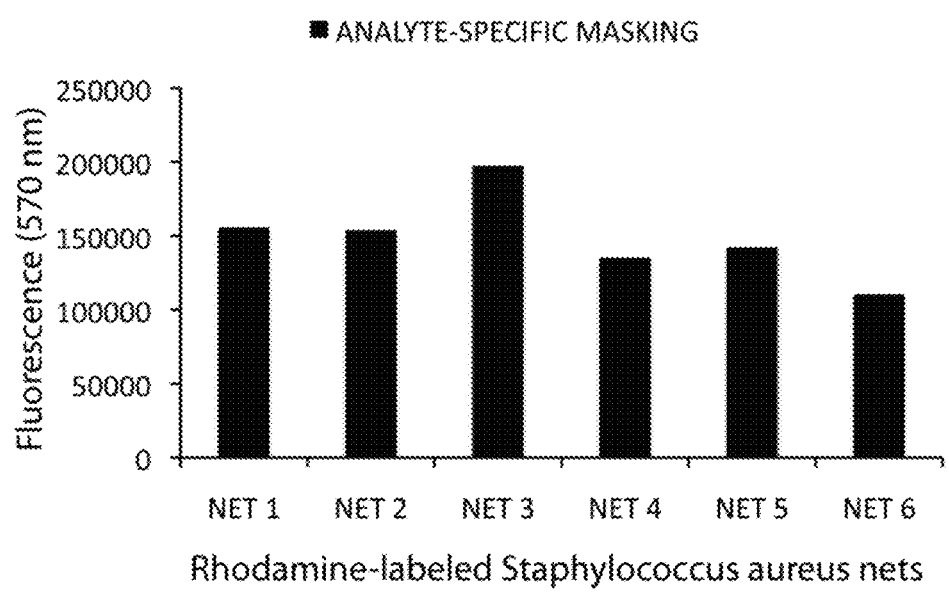
FIG. 20 shows that positive analyte binding to nets can induce altered net properties.

See FIG. 20 for the results. Analyte-specific alteration of net fluorescent properties or "masking" can be determined by measuring the absolute fluorescence intensity of molecular net pre- and post-incubation with sample. The results show that "masking" can be a way to determine analyte-binding events, as net fluorescence is masked by immobilized analytes.

Example 17: Effective Testing Format Using Molecular Nets to Bind *S. aureus*-Specific Analytes This example demonstrates that MRSA can be detected using a molecular net having capture components that enrich, isolate, bind, or immobilize a first set of analytes of interest (i.e., *S. aureus* and methicillin-resistance), and then using detection molecules against a second set of analytes which is a limited subset of the first set of analytes (i.e., methicillin resistance) in a sandwich assay format.

Nets were built with an avidin underlayer and two layers of antibodies against PBP2a and *S. aureus*-specific analytes and 4 species of DNA binding peptides as capture components, interlinked with BS3, BMPH, EMCS and EGS.

| Capture Agents | |
|---|---|
| 1) Albumin | (stock = 10%) |
| 2) Antibodies against PBP2a (clones AC10, 332/423, 198) | (stock = 1 µg/mL) |
| 3) DNA binding peptide 1 (VLFGKLA) | (stock = 1 mg/mL) |
| 4) DNA binding peptide 2 (VMFGKLA) | (stock = 1 mg/mL) |
| 5) DNA binding peptide 7 (RRRRRRRRRRR) | (stock = 1 mg/mL) |
| 6) DNA binding peptide 6 (VFFGRLA) | (stock = 1 mg/mL) |
| 7) pAb *S. aureus* | (stock = 1 µg/mL) |
| 8) mAb *S. aureus* IgM | (stock = 1 µg/mL) |
| 9) mAb Enterotoxin A/B/C1/C2/D/E clone S13 | (stock = 1 µg/mL) |
| 10) mAb *S. aureus* clone 704 | (stock = 1 µg/mL) |
| 11) pAb protein A | (stock = 1 µg/mL) |
| Linkers | |
| 1) BMPH | (stock = 285 nM) |
| 2) EGS | (stock = 5.9-6.03 uM) |
| 3) EMCS | (stock = 0.03 mM) |
| 4) BS³ | (stock = 14.4 uM) |
| 5) Formaldehyde | (stock = 37% w/v) |

TABLE 19

MRSA Detection reagents (ug/mL for antibodies and pM for probes):

| Capture Agent | Modification | Vendor | Amt of Stock Used (ug for Ab and pMol for probe) |
|---|---|---|---|
| mAb MRSA clone 332/423 | Biotin | AbD Serotec | 1 |
| mAb MRSA clone 198 | Biotin | AbCam | 1 |
| mAb MRSA clone AC10 | Biotin | AbCam | 1 |
| ACACCATTTTATATTGAGCATCTACT | Biotin | IDT | 1 |
| ACACCATTTTACCACGTTCTGATTTT | Biotin | IDT | 1 |
| ACACCATTCCACATTGTTT | Biotin | IDT | 1 |
| ACACCAGTCATTTCTACTTCACCATTA | Biotin | IDT | 1 |
| ACACCATGTTATGTTTTTAAGAAGC | Biotin | IDT | 1 |
| ACACCAGATAAATCTTTAAGTACAAG | Biotin | IDT | 1 |
| Human IgG Fc fragment* | none | Millipore | 4.3 |

*The human IgG Fc fragment is not an active part of the MRSA detection system, rather it binds and occludes *S. aureus* Protein A to minimize false positive detection of methicillin-sensitive *S. aureus*.

Underlayer
1) Pre-mix a batch of underlayer: 1:1 ratio of albumin and formaldehyde
2) Immediately add [pipette] 1 or 2 µL underlayer mixture on a surface
3) Let cure for 15 minutes to 1 hour at room temperature First Layer
4) Dilute linker stock at 1:40 into amine-free PBS pH 7.4, use that day only
5) Pre-mix a batch of capture and linker at 2:0.5 ratio of capture to linker stocks to generate $1^{st}$ layer materials
6) Immediately add [pipette] 1.25 or 2.5 µL of first capture layer onto the top of the underlayer drop (if cured at higher temperature, evaporation occurs; place first capture layer onto the remnant underlayer)
7) Let cure for 15 minutes to 1 hour at room temperature Second Layer
8) Pre-mix a batch of capture and linker at 2:0.5 ratio of capture to linker stocks to generate $2^{nd}$ layer
9) Immediately add [pipette] 1.25 or 2.5 µL of second capture layer onto the top of the $1^{st}$ layer drop (if cured at higher temperature, evaporation occurs; place second capture layer onto the remnant $1^{st}$ layer)
10) Let cure for 15 minutes to 1 hour at room temperature Third Layer
11) Pre-mix a batch of capture and linker at 2:0.5 ratio of capture to linker stocks to generate 3rd layer
12) Immediately add [pipette] 1.25 or 2.5 µL of second capture layer onto the top of the 2nd layer drop (if cured at higher temperature, evaporation occurs; place second capture layer onto the remnant 2nd layer)
13) Let cure for 15 minutes to 2 hours at room temperature to quench linkers 14) Let absorb to surface by storing overnight at 4° C.
15) Block nets with 200 μL of 0.5% BSA in PBS pH 7.4 for 12 hours at 4° C. or for 2 hours at 37° C.

Assay Procedure

1. Triple layered nets were built in triplicate according to methods above.
2. Block was removed from the wells containing nets and washed with PBS
3. To samples, detection molecules were added at 10 μL/well (detection has also been added directly to nets prior to sample addition, this also works well)
4. Samples and detection molecules were incubated with each net for 30 minutes
5. Wells were washed with 0.3 mL PBS, 0.005% Tween-20, and 2.5% egg albumin (wash buffer) and quickly rinsed with PBS
6. The absorbance in each well was measured by plate reader Nets were blocked and incubated in the presence of saline (assay control) or saline samples containing mixed microbial populations from patient nares swabs (MRSA positive and MRSA negative) and FITC-conjugated MRSA detection agents (a combination PBP2a antibodies and SCCmec DNA probes) (See Table 17 for the composition of the net) for 30 minutes. Nets were washed and read by fluorometer at A520.

Figure 21:
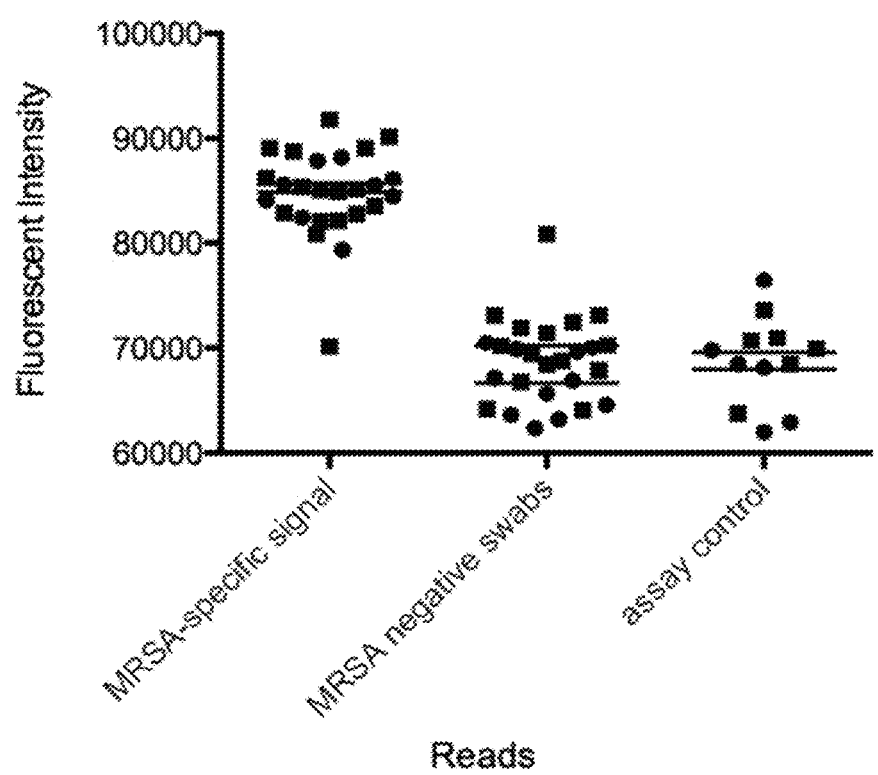
FIG. 21 shows that molecular nets can be effectively used to bind MRSA-specific analytes.

See FIG. 21 for the results. Data represents the fluorescent intensity produced from 7 or 14 uL nets incubated with MRSA positive swab samples. Error bars represent the SEM.

Data demonstrate the use of a molecular net to immobilize and facilitate detection of MRSA within 30 minutes in a complex sample without the need for sample prep.

Example 18: Smaller Nets Produce Higher Signals

Nets, totaling 7 or 14 uL of total volume, were built with an avidin underlayer and two layers of antibodies against PBP2a and S. aureus-specific analytes and 3 species of DNA binding peptides (See Table 17 for the composition of the net) as capture components, interlinked with BS3, BMPH, EMCH and EGS.

Nets were blocked and incubated in the presence of samples containing mixed microbial populations from patient nares swabs (MRSA positive and MRSA negative) and FITC-conjugated MRSA detection agents (See Table 17 for the composition of the net) for 30 minutes. Nets were washed and read by fluorometer at A520.

Figure 22:
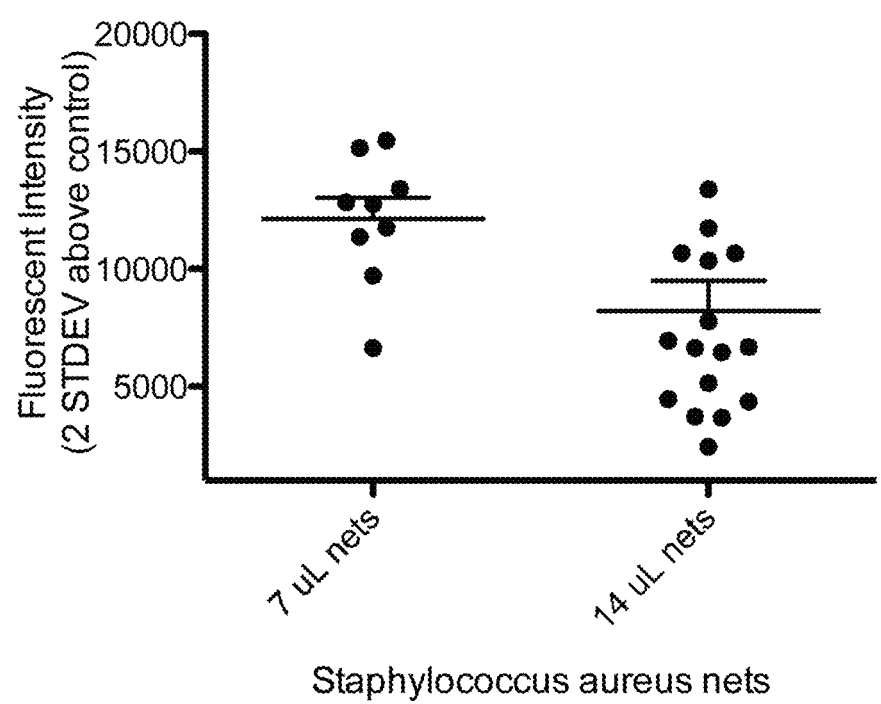
FIG. 22 shows that smaller nets produce higher signals.

See FIG. 22 for the results. Data represents the fluorescent signal above background (background=2 standard deviations above the average fluorescent intensity for 25 MRSA-negative swabs) produced from 7 or 14 uL nets incubated with MRSA positive swab samples. Error bars represent the SEM. The data demonstrate that smaller nets produce a stronger signal and less noise than larger nets. The goal of most molecular diagnostics is to increase signal and to reduce noise. The molecular net enables higher signal and lower noise to be achieved compared to conventional 2D immunoassays. Decreasing the diameter of the nets further increases the signal and lowers the noise. Additionally, increasing the layers of molecular nets also increases the signal.

Example 19: Smaller Nets Produce Less Noise (Non-Specific Binding)

Nets, totaling 7 or 14 uL of total volume, were built with an avidin underlayer and two layers of antibodies against PBP2a and S. aureus-specific analytes and 3 species of DNA binding peptides (See Table 17 for the composition of the net) as capture components, interlinked with BS3, BMPH, EMCH and EGS.

Nets were blocked and incubated with samples containing mixed microbial populations from patient nares swabs (MRSA negative) and FITC-conjugated MRSA detection agents (a combination of PBP2a antibodies and SCCmec DNA probes) for 30 minutes. Nets were washed and read by fluorometer at A520.

Figure 23:
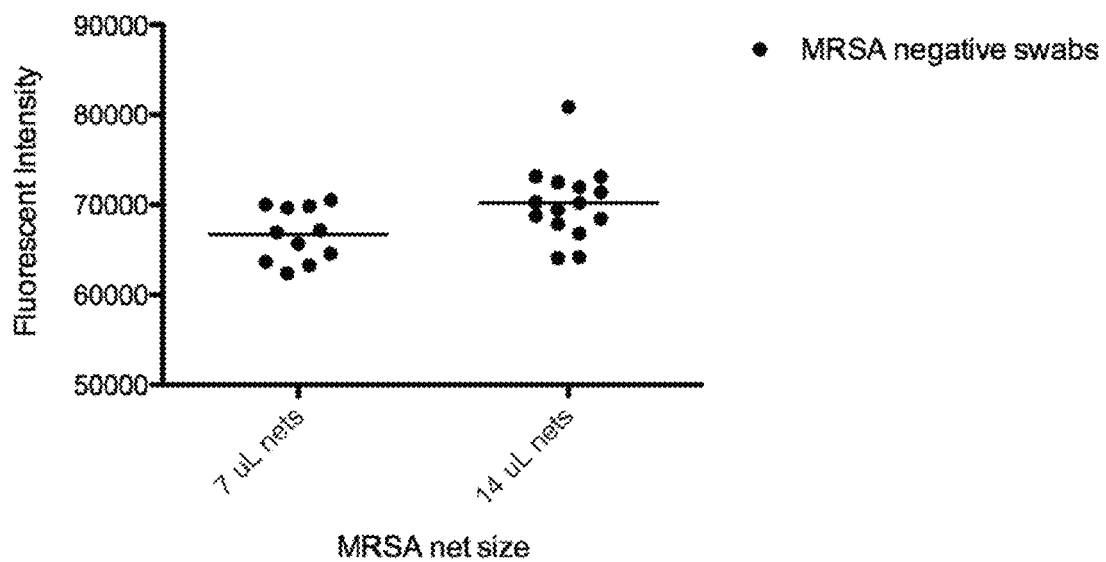
FIG. 23 shows that smaller nets produce less noise (non-specific binding).

See FIG. 23 for the results. Data represents the fluorescent intensity produced from 7 or 14 uL nets incubated with MRSA negative swab samples. Error bars represent the SEM. The significance of these data demonstrate that smaller nets produce less noise than larger nets. The goal of most molecular diagnostics is to increase signal and to reduce noise. The molecular net achieves lower noise in the presence of complex samples than conventional immunoassays and the like. The 3D arrangement of the molecular net contributes to this property.

Figure 24:
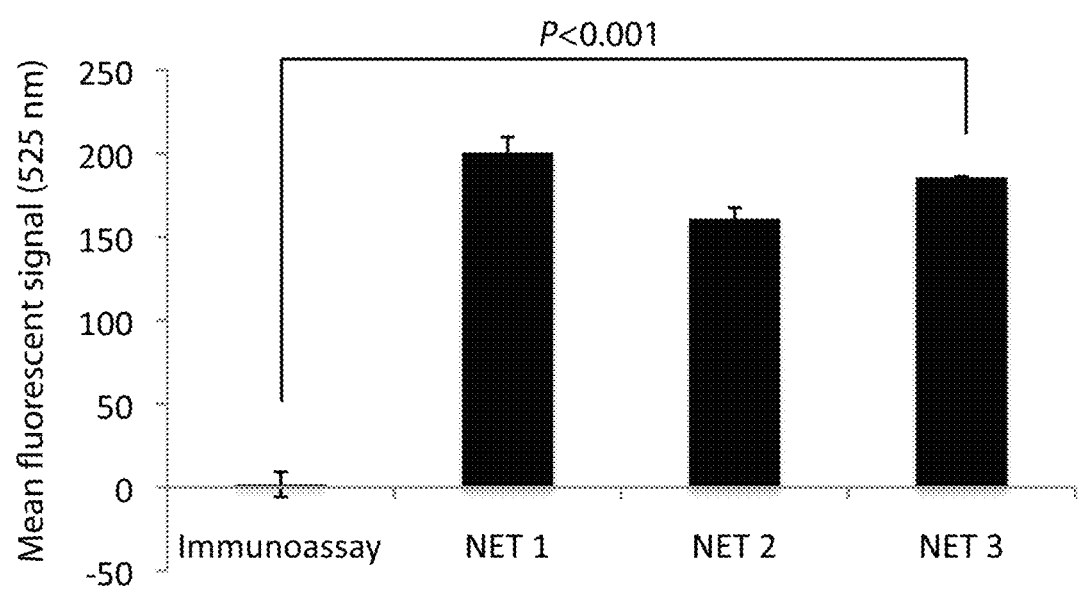
FIG. 24 shows that use of a net enables as faster positive signal as compared to a standard 2D immunoassay for MRSA-specific analytes.

Example 20: Net Enables Faster Positive Signal Compared to Standard 2D Immunoassay S. aureus-specific signal between 3D 3-layered net and standard immunoassay 2D format—each at 15 min. See FIG. 24 for the results. Data represent the mean fluorescent signal above background.

| Capture Agents | |
|---|---|
| 1) Albumin (CalBiochem) | (stock = 10%) |
| 2) DNA binding peptide 1 (VLFGKLA) | (stock = 1 mg/mL) |
| 3) DNA binding peptide 2 (VMFGKLA) | (stock = 1 mg/mL) |
| 4) DNA binding peptide 7 (RRRRRRRRRRRR) | (stock = 1 mg/mL) |
| 5) DNA binding peptide 6 (VFFGRLA) | (stock = 1 mg/mL) |
| 6) pAb S. aureus | (stock = 1 μg/mL) |
| 7) mAb S. aureus IgM | (stock = 1 μg/mL) |
| 8) mAb Enterotoxin A/B/C1/C2/D/E clone S13 | (stock = 1 μg/mL) |
| 9) mAb S. aureus clone 704 | (stock = 1 μg/mL) |
| 10) pAb protein A | (stock = 1 μg/mL) |
| Linkers | |
| 1) BMPH | (stock = 285 nM) |
| 2) EGS | (stock = 5.9-6.03 uM) |
| 3) EMCS | (stock = 0.03 mM) |
| 4) BS$^3$ | (stock = 14.4 uM) |
| 5) Formaldehyde | (stock = 37% w/v) |

Underlayer
1) Pre-mix a batch of underlayer: 1:1 ratio of albumin and formaldehyde
2) Immediately add [pipette] 2 μL underlayer mixture on a surface
3) Let cure for 15 minutes to 1 hour at room temperature First Layer
4) Dilute linker stock at 1:40 into amine-free PBS pH 7.4, use that day only
5) Pre-mix a batch of capture and linker at 2:0.5 ratio of capture to linker stocks to generate $1^{st}$ layer materials
6) Immediately add [pipette] 2.5 μL of first capture layer onto the top of the underlayer drop (if cured at higher temperature, evaporation occurs; place first capture layer onto the remnant underlayer)
7) Let cure for 15 minutes to 1 hour at room temperature Second Layer
8) Pre-mix a batch of capture and linker at 2:0.5 ratio of capture to linker stocks to generate $2^{nd}$ layer 9) Immediately add [pipette] 2.5 µL of second capture layer onto the top of the 1st layer drop (if cured at higher temperature, evaporation occurs; place second capture layer onto the remnant 1$^{st}$ layer)
10) Let cure for 2 hours at room temperature to quench linkers
11) For the 2D format, 7 uL of identical capture components were absorbed in 100 uL PBS pH 7.4
12) The plate was incubated overnight at 4° C.

Assay Procedure
1. Layered nets and 2D format were built in replicates according to methods above.
2. Block was removed from the wells containing nets and washed with PBS
3. Colonies of plated *S. aureus* were picked, serially-diluted in PBS and counted
4. Human biofilm nares swab samples were spiked with ~20 CFU MSSA or control
5. Samples were then incubated with each net and a 1:46 dilution of FITC-labeled *S. aureus* detection system for 30 minutes at RT in the dark (refer to table 17 for detection system)
6. Nets were washed with 0.3 mL PBS, 0.005% Tween-20, and 2.5% egg albumin (wash buffer) and quickly rinsed with PBS
7. The fluorescence at 520 nm was measured in each well by plate reader It is well known in the art that antibodies can bind to the respective epitopes very rapidly. Antibody-epitope binding is dependent upon molecular interaction frequency and can occur within 300 seconds in non-complex samples and up to 120 minutes in complex samples. The molecular net is constructed to have a 3D architecture with numerous topological features within the structure and on the surface. In this example, the pre-mixing of capture and linker produces small conjugates in solution that are then added to the growing end of the molecular net. Prior construction methods for net generation required mixing of capture and linker molecules within the layer. The purpose of the 3D features is to maximize interaction of the net capture components with the respective epitopes in a complex sample. Traditional 2D immunoassays (e.g., ELISAs) have a 60 to 120 minute incubation of capture antibody with sample. In the 2D immunoassay format, analytes diffuse through solution and interact with absorbed capture components on a large planar surface. In the 3D net format, analytes diffuse through solution (or can be pushed or pulled) and interact with a multi-layered topologically-enriched net of small diameter and a height above conventional 2D immunoassays. The 3D net architecture facilitates capture-to-epitope interactions and therefore reduces incubation times. Using simple optics and fluorescence-labeled detection components, a net can speed up a traditional sandwich immunoassay.

Example 22: Specific Binding of MRSA and *S. epidermidis* to Molecular Nets Designed to Immobilize *S. aureus* & Methicillin-Resistant *S. aureus* (MRSA) Signatures in a Sample As shown in this example, molecular nets can also be used to detect MRSA directly in a non-sandwich assay format by pre-labeling cells in a sample, incubating the net with sample, and looking for label immobilized on a net. Multi-layered molecular nets composed of DNA-binding peptides, non-cross-reactive anti-*S. aureus* polyclonal and monoclonal antibodies, and anti-Protein A were liked together with BS3, BMPH, EMCH, and EGS in 96 well plates, cured and blocked with a 1:20 dilution of 10% BSA in PBS (Pierce).

| Capture Agents | |
|---|---|
| 1) Albumin (CalBiochem) | (stock = 10%) |
| 2) DNA binding peptide 1 (VLFGKLA) | (stock = 1 mg/mL) |
| 3) DNA binding peptide 2 (VMFGKLA) | (stock = 1 mg/mL) |
| 4) DNA binding peptide 7 (RRRRRRRRRRRR) | (stock = 1 mg/mL) |
| 5) DNA binding peptide 6 (VFFGRLA) | (stock = 1 mg/mL) |
| 6) pAb *S. aureus* | (stock = 1 µg/mL) |
| 7) mAb *S. aureus* IgM | (stock = 1 µg/mL) |
| 8) mAb Enterotoxin A/B/C1/C2/D/E clone S13 | (stock = 1 µg/mL) |
| 9) mAb *S. aureus* clone 704 | (stock = 1 µg/mL) |
| 10) pAb protein A | (stock = 1 µg/mL) |
| Linkers | |
| 1) BMPH | (stock = 285 nM) |
| 2) EGS | (stock = 5.9-6.03 uM) |
| 3) EMCS | (stock = 0.03 mM) |
| 4) BS$^3$ | (stock = 14.4 uM) |
| 5) Formaldehyde | (stock = 37% w/v) |

Underlayer
1) Pre-mix a batch of underlayer: 1:1 ratio of albumin and formaldehyde
2) Immediately add [pipette] 1 or 2 µL underlayer mixture on a surface
3) Let cure for 15 minutes to 1 hour at room temperature First Layer
4) Dilute linker stock at 1:40 into amine-free PBS pH 7.4, use that day only
5) Pre-mix a batch of capture and linker at 2:0.5 ratio of capture to linker stocks to generate 1$^{st}$ layer materials
6) Immediately add [pipette] 1.25 or 2.5 µL of first capture layer onto the top of the underlayer drop (if cured at higher temperature, evaporation occurs; place first capture layer onto the remnant underlayer)
7) Let cure for 15 minutes to 1 hour at room temperature Second Layer
8) Pre-mix a batch of capture and linker at 2:0.5 ratio of capture to linker stocks to generate 2$^{nd}$ layer
9) Immediately add [pipette] 1.25 or 2.5 µL of second capture layer onto the top of the 1$^{st}$ layer drop (if cured at higher temperature, evaporation occurs; place second capture layer onto the remnant 1$^{st}$ layer)
10) Let cure for 15 minutes to 1 hour at room temperature Third Layer
11) Pre-mix a batch of capture and linker at 2:0.5 ratio of capture to linker stocks to generate 3rd layer
12) Immediately add [pipette] 1.25 or 2.5 µL of second capture layer onto the top of the 2nd layer drop (if cured at higher temperature, evaporation occurs; place second capture layer onto the remnant 2nd layer)
13) Let cure for 15 minutes to 2 hours at room temperature to quench linkers
14) Let absorb to surface by storing overnight at 4° C.
15) Block nets with 200 µL of 0.5% BSA in PBS pH 7.4 for 12 hours at 4° C. or for 2 hours at 37° C.

Figure 25:
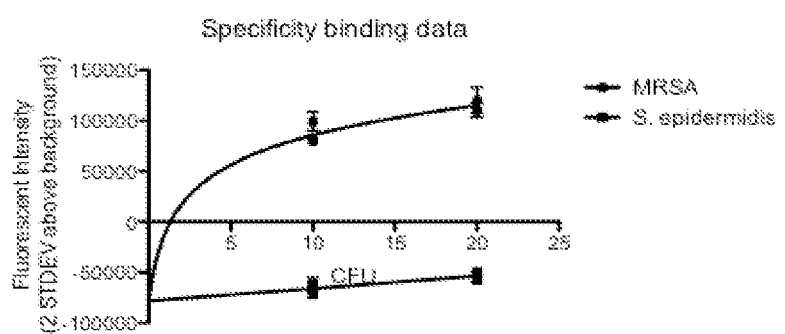
FIG. 25 shows specific binding of MRSA and *S. epidermidis* to molecular nets designed to immobilize *S. aureus* and methicillin-resistant *S. aureus* (MRSA) signatures in a sample.

Assay Procedure
1. Layered nets were built in triplicate according to methods above.
2. Block was removed from the wells containing nets and washed with PBS
3. Colonies of plated *S. aureus* and MRSA were picked, serially-diluted in PBS, counted and pre-loaded with FITC (Invitrogen) at 37° C. for 30 minutes, according to manufacturer instructions 4. Human biofilm nares swab samples were spiked with ~20 CFU of FITC-labeled MSSA or MRSA
5. Samples were then incubated with each net for 30 minutes
6. Nets were washed with 0.3 mL PBS, 0.005% Tween-20, and 2.5% egg albumin (wash buffer) and quickly rinsed with PBS
7. The fluorescence at 520 nm was measured in each well by plate reader Samples containing FITC-loaded *S. aureus* and MRSA cells (Invitrogen) at 10 or 20 CFU were incubated with nets for 30 minutes, washed and read at 520 nm. Error bars represent SEM. See FIG. 25. This Example demonstrates that direct binding of analyte to a net can be detected by pre-loading a sample with a fluorescent signal.

Example 23: Detection System Components and Limits of MRSA Detection in the MRSA Test Molecular nets constructed as described above in Example 22 were incubated with 500 CFU of MRSA and a serial dilution of detection system components (DNA probes or antibodies) for 30 minutes prior to test processing and reading at 520 nm. FIG. 26 shows serial dilutions of the probe-based detection component which is composed of FITC-conjugated DNA probes against the SCCmec region. FIG. 27 shows serial dilutions of the antibody-based detection component which is composed of FITC-conjugated anti-MRSA monoclonal antibody clone AC10, anti-MRSA monoclonal antibody clone 332/423, and anti-MRSA monoclonal antibody clone 198. Linear regression analysis was performed by Prism. These studies were performed to determine the minimum levels of detection system that must be immobilized onto a net in order to be detected by conventional fluorescent plate readers. Linear regression was performed to determine the x-intercept for the MRSA probes and the MRSA antibodies. The minimum concentration of probe mixture needed to produce a statistically significant signal above background was determined to be <1 pMol per test. The minimum concentration of antibody mixture was determined to be 40 uMol per test.

The MRSA detection system may also 3 distinct mAbs against different epitopes of Pbp2a. The MRSA detection system can also contain 4 probes directed against mecA and the remaining probes against sequences towards the 5' and 3' ends of SCCmec. We are currently designing additional probes against this region, including sequences in mecR. We are also designing probes with nuclease-resistant modifications to increase stability in nuclease-rich samples.

```
mecA probe 1    5'-AGATTTTTGATCGGCGAAGGCAATAAAC-3' mecA probe 2    5'-AAAGAAATCATGTCACAAAAAAGTATT-3'

ΔmecR1          5'-ACAATTTTTGATTTCTATTTCTTTTAGAG-3'
probe 1 mecR1 probe 1   5'-GGAACAGGAATCGTGAATCACAAAGAA-3'
```

Example 24: MRSA Test Specificity—the Importance of *S. aureus*-Specific Nets and MRSA-Specific Detection This example demonstrates that MRSA can be detected using a molecular net having capture components that enrich, isolate, bind, or immobilize a first set of analytes of interest (i.e., *S. aureus*), and then detection molecules against different analytes (indicators of methicillin-resistance) in a sandwich assay format.

Multi-layered molecular nets were composed of DNA-binding peptides, non-cross-reactive anti-*S. aureus* polyclonal and monoclonal antibodies, and anti-Protein A, were linked together with BS3, BMPH, EMCH, and EGS in 96 well plates, cured and blocked with a 1:20 dilution of 10% BSA in PBS pH 7.4 (Pierce). The MRSA detection system, composed of anti-MRSA monoclonal antibody clone AC10, anti-MRSA monoclonal antibody clone 332/423, and anti-MRSA monoclonal antibody clone 198 (each at 1 ug/mL) were combined with anti-SCCmec DNA probes (each at 1 uM). All detection molecules were biotinylated and incubated with avidin-FITC at 3:1 molar ratio.

| Capture Agents | |
|---|---|
| 1) Albumin (CalBiochem) | (stock = 10%) |
| 2) DNA binding peptide 1 (VLFGKLA) | (stock = 1 mg/mL) |
| 3) DNA binding peptide 2 (VMFGKLA) | (stock = 1 mg/mL) |
| 4) DNA binding peptide 7 (RRRRRRRRRRRR) | (stock = 1 mg/mL) |
| 5) DNA binding peptide 6 (VFFGRLA) | (stock = 1 mg/mL) |
| 6) pAb *S. aureus* | (stock = 1 µg/mL) |
| 7) mAb *S. aureus* IgM | (stock = 1 µg/mL) |
| 8) mAb Enterotoxin A/B/C1/C2/D/E clone S13 | (stock = 1 µg/mL) |
| 9) mAb *S. aureus* clone 704 | (stock = 1 µg/mL) |
| 10) pAb protein A | (stock = 1 µg/mL) |
| Linkers | |
| 1) BMPH | (stock = 285 nM) |
| 2) EGS | (stock = 5.9-6.03 uM) |
| 3) EMCS | (stock = 0.03 mM) |
| 4) BS$^3$ | (stock = 14.4 uM) |
| 5) Formaldehyde | (stock = 37% w/v) |

TABLE 20

MRSA Detection reagents (ug/mL for antibodies and pM for probes):

| Capture Agent | Modification | Vendor | Amt of Stock Used (ug for Ab and pMol for probe) |
|---|---|---|---|
| mAb MRSA clone 332/423 | Biotin | AbD Serotec | 1 |
| mAb MRSA clone 198 | Biotin | AbCam | 1 |
| mAb MRSA clone AC10 | Biotin | AbCam | 1 |
| ACACCATTTTATATTGAGCATCTACT | Biotin | IDT | 1 |
| ACACCATTTTACCACGTTCTGATTTT | Biotin | IDT | 1 |
| ACACCATTCCACATTGTTT | Biotin | IDT | 1 |
| ACACCAGTCATTTCTACTTCACCATTA | Biotin | IDT | 1 |
| ACACCATGTTATGTTTTTAAGAAGC | Biotin | IDT | 1 |
| ACACCAGATAAATCTTTAAGTACAAG | Biotin | IDT | 1 |
| Human IgG Fc fragment* | none | Millipore | 4.3 |

The human IgG Fc fragment is not an active part of the MRSA detection system, rather it binds and occludes *S.*

*aureus* Protein A to minimize false positive detection of methicillin-sensitive *S. aureus*.

Underlayer
1) Pre-mix a batch of underlayer: 1:1 ratio of albumin and formaldehyde
2) Immediately add [pipette] 2 μL underlayer mixture on a surface
3) Let cure for 15 minutes to 1 hour at room temperature First Layer
4) Dilute linker stock at 1:40 into amine-free PBS pH 7.4, use that day only
5) Pre-mix a batch of capture and linker at 2:0.5 ratio of capture to linker stocks to generate $1^{st}$ layer materials
6) Immediately add [pipette] 2.5 μL of first capture layer onto the top of the underlayer drop (if cured at higher temperature, evaporation occurs; place first capture layer onto the remnant underlayer)
7) Let cure for 15 minutes to 1 hour at room temperature Second Layer
8) Pre-mix a batch of capture and linker at 2:0.5 ratio of capture to linker stocks to generate $2^{nd}$ layer
9) Immediately add [pipette] 2.5 μL of second capture layer onto the top of the $1^{st}$ layer drop (if cured at higher temperature, evaporation occurs; place second capture layer onto the remnant $1^{st}$ layer)
10) Let cure for 2 hours at room temperature to quench linkers
11) Let absorb to surface by storing overnight at 4° C.
12) Block nets with 200 μL of 0.5% BSA in PBS pH 7.4 for 12 hours at 4° C. or for 2 hours at 37° C.

Figure 28:
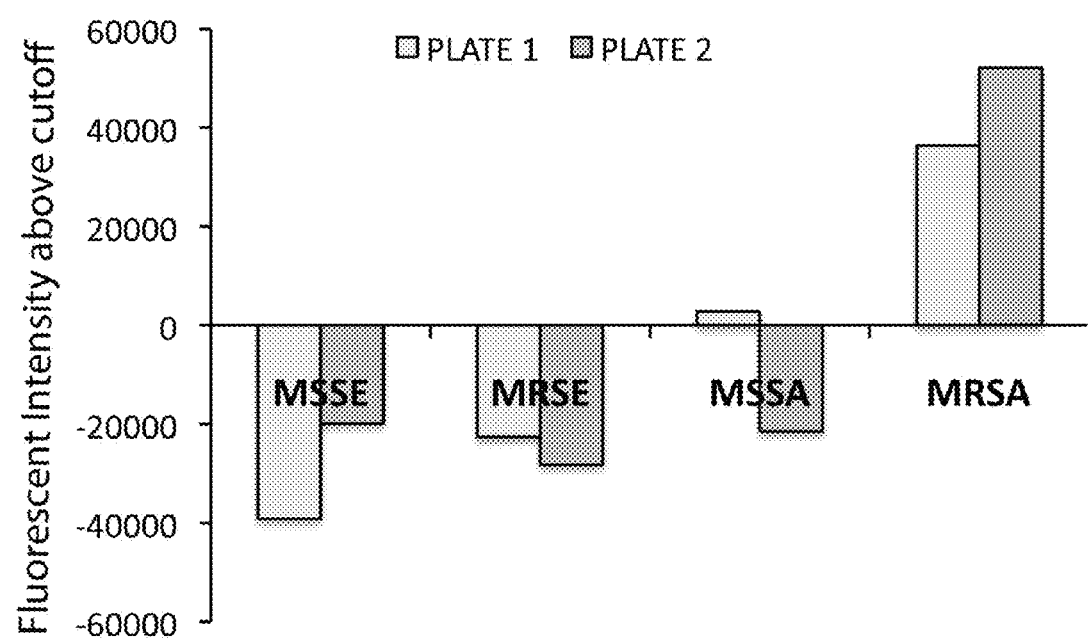
FIG. 28 shows results for testing of MRSA specificity.

Assay Procedure
1. Layered nets were built in replicates according to methods above.
2. Block was removed from the wells containing nets and washed with PBS
3. Colonies of plated *S. aureus* (MSSA), MRSA, *S. epidermidis* (MSSE), and MRSE were picked, serially-diluted in PBS, and counted
4. Human biofilm nares swab samples were spiked with ~20 CFU MSSA, MRSA, MRSE, or MSSE
5. Samples were then incubated with 10 uL of a 1:46 dilution of FITC-labeled MR detection system with each net for 30 minutes
6. Nets were washed with 0.3 mL PBS, 0.005% Tween-20, and 2.5% egg albumin (wash buffer) and quickly rinsed with PBS
7. The fluorescence at 520 nm was measured in each well by plate reader See FIG. 28. Samples containing unlabeled methicillin-sensitive *S. epidermidis* (MSSE) and *S. aureus* (MSSA) and methicillin-resistant *S. epidermidis* (MRSE) and *S. aureus* (MRSA) at 20 CFU were incubated with nets and FITC-labeled detection system for 30 minutes, washed and read at 520 nm. Error bars represent the SEM.

The significance of these studies are:
(I) The dual levels of specificity: the net binds *S. aureus*-specific analytes (and immobilizes MSSA and MRSA) and the detection system binds to MRSA-specific analytes (SCCmec and PBP2a).
(II) The net enriches and focuses the localization of immobilized *S. aureus*-specific analytes for the detection system to label said analytes. In this example, a test using a molecular net capable of binding and enriching for the presence of analytes (the pathogen *S. aureus*) combined with a detection system capable of binding low abundant analytes that associate to a high degree with *S. aureus* (that confer antibiotic resistance) can be useful.
(III) The net can be used in a test to detect the presence of a dependent analyte. In this example, the net binds analyte A, which is highly correlated with the presence of analyte B, which the detection system is directed against. Therefore, in this example, a positive test indicates the presence of MRSA (the net binds SA and the detection detects MR; MR can only bind if SA binds the net; importantly, the MR detection system does not bind when methicillin-resistant *S. epidermidis* is incubated with nets).

Example 25: ROC of MRSA Test

Figure 29:
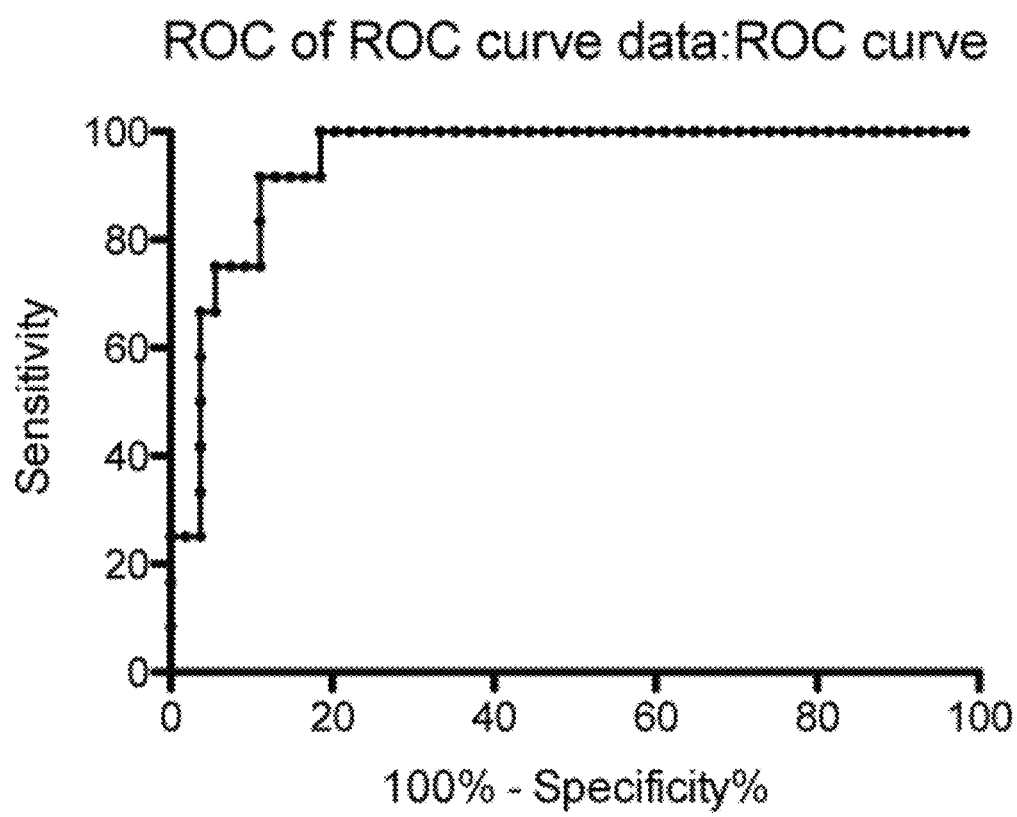
FIG. 29 shows receiver-operator characteristic (ROC) analysis of MRSA testing.

Sensitivity and specificity testing was performed on the 30 minute MRSA test as described in above Example 22 with 10 & 20 CFU of MRSA and *S. epidermidis*. ROC analysis was performed using Prism. See FIG. 29. Conditions for these analyses were done according to Example 24. Test results from numerous studies with molecular nets constructed to bind *S. aureus* analytes and the detection system designed to bind SCCmec and Pbp2a were used.

Assay Procedure
1. Layered nets were built in replicates according to methods above.
2. Block was removed from the wells containing nets and washed with PBS
3. Colonies of plated *S. aureus* (MSSA), MRSA, *S. epidermidis* (MSSE), and MRSE were picked, serially-diluted in PBS, and counted
4. Human biofilm nares swab samples were spiked with ~10 or 20 CFU MSSA, MRSA, MRSE, or MSSE
5. Samples were then incubated with 10 uL of a 1:46 dilution of FITC-labeled MR detection system with each net for 30 minutes
6. Nets were washed with 0.3 mL PBS, 0.005% Tween-20, and 2.5% egg albumin (wash buffer) and quickly rinsed with PBS
7. The fluorescence at 520 nm was measured in each well by plate reader These data demonstrate the potential for a molecular net-based test to produce statistically significant results within 30 minutes, with very few procedural steps (steps 5-7) with nothing more than a simple plate reader to determine test positivity. Many current approaches require large machines, more time and complicated sample-treatment protocols to achieve similar results.

Example 26: Effect of Net Configuration on Test Performance

Surface Curvature

Figure 30:
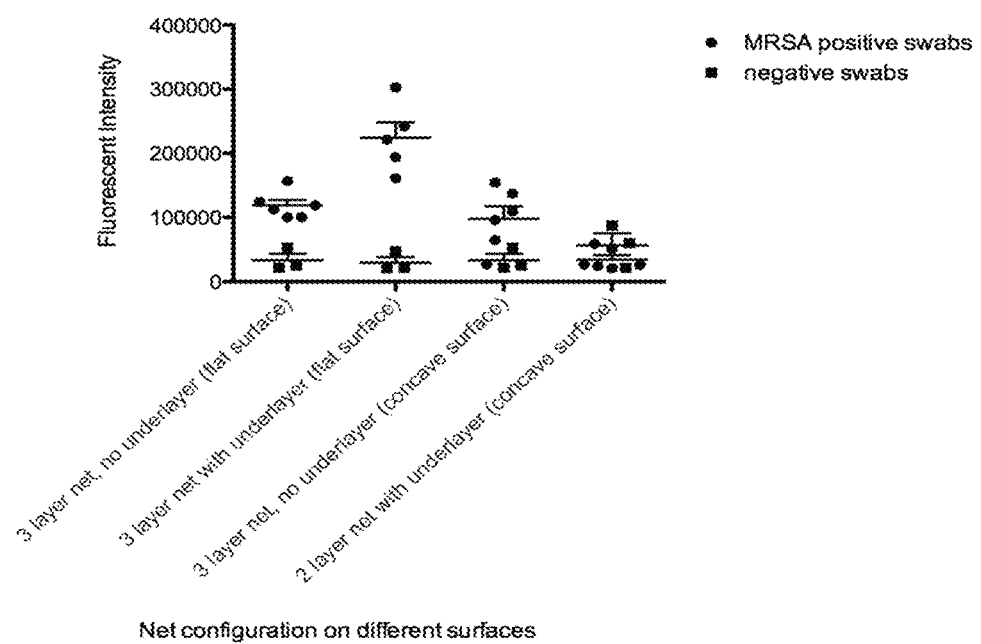
FIG. 30 shows test results for the impact of net configuration.

Different configurations of molecular nets were constructed and cured on flat or round wells in 96 well plates. The different net configurations were evaluated for performance in the MRSA test with MRSA positive swabs or negative swabs. Error bars represent the SEM. See FIG. 30. On a concave surface, the signal is the best without an underlayer. On a flat surface, signal is the best with an underlayer, such as 0.5-2.5 uL/layer or >2 layers.

On Beads

Figure 31:
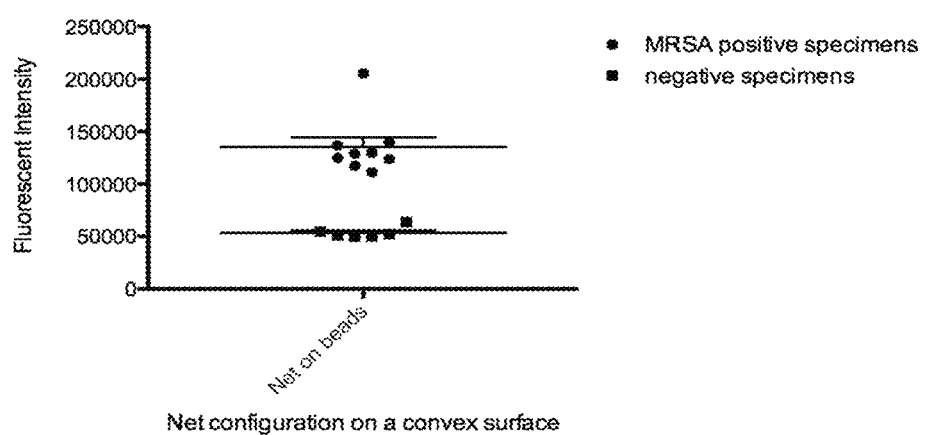
FIG. 31 shows the impact of configuration on test results.

Three-layered molecular nets (without underlayers) were constructed on magnetic beads and placed in 96 well plates. The beads were evaluated for performance in the MRSA test with MRSA positive swabs or negative swabs. Plates were placed in a magnetic field during the removal of the wash. Plates were read at 520 nm. Error bars represent the SEM. See FIG. 31. Nets built on beads (convex surface) have lower background auto-fluorescence relative to beads alone (data not shown) and can be effective in a MRSA test.

Example 27: Net to Detect Signs of Viral Infection in Patient Blood

This example describes fabrication of a three-layer molecular net for detection of a viral infection. The net binds 1) Interferon alpha; and 2) Interferon beta in this example. Other binding targets can include 1) Interferon alpha; and 2) Interferon beta 3) Viral MAVS and 4) Viral Viperin.

Materials

| Capture Agents | |
|---|---|
| 1) Polyclonal Antibodies against interferon-alpha | (stock = 1 mg/mL) |
| 2) Polyclonal Antibodies against interferon-beta | (stock = 1 mg/mL) |
| Linkers | |
| 3) EGS | (stock = 0.00275 g/mL in DMSO) |
| 4) EMCS | (stock = 0.00225 g/mL in DMSO) |
| 5) BS$^3$ | (stock = 0.0025 g/mL in DMSO) |
| 6) Formaldehyde | (stock = 37% w/v) |

Methods
1. Mix capture agents 1-2 or 1-4 (antibodies) in a 1:1:1:1 ratio.
2. Underlayer—Add a 5 uL aliquot containing 2 uL of formaldehyde and 3 uL of antibody mixture to surface. Let absorb overnight at 4° C. Remove remaining liquid including any non-immobilized antibodies.

First Layer
3. Pipette 6 uL of the antibody mixture and linker mixture onto the underlayer. Let cure for 1 hr at room temperature or for 15-30 minutes at 30° C.

Additional Layers
4. Repeat steps 3 to generate second layer
5. Repeat steps 3 to generate third layer Lyophilize or add PBS+0.001% sodium azide and store at 4° C. until use

TABLE 21

Multilayer Molecular Net Content

| Layer | Capture Agent(s) | Linker(s) |
|---|---|---|
| First | Antibodies against IFN-α and IFN-β | Formaldehyde |
| Second | " | EGS, EMCS, BS$^3$ |
| Third | " | " |

Figure 41:
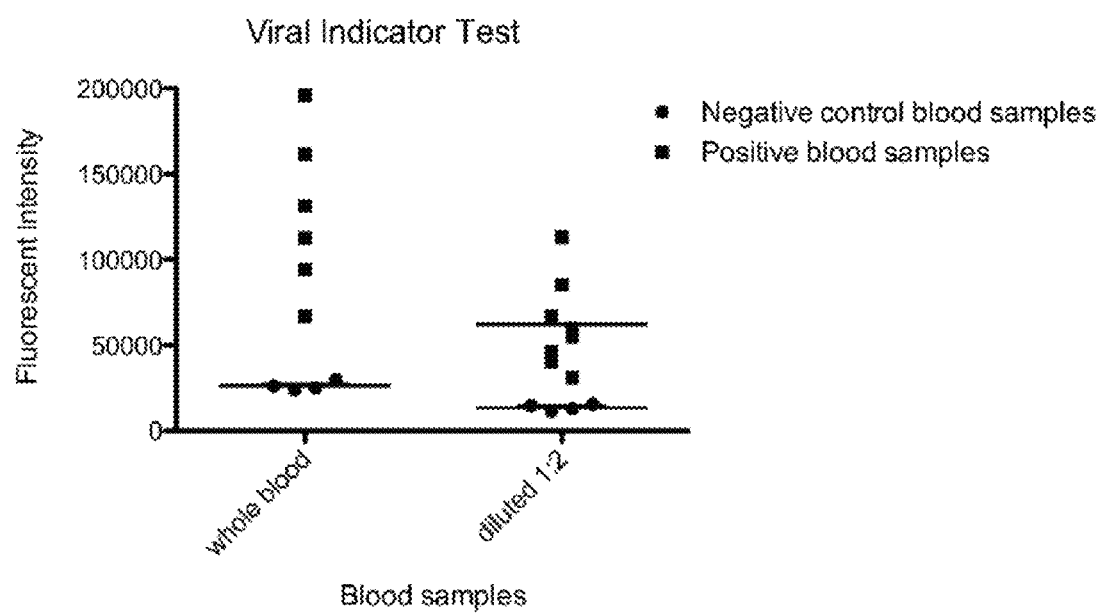
FIG. 41 shows detection of viral infection in whole and diluted blood.

Control blood samples and CMV and EBV clinical blood samples were tested in the viral infection indicator test. 20 uL of whole blood or 20 uL of diluted blood samples (1:2 dilution) were added concomitantly with detection system to viral infection indicator nets in a 384 well plate format and incubated for 15 minutes at RT prior to wash. Wells were read at 520 nm. Data represents the fluorescent intensity (FI) of the wells post-wash. Bars represent the mean FI for positive and negative blood tests. See FIG. 41.

Figure 42:
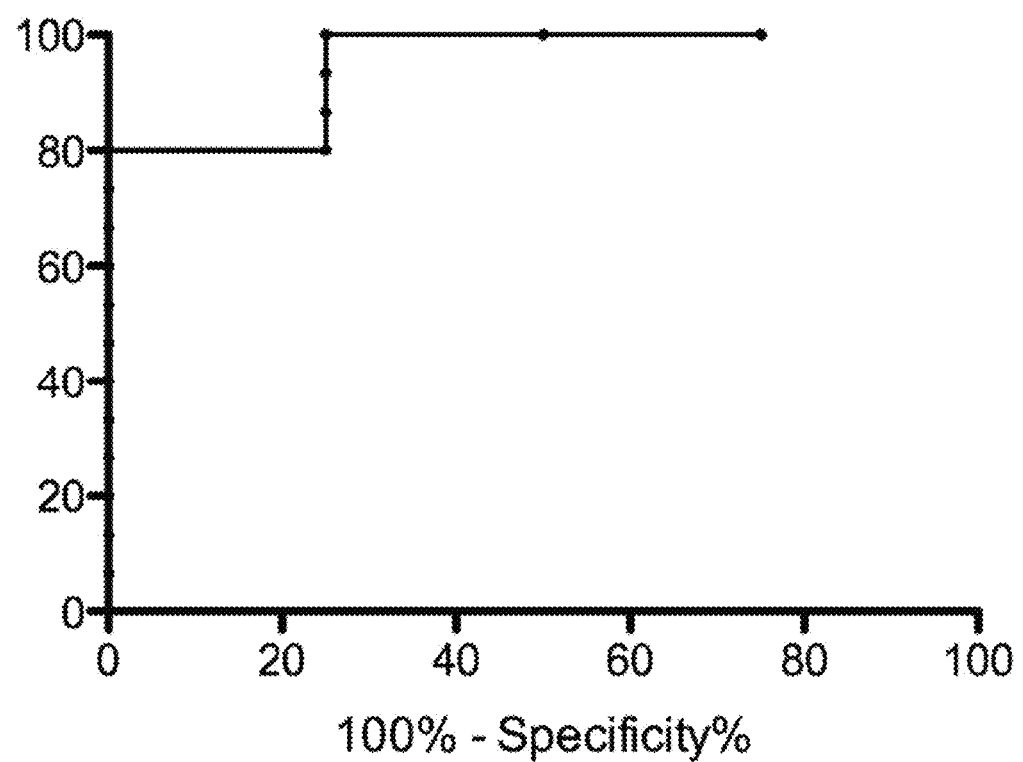
FIG. 42 shows ROC analysis of a viral infection indicator test.

Initial ROC analysis of viral infection indicator test on 6 clinical blood samples. Known clinical blood samples, 2 known positive samples, (i) CMV and (ii) EBV and 2 suspected viral samples were tested in parallel with 2 known negative blood samples in the presence of FITC-conjugated detection system for 15 minutes at RT prior to washing. Wells were read at 520 nm and the data was analyzed by Prism. See FIG. 42.

Current viral infection panels are serovar specific and are antibody or PCR based. Current methods for assessing viral infection require a 5-10 cc blood draw, sample prep, are time-consuming and fall outside the clinically-actionable window. There is a clinical need for a viral infection indicator test that can provide actionable information at the initial clinical encounter. The infection indicator test does not need sample processing, and with a few drops of blood, the viral infection indicator test can indicate the molecular symptoms of a viral infection within 15 minutes at ambient temperature. The above data suggest that the rapid detection of the viral response biomarkers (Type I interferons) can also be tested for and can be useful information.

Example 28: Molecular Net to Detect Bacterial Infection

The data in FIGS. 2 and 7 demonstrates that relates to bacterial cells/analytes spiked into whole blood can be detected using molecular nets have the composition as described in Example 2.

Current gold standard procedures for analyzing bacterial blood infections require a 5-10 cc blood draw, blood cultures or plating, are time-consuming (48 h) and fall outside the clinically-actionable window. There is a clinical need for a bacterial blood infection indicator test that can provide actionable information at the initial clinical encounter. The infection indicator test does not need sample processing, and with 100-300 uL of blood, the bacterial infection indicator test can indicate the molecular signatures of a bacterial infection within 15-30 minutes at ambient temperature.

The below molecular net recipe may be used to detect more specific signatures of bacteria known to cause bloodstream infections. The nets may be designed to immobilize signatures common to gram-negative bacteria (lipid A) and to gram-positive bacteria (peptidoglycan), in addition to immobilizing more specific signatures from the most common pathogens involved in bloodstream infections in most industrialized countries. The detection system for this test is formulated as a mixture of biotinylated antibodies from table 22.

TABLE 22

Bacterial net capture components

| BACT NET Components | Amount used (uL/50 mL) | Description of the build |
|---|---|---|
| pAb Strep Group B | 10.0 | Pipette 49.32 mL PBS |
| pAb Lipid A | 2.5 | add antibodies |
| pAb L monocytogenes | 2.5 | add sodium azide |
| pAb E coli | 5.0 | Mix, store at 4° C. until use |
| pAb E coli O + K | 2.0 | |
| mAb S aureus | 10.0 | |
| pAb Pseudomonas | 2.2 | |
| pAb Strep Group A | 10.0 | |
| mAb Klebsiella | 10.0 | |
| mAb peptidoglycan | 10.0 | |
| mAb Lipid A | 2.5 | |
| pAb S aureus | 5.0 | |

TABLE 22-continued

Bacterial net capture components

| BACT NET Components | Amount used (uL/50 mL) | Description of the build |
|---|---|---|
| pAb Enterococcus | 10.0 | |
| DNABP 1 | 4.3 | |
| DNABP 4 | 5.0 | |
| DNABP 6 | 6.0 | |
| DNABP 10 | — | |
| DNABP 11 | | |
| DNABP 12 | 10.0 | |
| PBS | 49322.78 | |
| Sodium azide | 0.1 | |

Vendors:
  AbCam
  Millipore
  AbD Serotec
Linker for Underlayer:
  Formaldehyde (37% w/v)
Linker for Net Layers:
  EMCS (0.00275 g/mL in DMSO)
  EGS (0.00325 g/mL in DMSO)
  BS$^3$ (0.075 g/mL in DMSO)
  BMPH (0.00225 g/mL in DMSO)
Method:
Underlayer—
  Mix 10% albumin (w/v) at 1:1 ratio with formaldehyde.
  Spot 2 uL per well
  Cure greater than 15 min at ambient temperature
$1^{st}$ Layer of Capture—
  Prepare linker solution by diluting linker mixture (from DMSO stock) 1:40 into amine-free PBS pH 7.4
  Mix 1:4 volume to volume of linker-to-capture
  Spot 2.5 uL directly onto the top of the underlayer
  Cure greater than 15 min at ambient temperature
$2^{nd}$ Layer of Capture—
  Mix 1:4 volume to volume of linker into capture
  Spot 2.5 uL directly onto the underlayer
  Cure greater than 15 min at ambient temperature
$3^{rd}$ Layer of Capture—
  Mix 1:4 volume to volume of linker into capture
  Spot 2.5 uL directly onto the underlayer
  Cure greater than 15 min at ambient temperature, then shift nets to 4° C. overnight Example 29: Nets to Bind S. aureus S. aureus Net Capture Components:

TABLE 23

| SA NET Components | Amount used (uL/50 mL) | Description of the build |
|---|---|---|
| pAb S aureus | 10.0 | Pipette 49.865 mL PBS |
| mAb S. aureus IgM | 20.0 | add antibodies |
| mAb Enterotoxin A/B/C1/C2/D/E clone S13 | 40.0 | add sodium azide |
| mAb S. aureus clone 704 | 24.1 | mix |
| DNABP 1 | 2.9 | |
| DNABP 4 | 3.3 | |
| DNABP 6 | 4.0 | |
| DNABP 10 | 10.0 | |
| DNABP 11 | 9.5 | |
| DNABP 12 | 11.0 | |
| PBS | 49865.2 | |
| Sodium azide | 0.1 | |

Vendors:
  Thermo Pierce
  AbCam
  Millipore
  AbD Serotec
Linker for Underlayer:
  Formaldehyde (37% w/v)
Linker for Net Layers:
  EMCS (0.00278 g/mL in DMSO)
  EGS (0.00302 g/mL in DMSO)
  BS$^3$ (0.0693 g/mL in DMSO)
  BMPH (0.00208 g/mL in DMSO)
Method:
Underlayer—
  Mix 10% albumin (w/v) at 1:1 ratio with formaldehyde.
  Spot 1 or 2 uL per well
  Cure greater than 15 min at ambient temperature
$1^{st}$ Layer of Capture—
  Prepare linker solution by diluting linker mixture (from DMSO stock) 1:40 into amine-free PBS pH 7.4
  Mix 1:4 volume to volume of linker-to-capture
  Spot 1.25 or 2.5 uL or 3 uL directly onto the top of the underlayer
  Cure greater than 15 min at ambient temperature
$2^{nd}$ Layer of Capture—
  Mix 1:4 volume to volume of linker into capture
  Spot 1.25 or 2.5 uL directly onto the underlayer
  Cure greater than 15 min at ambient temperature
$3^{rd}$ Layer of Capture—
  Mix 1:4 volume to volume of linker into capture
  Spot 1.25 or 2.0 or 2.5 uL directly onto the underlayer
  Cure greater than 15 min at ambient temperature, then shift nets to 4° C. overnight Three differentially constructed S. aureus nets and their respective ability to bind S. aureus in a complex sample within 15 minutes compared to a 2-dimensional immunoassay format.

Figure 32:
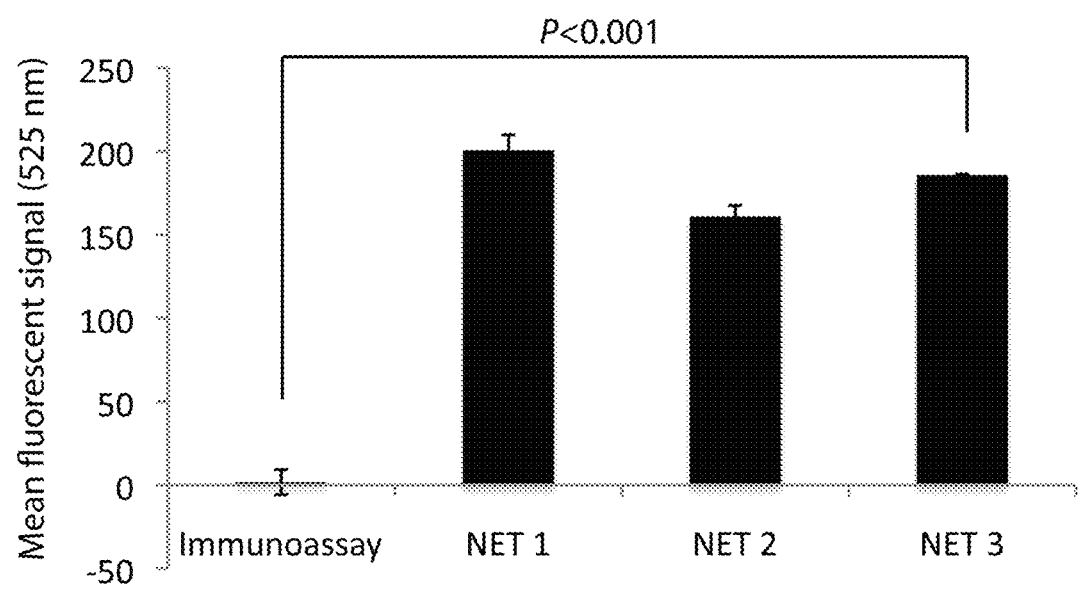
FIG. 32 shows *S. aureus* binding results for three different configurations of molecular net.

Two layered nets with an underlayer were built with the capture components from table 18. Net 1 was composed of underlayer, first (2 uL capture+1 uL linker), second (2 uL capture+0.5 uL linker), and third (1 uL capture+1 uL linker) layers. Net 2 was composed of underlayer and first (4 uL capture+1.5 uL linker) layer. Net 3 was composed of underlayer and first (5 uL+2.5 uL linker) layer. Nets composed of underlayer+6 uL capture+2.5 uL, underlayer+3 uL capture 1.5 uL linker and underlayer+2 uL capture+1 uL linker, +2 uL capture+1 uL linker, +1 uL capture+1 uL linker did not perform better than nets 1 through 3 (data not shown). Immunoassay format contained identical capture mixture (5 uL) and was absorbed overnight. Wells were incubated with 20 CFU of S. aureus and detection system at RT for 15 minutes prior to washing. Wells were read on a plate reader at 525 nm. Bars represent the mean fluorescent signal of triplicate wells. Error bars represent SEM. P values were obtained by the student t-test. See FIG. 32. This data demonstrates that molecular nets can increase the time-to-detection of S. aureus analytes compared to the conventional immunoassay format, as 15 minutes was insufficient for the immunoassay format to produce a signal.

Figure 33:
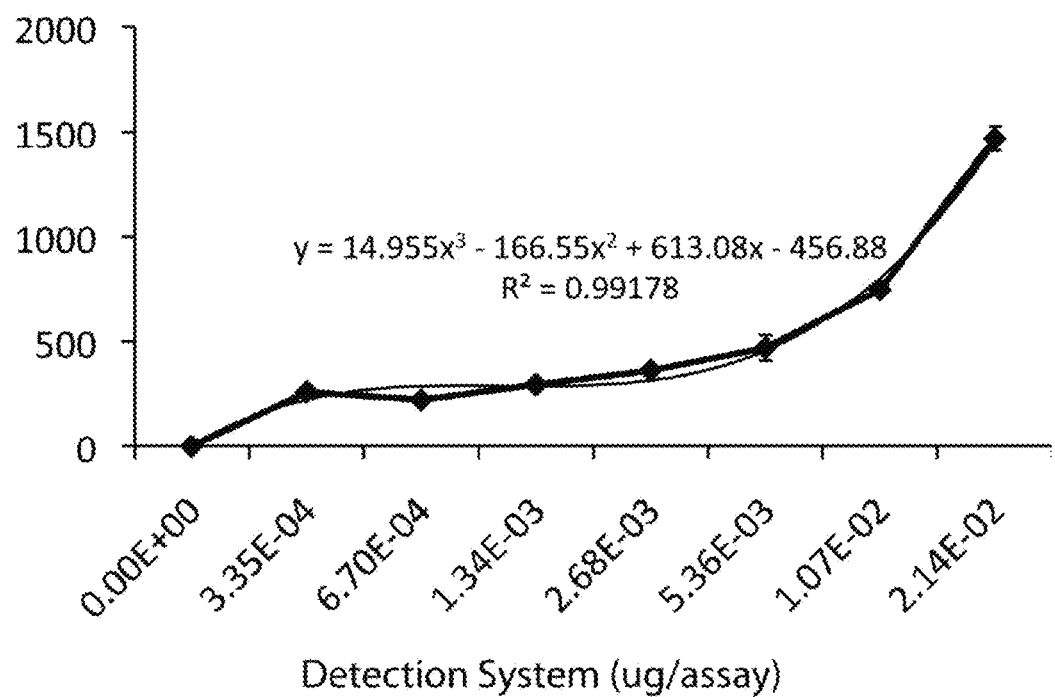
FIG. 33 shows detection of *S. aureus* immobilized on molecular nets.

Detection of S. aureus Immobilized to Nets
  S. aureus or S. epidermidis were incubated with molecular nets at 200 CFU/well and S. aureus detection system (10 uL of 0 to 21.4 ng/test well). See FIG. 33. S. aureus and S. epidermidis both inhabit the same environments and are very similar genetically and morphologically. Current tests to differentiate these species rely on the phenotypic catalase test performed on the cultured organism. The results from FIG. 33 demonstrate a timely and accurate approach to identify *S. aureus* analytes in a complex sample.

The *S. aureus* Test Utilizing a Molecular Net

Figure 34:
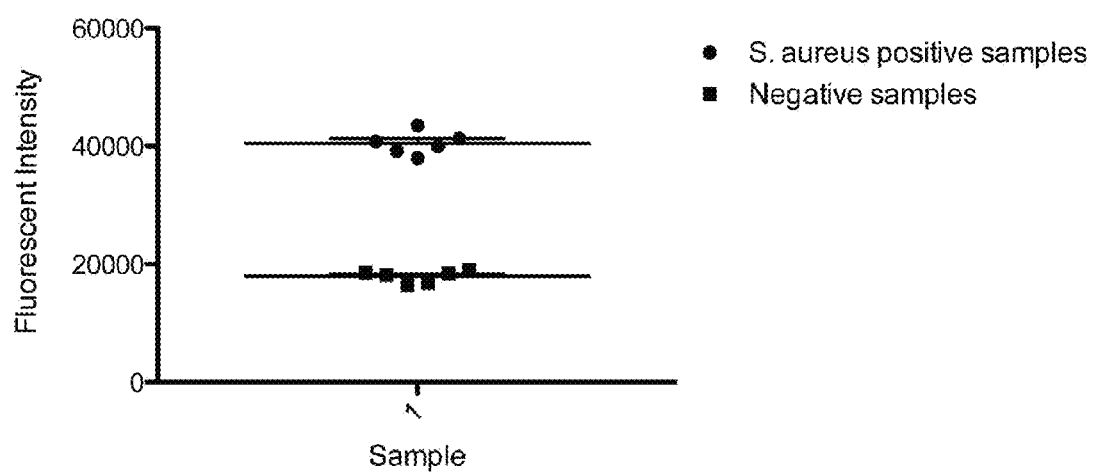
FIG. 34 shows detection of *S. aureus* using a fluorescent detection system.

Samples with *S. aureus* or non-*S. aureus* species were incubated with molecular nets and *S. aureus* detection system for 30 minutes at RT. Bars represent the average fluorescent intensity of the samples for each group. Small error bars represent the SEM. See FIG. 34.

The ability to bind signatures of *S. aureus* in complex samples within 15 to 30 minutes enables rapid testing of samples from clinical, environmental, industrial settings.

Example 30: Synergy of Multi-Signature Detection

Conditions for these analyses were done according to Example 24. Test results from numerous studies with molecular nets constructed to bind *S. aureus* analytes and the detection system components. The study was performed to analyse the individual contribution of the probe-based system designed to bind SCCmec and the antibody-based system designed to bind Pbp2a. The study was also designed to compare the individual probe-based signal with the antibody-based signal and with the combined contribution of both in a net-based test format.

Figure 40:
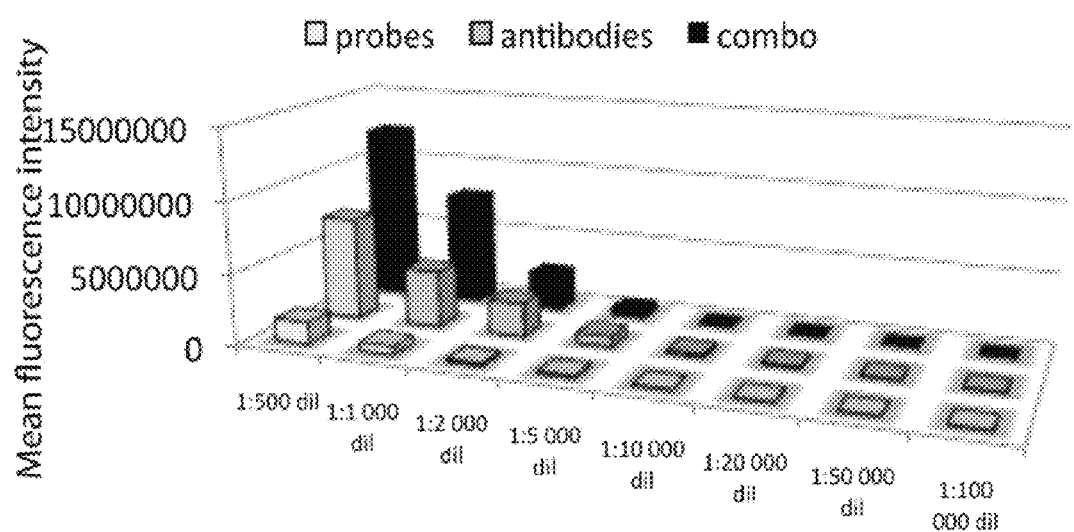
FIG. 40 shows synergistic results of multi-signature detection.

Assay Procedure
1. Layered nets were built in replicates according to methods above.
2. Block was removed from the wells containing nets and washed with PBS
3. Colonies of plated MRSA
4. Samples containing 1,000 CFU MRSA were placed in wells containing nets
5. Samples were then incubated with 10 uL of a serial dilution of FITC-labeled MR detection system (probes or antibodies or both) with each net for 30 minutes
6. Nets were washed with 0.3 mL PBS, 0.005% Tween-20, and 2.5% egg albumin (wash buffer) and quickly rinsed with PBS
7. The fluorescence at 520 nm was measured in each well by plate reader Probe hybridization to net-immobilized analytes accounts for a small percent of the readable signal. The antibody contribution is significantly greater. The results from this study suggest synergism exists when FITC-labeled probes are in the same testing location as FITC-labeled antibodies. See FIG. 40. The amplification of signal is very significant and is an important aspect in the ability to detect low abundant analytes. Positioning of the analytes by the net contributes to this result (See Example 20).

Example 31: Direct Detection of MRSA in Sandwich Assay

This prophetic example demonstrates direct detection of MRSA in a sandwich assay format. Molecular nets with the composition described in the below tables with capture components are used to immobilize analytes from a sample and the immobilized analytes are detected with components with directed against the same analytes. See Tables 23 and 24.

The advantage of this method over current immunoassays is the use of multiple capture antibodies and detection antibodies simultaneously. Conventional immunoassays use one capture antibody and a different detection antibody that recognize 2 distinct epitopes on an analyte. The use of multiple distinct antibodies that recognize different epitopes increases the probability of detection.

TABLE 23

Capture Components

| Capture Component | Modification | Vendor | Conc. (Ug) |
|---|---|---|---|
| mAb MRSA clone 332/423 | unmodified | AbD Serotec | 1 |
| mAb MRSA clone 198 | unmodified | AbCam | 1 |
| mAb MRSA clone AC10 | unmodified | AbCam | 1 |

TABLE 24

Detection Components

| Detection Component | Modification | Vendor | Conc. (Ug) |
|---|---|---|---|
| mAb MRSA clone 332/423 | Biotin | AbD Serotec | 1 |
| mAb MRSA clone 198 | Biotin | AbCam | 1 |
| mAb MRSA clone AC10 | Biotin | AbCam | 1 |

Net Construction

Nets are built by the following: 1 ug/mL of each unmodified antibody is mixed with a working linker stock containing $BS^3$ (363 nM), BMPH (27.5 nM), EMCS (750 nM) and EGS (150 nM) at a 2:0.5 ratio of capture-to-linker. 3-layered nets with underlayers (2 uL each) are built using a mixture of 1:1 10% (w/v) albumin and 37% (w/v) formaldehyde and cured for 15 minutes. Three layered nets are constructed (2.5 uL per layer). Nets are cured, quenched and blocked with 0.5% BSA in PBS prior to use.

Detection

Biotinylated detection components are pre-incubated for 30 minutes at 37° C. with avidin-FITC (Invitrogen) at a 1:3 ratio.

Assay Protocol

Samples containing MRSA or controls are incubated with nets and 10 uL of a 1:46 dilution of detection system for 30 minutes at RT. Wells are washed and rinsed and read with a conventional fluorescent plate reader.

Example 32: Personalized Medicine: Drug as Capture Agent for Cytochrome P450

There are over 50 genes encoding different cytochrome P450 enzymes (isozymes) in the human genome and these enzymes account for over 70% of drug metabolism. It is known that numerous drugs affect the activity of the P450 isozymes. For example, if drug A inhibits the P450-mediated metabolism of drug B, there can be a bioaccumulation of drug B in a human that approaches toxic levels. As another example, if drug A binds a P450 isozyme with high avidity, the biologic effect of the drug is abolished in an individual.

Furthermore, drug side effects are dependent on the P450 polymorphisms of individuals.

This prophetic example illustrates the use of molecular nets having an experimental drug or a known drug as a capture agent. These nets can be contacted with a patient blood sample. Detection of binding between the molecular net and cytochrome P450 isozymes and polymorphisms can be used to as an indicator of a potential adverse drug interaction within a clinically actionable timeframe (~30 minutes). The test is designed to detect the majority of the cytochrome P450 enzymes that are immobilized to the drug net.

TABLE 25

Capture Components

| Net Component | Vendor | Concentration | Significance |
|---|---|---|---|
| Carbamazepine | Novartis | 5 mM | Capture agent |
| NH2-AGKATRKG-COOH | Anaspec | 1 ug | Structural role, multiple amines |
| NH2-AGKAPAKD-COOH | Anaspec | 1 ug | Structural role, β-bend for net |
| NH2-GSKAGKANAKK-COOH | Anaspec | 1 ug | Structural role, multiple amines |

TABLE 26

Linkers

| Linker | Spacer Arm (Ångstrom) | Linkages | Concentration Used (Nm) |
|---|---|---|---|
| SANPAH | 18.2 | Amine to nonselective | 600 |
| NHS-ASA | 5.7 | Amine to nonselective | 260 |
| LC-SDA(NHS-LC-Diazirine) | 12.5 | Amine to nonselective | 335 |
| Formaldehyde | 0 | Nonselective | 37% (w/v) |

TABLE 27

Detection Components

| Antibody | Vendor | Modification | Concentration Used (Ug) |
|---|---|---|---|
| CYP1A2 | OriGene | Biotin | 1 |
| CYP2E1 | OriGene | Biotin | 1 |
| CYP7B1 | OriGene | Biotin | 1 |
| TBXAS1 | OriGene | Biotin | 1 |
| POR | OriGene | Biotin | 1 |
| CYP3A5 | OriGene | Biotin | 1 |
| ACYP1 | OriGene | Biotin | 1 |
| LDB3 | OriGene | Biotin | 1 |
| MUTYH | OriGene | Biotin | 1 |
| PPID | OriGene | Biotin | 1 |
| PPIA | OriGene | Biotin | 1 |
| CYP17A1 | OriGene | Biotin | 1 |
| CYP19A1 | OriGene | Biotin | 1 |
| CYP46A1 | OriGene | Biotin | 1 |
| CYP19A1 | OriGene | Biotin | 1 |
| CYP2B6 | Sigma | Biotin | 1 |
| CYP2C19 | Sigma | Biotin | 1 |
| CYP2D6 | Pierce | Biotin | 1 |
| CYP3A4 | Pierce | Biotin | 1 |

Net Build Protocol—
1. Underlayer is constructed with a 50:1 molar ratio of formaldehyde to peptides and cured at RT for 120 minutes
2. The initial layer of molecular net is constructed by pre-mixing capture components in PBS (carbamazepine and peptides) with a 1:400 dilution of linker mixture in PBS and applying a volume directly onto an underlayer
3. Photoactivation of linker within the initial capture layer is performed by UV light exposure and curing at RT for 30 minutes
4. The second layer of molecular net is constructed by pre-mixing capture components (carbamazepine and peptides) with a 1:400 dilution of linker mixture and applying a volume directly onto an underlayer
5. Photoactivation of linker within the initial capture layer is performed by UV light exposure and curing at RT for 30 minutes
6. The third layer of molecular net is constructed by pre-mixing capture components (carbamazepine and peptides) with a 1:400 dilution of linker mixture and applying a volume directly onto an underlayer
7. Photoactivation of linker within the initial capture layer is performed by UV light exposure and curing at RT for 30 minutes
8. The reaction is quenched from a final RT incubation for 2 hrs
9. Nets are blocked with 0.5% BSA in PBS and stored until use.

Detection Build Protocol—
1. A mixture of detection antibodies is generated to give a 1 ug/mL and is biotinylated at 20:1 molar ratio using the NHS-biotin reagent (Pierce) according to manufacturer specifications
2. Unreacted biotin is removed by size exclusion chromatography
3. Avidin-FITC is incubated with detection antibodies at 3:1 molar ratio for 30 minutes at 37° C.

Assay Protocol
1. Blocked nets are washed with PBS pH 7.4
2. Whole blood samples are incubated with nets and 10 uL of a 1:50 dilution of detection system
3. Nets are washed with 0.5% BSA and 0.05% Tween in PBS after 30 minutes
4. Nets are rinsed with PBS and are read using a fluorescent plate reader

Example 33: Sepsis/BVF Detection

Sepsis organism etiology can be determined using molecular nets. The advantage of this testing strategy over current methods to determine bloodstream infection is the use of multiple capture antibodies and detection antibodies simultaneously that can recognize a multitude of shared epitopes common amongst the leading gram-negative and gram-positive bacteria known to cause the majority of bloodstream infections. Conventional methods require the growth of a blood culture and microbial growth for certain organisms may not occur under the clinical laboratory conditions. Additionally, the employment of 2 separate detection systems, one for gram-negative and the other for gram-positive bacteria, enables a rapid method to distinguish between two of the largest classes of bacteria. The use of a molecular net-based test that does not rely on viable bacteria and that can produce a readable signal within a 30-minute timeframe is useful in many clinical settings.

The Bacterial Test

TABLE 28

Bacterial Net

| Bacterial Net Components | Amount used (uL/50 mL) | Description of the build |
|---|---|---|
| pAb Strep Group B | 10.0 | Pipette 49.32 mL PBS |
| pAb Lipid A | 2.5 | add antibodies |
| pAb L monocytogenes | 2.5 | add sodium azide |
| pAb E coli | 5.0 | Mix, store at 4° C. until use |
| pAb E coli O + K | 2.0 | |
| mAb S aureus | 10.0 | |
| pAb Pseudomonas | 2.2 | |
| pAb Strep Group A | 10.0 | |
| mAb Klebsiella | 10.0 | |

TABLE 28-continued

Bacterial Net

| Bacterial Net Components | Amount used (uL/50 mL) | Description of the build |
|---|---|---|
| mAb peptidoglycan | 10.0 | |
| mAb Lipid A | 2.5 | |
| pAb S aureus | 5.0 | |
| pAb Enterococcus | 10.0 | |
| DNABP 1 | 4.3 | |
| DNABP 4 | 5.0 | |
| DNABP 6 | 6.0 | |
| DNABP 10 | — | |
| DNABP 11 | | |
| DNABP 12 | 10.0 | |
| PBS | 49322.78 | |
| Sodium azide | 0.1 | |

Detection System Construction

TABLE 29

Gram positive detection

| Component | Modification | Vendor | Volume (uL) | Notes |
|---|---|---|---|---|
| pAb Strep Group A | Biotin | AbCam | 5.0 | Biotinylate all at 30:1 molar ratio and then freeze aliquots |
| pAb Strep Group B | Biotin | AbCam | 5.0 | Remove all unreacted biotin |
| pAb L monocytogenes | Biotin | AbCam | 1.3 | Add all biotinylated Abs into 71.54 uL PBS and added streptavidin-FITC at 4:1 ratio, incubate 37 C. for 30 min |
| mAb S aureus | Biotin | AbCam | 3.8 | |
| pAb Enterococcus | Biotin | AbCam | 5.0 | |
| mAb peptidoglycan | Biotin | Millipore | 5.5 | |
| mAb Enterotoxin A/B/C1/C2/D/E clone S13 | Biotin | AbD Serotec | 5.5 | |
| PBS | | Mediatech | 79.40 | |
| avidin-FITC | FITC | Invitrogen | 6.18 | |

TABLE 30

Gram negative detection

| Component | Modification | Vendor | Volume (uL) | Notes |
|---|---|---|---|---|
| pAb E coli | Biotin | AbCam | 1.3 | Biotinylate all at 30:1 molar ratio and then freeze aliquots |
| pAb E coli O + K | Biotin | AbCam | 2.5 | Remove all unreacted biotin |
| pAb Pseudomonas | Biotin | AbCam | 1.1 | Add all biotinylated Abs into 71.54 uL PBS and added |
| pAb Klebsiella | Biotin | AbCam | 1.3 | Streptavidin-FITC at 4:1 ratio, incubate 37 C. for 30 min |
| pAb Legionella | Biotin | AbCam | 2.6 | |
| pAb Lipid A | Biotin | AbD Serotec | 1.8 | |
| pAb Lipid A | Biotin | AbCam | 1.8 | |
| PBS | | Mediatech | 92.13 | |
| avidin-FITC | FITC | Invitrogen | 2.88 | |

Bacterial Net Construction

Nets are built by the following: 1 ug/mL of each unmodified antibody is mixed with a working linker stock containing $BS^3$ (363 nM), BMPH (27.5 nM), EMCS (750 nM) and EGS (150 nM) at a 2:0.5 ratio of capture-to-linker. 3-layered nets with underlayers (2 uL each) are built using a mixture of 1:1 10% (w/v) albumin and 37% (w/v) formaldehyde and cured for 15 minutes. Three layered nets are constructed (2.5 uL per layer). Nets are cured, quenched and blocked with 0.5% BSA in PBS prior to use.

Detection Construction

Biotinylated detection components are pre-incubated for 30 minutes at 37° C. with avidin-FITC (Invitrogen) at a 1:3 ratio.

Assay Protocol for Clinical Lab Settings

Blood samples positive for microbial growth or controls are incubated with nets and 10 uL of a 1:50 dilution of detection system for 30 minutes at RT. Wells are washed and rinsed and read with a conventional fluorescent plate reader.

Assay Protocol for Non-Lab Settings

Blood samples from patients suspected of having bloodstream infections or controls are incubated with nets and 10 uL of a 1:50 dilution of detection system for 30 minutes at RT. Nets are washed once and rinsed and read with a conventional fluorometer.

Fungal Test

TABLE 31

Fungal net capture components

| Component | Modification | Vendor | Concentration (ug) | Notes |
|---|---|---|---|---|
| pAb C albicans | None | AbCam | 1 | Add antibodies and repeat up to 50 mL of PBS pH 7.4 |
| pAb Aspergillus | None | AbCam | 3 | Add 0.01% sodium azide |
| pAb C albicans | None | Novus | 2 | Store at 4 C. until use |
| pAb chitin | None | Pierce | 3 | |
| mAb Aflatoxin | None | AbCam | 1.1 | |
| pAb ochratoxin A | None | AbCam | 1.5 | |
| pAb ergosterol | None | Pierce | 2.5 | |
| PBS | | Mediatech | — | |
| LINKERS | | | | |
| $BS^3$ | None | Pierce | 300 nM | Resuspend linkers in DMSO stock |
| BS(PEG)$_9$ | None | Pierce | 600 nM | Dilute stock 1:40 in amine free PBS |
| EGS | None | Pierce | 216 nM | Mix capture-to-linker at 2.0:0.6 ratio |
| UNDERLAYER | | | | |
| Albumin | None | Calbiochem | 10% w/v | Reconstitute in PBS |
| Formaldehyde | None | Pierce | 37% w/v | Mix albumin-to-linker at 1:1 ratio |

TABLE 32

Fungal detection components

| Component | Modification | Vendor | Volume | Notes |
|---|---|---|---|---|
| pAb C albicans | Biotin | AbCam | 5.0 | Biotinylate at 30:1 molar ratio and then freeze aliquots |

TABLE 32-continued

Fungal detection components

| Component | Modification | Vendor | Volume | Notes |
|---|---|---|---|---|
| pAb Aspergillus | Biotin | AbCam | 1.1 | Remove unbound biotin |
| pAb C albicans | Biotin | Novus | 5.0 | added all biotinylated Abs into 71.54 uL PBS and add streptavidin-FITC at 4:1 ratio, incubate 37 C. for 30 min |
| pAb chitin | Biotin | Pierce | 6.0 | |
| mAb Aflatoxin | Biotin | AbCam | 5.5 | |
| pAb ochratoxin A | Biotin | AbCam | 5.5 | |
| pAb ergosterol | Biotin | Pierce | 4.5 | |
| PBS | | Mediatech | 77.89 | |

Fungal Net Construction

Nets are built by the following: 1 ug/mL of each unmodified antibody is mixed with a working linker stock containing $BS^3$ (300 nM), $BS(PEG)_9$ (600 nM), and EGS (216 nM) at a 2:0.75 ratio of capture-to-linker. 3-layered nets with underlayers (2 uL each) are built using a mixture of 1:1 10% (w/v) albumin and 37% (w/v) formaldehyde and cured for 15 minutes. Three layered nets are constructed (2.5 uL per layer). Nets are cured, quenched and blocked with 0.5% BSA in PBS prior to use.

Detection Construction

Biotinylated detection components are pre-incubated for 30 minutes at 37° C. with avidin-FITC (Invitrogen) at a 1:3 ratio.

Assay Protocol for Clinical Lab Settings

Blood samples positive for microbial growth or controls are incubated with nets and 10 uL of a 1:50 dilution of detection system for 30 minutes at RT. Wells are washed and rinsed and read with a conventional fluorescent plate reader.

Assay Protocol for Non-Lab Settings

Blood samples from patients suspected of having bloodstream infections or controls are incubated with nets and 10 uL of a 1:50 dilution of detection system for 30 minutes at RT. Nets are washed once and rinsed and read with a conventional fluorometer.

The Viral Test

The components of the test and the methods for construction of the net and the assay are as described in Example 24.

Example 34: Infection Screening

Molecular nets can be used to screen for infection. The advantage of this testing strategy over current methods is the use of molecular approaches. Conventional methods for infection survey the individual for a fever or an increase in white blood cell (leukocytes) counts (also known as a CBC). The net-based infection indicator test enables the detection of molecules produced by innate immune cells at the initial encounter of a foreign agent. This precedes the TNF response that leads to a fever and also precedes the increase in blood leukocytes that result from an infection. The use of a robust molecular net-based test that can be used rapidly in numerous clinical settings and produce readable signal within a 30-minute timeframe is useful for post-operative, critical care, burn, bone marrow transplant, and intensive care settings.

TABLE 33

Infection screening test - Net components

| Component | Vendor | Volume (uL) | Notes |
|---|---|---|---|
| pAb LBP (N-17) | Santa Cruz | 50 | Pipette 48.13 mL PBS |
| pAb LBP (K-15) | Santa Cruz | 50 | add antibodies |
| pAb Azurocidin | AbCam | 27 | add sodium azide |
| mAb Ficolin 2 | AbCam | 10 | mix |
| pAb Cathelicidin | AbCam | 3 | |
| pAb beta 2 Defensin | AbCam | 20 | |
| pAb beta Defensin 1 | AbCam | 3 | |
| mAb alpha Defensin 1 + 2 + 3 | AbCam | 5 | |
| mAb beta Defensin 3 | AbCam | 10 | |
| pAb beta Defensin 4 | AbCam | 20 | |
| PBS | Mediatech | 48013.06 | |
| Sodium azide | Pierce | 0.1 | |
| LINKERS | | | |
| $BS^3$ | Pierce | 380 nM | Resuspend linkers in DMSO stock |
| EMCS | Pierce | 500 nM | Dilute stock 1:40 in amine free PBS |
| EGS | Pierce | 245 nM | Mix capture-to-linker at 2.0:0.6 ratio |
| UNDERLAYER | | | |
| Albumin | Calbiochem | 10% w/v | Reconstitute in PBS |
| Formaldehyde | Pierce | 37% w/v | Mix albumin-to-linker at 1:1 ratio |

TABLE 34

Infection screening test - Detection system

| Component | Modification | Vendor | Volume (uL) | Notes |
|---|---|---|---|---|
| pAb Azurocidin | Biotin | AbCam | 0.915 | Biotinylate at 30:1 molar ratio and then freeze aliquots |
| pAb beta Defensin 1 | Biotin | AbCam | 1 | Remove unbound biotin |
| pAb beta 4 Defensin | Biotin | AbCam | 1 | add all biotinylated Abs into 71.54 uL PBS and add streptavidin-FITC at 4:1 ratio, incubate 37 C. for 30 min |
| pAb beta Defensin | Biotin | AbCam | 1 | |
| mAb LBP | Biotin | Antibodies Online | 1 | |
| mAb Ficolin 2 | none | AbCam | 1 | |
| pAb beta 2 Defensin | none | AbCam | 0.5 | |
| mAb alpha Defensin 1 + 2 + 3 | none | AbCam | 2 | |
| PBS | | Mediatech | 91.5 | |
| avidin-FITC | FITC | Invitrogen | | |

Infection Indicator Net Construction

Nets are built by the following: 1 ug/mL of each unmodified antibody is mixed with a working linker stock containing $BS^3$ (380 nM), EMCS (500 nM), and EGS (245 nM) at a 2:0.75 ratio of capture-to-linker. 3-layered nets with underlayers (2 uL each) are built using a mixture of 1:1 10% (w/v) albumin and 37% (w/v) formaldehyde and cured for 15 minutes. Three layered nets are constructed (2.5 uL per layer). Nets are cured, quenched and blocked with 0.5% BSA in PBS prior to use.

Detection Construction

Biotinylated detection components are pre-incubated for 30 minutes at 37° C. with avidin-FITC (Invitrogen) at a 1:3 ratio.

Assay Protocol for Clinical Settings

Blood or urine samples from patients suspected of having an infection or controls are incubated with nets and 10 uL of a 1:50 dilution of detection system for 30 minutes at RT. Wells are washed and rinsed and read with a conventional fluorescent plate reader.

Assay Protocol for Non-Clinical Settings

Blood or urine samples from individuals suspected of having an infection or controls are incubated with nets and 10 uL of a 1:50 dilution of detection system for 30 minutes at RT. Nets are washed once and rinsed and read with a conventional fluorometer.

Example 35: Molecular Nets for Field Testing

A *S. aureus* molecular net that can immobilize analytes from methicillin-sensitive and methicillin-resistant *S. aureus* is constructed on a sampling swab. This swab can be for sampling a person, food, a surface or an environment.

The sampling swab is used as follows:
1) Swab sampling source
2) Place swab in detection system
3) Remove swab from detection system
4) Place swab in wash solution
5) Remove swab from wash solution
6) Place swab in rinse solution
7) Remove swab from rinse solution
8) Place swab in a reader Additional Molecular Nets and Uses of the Same Applications, tests, devices and composition of matter for immobilizing and/or detecting analytes in a sample have been described in U.S. patent application Ser. Nos. 61/281,991 (filed Nov. 24, 2009), 61/337,257 (filed Feb. 1, 2010), 61/340,287 (filed Mar. 15, 2010), 61/343,467 (filed Apr. 29, 2010), 61/410,837 (filed Nov. 5, 2010), 61/669,261 (filed Jul. 9, 2012), and 61/669,265 (filed Jul. 9, 2012), all of which are hereby incorporated by reference as if fully set forth herein.

The inventive use of molecular nets in combination with tests, devices and methods of this invention overcome the problems found in the prior art providing devices and methods for the simultaneous testing of sample protein, lipid, carbohydrate and nucleic acid analytes, and combinations thereof, using affinity-based, physicochemical, electrochemical, magnetic and enzymatic analyses; and for devices and methods to detect or immobilize multiple specific analytes in a sample which are limited to one-to-five kinds of recombinant polypeptides or nucleic acids to be absorbed or attached to a device and the corresponding recognition of antibodies that bind the one-to-five kinds of recombinant polypeptides or nucleic acid probes, respectively; which require precise pipetting of sample; which require even flow of reagents through a device; which require capillary action of reagents to migrate through a device; and which require uniform binding of reagents to the test surface of a device.

The concept of the present invention and any arrangement, use, method, test and device that employs said invention wherein the construction of a dense heterogeneous network of multiple different types of capture components that can be mixed with metal nanoparticles and that can contain unique and distinct topologies and binding surfaces and physical, electrical, vibrational, thermal, spatial, magnetic, and chemical properties is referred to as a molecular net; whereby small channels and small pockets can be present throughout the molecular net in an irregular manner; and whereby a molecular net is covalently or non-covalently linked via chemical crosslinkers or mixed with polyethylene glycol to increase the stability of the capture molecules and to increase the density of the potential analyte binding sites per volume of molecular net and/or to confer a unifying property in relation to physical, vibrational, spatial, magnetic and chemical properties of said molecular net; and whereby said small channels and pockets within and throughout said molecular net can contain multiple unique surface chemistries and can confer properties to the molecular net and to the manner in which analyte moves through and around the molecular net by microfluidics, nanofluidics, capillary action, and other means of solute movement through a dense network of molecules. The two- and three-dimensional topology of the molecular net is undefined, non-uniform and is optimal for the specific binding and immobilization of multiple analytes in complex samples.

Additionally, the invention herein also pertains to the ways in which molecular nets can be constructed, processed and arranged via moldings, sectioning, cutting, etching, extruding or other to generate molecular net of specified dimensions for the purpose of filling a testing area, volume or other; or for the purpose of filling a column, tubing, piping, hosing, cartridge or other; and whereby said molecular net can be constructed to generate neighboring sections of different molecular nets containing capture components and/or chemical crosslinkers of different chemical specificity; and can be attached or fitted to one or more test areas in a polymeric device; or can be attached or fitted into a porous polymeric device; or can be fitted into a polymeric column, pipe, cartridge, tubing, hosing or other.

Disclosed is a device employing multiple different molecular nets or pieces of molecular nets configured within one or more testing area to facilitate multi-analyte capture, immobilization and detection; whereby molecular net surfaces comprise a plurality of textures and structures and surface chemistries and topologies and fluidics; and whereby a plurality of molecular nets in a single testing area can be configured; or whereby a plurality of molecular nets in a single column, tube, pipe, cassette, cartridge or other can be configured. Surfaces, topologies, arrangements, and physical properties in accordance with the invention, and devices comprising such surfaces, topologies, arrangements and physical properties, are used to facilitate the binding, immobilization and/or detection of multiple different analytes simultaneously from an environmental, food or biologic sample.

Unlike assay devices of the prior art, the inventive assay devices described herein do not require the use of bibulous materials, such as papers or membranes. The inventive devices of the present invention rely on the use of any defined surface that contains amines, sulfhydryls, carboxyls, and/or hydroxyls that can serve as attachment points to promote the construction or the deposit of molecular nets into or onto a device; and whereby the molecular nets can be absorbed, fitted, bound, or linked to said defined surface. The inventive devices described herein can require injection, pushing, suctioning, swiping, swabbing, scooping, shoveling, clipping, cutting, entrapment and/or exposure of a sample to one or more molecular net; that can be introduced into one or more inlet port of a device, and do not require precise pipetting steps. The concepts and devices of the present invention are especially useful in the performance of affinity assays such as immunoassays, enzymatic assays, protein binding assays and nucleic acid binding assays of a plurality of samples such as: environmental samples, food samples, tissues, cells, microbes, drugs, biologics, antibodies, antigens, nucleic acids, steroids, hormones, and other molecules found in fluids and products, such as but not limited to: wastewater, well water, municipal water sources, bodies of water, cerebrospinal fluid, amniotic fluid, serum, plasma, blood, sputum, sebum, pleural effusion, buccal swab, throat swab and urine simultaneously.

Disclosed is an analytical device for determining the presence or amount of one or more analyte in a sample using molecular nets. The device can comprise an array of internal structures, chambers and channels; whereby one or more of said structures can have a surface supporting and/or immobilizing one or more molecular net that can be covalently or non-covalently attached; or fitted; to a polymeric surface, and whereby the immobilized molecular net can be capable of binding more than one different kind of analyte in a sample. The device can also comprise a plurality of molecular nets in one or more arrangement; in one or more testing area of a device, or whereby individual molecular nets can be separated into separate testing areas, wherein all testing areas can be exposed to said test sample or a separated, semi-purified, or fractionated test sample to enable one or more analyte to be immobilized by multiple capture molecules in one or more molecular net in one or more testing area of said device.

Disclosed is one or more molecular net and/or an arrangement of molecular net pieces; whereby the arrangement of capture molecules and the respective specific surface chemistries of capture molecules and the respective binding preferences for specific analytes can be arranged in sections within the molecular net; whereby the binding and immobilization of specific analytes to specific capture molecules can generate a pattern of detection; and whereby the pattern of detection can be determined by the immobilization of specifically labeled analyte detection molecules; and whereby said labeled detection molecules can provide one or more signal; and whereby the patterning and/or arrangement and/or timing of signal can provide information in a binary or analytical test.

Disclosed is a molecular net and/or an arrangement of molecular net pieces that can comprise an array of structures such as one or more than one of the following: a wall of molecular net; a section of molecular net; a brick of molecular net; a patchwork of molecular net; a striated pattern of molecular net or other arrangement that can be formed; whereby molecular nets or pieces thereof can be layered; stacked; linked in a patchwork; woven; glued; adhered; crosslinked; and/or adsorbed together; whereby each molecular net, piece or section of molecular net can possess unique physical features and physical properties that confer enhanced binding of specific analytes per unit volume; and whereby said arrangements can generate an enhanced multiplexing ability, or superplexing, whereby the density and binding specificities of the multiple different capture molecules can capture and immobilize a large population of specific analytes of different compositions in a sample; and whereby said invention is a great improvement over the capture and immobilization capacities of current technologies.

Disclosed is one or more molecular net, and tests and devices that can contain one or more molecular net, with capture molecules and metal nanoparticles that are linked together with chemical crosslinkers; whereby said metal nanoparticles are covalently linked to one or more amine, sulfhydryl, carboxyl, and/or hydroxyl group to facilitate crosslinking to one another and to capture molecules; and the construction of a molecular net with unique thermal, magnetic, electric, chemical, vibrational, compressive, spatial and colorimetric properties; whereby the binding of and the degree of binding of specific analytes to the capture molecules can change the properties of the molecular net; and whereby the changes of molecular net properties can be a signal and can be detected in a binary or analytical test.

Disclosed is a device containing one or more molecular net, or molecular net walls, containing interspersed capture molecules and modified metal nanoparticles; whereby analyte binding can alter the physical, magnetic, electrical, chemical, vibrational, compressive, colorimetric, thermal, and spatial properties of said molecular nets or molecular net walls; whereby said altered properties can be a signal and can be detected by sensors to produce information in a binary or analytical test of said device.

Disclosed is a device and methods within said device that can contain one or more molecular net that can perform PCR and/or RT-PCR under isothermal and/or thermal-cycling conditions; whereby said molecular net can contain capture molecules such as nucleic acid binding molecules and/or gyrases and topoisomerases, and polymerases; and whereby the buffer surrounding the molecular net can contain water and specific nucleic acid primers and Mg2+ and nucleosides and/or dimethyl sulfoxide and/or glycerol; and whereby nucleic acid analytes can be processed prior to or simultaneously with immobilization to the molecular net with processing agents such as: nucleases, gyrases, topoisomerases, heat, and/or chemical; and whereby primers can hybridize to specific nucleotides of the nucleic acid analytes analytes; and whereby polymerases of the molecular net can replicate said nucleic acid analyte; and whereby replicated nucleic acid analyte can bind and be immobilized to specific capture molecules within specific regions, sections, and pieces of the molecular net; or can bind and be immobilized by capture molecules within specific regions, sections, and pieces of a neighboring molecular net; and whereby the immobilized replicated analyte can be detected by detection molecules; whereby detection molecules can be labeled nucleic acid probes or other labeled detection molecule; and whereby the binding of detection molecules can be a signal and can be detected in a binary or an analytical test.

Disclosed is a device that contains one or more PCR and/or RT-PCR chamber and chamber containing one or more molecular net that can capture and immobilize replicated nucleic acid analyte products from one or more PCR and/or RT-PCR; whereby PCR and/or RT-PCR can be conducted in a chamber preceding the chamber containing one or more molecular net; and whereby immobilized replicated nucleic acid analyte products can be detected and can produce a signal in a binary or an analytical test.

Disclosed is a device that can partition sample into separate chambers; and whereby said device contains one or more PCR and/or RT-PCR chamber and one or more analyte binding chamber containing one or more molecular net or arrangements of molecular nets and pieces thereof; whereby sample can be partitioned into PCR chamber and/or RT-PCR chamber and analyte binding chamber simultaneously; whereby the replicated nucleic acid analytes produced in the PCR and/or RT-PCR chamber can be moved into the analyte binding chamber and can be immobilized by molecular net capture molecules in concert with non-nucleic acid analytes that can be immobilized by different molecular net capture molecules; and whereby non-nucleic acid analytes and nucleic acid analytes can be detected simultaneously by labeled analyte detection molecules; and whereby immobilized labeled detection molecules can produce a signal in a binary or an analytical test.

Disclosed is a filtration unit device containing a single volume, whereby molecular net; layers of molecular net; arrangements of sections of molecular nets; can be fitted into a cartridge, column, piping, tubing, cassette or other polymeric containment unit; and whereby molecular net can serve as a filtration unit to specifically immobilize a plurality of analytes from a liquid sample and simultaneously allow liquid sample and unbound non-analytes to pass through said filtration volume; and whereby liquid sample and non-immobilized non-analytes can be returned to the sample source.

Disclosed is the use of and devices using molecular net as a molecular sponge to immobilize and remove specific analytes from a liquid sample; whereby emersion of one or more molecular sponge or device containing molecular sponge into a liquid sample can selectively remove all or a significant percentage of analytes of interest from said liquid sample; and whereby non-analytes of interest are not removed from said liquid sample.

FIGS. 43A-43B show two embodiments of a superplexing net. Superplexing nets are nets that capture multiple analytes related to a specific disease state. In some embodiments, superplexing nets comprise a number of molecular nets of the same composition. In other embodiments, superplexing nets comprise a number of molecular nets having different compositions. Superplexing nets can be fabricated by covalently interconnecting individual molecular nets together or can be fabricated by mixing individual pre-formed molecular nets together. In one example of a superplexing net, said superplexing net 4300 comprises an arranged pattern of molecular nets 4301, 4304, and 4307. FIGS. 43A-43B show top views of superplexing nets 4300 in a test volume. In a given superplexing net 4300, a net 4300 can comprise a patterned array (or patchwork) of nets 4301, 4304, and 4307 interconnected to one another through covalent linkers, or can be placed near one another. Said superplexing net 4300 can be on a solid-phase surface or can be in fluid-phase. Said superplexing net 4300 can be placed in a container with a known testing volume comprising one or more sensor and amplifier 4312 near one or more molecular net 4301, 4304, and/or 4307 of a superplexing net 4300.

In its simplest form, a superplexing net can comprise an array of a single type of molecular net. In other forms, a superplexing net 4300 can comprise an array of multiple molecular nets arranged in an array wherein the molecular nets, such as molecular nets 4301, 4304, and 4307, comprising said superplexing net 4300 are arranged in an array to maximize the capture of analytes by individual molecular nets 4301, 4304, and 4307 of a superplexing net 4300 in a sequential manner, such as arrangement 4310 shown in FIG. 43A. Another example of superplexing net arrangement is depicted in arrangement 4311 shown in FIG. 43B, whereby the arrangement of individual molecular nets 4301, 4304, and 4307 in a superplexing net 4300 maximizes the capture of specific analytes from a sample. Arrow 4313 depicts the flow of sample through arrangements 4310 and 4311 of various molecular nets 4301, 4304, and 4307 within a superplexing net 4300 to achieve optimal analyte capture for a given test.

FIGS. 43C-43E show various embodiments of molecular nets 4301, 4304, and 4307, respectively. Said superplexing nets 4300 comprises more than one molecular net comprising one or more layer, wherein each molecular net 4301, 4304, and 4307 comprises a mixture of different capture agents 4302, 4305, and 4308, respectively, that are directed against specific analytes known to be important for a disease state, wherein each capture agent provides binding affinity directed against a specific antigen based on the physicochemical properties of said capture agent and wherein said capture agents 4302, 4305, and 4308 are arranged and covalently interconnected by selected linker agents 4304, 4306, and 4309, respectively, wherein each linker agent imparts structural and spacing characteristics for each portion of molecular net.

Figure 44A:
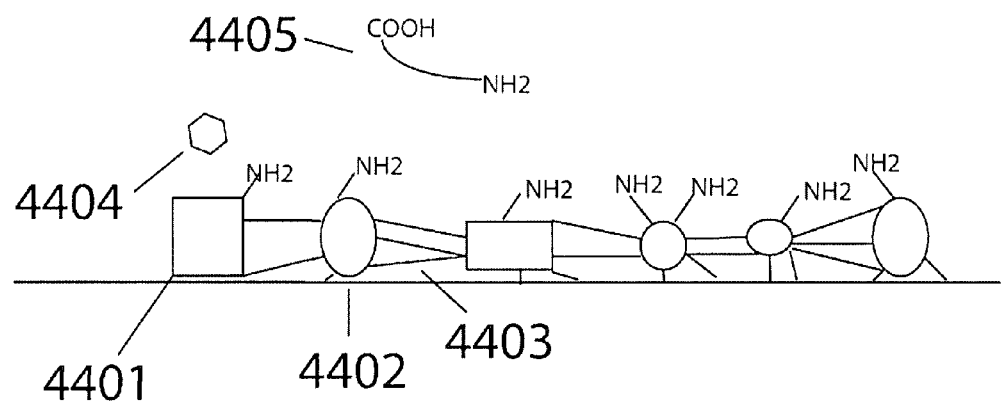
FIGS. 44A-44B show embodiments of modified molecular nets using cyanuric chloride linkers.
Figure 44B:
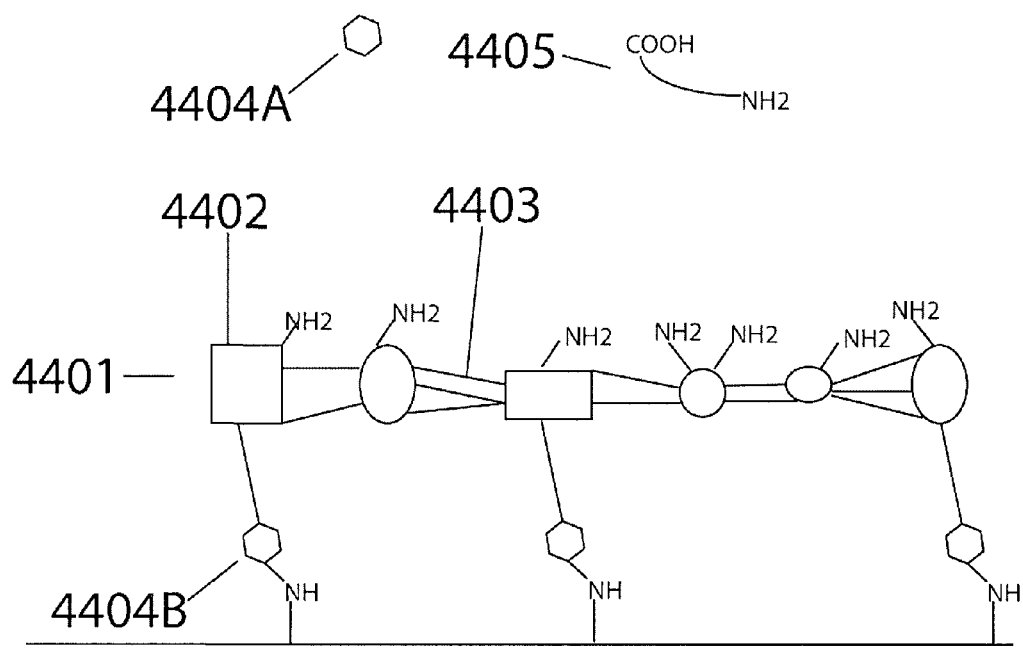

FIGS. 44A-44B show embodiments of modified molecular nets using cyanuric chloride linkers. Molecular nets can be used to capture single- and double-stranded nucleic acid analytes from a sample. Examples of molecular net compositions for the capture of single- and double-stranded nucleic acid analytes from a sample are presented in FIGS. 44A-44B. In one example shown in FIG. 44A, a portion of molecular net 4401 comprising capture agents 4402 and linker agents 4403 is fabricated on a solid phase surface. The capture agents 4402 for example are nucleic acid binding peptides, comprising poly-lysine and/or -arginine residues and/or nucleic acid binding motifs having primary amines, and are covalently linked together by linkers 4403 having predefined lengths. A step in the fabrication process involves the controlled exposure of the molecular net 4401 to cyanuric chloride 4404 for a period of time to generate reactive amines for the coupling of single- or double-stranded nucleic acids 4405 from a sample directly to a portion of molecular net 4401. Said molecular net portion can be used to bind nucleic acid in a non-specific manner to bind total nucleic acids in a sample, or can be used to bind specific nucleic acid sequences from a sample using pre-loaded capture nucleic acid sequences as capture components covalently linked in one or more portion of a molecular net 4401.

In another example as shown in FIG. 44B, a portion of molecular net 4401 comprising capture agents 4402 and linker agents 4403 is fabricated on a solid-phase surface by first treating said surface with cyanuric acid 4404B prior to the addition of a portion of capture agents 4402 and linker agents 4403. The capture agents 4402 are nucleic acid binding peptides, comprising poly-lysine and/or -arginine residues and/or nucleic acid binding motifs having primary amines, and are covalently linked together by linkers 4403 having predefined lengths. A step in the fabrication process can involve the controlled exposure of the molecular net 4401 to cyanuric chloride 4404A for a period of time to generate reactive amines for the coupling of single- or double-stranded nucleic acids 4405 from a sample directly to a portion of molecular net 4401. Said molecular net portion can be used to bind nucleic acid in a non-specific manner to bind total nucleic acids in a sample, or can be used to bind specific nucleic acid sequences from a sample using pre-loaded capture nucleic acid sequences as capture components covalently linked in one or more portion of a molecular net 4401.

Figure 45:
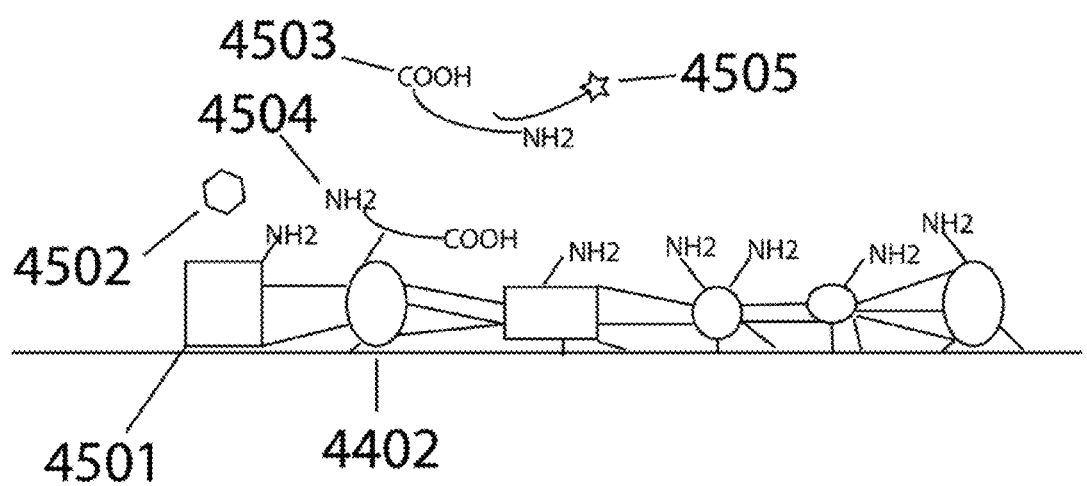
FIG. 45 shows attachment of amplified nucleic acid analytes to molecular nets.

FIG. 45 shows attachment of amplified nucleic acid analytes to molecular nets 4501. Molecular nets 4501 can also be chemically modified by cyanuric chloride 4502 in certain portion(s) of molecular net 4501 to capture nucleic acid analytes 4503 in a non-specific manner while other portions of molecular net can capture nucleic acid analytes in a sequence-specific manner by specific capture agents having complementary sequence 4504 to specific nucleic acid analytes in a sample. Specific analytes captured by said molecular net 4501 can be detected using specific detection probes having reporter agents against a portion of the captured nucleic acid 4505. Total nucleic acids captured by said molecular net 4501 can be detected using a non-specific detection reporter. In this example, the detection probes specifically recognize sequences and are labeled with Alexa647, while the non-specific (total) nucleic acid captured by the molecular net 4501 is labeled with propidium iodide, acridine orange, or other.

Figure 46:
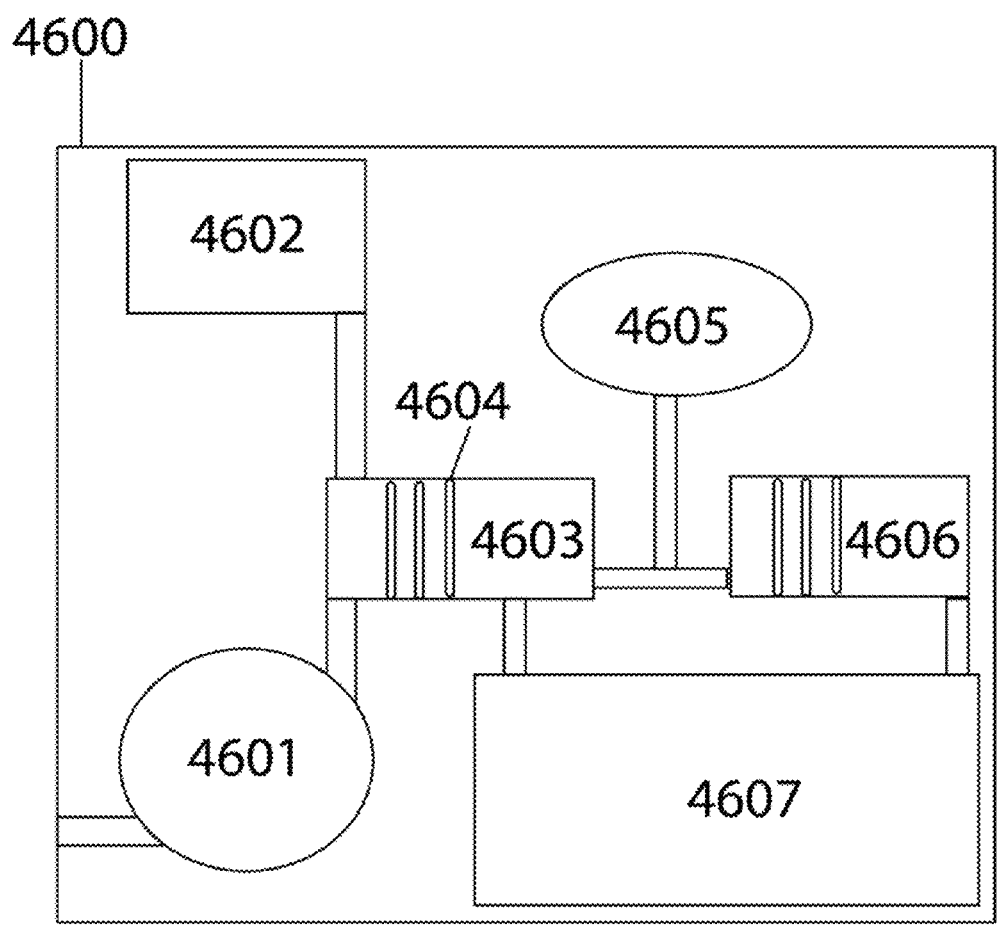
FIG. 46 shows an isothermal nucleic acid affinity test using molecular nets.

FIG. 46 shows an isothermal nucleic acid affinity test using molecular nets. Nucleic acid-capture nets can be used in thermocycling and isothermal PCR-mediated nucleic acid amplification for the improved amplification and measurement of target nucleic acid and amplicon. FIG. 46 depicts a device 4600 to capture one or more specific nucleic acid from a sample and to amplify said specific nucleic acid and to measure specific amplicons using molecular net. Said device 4600 comprises channels connecting: nucleic acid modification chamber 4601 to process, modify, denature and/or prepare nucleic acid analytes in a sample; buffer containment chamber 4602 to house buffer required in the amplification step; amplification chamber 4603 containing molecular nets 4604 comprised of specific nucleic acid capture agents that also serve as primers for nucleic acid polymerization; detection and wash chamber 4605 containing detection probes and wash buffer; amplicon detection chamber 4606 comprising molecular nets designed and fabricated to capture specific nucleic acid sequences and waste chamber 4607 to collect all flow-through and unbound sample.

Figure 47:
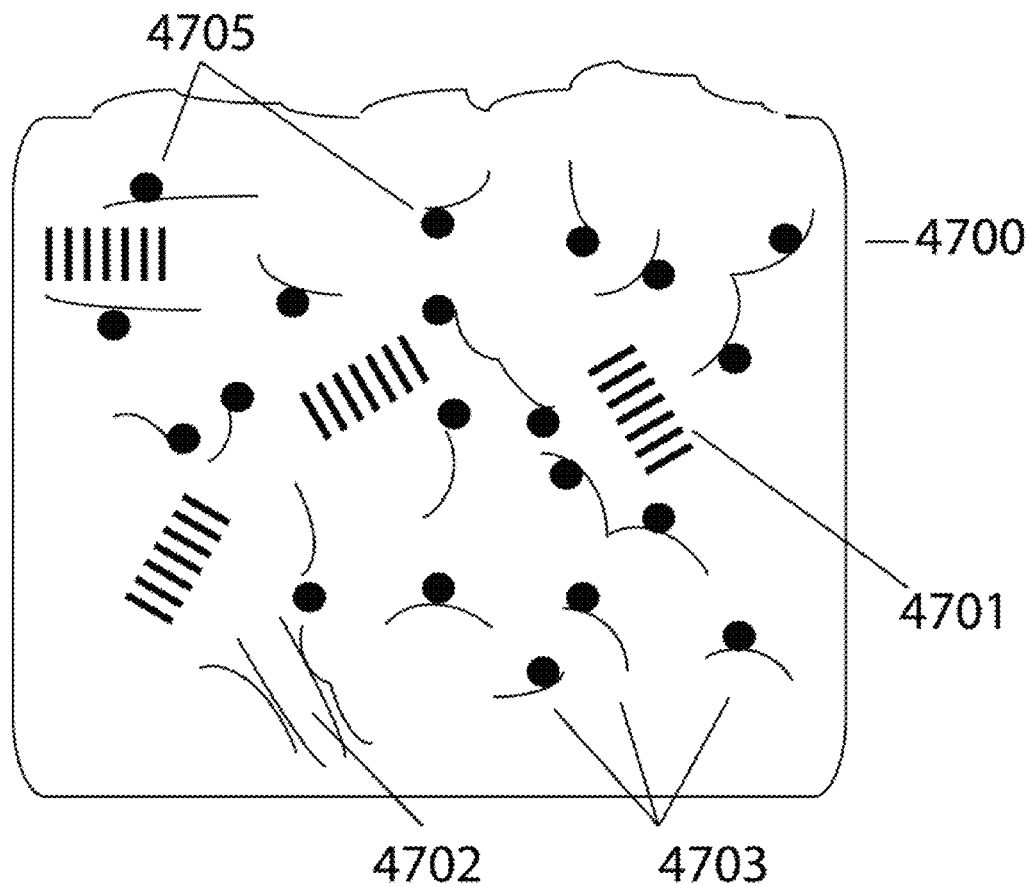
FIG. 47 shows molecular nets with capture molecules, colloidal metals, crosslinkers and various structural features.

FIG. 47 shows molecular nets with capture agents, colloidal metals, crosslinkers and various structural features. FIG. 47 shows a portion of a conductive molecular net 4700 depicting the three-dimensional topological features including the non-uniform structure, pockets 4701 and channels 4702 formed by different capture agents 4703 having different structures that are interconnected by covalent linkers having known lengths. In addition, said molecular net portion contains conductive metallic nanoparticles 4705 covalently linked to said capture agents 4703 to impart conductive properties to the net 4700. Upon specific binding of analyte to capture agent 4703, the conductive properties of said molecular net 4700 changes. Said conductive nanoparticles 4705 can be quantum dots, nanoparticles or microparticles comprised of semiconductive crystals, metals, metalloids or metal alloys.

Figure 48:
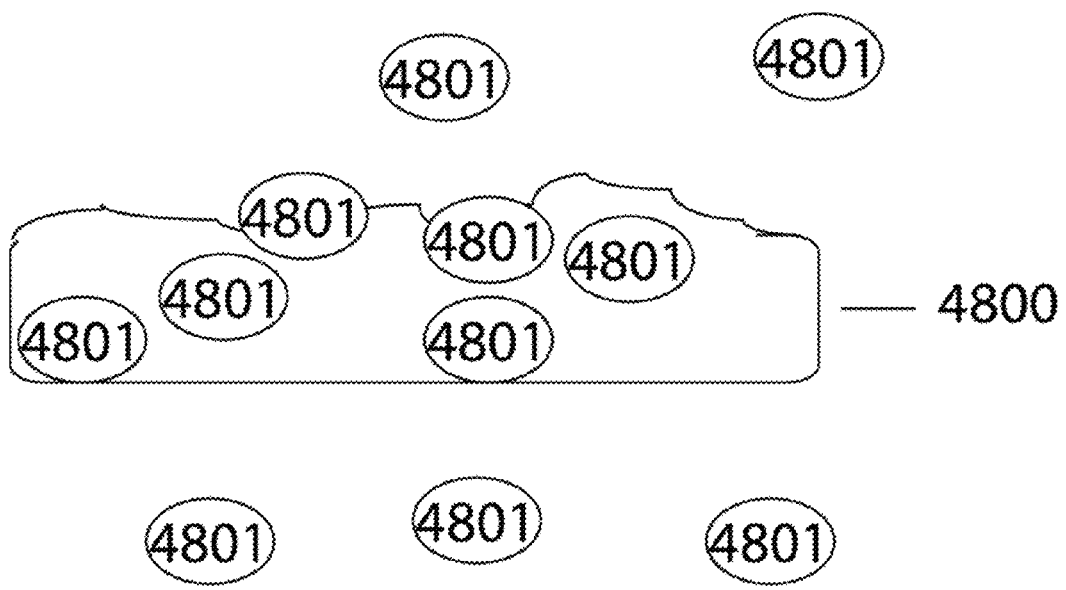
FIG. 48 shows molecular nets as sponges.

FIG. 48 shows molecular nets as sponges. Another attribute of molecular nets is that the three-dimensionality and non-uniform multi-layered structure imparts superior binding capacity compared to traditional capture technologies by alleviating stearic hindrance to maximize specific analyte binding. In this example a molecular net 4800 can have specific sponge-like properties to capture and bind specific analytes 4801 from a sample. Said molecular net 4800 can be applied to a liquid sample for the purposes of removal and/or detection of specific analytes 4801 from a liquid sample.

Figure 49:
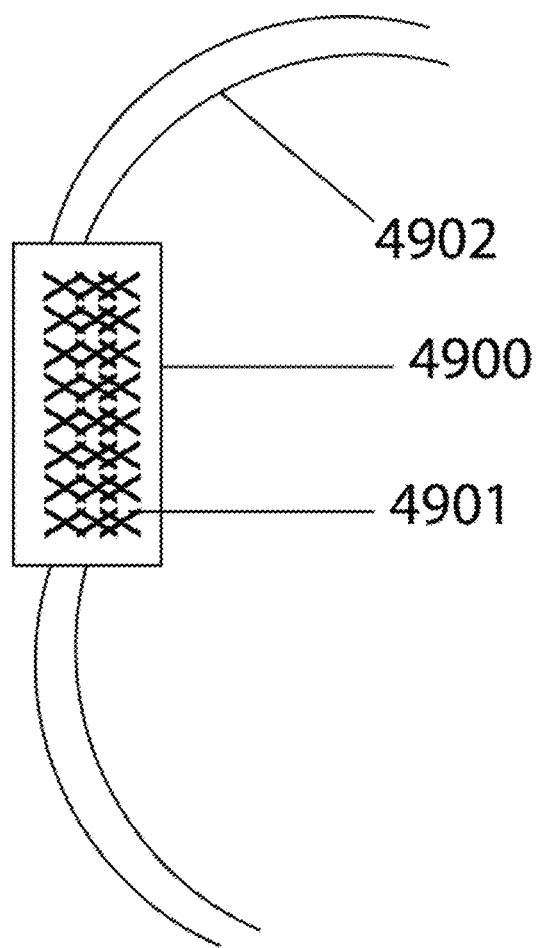
FIG. 49 shows molecular nets as filtration units.

FIG. 49 shows molecular nets as filtration units. The high capture capacity of molecular nets can be utilized to filter analytes from a sample. Molecular nets can be designed to capture analytes based on a combination of size, pattern recognition, and specific affinity. FIG. 49 presents an example of a removable cartridge 4900 comprising numerous multi-layered molecular nets packed in a manner to serve as a molecular filter 4901. Said multi-layered molecular nets can be covalently linked to receptive bead, mesh, paper or other surface comprised of one or more of the following: polystyrene, silica, polyethylene, polycarbonate, nylon, PTFE, semiconductive crystals, metals, metalloids, metal alloys, PVDF, nitrocellulose.

The removable cartridge 4900 can be connected by tubing 4902 from a sample source to guide sample flow through the cartridge 4900 in a directional manner, the flow-through of which can then be re-circulated to said sample source or can be directed to another reservoir. The sample source can be a biological sample including but not limited to an environmental sample containing microbes, a fermentation vessel, cell culture, blood, plasma, serum, urine, cerebral spinal fluid and interstitial tissue from an organism.

Said multi-layered molecular nets can be designed and fabricated to capture analytes such as but not limited to: cells, cellular debris, cellular products, metals, chelators, drugs, biologics, mitogens, cytokines, nucleic acids, proteins, lipids, cholesterols, hormones, bacteria, exosomes, viruses, fungi, toxins, protozoa and other agents and/or agents that can be removed from a biological sample by a molecular net based on a combination of size, pattern recognition and specific affinity.

Figure 50:
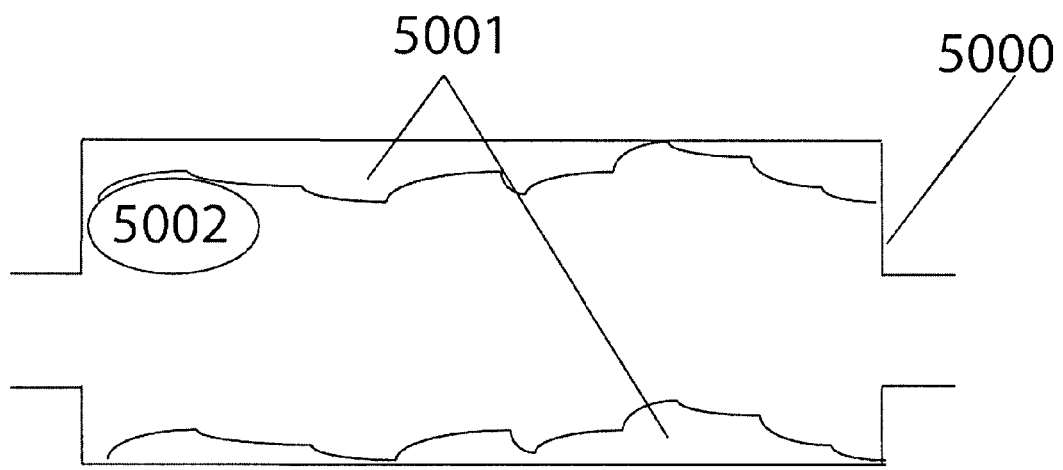
FIG. 50 shows molecular nets as walls.

FIG. 50 shows molecular nets as walls. In some cases, a vessel comprising molecular net covalently linked to the walls of said vessel is desirable for the capture of analytes from a sample. FIG. 50 presents an example of a vessel 5000 having molecular nets covalently linked to its walls 5001 for the capture and detection of analytes 5002 immobilized to a molecular net. Multi-layered molecular nets can be covalently linked to the walls 5001 of a vessel 5000 using traditional covalent chemical linker agents in a manner to enable maximal analyte capture as a sample flows through said vessel 5000. Examples of vessels of the current invention include cartridges, tubing, piping, bottles, columns, plates, slides, optical fibers, tips, cuvettes, semi-conducting nanowires, and other.

Said molecular net can have various measurable physical and/or chemical properties and the binding of one or more analyte to the molecular net can alter the physical and/or chemical properties of said molecular net, the change in said physical and/or chemical properties can be detected by a sensor. Said sensor will be calibrated to measure the baseline properties of said molecular net prior to administration of a sample. Said sensor will then measure said property(s) of said molecular net following administration of sample. A measurable change in molecular net property(s) indicates the presence of bound analyte(s).

Physical and chemical properties of the molecular net that can be sensed include magnetic, refractive index, electrical, thermal, compressiveness, scattering, acidity, basicity or other.

Figure 51:
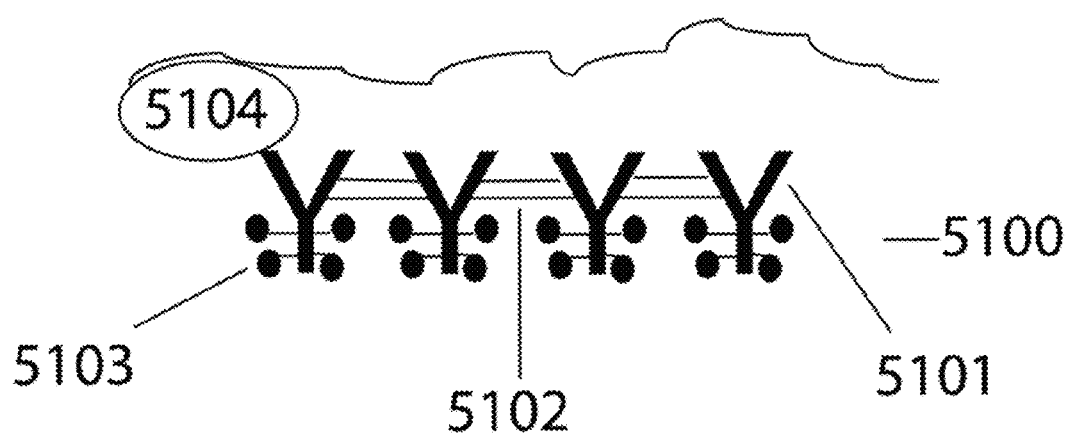
FIG. 51 shows analyte detection using crosslinked molecules and/or PEGylated with signal amplification molecules.

FIG. 51 shows analyte detection using crosslinked agents and/or PEGylated with signal amplification agents. Analyte capture can also be detected using molecular net nano-aggregates. Said molecular net nano-aggregates 5100 are fabricated in fluid-phase prior to use, comprising analyte capture agents 5101 covalently linked by linker agents 5102, wherein said capture agents 5101 are covalently bound to a signal amplification factor 5103. Said amplification factor 5103 can be: enzyme, metal, metalloid, metal alloy, visible dye, fluorophore, chemical, co-factor, substrate and combinations thereof. Said amplification factors 5103 can be directly linked to each capture agent 5101 prior to molecular net nano-aggregate fabrication or can be directly linked to the assembled molecular net nano-aggregate 5100.

In this example, analyte 5104 detection can be accomplished by co-incubation of molecular net nano-aggregates 5100 with captured analyte from a sample. Said molecular net nano-aggregates 5100 are comprised of analyte capture agents 5101 pre-linked with signal amplification factors 5103, the analyte capture agents 5101 of which are covalently linked together by linking agents 5102 comprising one or more PEG to generate a multi-Angstrom spacer. The length of each nano-aggregate 5100 is dictated by the size of the analyte to be detected and the optimal separation distance between signal amplification factors 5103 linked to each capture agents 5101. An increase in separation distance is achieved by the use of a multi-PEG linker.

While the present invention has been described with reference to the specific embodiments thereof, it should be understood by those skilled in the art that various changes can be made and equivalents can be substituted without departing from the scope of the invention. In addition, many modifications can be made to adapt a particular situation, material, composition of matter, process, process step or steps, to achieve the benefits provided by the present invention without departing from the scope of the present invention. All such modifications are intended to be within the scope of the claims appended hereto.

What is claimed is:

1. A layered, multipolymeric molecular net structure, the molecular net structure comprising:
    a base comprising a surface;
    a plurality of first capture agents, wherein at least one of the first capture agents selected from the plurality of first capture agents is directly connected to the base surface, or wherein at least one of the first capture agents is connected to the base surface by one or more of a first linker agent selected from a plurality of first linker agents; and
    a plurality of second capture agents, wherein at least one of the second capture agents selected from the plurality of second capture agents is indirectly connected to the base surface by a shortest linkage comprising (a) no more than one of the first capture agents and (b) (i) one or more of the first linker agents, (ii) one or more of a second linker agent, or (iii) both;
    wherein at least one of the second capture agents, in combination with its shortest linkage, forms a first multimer comprising at least (a) the second capture agent, (b) the first capture agent, and (c) (i) one or more of the first linker agents, (ii) one or more of the second linker agents, or (iii) both;
    wherein each first capture agent from the plurality of first capture agents is capable of specifically binding to one or more first analytes; and
    wherein each second capture agent from the plurality of second capture agents is capable of specifically binding to one or more second analytes.

2. The molecular net structure of claim 1, wherein the first capture agents of two first multimers are crosslinked by a linkage comprising (i) one or more of the first linker agents, (ii) one or more of the second linker agents, or (iii) both.

3. The molecular net structure of claim 1, wherein the second capture agents of two first multimers are crosslinked by a linkage comprising (i) one or more of the first linker agents, (ii) one or more of the second linker agents, or (iii) both.

4. The molecular net structure of claim 1, wherein the first capture agent of a first multimer is crosslinked to the second capture agent of another first multimer by a linkage comprising (i) one or more of the first linker agents, (ii) one or more of the second linker agents, or (iii) both.

5. The molecular net structure of claim 1, further comprising:
    a plurality of third capture agents, wherein at least one of the third capture agents are indirectly connected to the base surface by a shortest linkage comprising (a) no more than one of the second capture agents, (b) no more than one of the first capture agents, and (c) (i) one or more of the first linker agents, (ii) one or more of the second linker agents, (iii) one or more of a third linker agent, or (iv) a combination thereof;
    wherein at least one of the third capture agents selected from the plurality of third capture agents, in combination with its shortest linkage, forms a second multimer comprising at least (a) the second capture agent, (b) the first capture agent, (c) the third capture agent, and (d) (i) one or more of the first linker agents, (ii) one or more of the second linker agents, (iii) one or more of the third linker agents, or (iv) a combination thereof;
    wherein each third capture agent from the plurality of third capture agents is capable of specifically binding to one or more third analytes.

6. The molecular net of claim 5, wherein the second multimer comprises one or more of the third linker agents.

7. The molecular net of claim 5, wherein the first multimer comprises one or more of the second linker agents and the second multimer comprises one or more of the third linker agents.

8. The molecular net of claim 5, wherein the first multimer comprises one or more of the second linker agents, the second multimer comprises one or more of the third linker agents, and each layer has a different porosity.

9. The molecular net structure of claim 1, wherein the plurality of first capture agents is heterogeneous and comprise at least a first species of the first capture agent and a second species of the first capture agent that are specific to different targets.

10. The molecular net structure of claim 9, wherein at least one linker agent of the plurality of second linker agents is incapable of releasably binding a target to which either the first species of the first capture agent or the second species of the first capture agent is specific.

11. The molecular net structure of claim 1, wherein at least one capture agent in the molecular net is capable of releasably binding to at least one target, and wherein at least one linker agent of the plurality of second linker agents is incapable of releasably binding to any target for which at least one capture agent in the molecular net is capable of releasably binding.

12. The molecular net structure of claim 1, wherein the plurality of second linker agents are heterogeneous and comprise at least a first species of the second linker agent and a second species of the second linker agent, wherein the first species and the second species each have at least two reactive groups, and wherein the first species has different reactive groups than the second species.

13. The molecular net structure of claim 1, wherein a subset of the plurality of second linker agents is directly connected to at least two second capture agents.

14. The molecular net structure of claim 1, wherein a subset of the plurality of second capture agents is indirectly connected to at least two first capture agents.

15. The molecular net structure of claim 1, wherein the first capture agents are indirectly connected to the base surface by the one or more first linker agents, and wherein the second capture agents are indirectly connected to the base surface by a shortest linkage that comprises (a) no more than one first capture agent and (b) two or more of first linker agents, second linker agents, or both.

16. The molecular net structure of claim 1, wherein no greater than 70% of the capture agents in the molecular net structure are first capture agents.

17. The molecular net structure of claim 1, wherein the ratio of first capture agents to second capture agents in the molecular net structure is at least 1.5:1.

18. The molecular net structure of claim 1, wherein the base is selected from the group consisting of nitrocellulose, polystyrene, and polyurethane.

19. The molecular net structure of claim 1, wherein at least a portion of the surface of the base is formed of a different material than the base.

20. The molecular net structure of claim 19, wherein at least a portion of the surface of the base is a layer of polypeptides or carbohydrates.

21. The molecular net structure of claim 20, wherein at least a portion of the surface of the base is a layer of a polypeptide and the polypeptide is selected from a polypeptide comprising SEQ ID NO: 4, a polypeptide comprising SEQ ID NO: 5, a polypeptide comprising SEQ ID NO: 6, or a polypeptide comprising polyarginine, wherein the polypeptide forms a structural underlayer, and wherein the structural underlayer forms a portion of the surface.

22. The molecular net of claim 1, wherein each layer has a different porosity.

23. The molecular net of claim 1, wherein the first multimer comprises one or more of the second linker agents.

24. The molecular net of claim 1, wherein the first multimer comprises one or more of the second linker agents and each layer has a different porosity.

25. A branched, pseudorandom, multi polymeric molecular net, the molecular net comprising:
  a plurality of first capture agents and a plurality of second capture agents;
  wherein at least one first capture agent is connected to at least three other capture agents and each connection consists of (a) one or more of a first linker agent, (b) one or more of a second linker agent, or (c) both;
  wherein at least one second capture agent is connected to no more than two other capture agents and each connection consists of (a) one or more of the first linker agents, (b) one or more of the second linker agents, or (c) both;
  wherein each first capture agent from the plurality of first capture agents is capable of specifically binding to one or more first analytes; and
  wherein each second capture agent from the plurality of second capture agents is capable of specifically binding to one or more second analytes.

26. The molecular net of claim 25, further comprising a plurality of third capture agents, wherein each third capture agent is connected to no more than one other capture agent by (a) one or more of the first linker agents, (b) one or more of the second linker agents, (c) one or more of a third linker agent, or (d) a combination thereof.

27. The molecular net of claim 25, wherein at least 30% of the capture agents in the molecular net are first capture agents.

28. The molecular net of claim 25, wherein no more than 20% of the capture agents in the molecular net are second capture agents.

29. The molecular net of claim 26, wherein prior to forming the molecular net, each first capture agent comprises a capture agent reactive group and wherein a subset of the plurality of first linker agents comprises a linker reactive group that is reactive to the capture agent reactive group.

30. A branched, pseudorandom, multipolymeric molecular net, the molecular net comprising:
  an outer layer region comprising a plurality of first capture agents and a plurality of first linker agents, wherein at least one first capture agent is connected to no more than one other capture agent where each connection consists of a first linkage comprising one or more of the first linker agents and no capture agents;
  a first inner layer region comprising a plurality of second capture agents, wherein at least one second capture agent is connected to two other capture agents where each connection consists of a second linkage comprising (i) one or more of the first linker agents, one or more of a second linker agent, or both, and (ii) no capture agents;
  a second inner layer region comprising a plurality of third capture agents, wherein at least one third capture agent is connected to at least three other capture agents where each connection consists of a third linkage comprising (i) one or more of the first linker agents, one or more of the second linker agents, one or more of a third linker agent, or a combination thereof, and (ii) no capture agents;
  wherein
    (a) at least one second capture agent is directly connected to at least one first capture agent by a linkage comprising (i) one or more of the first linker agents, one or more of the second linker agents, one or more of the third linker agents, or a combination thereof, and (ii) no capture agents,
    or at least one second capture agent is indirectly connected to at least one first capture agent by a linkage comprising (i) one or more of the first linker agents, one or more of the second linker agents, one or more of the third linker agents, or a combination thereof, and (ii) one or more capture agents;
    (b) at least one third capture agent is directly connected to at least one first capture agent by a linkage comprising (i) one or more of the first linker agents, one or more of the second linker agents, one or more of the third linker agents, or a combination thereof, and (ii) no capture agents,
    or at least one third capture agent is indirectly connected to at least one first capture agent by a linkage comprising (i) one or more of the first linker agents, one or more of the second linker agents, one or more of the third linker agents, or a combination thereof, and (ii) one or more capture agents;
    (c) the second inner layer is between the first inner layer and the outer layer;
    (d) each first capture agent from the plurality of first capture agents is capable of specifically binding to one or more first analytes;
    (e) each second capture agent from the plurality of second capture agents is capable of specifically binding to one or more second analytes; and
    (f) each third capture agent from the plurality of third capture agents is capable of specifically binding to one or more third analytes.

31. The molecular net of claim 30, wherein the outer layer region, the first inner layer region, and the second inner layer region, each has a porosity that is different than the porosities of the other two regions.

* * * * *

SEQUENCE LISTING

```
<160> NUMBER OF SEQ ID NOS: 38

<210> SEQ ID NO 1
<211> LENGTH: 4
<212> TYPE: PRT
<213> ORGANISM: Artificial Sequence
<220> FEATURE:
<223> OTHER INFORMATION: motif
<220> FEATURE:
<221> NAME/KEY: VARIANT
<222> LOCATION: (2)..(2)
<223> OTHER INFORMATION: X is glycine, serine, proline or threonine
<220> FEATURE:
<221> NAME/KEY: VARIANT
<222> LOCATION: (3)..(3)
<223> OTHER INFORMATION: X is asparagine, arginine, glycine or threonine

<400> SEQUENCE: 1

Leu Xaa Xaa Leu
1

<210> SEQ ID NO 2
<211> LENGTH: 4
<212> TYPE: PRT
<213> ORGANISM: Artificial Sequence
<220> FEATURE:
<223> OTHER INFORMATION: motif
<220> FEATURE:
<221> NAME/KEY: VARIANT
<222> LOCATION: (2)..(2)
<223> OTHER INFORMATION: X is glycine, serine, proline or threonine
<220> FEATURE:
<221> NAME/KEY: VARIANT
<222> LOCATION: (3)..(3)
<223> OTHER INFORMATION: X is asparagine, arginine, glycine or threonine

<400> SEQUENCE: 2

Phe Xaa Xaa Leu
1

<210> SEQ ID NO 3
<211> LENGTH: 4
<212> TYPE: PRT
<213> ORGANISM: Artificial Sequence
<220> FEATURE:
<223> OTHER INFORMATION: motif
<220> FEATURE:
<221> NAME/KEY: VARIANT
<222> LOCATION: (2)..(2)
<223> OTHER INFORMATION: X is glycine, serine, proline or threonine
<220> FEATURE:
<221> NAME/KEY: VARIANT
<222> LOCATION: (3)..(3)
<223> OTHER INFORMATION: X is asparagine, arginine, glycine or threonine

<400> SEQUENCE: 3

Val Xaa Xaa Leu
1

<210> SEQ ID NO 4
```

```
<211> LENGTH: 20
<212> TYPE: PRT
<213> ORGANISM: Artificial Sequence
<220> FEATURE:
<223> OTHER INFORMATION: Nucleic acid binding sequence

<400> SEQUENCE: 4

Val Pro Thr Leu Glu Glu Leu Asn Leu Ser Tyr Asn Asn Ile Met Thr
1               5                   10                  15

Val Pro Ala Leu
            20

<210> SEQ ID NO 5
<211> LENGTH: 42
<212> TYPE: PRT
<213> ORGANISM: Artificial Sequence
<220> FEATURE:
<223> OTHER INFORMATION: Nucleic acid binding polypeptides

<400> SEQUENCE: 5

Leu Gly Asn Leu Thr His Leu Ser Leu Lys Tyr Asn Asn Leu Thr Val
1               5                   10                  15

Val Pro Arg Asn Leu Pro Ser Ser Leu Glu Tyr Leu Leu Ser Tyr
            20                  25                  30

Asn Arg Ile Val Lys Leu Ala Pro Glu Asp
            35                  40

<210> SEQ ID NO 6
<211> LENGTH: 28
<212> TYPE: PRT
<213> ORGANISM: Artificial Sequence
<220> FEATURE:
<223> OTHER INFORMATION: Nucleic acid binding peptide

<400> SEQUENCE: 6

Leu Ser Arg Leu Glu Gly Leu Val Leu Lys Asp Ser Ser Leu Ser Trp
1               5                   10                  15

Leu Asn Ala Ser Trp Phe Arg Gly Leu Gly Asn Leu
            20                  25

<210> SEQ ID NO 7
<211> LENGTH: 4
<212> TYPE: PRT
<213> ORGANISM: Artificial Sequence
<220> FEATURE:
<223> OTHER INFORMATION: motif
<220> FEATURE:
<221> NAME/KEY: VARIANT
<222> LOCATION: (3)..(3)
<223> OTHER INFORMATION: X is argnine or lysine
<220> FEATURE:
<221> NAME/KEY: VARIANT
<222> LOCATION: (4)..(4)
<223> OTHER INFORMATION: X is leucine or valine or serine or alanine or
      glycine or phenylalanine or tryptophan or aspartate or histidine

<400> SEQUENCE: 7

Phe Gly Xaa Xaa
1

<210> SEQ ID NO 8
<211> LENGTH: 4
<212> TYPE: PRT
<213> ORGANISM: Artificial Sequence
<220> FEATURE:
<223> OTHER INFORMATION: motif
<220> FEATURE:
```

```
<221> NAME/KEY: VARIANT
<222> LOCATION: (3)..(3)
<223> OTHER INFORMATION: X is arginine or lysine
<220> FEATURE:
<221> NAME/KEY: VARIANT
<222> LOCATION: (4)..(4)
<223> OTHER INFORMATION: X is leucine, valine, serine, alanine, glycine,
      phenylalanine, tryptophan, asparagine or histidine.

<400> SEQUENCE: 8

Phe Gly Xaa Xaa
1

<210> SEQ ID NO 9
<211> LENGTH: 4
<212> TYPE: PRT
<213> ORGANISM: Artificial Sequence
<220> FEATURE:
<223> OTHER INFORMATION: motif

<400> SEQUENCE: 9

Phe Gly Lys Ile
1

<210> SEQ ID NO 10
<211> LENGTH: 34
<212> TYPE: PRT
<213> ORGANISM: Artificial Sequence
<220> FEATURE:
<223> OTHER INFORMATION: binding peptide

<400> SEQUENCE: 10

Met Gln Met Thr Lys Ala Glu Phe Thr Phe Ala Asn Arg Leu Lys His
1               5                   10                  15

Asp Asp Leu Glu Glu Ile Tyr Ser Glu Leu Ser Asp Gln Phe Pro Tyr
            20                  25                  30

Trp Asp

<210> SEQ ID NO 11
<211> LENGTH: 42
<212> TYPE: PRT
<213> ORGANISM: Artificial Sequence
<220> FEATURE:
<223> OTHER INFORMATION: binding peptide

<400> SEQUENCE: 11

Tyr Ile Thr Cys Leu Phe Arg Gly Ala Arg Cys Arg Val Tyr Ser Gly
1               5                   10                  15

Arg Ser Cys Cys Phe Gly Tyr Tyr Cys Arg Arg Asp Phe Pro Gly Ser
            20                  25                  30

Ile Phe Gly Thr Cys Ser Arg Arg Asn Phe
            35                  40

<210> SEQ ID NO 12
<211> LENGTH: 7
<212> TYPE: PRT
<213> ORGANISM: Artificial Sequence
<220> FEATURE:
<223> OTHER INFORMATION: DNA binding peptide 1

<400> SEQUENCE: 12

Val Leu Phe Gly Lys Leu Ala
1               5

<210> SEQ ID NO 13
```

```
<211> LENGTH: 7
<212> TYPE: PRT
<213> ORGANISM: Artificial Sequence
<220> FEATURE:
<223> OTHER INFORMATION: DNA binding peptide 2

<400> SEQUENCE: 13

Val Met Phe Gly Lys Leu Ala
1               5

<210> SEQ ID NO 14
<211> LENGTH: 7
<212> TYPE: PRT
<213> ORGANISM: Artificial Sequence
<220> FEATURE:
<223> OTHER INFORMATION: DNA binding peptide 6

<400> SEQUENCE: 14

Val Phe Phe Gly Arg Leu Ala
1               5

<210> SEQ ID NO 15
<211> LENGTH: 29
<212> TYPE: DNA
<213> ORGANISM: Artificial Sequence
<220> FEATURE:
<223> OTHER INFORMATION: S. aureus probe

<400> SEQUENCE: 15
ggtatgtgga agttagattg ggatatagg                                    29

<210> SEQ ID NO 16
<211> LENGTH: 28
<212> TYPE: DNA
<213> ORGANISM: Artificial Sequence
<220> FEATURE:
<223> OTHER INFORMATION: S. aureus probe

<400> SEQUENCE: 16
aatagagaaa aaaaaaaga tggcaaag                                      28

<210> SEQ ID NO 17
<211> LENGTH: 28
<212> TYPE: DNA
<213> ORGANISM: Artificial Sequence
<220> FEATURE:
<223> OTHER INFORMATION: S. aureus probe

<400> SEQUENCE: 17
aatagagaaa agaaaaaaga tggcaaag                                     28

<210> SEQ ID NO 18
<211> LENGTH: 25
<212> TYPE: DNA
<213> ORGANISM: Artificial Sequence
<220> FEATURE:
<223> OTHER INFORMATION: S. aureus probe

<400> SEQUENCE: 18
agatgtgcac agttattaca catat                                        25

<210> SEQ ID NO 19
<211> LENGTH: 40
<212> TYPE: DNA
<213> ORGANISM: Artificial Sequence
<220> FEATURE:
<223> OTHER INFORMATION: S. aureus probe
```

```
<400> SEQUENCE: 19
gctattattt acttgaaatg aaagactgcg gaggctaact                              40

<210> SEQ ID NO 20
<211> LENGTH: 21
<212> TYPE: DNA
<213> ORGANISM: Artificial Sequence
<220> FEATURE:
<223> OTHER INFORMATION: S. aureus probe

<400> SEQUENCE: 20
acgacaavva tgcavvavvt g                                                 21

<210> SEQ ID NO 21
<211> LENGTH: 26
<212> TYPE: DNA
<213> ORGANISM: Artificial Sequence
<220> FEATURE:
<223> OTHER INFORMATION: mecA probe

<400> SEQUENCE: 21
gcaatacaat cgcactacat taatag                                            26

<210> SEQ ID NO 22
<211> LENGTH: 22
<212> TYPE: DNA
<213> ORGANISM: Artificial Sequence
<220> FEATURE:
<223> OTHER INFORMATION: mecA probe

<400> SEQUENCE: 22
cattttgagt tctgcagtac cg                                                22

<210> SEQ ID NO 23
<211> LENGTH: 18
<212> TYPE: DNA
<213> ORGANISM: Artificial Sequence
<220> FEATURE:
<223> OTHER INFORMATION: mecA probe

<400> SEQUENCE: 23
tcatagcgtc attattcc                                                     18

<210> SEQ ID NO 24
<211> LENGTH: 21
<212> TYPE: DNA
<213> ORGANISM: Artificial Sequence
<220> FEATURE:
<223> OTHER INFORMATION: mecA probe

<400> SEQUENCE: 24
atcacttggt atatcttcac c                                                 21

<210> SEQ ID NO 25
<211> LENGTH: 24
<212> TYPE: DNA
<213> ORGANISM: Artificial Sequence
<220> FEATURE:
<223> OTHER INFORMATION: mecA probe

<400> SEQUENCE: 25
tatccaccct caaacaggtg aatt                                              24

<210> SEQ ID NO 26
```

```
<211> LENGTH: 17
<212> TYPE: DNA
<213> ORGANISM: Artificial Sequence
<220> FEATURE:
<223> OTHER INFORMATION: mecA-mecRI probe

<400> SEQUENCE: 26
ccaaacccga caactac                                                      17

<210> SEQ ID NO 27
<211> LENGTH: 18
<212> TYPE: DNA
<213> ORGANISM: Artificial Sequence
<220> FEATURE:
<223> OTHER INFORMATION: mecA-mecRI

<400> SEQUENCE: 27
cgtgtcagat acatttcg                                                     18

<210> SEQ ID NO 28
<211> LENGTH: 24
<212> TYPE: DNA
<213> ORGANISM: Artificial Sequence
<220> FEATURE:
<223> OTHER INFORMATION: mecI probe

<400> SEQUENCE: 28
ccggaattcg catatggatt tcac                                              24

<210> SEQ ID NO 29
<211> LENGTH: 21
<212> TYPE: DNA
<213> ORGANISM: Artificial Sequence
<220> FEATURE:
<223> OTHER INFORMATION: mecI probe

<400> SEQUENCE: 29
gatggttcgt aggttatgtt g                                                 21

<210> SEQ ID NO 30
<211> LENGTH: 27
<212> TYPE: DNA
<213> ORGANISM: Artificial Sequence
<220> FEATURE:
<223> OTHER INFORMATION: mecI probe

<400> SEQUENCE: 30
cggatccgaa atggaattaa tataatg                                           27

<210> SEQ ID NO 31
<211> LENGTH: 24
<212> TYPE: DNA
<213> ORGANISM: Artificial Sequence
<220> FEATURE:
<223> OTHER INFORMATION: mecI probe

<400> SEQUENCE: 31
cggaattcga cttgattgtt tcct                                              24

<210> SEQ ID NO 32
<211> LENGTH: 24
<212> TYPE: DNA
<213> ORGANISM: Artificial Sequence
<220> FEATURE:
<223> OTHER INFORMATION: probe

<400> SEQUENCE: 32
```

```
ccttcctccc aacttaaagt gctt                                             24

<210> SEQ ID NO 33
<211> LENGTH: 27
<212> TYPE: DNA
<213> ORGANISM: Artificial Sequence
<220> FEATURE:
<223> OTHER INFORMATION: probe

<400> SEQUENCE: 33
ggagtaaagt taatacctttt gctcatt                                         27

<210> SEQ ID NO 34
<211> LENGTH: 20
<212> TYPE: DNA
<213> ORGANISM: Artificial Sequence
<220> FEATURE:
<223> OTHER INFORMATION: probe

<400> SEQUENCE: 34
acgacagcca tgcagcacct                                                  20

<210> SEQ ID NO 35
<211> LENGTH: 20
<212> TYPE: DNA
<213> ORGANISM: Artificial Sequence
<220> FEATURE:
<223> OTHER INFORMATION: S. aureus probe

<400> SEQUENCE: 35
gccagcagcg cggtaatacg                                                  20

<210> SEQ ID NO 36
<211> LENGTH: 22
<212> TYPE: DNA
<213> ORGANISM: Artificial Sequence
<220> FEATURE:
<223> OTHER INFORMATION: S. aureus probe

<400> SEQUENCE: 36
ggactaccag ggtatctaat cc                                               22

<210> SEQ ID NO 37
<211> LENGTH: 21
<212> TYPE: DNA
<213> ORGANISM: Artificial Sequence
<220> FEATURE:
<223> OTHER INFORMATION: Gram-positive bacterial probe

<400> SEQUENCE: 37
acgacaacca tgcaccacct g                                                21

<210> SEQ ID NO 38
<211> LENGTH: 12
<212> TYPE: PRT
<213> ORGANISM: Artificial Sequence
<220> FEATURE:
<223> OTHER INFORMATION: DNA binding peptide 7

<400> SEQUENCE: 38

Arg Arg Arg Arg Arg Arg Arg Arg Arg Arg Arg Arg
1               5                   10
```